United States Patent
Davis et al.

(10) Patent No.: US 9,845,460 B2
(45) Date of Patent: Dec. 19, 2017

(54) TREATMENT OF PLURIPOTENT CELLS

(71) Applicant: Janssen Biotech, Inc., Horsham, PA (US)

(72) Inventors: Janet Davis, Raritan, NJ (US); Jiajian Liu, Princeton, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 0 days.

(21) Appl. No.: 14/085,068

(22) Filed: Nov. 20, 2013

(65) Prior Publication Data

US 2014/0080210 A1   Mar. 20, 2014

Related U.S. Application Data

(62) Division of application No. 12/108,852, filed on Apr. 24, 2008, now Pat. No. 8,623,648.

(51) Int. Cl.
| | |
|---|---|
| *A61K 31/00* | (2006.01) |
| *C12N 5/02* | (2006.01) |
| *C12N 5/08* | (2006.01) |
| *C12N 5/071* | (2010.01) |
| *C12N 5/0735* | (2010.01) |

(52) U.S. Cl.
CPC ......... *C12N 5/0676* (2013.01); *C12N 5/0606* (2013.01); *A61K 31/00* (2013.01); *C12N 2501/105* (2013.01); *C12N 2501/115* (2013.01); *C12N 2501/117* (2013.01); *C12N 2501/119* (2013.01); *C12N 2501/16* (2013.01); *C12N 2501/415* (2013.01); *C12N 2501/48* (2013.01); *C12N 2501/70* (2013.01); *C12N 2506/00* (2013.01); *C12N 2506/02* (2013.01)

(58) Field of Classification Search
CPC .. A61K 31/00; C12N 5/0606; C12N 2506/00; C12N 2506/02
USPC ...................... 435/366, 377; 514/1
See application file for complete search history.

(56) References Cited

U.S. PATENT DOCUMENTS

| | | |
|---|---|---|
| 3,935,067 A | 1/1976 | Thayer |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,834,308 A | 11/1998 | Peck et al. |
| 5,843,780 A | 12/1998 | Thomson |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |
| 6,703,017 B1 | 3/2004 | Peck et al. |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomson et al. |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |

(Continued)

FOREIGN PATENT DOCUMENTS

| | | |
|---|---|---|
| EP | 0363125 A2 | 4/1990 |
| EP | 348969 B1 | 5/1993 |

(Continued)

OTHER PUBLICATIONS

Allegrucci et al., 2006, Human Reproduction Update, vol. Advance Access published on Aug. 26, 2006, p. 1-18.*

(Continued)

*Primary Examiner* — Shin Lin Chen
(74) *Attorney, Agent, or Firm* — Lois A. Gianneschi

(57) ABSTRACT

The present invention is provides a method for treating human pluripotent cells. In particular, the methods of the invention are directed to the treatment of human pluripotent cells, whereby the human pluripotent cells can be efficiently expanded in culture and differentiated by treating the pluripotent cells with an inhibitor of glycogen synthase kinase 3β (GSK-3B) enzyme activity.

9 Claims, 20 Drawing Sheets

(56) References Cited

U.S. PATENT DOCUMENTS

| | | |
|---|---|---|
| 7,993,920 B2 | 8/2011 | Martinson et al. |
| 2002/0072117 A1 | 6/2002 | Xu |
| 2003/0082155 A1 | 5/2003 | Habener |
| 2003/0138948 A1 | 7/2003 | Fisk et al. |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037488 A1 | 2/2005 | Mitalipova |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson et al. |
| 2005/0158852 A1 | 7/2005 | Wang et al. |
| 2005/0187298 A1 | 8/2005 | Vasudevan et al. |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0154981 A1 | 7/2007 | Hori et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0241107 A1 | 10/2008 | Copland, III et al. |
| 2008/0268533 A1 | 10/2008 | Dalton et al. |
| 2008/0268534 A1 | 10/2008 | Robins et al. |
| 2009/0203141 A1 | 8/2009 | Lin et al. |
| 2009/0298178 A1 | 12/2009 | D'Amour |
| 2010/0003749 A1 | 1/2010 | Uchida et al. |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0255580 A1 | 10/2010 | Rezania |
| 2011/0014703 A1 | 1/2011 | Xu et al. |
| 2012/0045830 A1 | 2/2012 | Green et al. |

FOREIGN PATENT DOCUMENTS

| | | |
|---|---|---|
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| WO | WO9219759 A2 | 2/1992 |
| WO | 9847892 A1 | 10/1998 |
| WO | WO9920741 A1 | 4/1999 |
| WO | 0029549 A1 | 5/2000 |
| WO | WO0151616 A2 | 7/2001 |
| WO | WO0181549 A3 | 11/2001 |
| WO | 0246183 A2 | 6/2002 |
| WO | 0246197 A1 | 6/2002 |
| WO | 02092756 A2 | 11/2002 |
| WO | 03026584 A2 | 4/2003 |
| WO | 03033697 A1 | 4/2003 |
| WO | 03042405 A2 | 5/2003 |
| WO | WO0305049 A1 | 6/2003 |
| WO | 03062405 A2 | 7/2003 |
| WO | 03095452 A1 | 11/2003 |
| WO | WO03102134 A2 | 12/2003 |
| WO | 2004016747 A2 | 2/2004 |
| WO | WO2004011621 A2 | 2/2004 |
| WO | 2004055155 A2 | 7/2004 |
| WO | 2004073633 A1 | 9/2004 |
| WO | 2004087885 | 10/2004 |
| WO | WO2004090110 A2 | 10/2004 |
| WO | 2005080598 A1 | 1/2005 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005086845 A2 | 9/2005 |
| WO | WO2005116073 A3 | 12/2005 |
| WO | 2006020919 A2 | 2/2006 |
| WO | WO2006016999 A1 | 2/2006 |
| WO | 2006026473 A1 | 3/2006 |
| WO | 2006100490 A1 | 9/2006 |
| WO | WO2006094286 A2 | 9/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007003525 A2 | 1/2007 |
| WO | 2007012144 A1 | 2/2007 |
| WO | 2007016485 A2 | 2/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | WO2007103282 A1 | 9/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2008094597 | 8/2008 |
| WO | 2008102118 A1 | 8/2008 |
| WO | 2009012428 A1 | 1/2009 |
| WO | 2009018453 A1 | 2/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009131568 A1 | 10/2009 |
| WO | 2010000415 A1 | 1/2010 |

OTHER PUBLICATIONS

Sato et al., 2003, Developmental Biology, vol. 260, p. 404-413.*
Rao, M., 2004, Developmental Biology, vol. 275, p. 269-286.*
Abeyta et al., 2004, Human Molecular Genetics, vol. 13, No. 6, p. 601-608.*
Bellin et al., 2012, Nature reviews/Molecular Cell Biology, vol. 13, p. 713-726.*
Burridge et al., 2011, PLoS One, vol. 6, No. 4, e18293, p. 1-16).*
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.

(56) References Cited

OTHER PUBLICATIONS

Ackermann, et al., Molecular Regulation of Pancreatic B-Cell Mass Development, Maintenance, and Expansion, Journal of Molecular Endocrinology, 2007, pp. 193-206, vol. 38.

Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.

Allegrucci, et al., Differences between Human Embryonic Stem Cell Lines, Human Reproduction Update, Aug. 26, 2006, pp. 1-18, Advance Access.

Amit et al., Human Feeder Layers for Human Embryonic Stem Cells, Biology of Reproduction, Jan. 22, 2003, 2150-2156, 68, No. 6, Society for the Study of Reproduction, Inc..

Amit, et al., Clonally Derived Human Embryonic Stem Cell Lines Maintain Pluripotency and Proliferative Potential for Prolonged Periods of Culture, Developmental Biology, 2000, pp. 271-278, vol. 227.

Amit, et al., Feeder Layer-and Serum-Free Culture of Human Embryonic Stem Cells, Biology of Reproduction, 2004, pp. 837-845, vol. 70.

Arai, et al., Purification of Recombinant Activin A Using the Second Follistatin Domain of Follistatin-Related Gene (FLRG), Protein Expression & Purification, 2006, pp. 78-82, vol. 49.

Armstrong, et al., The Role of P13K/AKT, MAPK/ERK and $NFK_{\kappa\beta}$ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.

Baetge, Production of B-Cells from Human Embryonic Stem Cells, Diabetes, Obesity, Metabolism, 2008, pp. 186-194, vol. 10, Supplement 4.

Balsam, et al., Haematopoeitic Stem Cells Adopt Mature Haeatopoietic Fates in Ischaemic Myocardium, Nature, Apr. 8, 2004, pp. 668-673, ?, Nature Publishing Group.

Barclay, et al., The Leucocyte Antigen Facts Book, The Leucocyte Antigen Facts Book, 1997, Textbook, 2[sup] edition, Academic Press.

Beltrami, et al., Adult Cardiac Stem Cells are Multipotent and Support Myocardial Regeneration, Cell, Sep. 19, 2003, pp. 763-776, vol. 114, Cell Press.

Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.

Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.

Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.

Bocian-Sobkowska, et al., Polyhormonal Aspect of the Endocrine Cells of the Human Fetal Pancreas, Histochem Cell Biol, 1999, pp. 147-153, vol. 112, Issue 2.

Bonner-Weir et al., In vitro cultivation of human islets from expanded ductal tissue, Proceedings of the National Academy of Sciences, Jul. 5, 2000, 7999-8004, 97-14, National Academy of Sciences.

Borowiak, et al., How to Make AB Cells, Current Opinion Cell Biology, 2009, pp. 727-732, vol. 21, Issue 6.

Borowitz, et al., Prognostic Significance of Fluorescence Intensity of Surface Marker . . . , Blood, Jun. 1, 1997, 3960-3966, 89-11, American Society of Hematology, Washington, D.C., US.

Braam, et al., Improved Genetic Manipulation of Human Embryonic Stem Cells, Nature Methods, May 2008, pp. 389-392, vol. 5, No. 5.

Brakenhoff et al., Development of a Human Interleukin-6 Receptor Antagonist, Journal of Biological Chemistry, Jan. 7, 1994, 86-93, 269-1, US.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini, et al., No Shortcuts to Pig Embryonic Stem Cells, Theriogenology, 2010, pp. 544-550, vol. 74.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature Biotechnology, Apr. 1, 2004, 381-381, 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Rat Marrow Mesencymal Stem Cells in Pancreatic Islet Beta-Cells, World Journal of Gastroenterology, Oct. 15, 2004, 3016-3020, 10.

Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.

Cheon, et al., Defined Feeder-Free Culture System of Human Embryonic Stem Cells, Biol Reprod, 2005, 105.046870, DOI10/1095.

Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, and Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al., Efficient differentiation of human embryonic stem cells to definitive endoderm, Nature Biotechnology, Oct. 28, 2005, 1-8, :W.1038/nbt1163, Nature Publishing Group.

D'Amour et al., Production of pancreatic hormone-expressing endocrine cells from human embryonic stem cells, Nature Biotechnology, Oct. 19, 2006, 1392-1401, 24-11, Nature Publishing Group, US.

Damy, et al., Increased Neuronal Nitric Oxide Synthase-Derived NO Production in the Failing Human Heart, Research Letters, Apr. 24, 2004, pp. 1365-1367, vol. 363.

David M. Chacko, et al., Survival and Differentiation of Cultured Retinal Progenitors Transplanted in the Subretinal Space of the Rat,

(56) References Cited

OTHER PUBLICATIONS

Biochemical and Biophysical Research Communications, 2000, pp. 842-846, vol. 268, Academic Press.
De Rosa, 11-color, 13-parameter flow cytometry: Identification of . . . , Nature, Feb. 1, 2001, 245-248, 7-2, Nature Publishing Group, US.
Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.
Donovan, et al., The End of the Beginning for Pluripotent Stem Cells, Nature, Nov. 2001, pp. 92-97, vol. 414.
Dorrell, et al., Editorial, Stem Cell Research, 2008, pp. 155-156, vol. 1.
Doyle, et al., Cell and Tissue Culture: Laboratory Procedures in Biotechnology, Cell and Tiossue Culture: Laboratory Procedures in Biotechnology, 1995, Textbook, Textbook, Wiley.
Draper, et al., Recurrent Gain of Chromosomes 17q and 12 in Cultured Human Embryonic Stem Cells, Nature Biotechnology, 2004, pp. 53-54, vol. 22, No. 1.
Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.
Dupont-Gillain, et al., Plasma-Oxidized Polystyrene: Wetting Properties and Surface Reconstruction, Langmuir, 2000, pp. 8194-8200, vol. 16.
Edlund, Pancreatic Organogenisis—Pancreatic Mechanisims and Implications for Therapy, Nature, Jul. 1, 2002, 524-532, 3, Nature Publishing Group, US.
Ellerstrom, et al., Derivation of a Xeno-Free Human Embryonic Stem Cell Line, Stem Cells, 2006, pp. 2170-2176, vol. 24.
Ellerstrom, et al., Facilitated Expansion of Human Embryonic Stem Cells by Single-Cell Enzymatic Dissociation, Stem Cells, 2007, pp. 1690-1696, vol. 25, No. 7.
Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low 02 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Fok, et al., Shear-Controlled Single-Step Mouse Embryonic Stem Cell Expansion and Embryoid Body-Based Differentiation, Stem Cells, 2005, pp. 1333-1342, vol. 23.
Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gershengorn et al., Epithelial-to-Mesenchymal Transition Generates Proliferative Human Islet Precursor Cells, Science, Dec. 24, 2004, 2261-2264, 306, US.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, 360-380, vol. 269.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hasegawa, et al., A Method for the Selection of Human Embryonic Stem Cell Sublines with High Replating Efficacy After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Ho, et al., Animal Cell Bioreactors, Animal Cell Bioreactors, 1991, 1-512, Hardcover, Butterworth-Heinemann.

(56) References Cited

OTHER PUBLICATIONS

Hoehn, et al., Morphological and Biochemical Heterogeneity of Amniotic Fluid Cells in Culture, Methods in Cell Biology, 1982, pp. 11-34, vol. 26, Academic Press, Inc.

Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.

Hussain, et al., Stem-Cell Therapy for Diabetes Mellitus, Lancet, 2004, pp. 203-205, vol. 364.

Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.

Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.

Int' Anker, et al., Amniotic Fluid as a Novel Source of Mesenchymal Stem Cells for Therapeutic Transplantation, Blood, Aug. 15, 2003, pp. 1548-1549, vol. 102, No. 4.

Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.

Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.

Jeon, et al., Endocrine Cell Clustering During Human Pancreas Development, J Histochem Cytochem, 2009, pp. 811-824, vol. 57, Issue 9.

Jiang, et al., Generation of Insulin-Producing Islet-Like Clusters from Human Embryonic Stem Cells, Stem Cells, 2007, pp. 1940-1953, vol. 25, Issue 8.

Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.

Kahan, Pancreatic Precursors and Differentiated Islet Cell Types from Murine Embryonic Stem Cells, Diabetes, Aug. 2003, pp. 2016-2042, vol. 52.

Kelly, et al., Cell-Surface Markers for the Isolation of Pancreatic Cell Types Derived from Human Embryonic Stem Cells, Nature Biotechnology, 2011, pp. 750-756, vol. 29, Issue 8.

Kicic, et al., Differentiation of Marrow Stromal Cells into Photoreceptors in the Rat Eye, The Journal of Neuroscience, Aug. 27, 2003, pp. 7742-7749, vol. 23, Issue 21.

Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.

Kinkel, et al., Cyp26 Enzymes Function in Endoderm to Regulate Pancreatic Field Size, PNAS, May 12, 2009, pp. 7864-7869, vol. 106, No. 19.

Kleinman et al., Basement Membrane Complexes with Biological Activity, Biochemistry, 1986, 312-318, 25, American Chemical Society.

Klimanskaya, et al., Human Embryonic Stem Cells Derived without Feeder Cells, Lancet, May 2005, pp. 1636-1641, vol. 365, No. 9471.

Koblas, et al., Differentiation of CD133-Positive Pancreatic Cells Into Insulin-Producing Islet-Like Cell Clusters, Transplantation Proceedings, 2008, pp. 415-418, vol. 40.

Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.

Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.

Koyangi et al., Inhibitio not the Rho/ROCK Pathway Reduces Apoptosis During Transplantatation of Embryonic Stem Cell-Derived Neural Precursors, Journal of Neurosciene Research, Sep. 7, 2007, 270-280, 86, Wiley-Liss, Inc.

Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.

Ku et al., Committing Embryonic Stem Cells to Early Endocrine Pancreas In Vitro, Stem Cells, 2004, 1205-1217, 22, AlphaMed Press.

Kubo et al., Development of definitive endoderm from embryonic stem cells in culture, Development, 2004, 1651-1662, 131, The Company of Biologists.

Lanza, et al., Characteristics and Characterization of Human Pluripotent Stem Cells, Stem Cell Anthology, 2010, pp. 142, 144 and 146, 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Levenstein et al., Basic Fibroblast Growth Factor Support of Human Embryonic Stem Cell Self-Renewal, Stem Cells, Nov. 10, 2005, 568-574, 24, AlphaMed Press.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Lilja et al., Cyclin-dependent Kinase 5 Promotes Insulin Exocytosis, Journal of Biological Chemistry, Jul. 6, 2001, 34199-34205, 36-7, JBC Papers in Press.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

(56) References Cited

OTHER PUBLICATIONS

Loh, et al., Genomic Approaches to Deconstruct Puripotency, Annu Rev Genomics Hum Genet, 2011, pp. 165-185, vol. 12.
Ludwig, et al., Derivation of Human Embryonic Stem Cells in Defined Conditions, Nature Biotechnology, Feb. 2006, pp. 185-187, vol. 24 No. 2.
Lumelsky, et al., Differentiation of Embryonic Stem Cells to Insulin-Secreting Structures Similar to Pancreatic Islets, Science, 2001, 1389-1394, 292, HighWire Press.
Lund, et al., Cell Transplantation as a Treatment for Retinal Disease, Progress in Retinal and Eye Research, 2001, pp. 415-449, vol. 20, No. 4, Elsevier Science Ltd.
Lund, et al., Retinal Transplantation: Progress and Problems in Clinical Application, Journal of Leukocyte Biology, Aug. 2003, pp. 151-160, vol. 74.
Lyttle, et al., Transcription Factor Expression in the Developing Human Fetal Endocrine Pancreas, Diabetologica, 2008, pp. 1169-1180, vol. 51, Spring-Verlag.
Maherali, et al., Directly Reprogrammed Fibroblasts Show Global Epigenetic Remodeling and Widespread Tissue Cell Contribution, Cell Stem Cell, Jul. 2007, pp. 55-70, vol. 1, Elsevier, Inc.
Marshall, et al., Early Micro-and Macro-Angiopathy in the Streptozotocin, Research in Experimental Medicine, 1980, pp. 145-158, vol. 177, Springer-Verlag.
Marshall, et al., Isolation and Maintenance of Primate Embryonic Stem Cells, Methods in Molecular Biology, 2001, pp. 11-18, vol. 158.
Martin, et al., Bioreactors for Tissue Mass Culture: Design, Characterization, and Recent Advances, Biomaterials, Jul. 14, 2005, pp. 7481-7503, vol. 26.
Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.
McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.
McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.
McLin, et al., Repression of WNT/(szligbeta)-6atenin Signaling in the Anterior Endoderm is Essential for Liver and Pancreas Development, Development, 2007, pp. 2207-2217, vol. 134, Issue 12.
Meijer, et al., Pharmacological Inhibitors of Glycogen Synthase Kinase 3, Trends in Pharmacological Sciences, Sep. 2004, pp. 471-480, vol. 25, No. 9.
Micallef et al., Retinoic Acid Induces Pdx1-Positive Endoderm in Differentiating Mouse Embryonic Stem Cells, Diabetes, Feb. 2005, 301-305, 54, American Diabetes Association.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Mitalipova, et al., Preserving the Genetic Integrity of Human Embryonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, 433-440, 22, AlphaMed Press.
Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.
Moore, et al., The Corneal Epithelial Stem Cell, DNA and Cell Biology, 2002, pp. 443-451, vol. 21, No. 5/6.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Munoz, et al., Conventional Pluripotency Markers are Unspecific for Bovine Embryonic-Derived Cell-Lines, Theriogenology, 2008, pp. 1159-1164, vol. 69.
Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nicholas et al., A Method for Single-Cell Sorting and Expansion of Genetically modified Human Embryonic Stem Cells, Stem Cells and Development, 2007, 109-117, 16, Mary Ann Liebert, Inc.
Nishimura, et al., Expression of MafA in Pancreatic Progenitors is Detrimental for Pancreatic Development, Developmental Biology, 2009, pp. 108-120, vol. 333.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Oh, et al., Human Embryonic Stem Cells: Technological Challenges Towards Therapy, Clinical and Experimental and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Corning CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Peerani, et al., Niche-Mediated Control of Human Embryonic Stem Cell Self-Renewal and Differentiation, The EMBO Journal, 2007, pp. 4744-4755, vol. 26.
Phillips, et al., Attachment and Growth of Human Embryonic Stem Cells on Microcarriers, Journal of Biotechnology, 2008, pp. 24-32, vol. 138.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.

(56) References Cited

OTHER PUBLICATIONS

Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct-4-Expressing Cells in Human Amniotic Fluid: a New Source for Stem Cell Research?, Human Reproduction, 2003, pp. 1489-1493, vol. 18, No. 7.
Rajagopal, et al., Insulin Staining of ES Cell Progeny from Insulin Uptake, Science, Jan. 17, 2003, pp. 363, vol. 299.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, 399-404, 18, Nature America Inc.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Ricordi et al., Automated Method for Isolation of Human Pancreatic Islets, Diabetes, Apr. 1988, 413-420, 37, American Diabetes Association.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adultmesenchymal Stem Cells in the CNS, Society for Neuroscience Abstract Viewer and Itineray Planner, 2002, XP002519394, Program 237.18.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Scullica, et al., Diagnosis and Classification of Macular Degenerations: an Approach Based on Retinal Function Testing, Documenta Ophthalmologica, 2001, pp. 237-250, vol. 102.
Seaberg et al., Cfonal identification of multipotent precursors from adult~mouse pancreas that generate neural and pancreatic lineages, Nature Biotechnology, Sep. 2004, pp. 1115-1124, vol. 22, No. 9, Nature Publishing Group.
Segev, et al., Differentiation of Human Embryonic Stem Cells into Insulin-Producing Clusters, Stem Cells, Jan. 1, 2004, pp. 265-274.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.
Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.
Sherwood, et al., Transcriptional Dynamics of Endodermal Organ Formation, Developmental Dynamics, 2009, pp. 29-42, vol. 238, Issue 1.
Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.
Shindler et al., A synthetic nanofibrillar matrix promotes in vivo-like organization and morphogenesis for cells in culture, Biomaterials, Apr. 18, 2005, 5624-5631, 26, Elsevier.
Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.
Shiraki, et al., Guided Differentiation of Embryonic Stem Cells into Pdx1-Expressing Regional-Specific Definitive Endoderm, Stem Cells, 2008, pp. 874-885, vol. 26.
Sidhu et al., Derivation of Three Clones from Human Embryonic Stem Cell Lines by FACS Sorting and Their Characterization, Stem Cells and Development, 2006, 61-69, 15, Mary Ann Liebert, Inc.
Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.
Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.
Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.
Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.
Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.
Stadtfeld, et al., Defining Molecular Cornerstones During Fibroblast to iPS Cell Reprogramming in Mouse, Cell Stem Cell, Mar. 2008, pp. 230-240, vol. 2.
Stafford, et al., Retinoic Acid Signaling is Required for a Critical Early Step in Zebrafish Pancreatic Development, Current Biology, 2002, pp. 1215-1220, vol. 12, Issue 14.
Stojkovic et al., An Autogeneic Feeder Cell System That Efficiently Supports Growth of Undifferentiated Human Embryonic Stem Cells, Stem Cells, 2005, 306-314, 23, AlphaMed Press.
Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.
Sugiyama, et al., Fluorescence-Activated Cell Sorting Purification of Pancreatic Progenitor Cells, Diabetes, Obesity and Metabolism, 2008, pp. 179-185, vol. 10, Supplement 4.
Suh, et al., Characterization of His-X3-His Sites in a-Helices of Synthetic Metal-Binding Bovine Somatotropin, Protein Engineering, 1991, pp. 301-305, vol. 4, No. 3.
Sulbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.
Takahashi, et al., Homogenous Seeding of Mesenchymal Stem Cells into Nonwoven Fabric for Tissue Engineering, Tissue Engineering, 2003, pp. 931-938, vol. 9, No. 5.

(56) References Cited

OTHER PUBLICATIONS

Takahashi, et al., Induction of Pluripotent Stem Cells from Adult Human Fibroblasts by Defined Factors, Cell, 2007, pp. 861-872, vol. 131.
Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.
Tang, et al., Reprogramming Liver-Stem WB Cells into Functional Insulin-Producing Cells by Persistent Expression Pdx1-and Pdx1-VP16 Mediated by Lentiviral Vectors, Laboratory Investigation, 2006, pp. 83-93, vol. 86.
Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.
Teare, et al., Cellular Attachment to Ultraviolet Ozone Modified Polystyrene Surfaces, Langmuir, 2000, pp. 2818-2824, vol. 16.
Thomson et al., Embryonic Stem Cell Lines Derived from Human Blastocysts, Science, Nov. 6, 1998, 1145-1147, 282, HighWire Press.
Thomson et al., Isolation of a primate embryonic stem cell line, Developmental Biology, Aug. 1995, 7844-7848, 92, Proc. Natl. Acad. Sci, US.
Thomson et al., Primate Embryonic Stem Cells, Currenl Topics in Developmental Biology, 1998, 133-154, 38, Academic Press, US.
Tomita, et al., Bone Marrow-Derived Stem Cells Can Differentiate into Retinal Cells in Injured Rat Retina, Stem Cells, 2002, pp. 279-283, vol. 20.
Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediatric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: in vivo systems pathology and systems pharmacology, Nature, Dec. 1, 2005, 961-967, 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structurs of Anthraquinones with their Effects onthe Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Acitivity, The Journal of Cell Biology, 2005, pp. 443-445, vol. 170, No. 3.

(56) References Cited

OTHER PUBLICATIONS

Young, et al., Three-Dimensional Culture of Human Uterine Smooth Muscle Nyocytes on a Resorbably Scaffolding, Tissue Engineering, 2003, pp. 451-459, vol. 9, No. 3.

Yu, et al., Induced Pluripotent Stem Cell Lines Derived from Human Somatic Cells, Science, Dec. 21, 2007, pp. 1917-1920, vol. 318.

Yu, et al., Isolation of a Novel Population of Multipotent Adult Stem Cells from Human Hair Follicles, American Journal of Pathology, Jun. 6, 2006, pp. 1879-1888, vol. 168, No. 6.

Zhang et al., MafA Is a Key Regulator of Glucose-Stimulated Insulin Secretion, Molecular and Cellular Biology, Jun. 2005, 4969-4976, 25-12, American Society for MIcrobiology.

Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.

Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127.

ZHANG_et_al, Highly Efficient Differentiation of Human ES Cells and iPS Cells into Mature Pancreatic Insulin-Producing Cells, Cell Research, 2009, pp. 429-438, vol. 19, Issue 14.

Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.

Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.

Zorn, et al., Vertebrate Endoderm Development and Organ Formation, Annual Review Cell Development Biology, 2009, pp. 221-251, vol. 25.

Zubaty, et al., Transplantation of Mesenchymal Stem Cells into RCS Rats for Retinal Repair, Investigative Ophthalmology and Visual Science, 2005, pp. 4160-B518, vol. 46, Supplement S.

\* cited by examiner

Figure 10-A
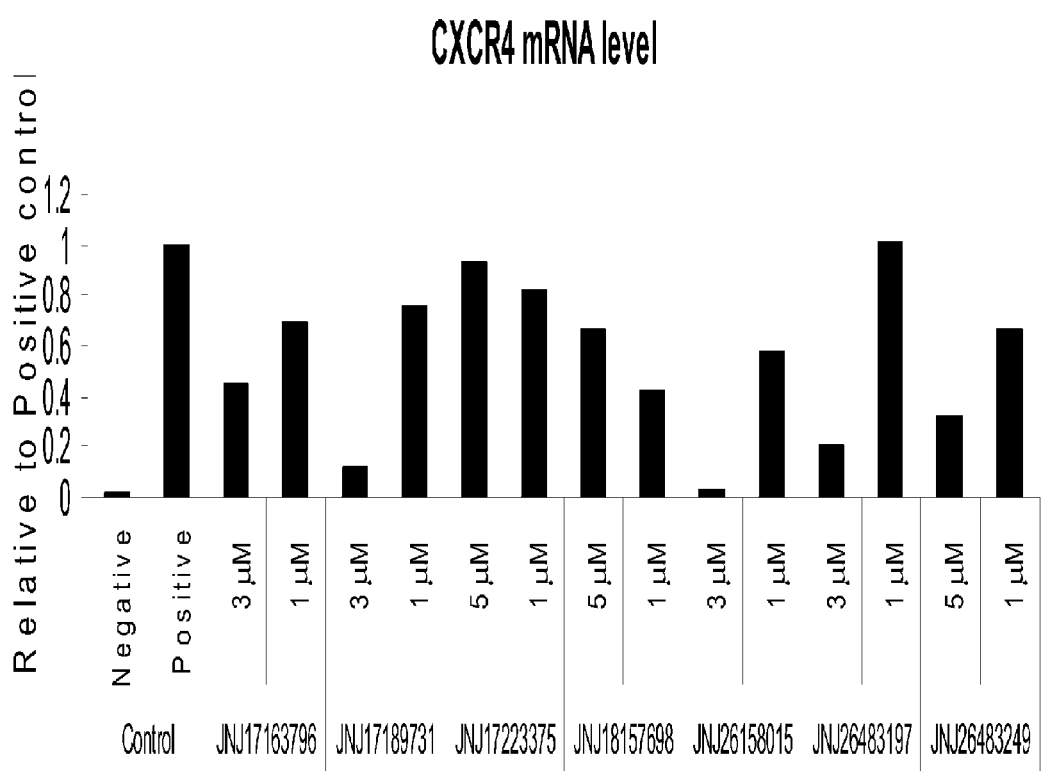

Figure 10-B
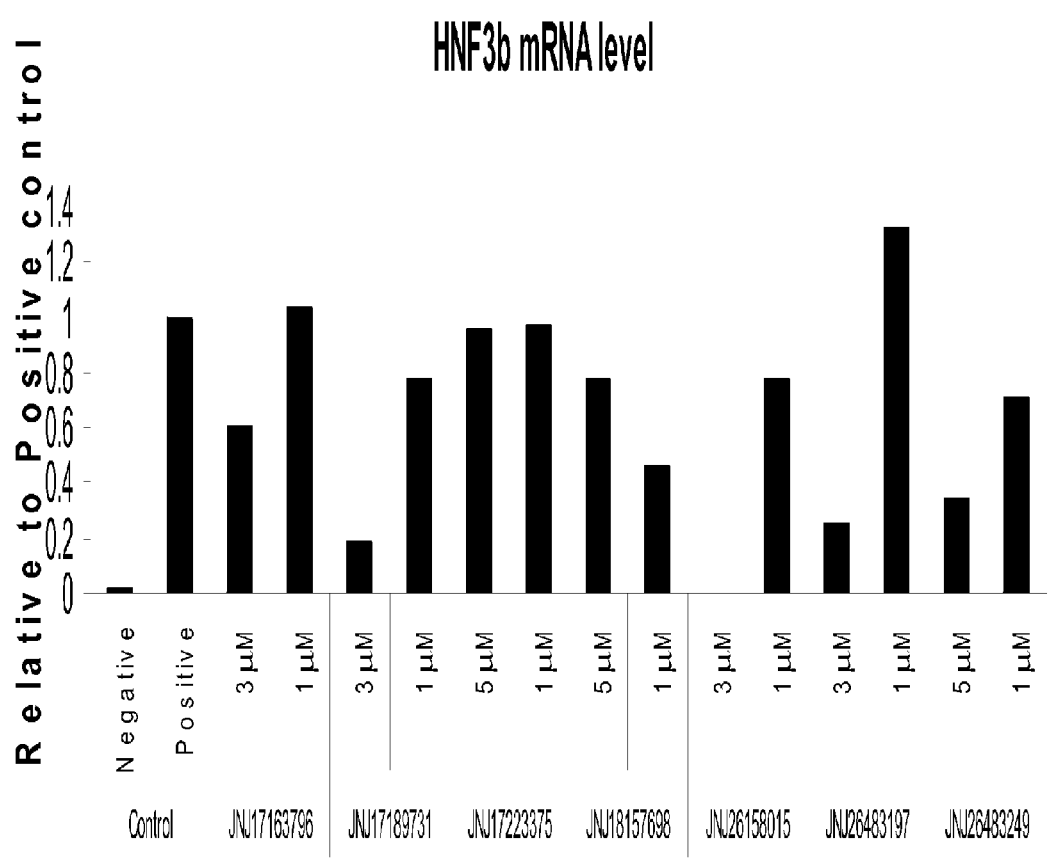

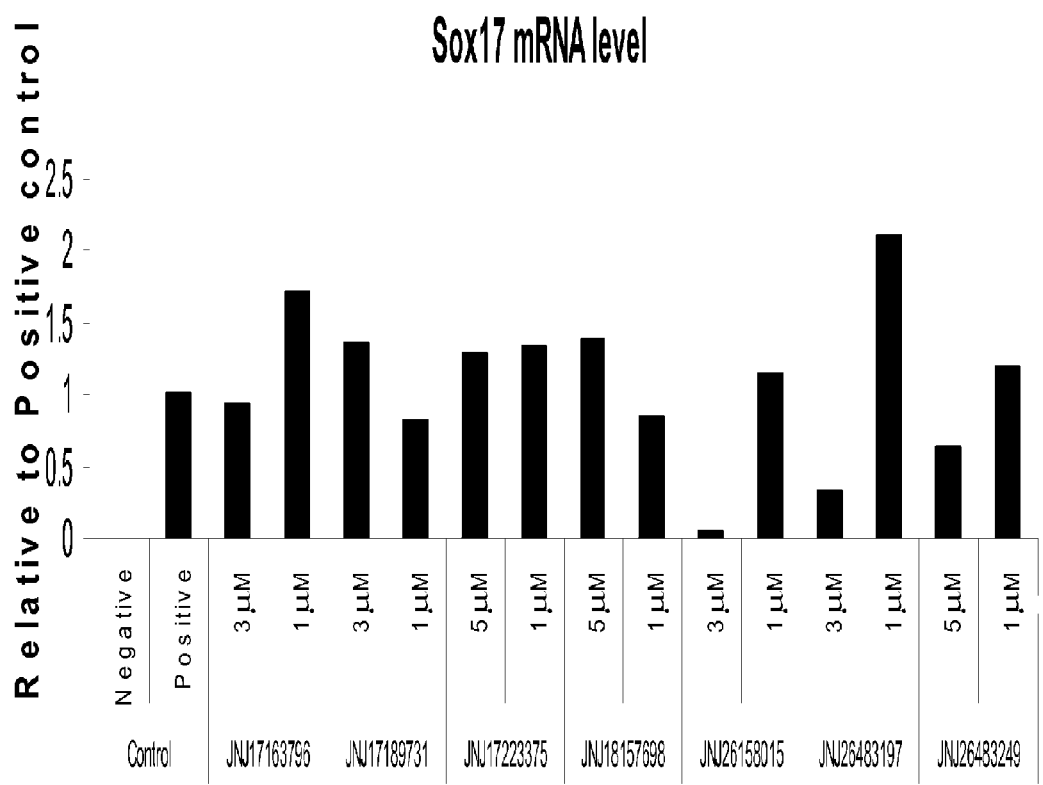
Figure 10-C

Figure 11-A
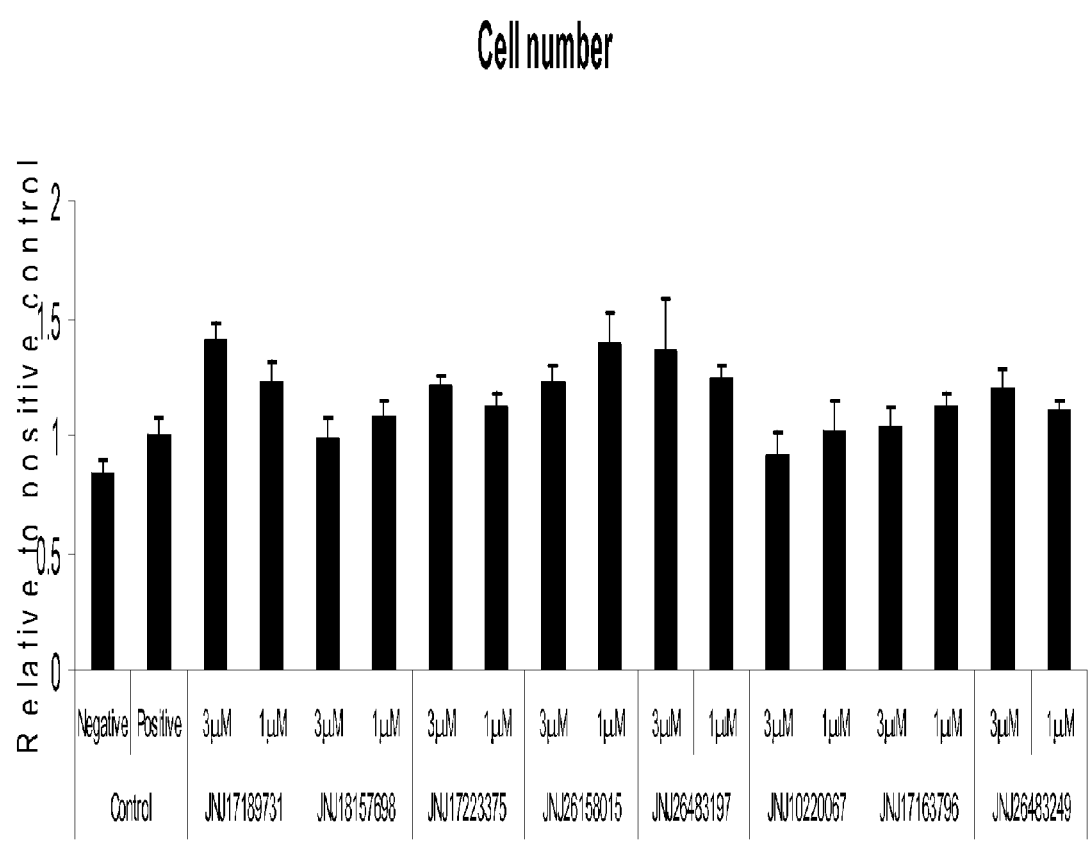

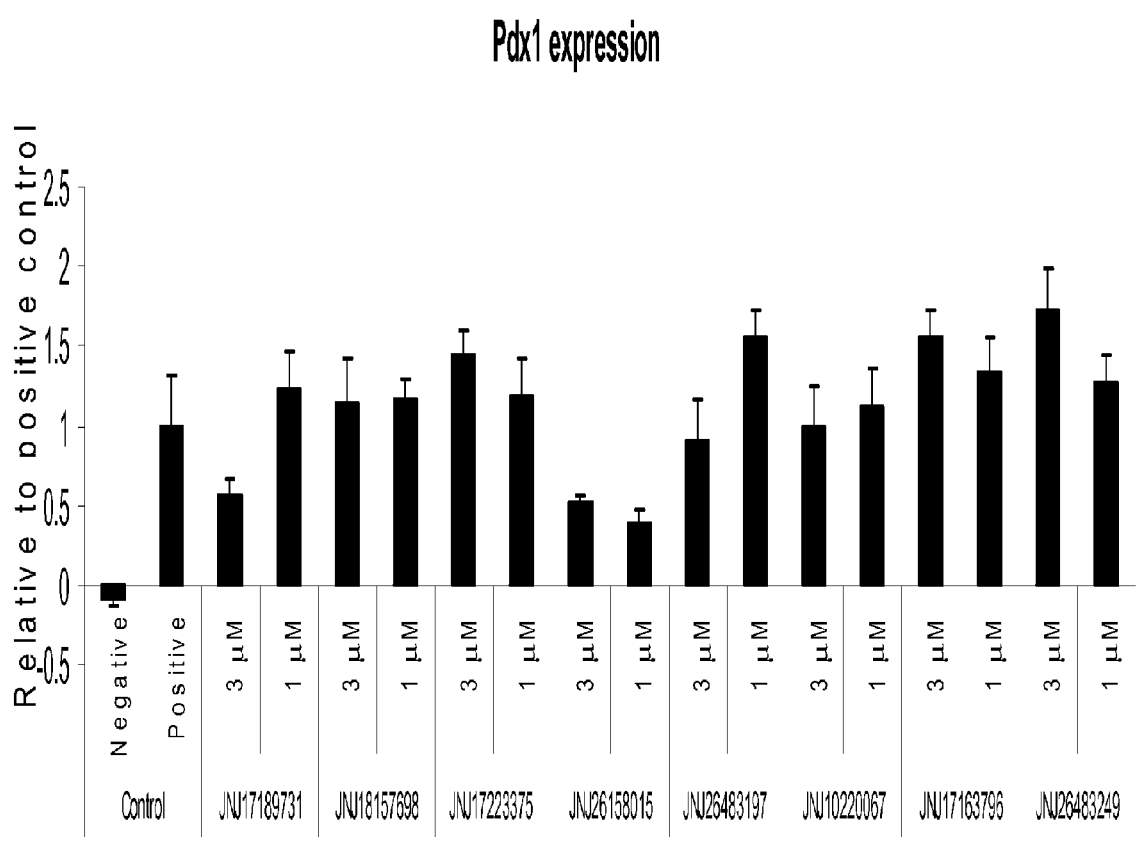
Figure 11-B

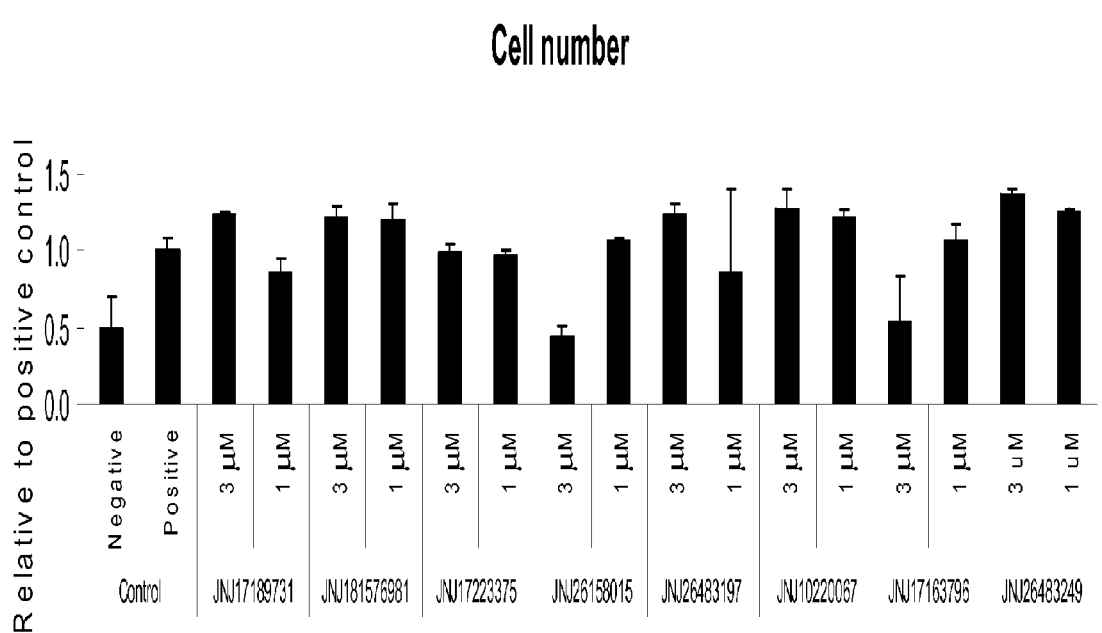
Figure 13-A

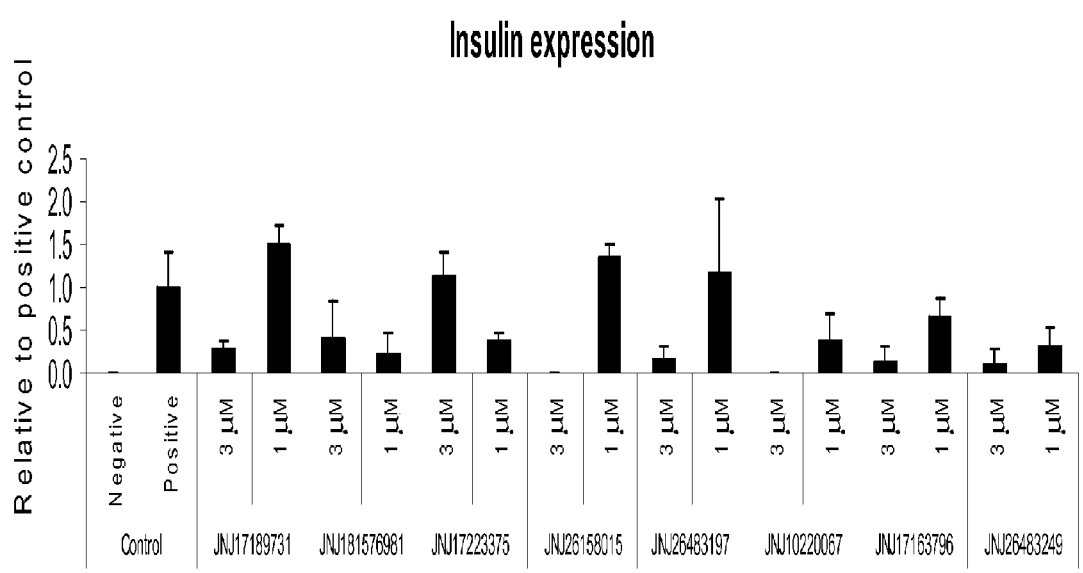
Figure 13-B

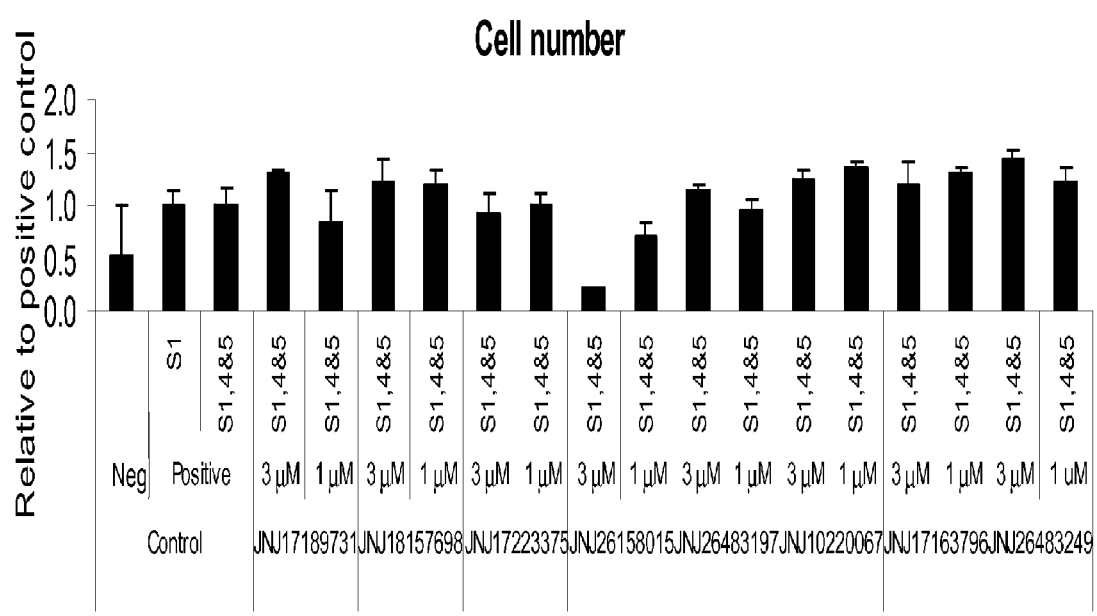
Figure 15-A

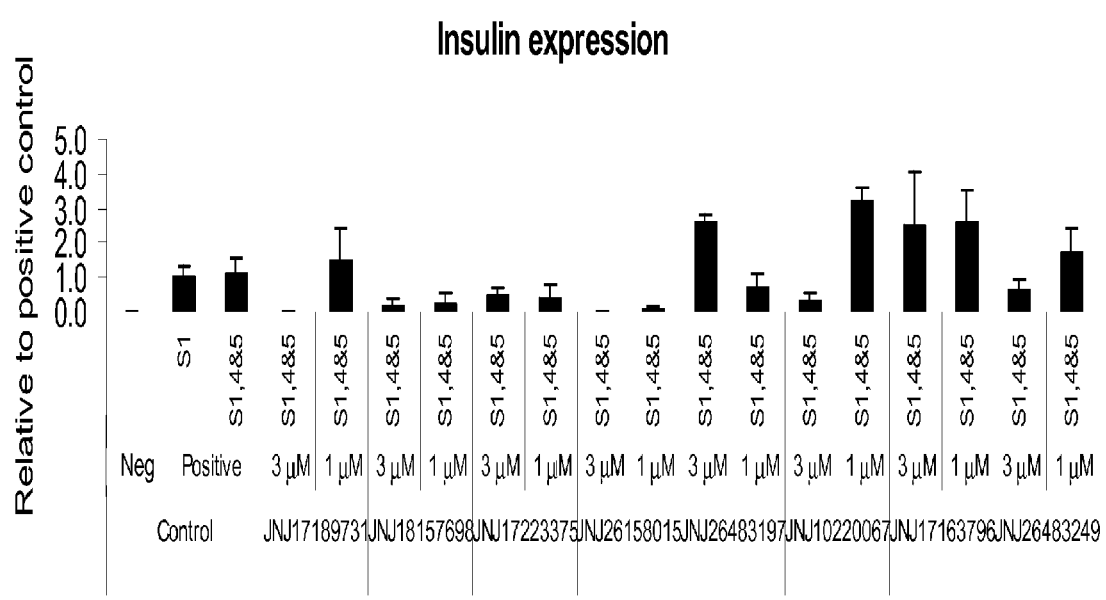
Figure 15-B

TREATMENT OF PLURIPOTENT CELLS

This application is a divisional of U.S. application Ser. No. 12/108,852 filed Apr. 24, 2008. The complete disclosures of the aforementioned related patent applications are hereby incorporated herein by reference for all purposes.

FIELD OF THE INVENTION

The present invention is directed to methods to treat pluripotent cells, whereby the pluripotent cells can be efficiently expanded in culture and differentiated by treating the pluripotent cells with an inhibitor of GSK-3B enzyme activity.

BACKGROUND

Advances in cell-replacement therapy for Type I diabetes mellitus and a shortage of transplantable islets of Langerhans have focused interest on developing sources of insulin-producing cells, or β cells, appropriate for engraftment. One approach is the generation of functional β cells from pluripotent cells, such as, for example, embryonic stem cells.

In vertebrate embryonic development, a pluripotent cell gives rise to a group of cells comprising three germ layers (ectoderm, mesoderm, and endoderm) in a process known as gastrulation. Tissues such as, for example, thyroid, thymus, pancreas, gut, and liver, will develop from the endoderm, via an intermediate stage. The intermediate stage in this process is the formation of definitive endoderm. Definitive endoderm cells express a number of markers, such as, HNF-3 beta, GATA-4, Mix11, CXCR4 and SOX-17.

Formation of the pancreas arises from the differentiation of definitive endoderm into pancreatic endoderm. Cells of the pancreatic endoderm express the pancreatic-duodenal homeobox gene, PDX-1. In the absence of PDX-1, the pancreas fails to develop beyond the formation of ventral and dorsal buds. Thus, PDX-1 expression marks a critical step in pancreatic organogenesis. The mature pancreas contains, among other cell types, exocrine tissue and endocrine tissue. Exocrine and endocrine tissues arise from the differentiation of pancreatic endoderm.

The generation of a sufficient amount of cellular material for transplantation requires a source of the cellular material that can be efficiently expanded in culture, and efficiently differentiated into the tissue of interest, for example, functional β cells.

Current methods to culture human embryonic stem cells are complex; they require the use of exogenous factors, or chemically defined media in order for the cells to proliferate without loosing their pluripotency. Furthermore differentiation of embryonic stem cells often results in a decrease in the cells to expand in culture.

In one example, Cheon et al (BioReprod DOI:10.1095/biolreprod.105.046870, Oct. 19, 2005) disclose a feeder-free, serum-free culture system in which embryonic stem cells are maintained in unconditioned serum replacement (SR) medium supplemented with different growth factors capable of triggering embryonic stem cell self-renewal.

In another example, US20050233446 discloses a defined media useful in culturing stem cells, including undifferentiated primate primordial stem cells. In solution, the media is substantially isotonic as compared to the stem cells being cultured. In a given culture, the particular medium comprises a base medium and an amount of each of bFGF, insulin, and ascorbic acid necessary to support substantially undifferentiated growth of the primordial stem cells.

In another example, WO2005086845 discloses a method for maintenance of an undifferentiated stem cell, said method comprising exposing a stem cell to a member of the transforming growth factor-beta (TGFβ) family of proteins, a member of the fibroblast growth factor (FGF) family of proteins, or nicotinamide (NIC) in an amount sufficient to maintain the cell in an undifferentiated state for a sufficient amount of time to achieve a desired result.

Inhibitors of glycogen synthase kinase-3 (GSK-3) are known to promote proliferation and expansion of adult stem cells. In one example, Tateishi et al. (Biochemical and Biophysical Research Communications (2007) 352: 635) show that inhibition of GSK-3 enhances growth and survival of human cardiac stem cells (hCSCs) recovered from the neonatal or adult human heart and having mesenchymal features.

For example, Rulifson et al (PNAS 144, 6247-6252, (2007)) states "Wnt signaling stimulates islet β cell proliferation.

In another example, WO2007016485 reports that addition of GSK-3 inhibitors to the culture of non-embryonic stem cells, including multipotent adult progenitor cells, leads to the maintenance of a pluripotent phenotype during expansion and results in a more robust differentiation response.

In another example, US2006030042 uses a method of inhibiting GSK-3, either by addition of Wnt or a small molecule inhibitor of GSK-3 enzyme activity, to maintain embryonic stem cells without the use of a feeder cell layer.

In another example, WO2006026473 reports the addition of a GSK-3B inhibitor, to stabilize pluripotent cells through transcriptional activation of c-myc and stabilization of c-myc protein.

In another example, WO2006100490 reports the use of a stem cell culture medium containing a GSK-3 inhibitor and a gp130 agonist to maintain a self-renewing population of pluripotent stem cells, including mouse or human embryonic stem cells.

In another example, Sato et al. (Nature Medicine (2004) 10:55-63) show that inhibition of GSK-3 with a specific pharmacological compound can maintain the undifferentiated phenotype of embryonic stem cells and sustain expression of pluripotent state-specific transcription factors such as Oct-3/4, Rex-1, and Nanog.

In another example, Maurer et al (Journal of Proteome Research (2007) 6:1198-1208) show that adult, neuronal stem cells treated with a GSK-3 inhibitor show enhanced neuronal differentiation, specifically by promoting transcription of β-catenin target genes and decreasing apoptosis.

In another example, Gregory et al (Annals of the New York Academy of Sciences (2005) 1049:97-106) report that inhibitors of GSK-3B enhance in vitro osteogenesis.

In another example, Feng et al (Biochemical and Biophysical Research Communications (2004) 324:1333-1339) show that hematopoietic differentiation from embryonic stem cells is associated with down-regulation of the Wnt/β-catenin pathway, where Wnt is a natural inhibitor of GSK3.

Therefore, there still remains a significant need to develop methods for treating pluripotent stem cell such that they can be expanded to address the current clinical needs, while retaining the potential to differentiate into pancreatic endocrine cells, pancreatic hormone expressing cells, or pancreatic hormone secreting cells.

SUMMARY

The present invention provides a method to expand and differentiate pluripotent cells by treating the pluripotent cells with an inhibitor of GSK-3B enzyme activity.

In one embodiment, the present invention provides a method to expand and differentiate pluripotent cells, comprising the steps of:
a. Culturing pluripotent cells, and
b. Treating the pluripotent cells with an inhibitor of GSK-3B enzyme activity.

In one embodiment, the pluripotent cells are differentiated into cells expressing markers characteristic of the definitive endoderm lineage.

The pluripotent cells may be human embryonic stem cells, or they may be cells expressing pluripotency markers derived from human embryonic stem cells, according to the methods disclosed in 60/913,475.

In one embodiment, the inhibitor of GSK-3B enzyme activity is a compound of the Formula (I):

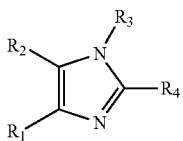

Formula (I)

In one embodiment, the inhibitor of GSK-3B enzyme activity is a compound of the Formula (II):

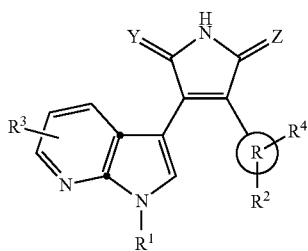

Formula (II)

In one embodiment, the inhibitor of GSK-3B enzyme activity is a compound of the Formula (III):

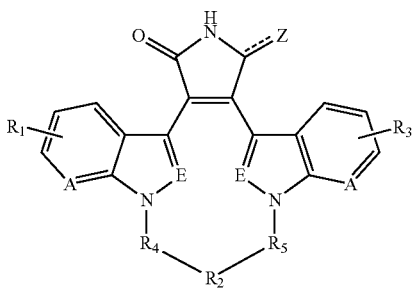

Formula (III)

BRIEF DESCRIPTION OF THE FIGURES

FIG. 10 shows the expression of CXCR4 (Panel A), HNF-3 beta (Panel B), and Sox-17 (Panel C), as determined by real-time PCR, in cells treated with the compounds shown, according to the methods described in Example 8.

FIG. 11 shows the effect of a range of concentrations of the compounds shown on cell number, as determined by the number of nuclei observed (Panel A) and Pdx-1 expression, as determined by intensity of immunofluorescent staining (Panel B), using the IN Cell Analyzer 1000 (GE Healthcare). Cells were treated according to the methods described in Example 9.

FIG. 13 shows the effect of a range of concentrations of the compounds shown on cell number, as determined by the number of nuclei observed (Panel A) and insulin expression, as determined by intensity of immunofluorescent staining (Panel B), using the IN Cell Analyzer 1000 (GE Healthcare). Cells were treated according to the methods described in Example 10.

FIG. 15 shows the effect of a range of concentrations of the compounds shown on cell number, as determined by the number of nuclei observed (Panel A) and insulin expression, as determined by intensity of immunofluorescent staining (Panel B), using the IN Cell Analyzer 1000 (GE Healthcare). Cells were treated according to the methods described in Example 11.

DETAILED DESCRIPTION

Figure 1A:
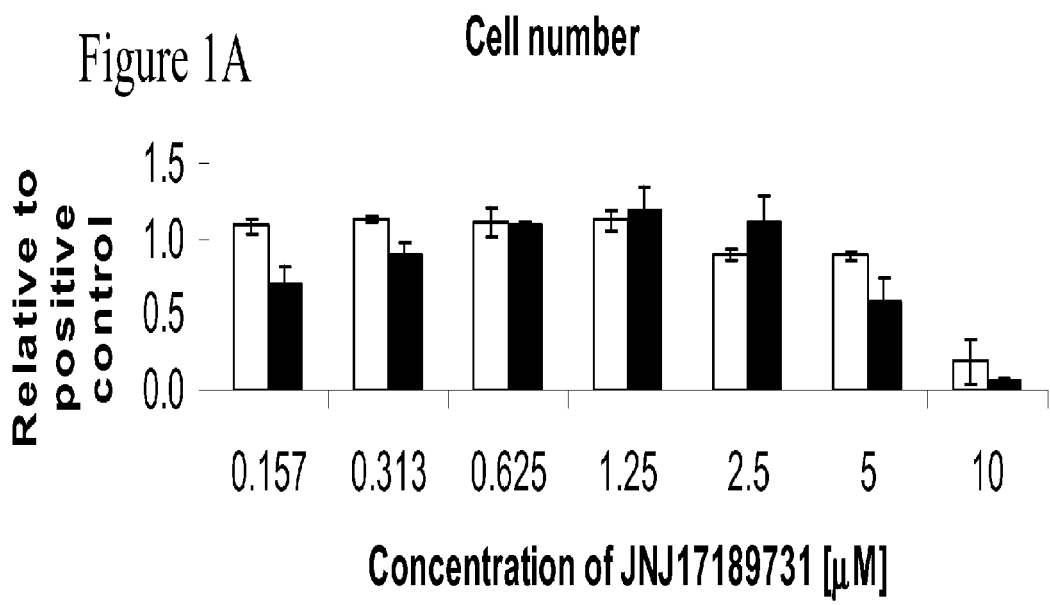
FIG. 1 shows the effect of a range of concentrations of the compound JNJ 17189731 on cell number, as determined by the number of nuclei observed (Panel A) and Sox-17 expression, as determined by intensity of immunofluorescent staining (Panel B). Results were obtained from cells of the human embryonic stem cell line H1 (white bars), or cells of the human embryonic stem cell line H9 (black bars), using the IN Cell Analyzer 1000 (GE Healthcare).
Figure 1B:
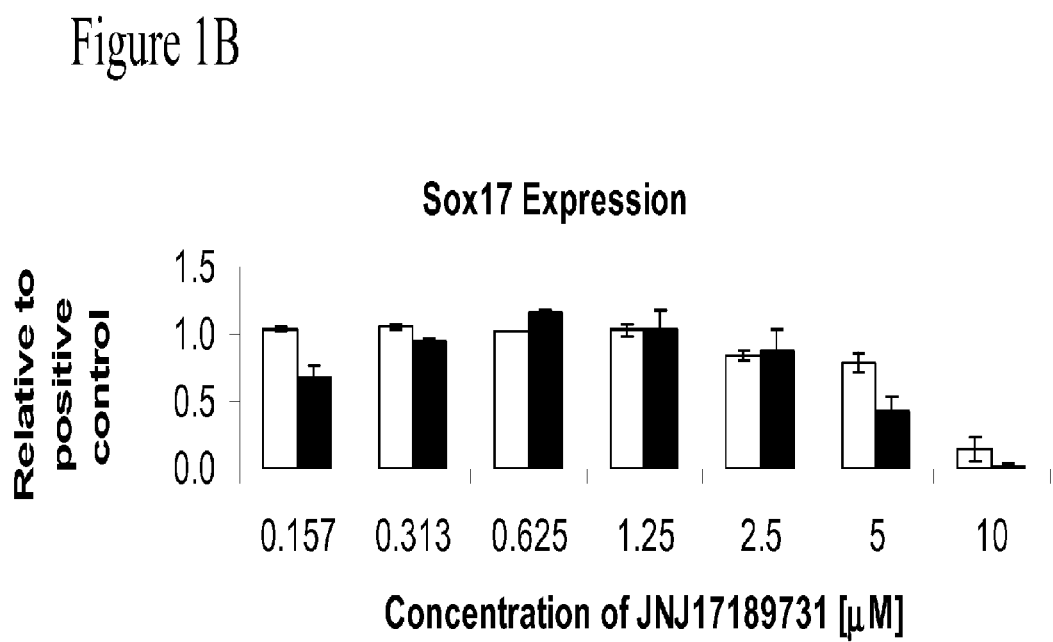
Figure 2A:
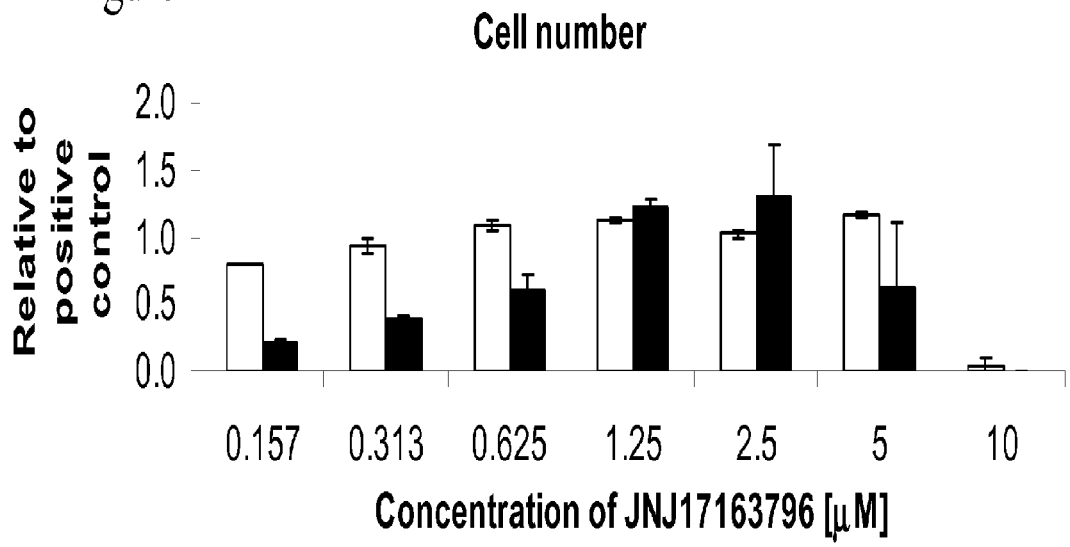
FIG. 2 shows the effect of a range of concentrations of the compound JNJ 17163796 on cell number, as determined by the number of nuclei observed (Panel A) and Sox-17 expression, as determined by intensity of immunofluorescent staining (Panel B). Results were obtained from cells of the human embryonic stem cell line H1 (white bars), or cells of the human embryonic stem cell line H9 (black bars), using the IN Cell Analyzer 1000 (GE Healthcare).
Figure 2B:
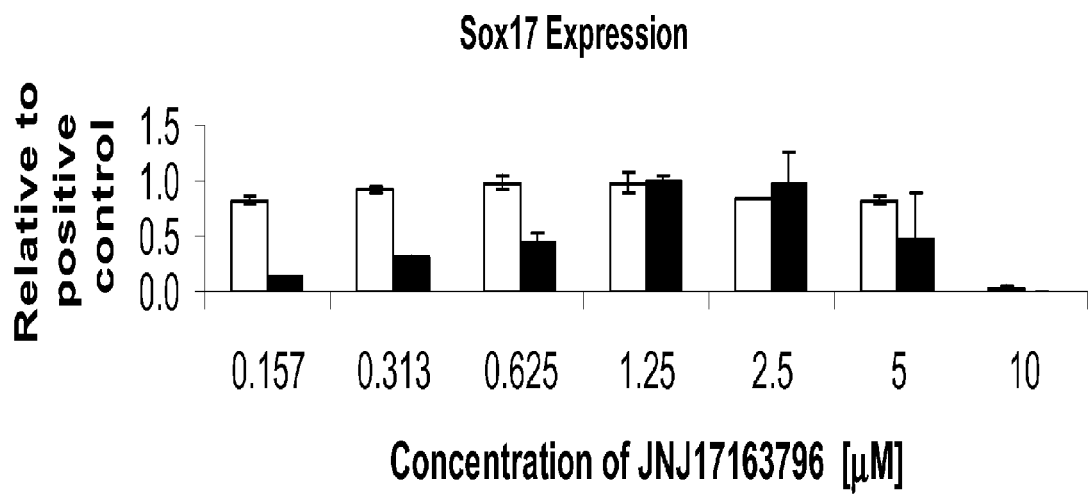
Figure 3A:
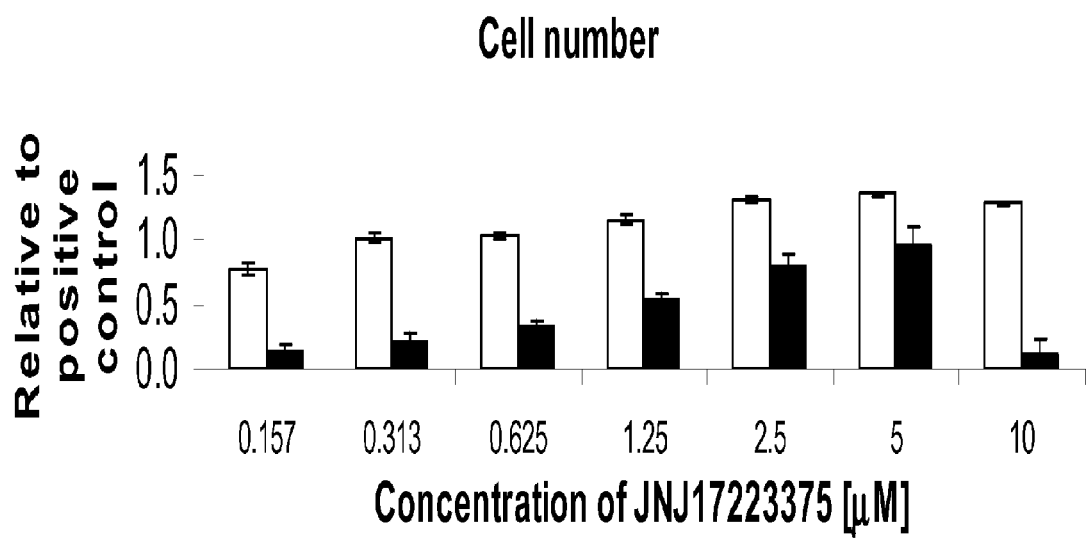
FIG. 3 shows the effect of a range of concentrations of the compound JNJ 17223375 on cell number, as determined by the number of nuclei observed (Panel A) and Sox-17 expression, as determined by intensity of immunofluorescent staining (Panel B). Results were obtained from cells of the human embryonic stem cell line H1 (white bars), or cells of the human embryonic stem cell line H9 (black bars), using the IN Cell Analyzer 1000 (GE Healthcare).
Figure 3B:
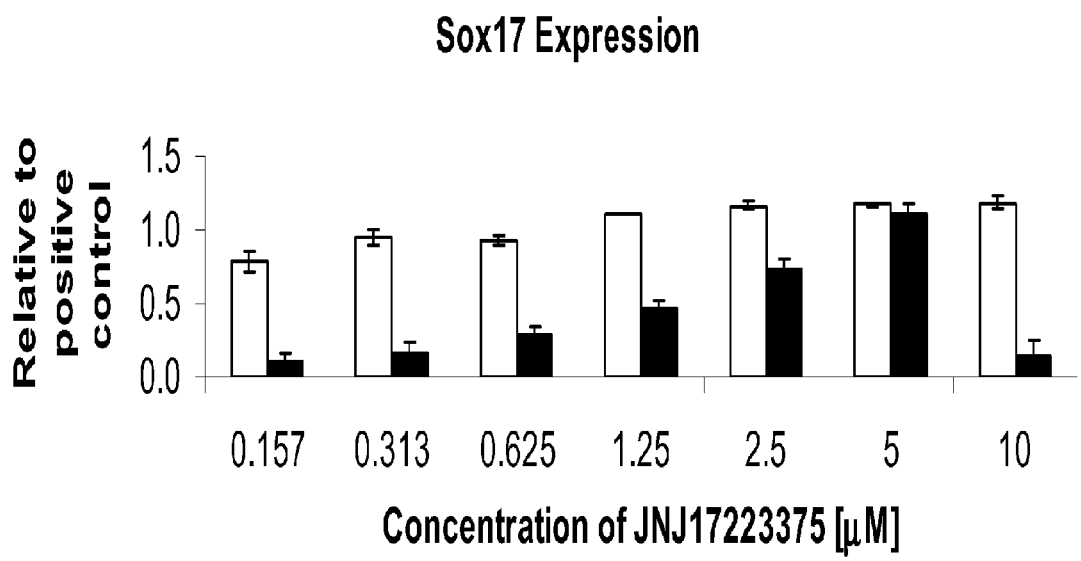
Figure 4A:
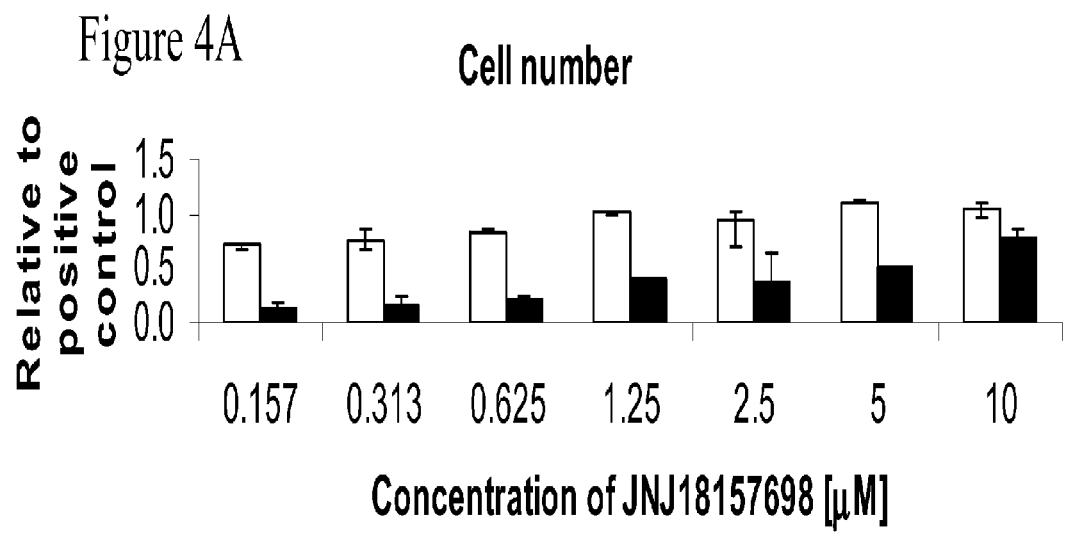
FIG. 4 shows the effect of a range of concentrations of the compound JNJ 18157698 on cell number, as determined by the number of nuclei observed (Panel A) and Sox-17 expression, as determined by intensity of immunofluorescent staining (Panel B). Results were obtained from cells of the human embryonic stem cell line H1 (white bars), or cells of the human embryonic stem cell line H9 (black bars), using the IN Cell Analyzer 1000 (GE Healthcare).
Figure 4B:
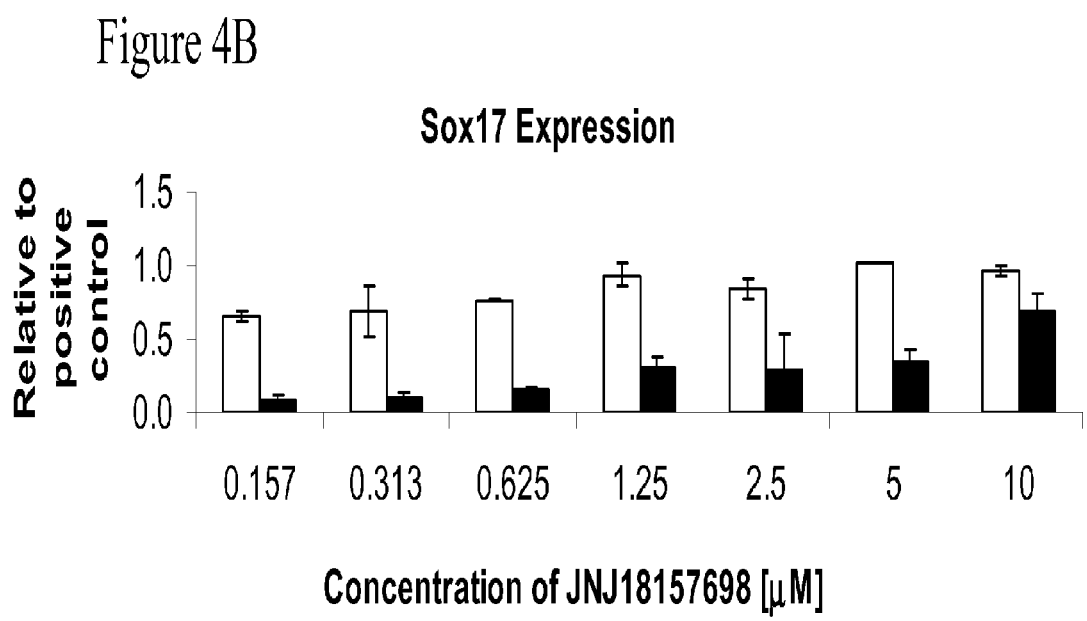
Figure 5A:
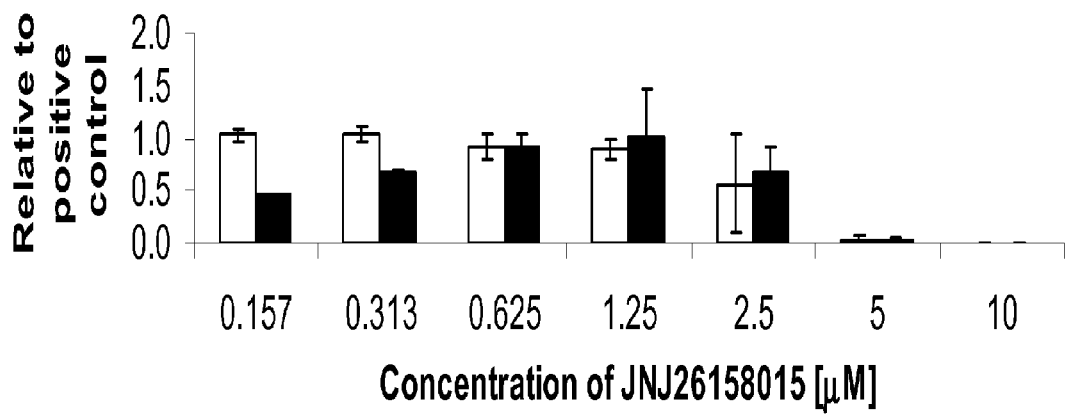
FIG. 5 shows the effect of a range of concentrations of the compound JNJ 26158015 on cell number, as determined by the number of nuclei observed (Panel A) and Sox-17 expression, as determined by intensity of immunofluorescent staining (Panel B). Results were obtained from cells of the human embryonic stem cell line H1 (white bars), or cells of the human embryonic stem cell line H9 (black bars), using the IN Cell Analyzer 1000 (GE Healthcare).
Figure 5B:
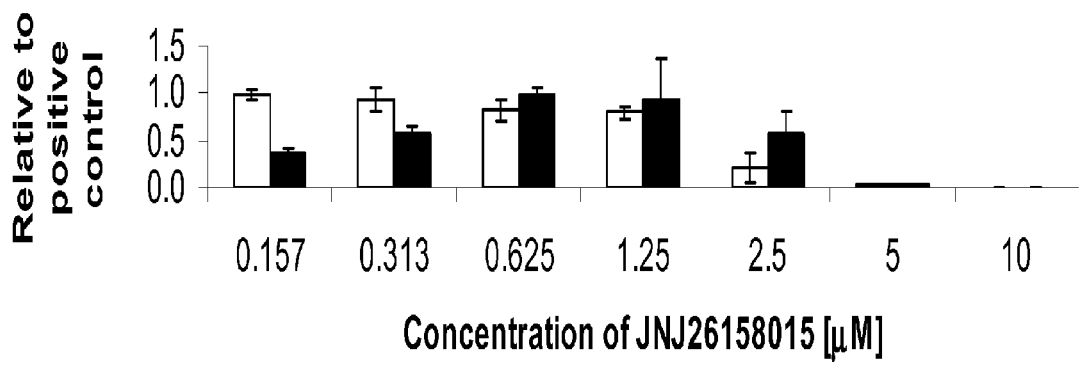
Figure 6A:
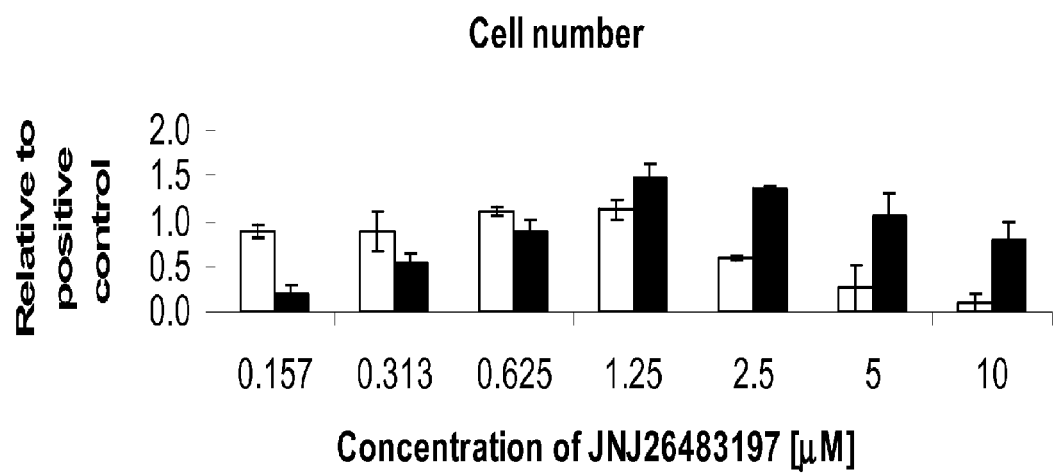
FIG. 6 shows the effect of a range of concentrations of the compound JNJ 26483197 on cell number, as determined by the number of nuclei observed (Panel A) and Sox-17 expression, as determined by intensity of immunofluorescent staining (Panel B). Results were obtained from cells of the human embryonic stem cell line H1 (white bars), or cells of the human embryonic stem cell line H9 (black bars), using the IN Cell Analyzer 1000 (GE Healthcare).
Figure 6B:
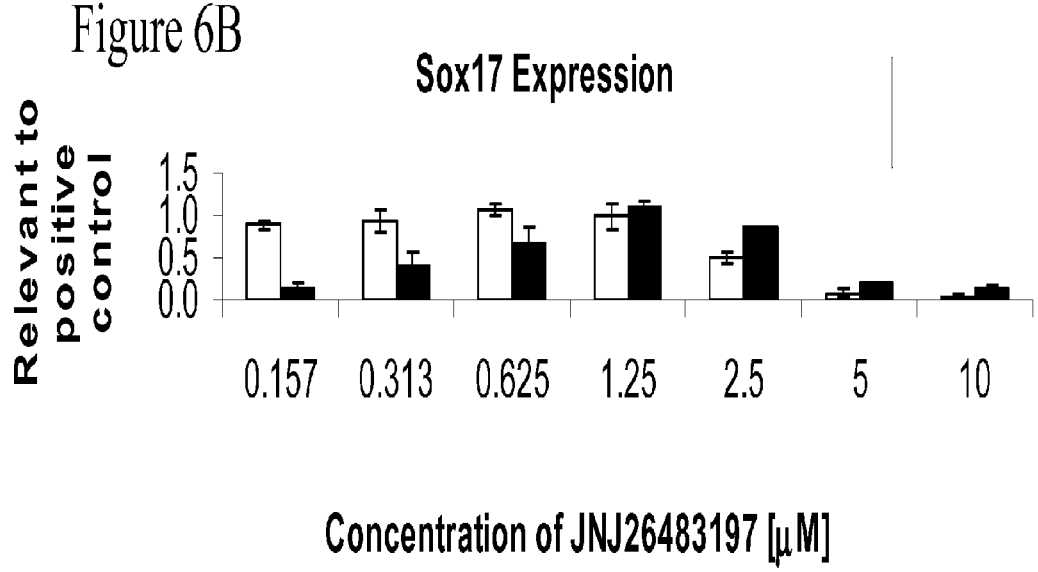
Figure 7A:
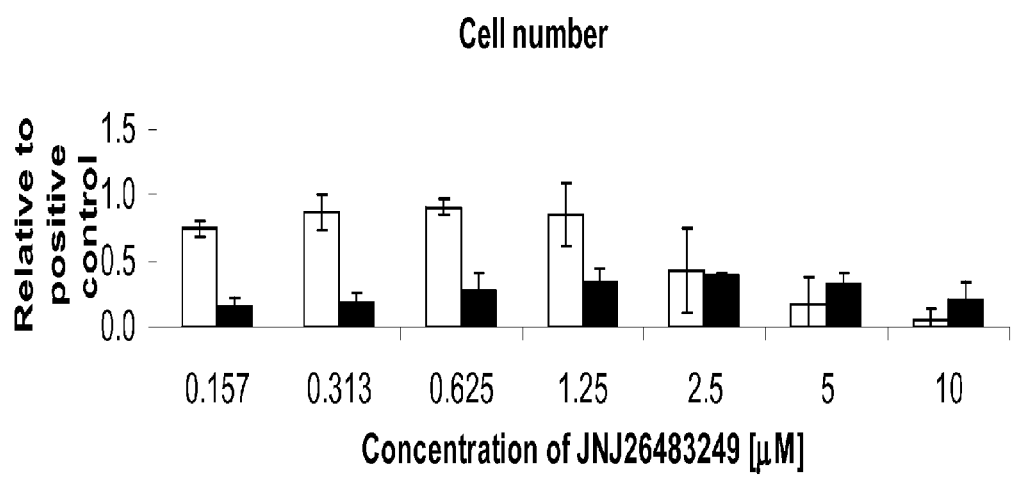
FIG. 7 shows the effect of a range of concentrations of the compound JNJ 26483249 on cell number, as determined by the number of nuclei observed (Panel A) and Sox-17 expression, as determined by intensity of immunofluorescent staining (Panel B). Results were obtained from cells of the human embryonic stem cell line H1 (white bars), or cells of the human embryonic stem cell line H9 (black bars), using the IN Cell Analyzer 1000 (GE Healthcare).
Figure 7B:
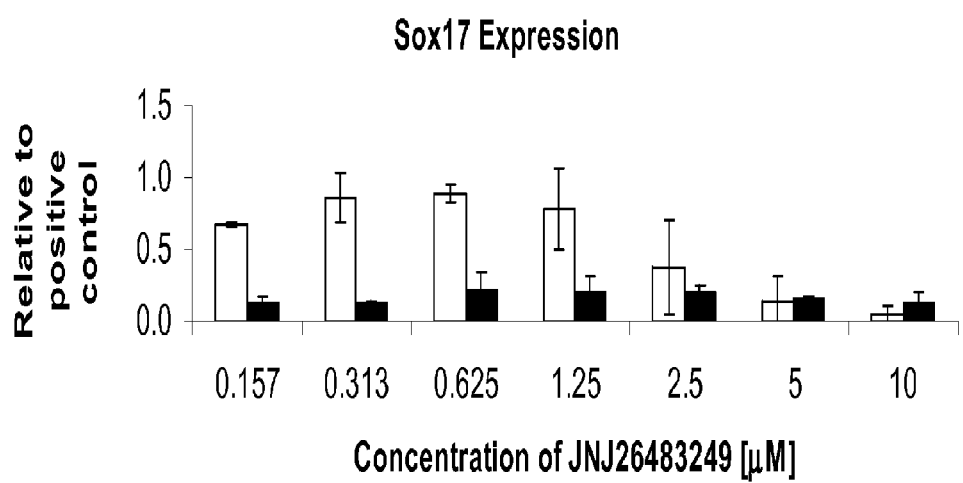
Figure 8A:
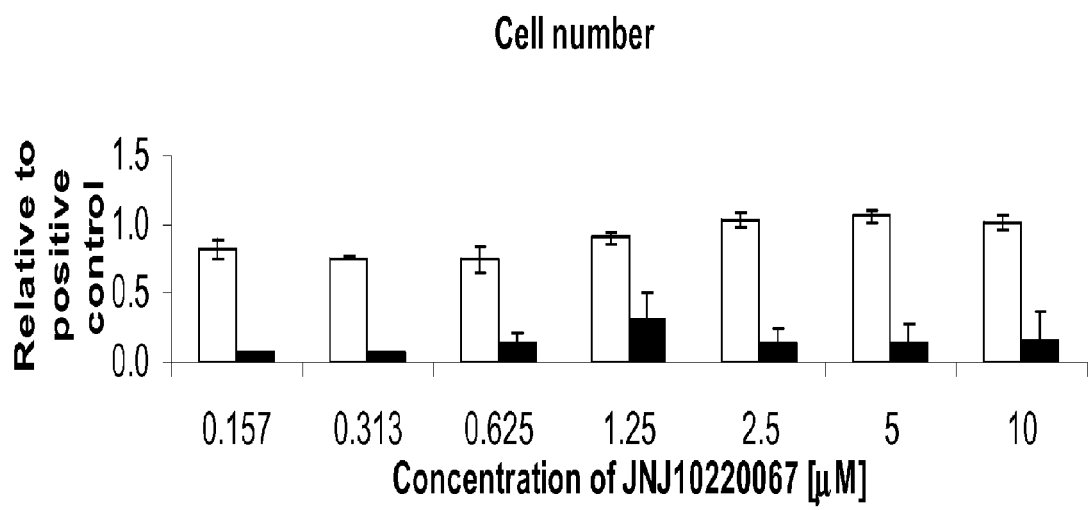
FIG. 8 shows the effect of a range of concentrations of the compound JNJ 10220067 on cell number, as determined by the number of nuclei observed (Panel A) and Sox-17 expression, as determined by intensity of immunofluorescent staining (Panel B). Results were obtained from cells of the human embryonic stem cell line H1 (white bars), or cells of the human embryonic stem cell line H9 (black bars), using the IN Cell Analyzer 1000 (GE Healthcare).
Figure 8B:
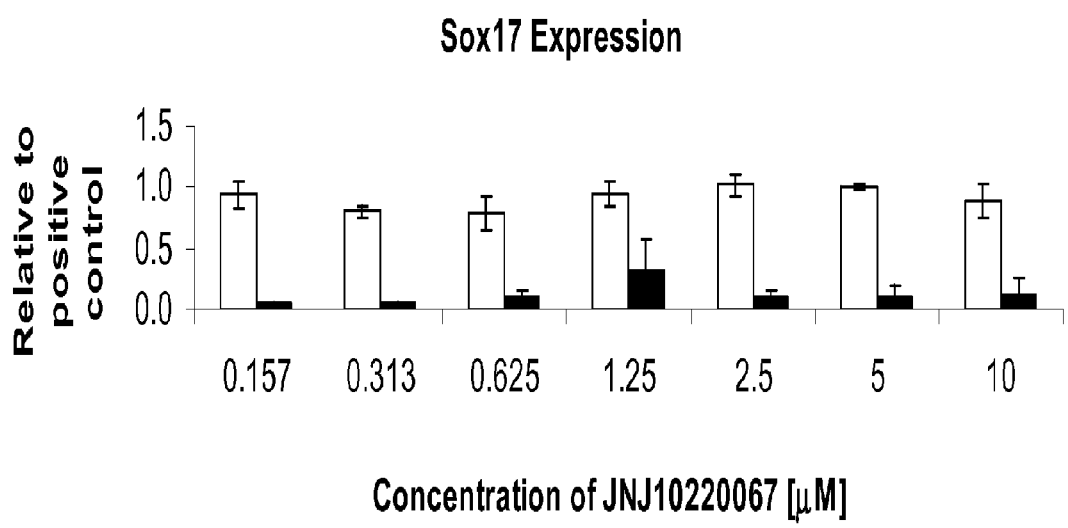

For clarity of disclosure, and not by way of limitation, the detailed description of the invention is divided into the following subsections that describe or illustrate certain features, embodiments, or applications of the present invention.

Definitions

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multipotent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g., spermatogenic stem cells).

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"β-cell lineage" refer to cells with positive gene expression for the transcription factor PDX-1 and at least one of the following transcription factors: NGN-3, NRx2.2, NRx6.1, NeuroD, Is1-1, HNF-3 beta, MAFA, Pax4, and Pax6. Cells expressing markers characteristic of the β cell lineage include β cells.

"Cells expressing markers characteristic of the definitive endoderm lineage" as used herein refer to cells expressing at least one of the following markers: SOX-17, GATA-4, HNF-3 beta, GSC, Cer1, Nodal, FGF8, Brachyury, Mix-like homeobox protein, FGF4 CD48, eomesodermin (EOMES), DKK4, FGF17, GATA-6, CXCR4, C-Kit, CD99, or OTX2. Cells expressing markers characteristic of the definitive endoderm lineage include primitive streak precursor cells, primitive streak cells, mesendoderm cells and definitive endoderm cells.

"Cells expressing markers characteristic of the pancreatic endoderm lineage" as used herein refer to cells expressing at least one of the following markers: PDX-1, HNF-1beta, PTF-1 alpha, HNF-6, or HB9. Cells expressing markers characteristic of the pancreatic endoderm lineage include pancreatic endoderm cells.

"Cells expressing markers characteristic of the pancreatic endocrine lineage" as used herein refer to cells expressing at least one of the following markers: NGN-3, NeuroD, Islet-1, PDX-1, NKX6.1, Pax-4, Ngn-3, or PTF-1 alpha. Cells expressing markers characteristic of the pancreatic endocrine lineage include pancreatic endocrine cells, pancreatic hormone expressing cells, and pancreatic hormone secreting cells, and cells of the β-cell lineage.

"Definitive endoderm" as used herein refers to cells which bear the characteristics of cells arising from the epiblast during gastrulation and which form the gastrointestinal tract and its derivatives. Definitive endoderm cells express the following markers: HNF-3 beta, GATA-4, SOX-17, Cerberus, OTX2, goosecoid, C-Kit, CD99, and Mix11.

"Extraembryonic endoderm" as used herein refers to a population of cells expressing at least one of the following markers: SOX-7, AFP, and SPARC.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

"Mesendoderm cell" as used herein refers to a cell expressing at least one of the following markers: CD48, eomesodermin (EOMES), SOX-17, DKK4, HNF-3 beta, GSC, FGF17, GATA-6.

"Pancreatic endocrine cell", or "pancreatic hormone expressing cell" as used herein refers to a cell capable of expressing at least one of the following hormones: insulin, glucagon, somatostatin, and pancreatic polypeptide.

"Pancreatic hormone secreting cell" as used herein refers to a cell capable of secreting at least one of the following hormones: insulin, glucagon, somatostatin, and pancreatic polypeptide.

"Pre-primitive streak cell" as used herein refers to a cell expressing at least one of the following markers: Nodal, or FGF8

"Primitive streak cell" as used herein refers to a cell expressing at least one of the following markers: Brachyury, Mix-like homeobox protein, or FGF4.

In one embodiment, the present invention provides a method for the expansion and differentiation of pluripotent cells comprising treating the pluripotent cells with an inhibitor of GSK-3B enzyme activity.

In one embodiment, the present invention provides a method to expand and differentiate pluripotent cells, comprising the steps of:

c. Culturing pluripotent cells, and
d. Treating the pluripotent cells with an inhibitor of GSK-3B enzyme activity.

In one embodiment, the pluripotent cells are differentiated into cells expressing markers characteristic of the definitive endoderm lineage.

Markers characteristic of the definitive endoderm lineage are selected from the group consisting of SOX17, GATA4, Hnf-3beta, GSC, Cer1, Nodal, FGF8, Brachyury, Mix-like homeobox protein, FGF4 CD48, eomesodermin (EOMES), DKK4, FGF17, GATA6, CXCR4, C-Kit, CD99, and OTX2. Contemplated in the present invention is a cell, derived from a pluripotent cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

The pluripotent cells may be treated with the inhibitor of GSK-3B enzyme activity for about one to about 72 hours. Alternatively, the pluripotent cells may be treated with the inhibitor of GSK-3B enzyme activity for about 12 to about 48 hours. Alternatively, the pluripotent cells may be treated with the inhibitor of GSK-3B enzyme activity for about 48 hours.

In one embodiment, the inhibitor of GSK-3B enzyme activity is used at a concentration of about 100 nM to about 100 µM. Alternatively, the inhibitor of GSK-3B enzyme activity is used at a concentration of about 1 µM to about 10 µM. Alternatively, the inhibitor of GSK-3B enzyme activity is used at a concentration of about 10 µM.

Compounds Suitable for Use in the Methods of the Present Invention

In one embodiment, the inhibitor of GSK-3B enzyme activity is a compound of the Formula (I):

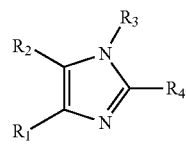

Formula (I)

wherein:

$R_1$ is phenyl, substituted phenyl wherein the phenyl substituents are selected from the group consisting of $C_{1-5}$alkyl, halogen, nitro, trifluoromethyl and nitrile, or pyrimidinyl;

$R_2$ is phenyl, substituted phenyl wherein the phenyl substituents are selected from the group consisting of $C_{1-5}$alkyl, halogen, nitro, trifluoromethyl and nitrile, or pyrimidinyl which is optionally $C_{1-4}$alkyl substituted, and at least one of $R_1$ and $R_2$ is pyrimidinyl;

$R_3$ is hydrogen, 2-(trimethylsilyl)ethoxymethyl, $C_{1-5}$alkoxycarbonyl, aryloxycarbonyl, aryl$C_{1-5}$alkyloxycarbonyl, aryl$C_{1-5}$alkyl, substituted aryl$C_{1-5}$alkyl wherein the one or more aryl substituents are independently selected from the group consisting of $C_{1-5}$alkyl, $C_{1-5}$alkoxy, halogen, amino, $C_{1-5}$ alkylamino, and di$C_{1-5}$ alkylamino, phthalimido$C_{1-5}$alkyl, amino$C_{1-5}$ alkyl, diamino$C_{1-5}$ alkyl, succinimido$C_{1-5}$ alkyl, $C_{1-5}$ alkylcarbonyl, arylcarbonyl, $C_{1-5}$ alkylcarbonyl$C_{1-5}$ alkyl and aryloxycarbonyl$C_{1-5}$ alkyl;

$R_4$ is -(A)-(CH_2)_q—X;

A is vinylene, ethynylene or

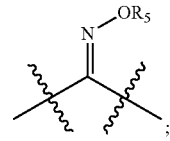

$R_5$ is selected from the group consisting of hydrogen, $C_{1-5}$alkyl, phenyl and phenyl$C_{1-5}$alkyl;

q is 0-9;

X is selected from the group consisting of hydrogen, hydroxy, vinyl, substituted vinyl wherein one or more vinyl substituents are each selected from the group consisting of fluorine, bromine, chlorine and iodine, ethynyl, substituted ethynyl wherein the ethynyl substituents are selected from the group consisting of fluorine, bromine chlorine and iodine, $C_{1-5}$alkyl, substituted $C_{1-5}$alkyl wherein the one or more alkyl substituents are each selected from the group consisting of $C_{1-5}$alkoxy, trihaloalkyl, phthalimido and amino, $C_{3-7}$cycloalkyl, $C_{1-5}$alkoxy, substituted $C_{1-5}$alkoxy wherein the alkyl substituents are selected from the group consisting of phthalimido and amino, phthalimidooxy, phenoxy, substituted phenoxy wherein the one or more phenyl substituents are each selected from the group consisting of $C_{1-5}$alkyl, halogen and $C_{1-5}$alkoxy, phenyl, substituted phenyl wherein the one or more phenyl substituents are each selected from the group consisting of $C_{1-5}$alkyl, halogen and $C_{1-5}$alkoxy, aryl$C_{1-5}$alkyl, substituted aryl$C_{1-5}$alkyl wherein the one or more aryl substituents are each selected from the group consisting of $C_{1-5}$alkyl, halogen and $C_{1-5}$alkoxy, aryloxy$C_{1-5}$alkylamino, $C_{1-5}$ alkylamino, di$C_{1-5}$ alkylamino, nitrile, oxime, benxyloxyimino, $C_{1-5}$ alkyloxyimino, phthalimido, succinimido, $C_{1-5}$ alkylcarbonyloxy, phenylcarbonyloxy, substituted phenylcarbonyloxy wherein the one or more phenyl substituents are each selected from the group consisting of $C_{1-5}$alkyl, halogen and $C_{1-5}$alkoxy, phenyl$C_{1-5}$alkylcarbonyloxy wherein the one or more phenyl substituents are each selected from the group consisting of $C_{1-5}$alkyl, halogen and $C_{1-5}$alkoxy, aminocarbonyloxy, $C_{1-5}$alkylaminocarbonyloxy, di$C_{1-5}$ alkylaminocarbonyloxy, $C_{1-5}$ alkoxycarbonyloxy, substituted $C_{1-5}$alkoxycarbonyloxy wherein the one or more alkyl substituents are each selected from the group consisting of methyl, ethyl, isopropyl and hexyl, phenoxycarbonyloxy, substituted phenoxycarbonyloxy wherein the one or more phenyl substituents are each selected from the group consisting of $C_{1-5}$alkyl, $C_{1-5}$ alkoxy and halogen, $C_{1-5}$ alkylthio, substituted $C_{1-5}$alkylthio wherein the alkyl substituents are selected from the group consisting of hydroxy and phthalimido, $C_{1-5}$alkylsulfonyl, phenylsulfonyl, substituted phenylsulfonyl wherein the one or more phenyl substituents are each selected from the group consisting of bromine, fluorine, chloride, $C_{1-5}$alkoxy and trifluoromethyl; with the proviso that if A is ![structure with N-OR5]

q is 0 and X is H, then $R_3$ may not be 2-(trimethylsilyl)ethoxymethyl; and pharmaceutically acceptable salts thereof.

An example of the invention includes a compound of Formula (I) wherein $R_1$ is substituted phenyl and $R_2$ is pyrimidin-3-yl.

An example of the invention includes a compound of Formula (I) wherein $R_1$ is 4-fluorophenyl.

An example of the invention includes a compound of Formula (I) wherein $R_3$ is hydrogen, aryl$C_{1-5}$alkyl, or substituted aryl$C_{1-5}$alkyl.

An example of the invention includes a compound of Formula (I) wherein $R_3$ is hydrogen or phenyl$C_{1-5}$alkyl.

An example of the invention includes a compound of Formula (I) wherein A is ethynylene and q is 0-5.

An example of the invention includes a compound of Formula (I) wherein X is succinimido, hydroxy, methyl, phenyl, $C_{1-5}$alkylsulfonyl, $C_{3-6}$cycloalkyl, $C_{1-5}$alkylcarbonyloxy, $C_{1-5}$alkoxy, phenylcarbonyloxy, $C_{1-5}$alkylamino, di$C_{1-5}$alkylamino or nitrile.

Compounds of Formula (I) are disclosed in commonly assigned U.S. Pat. No. 6,214,830, the complete disclosure of which is herein incorporated by reference.

An example of the invention includes a compound of Formula (I) wherein the compound is selected from the group consisting of:

| Compound | Name |
|---|---|
| 1 | 5(4)-(4-fluorophenyl)-4(5)-(4-pyridyl)imidazole, |
| 2 | 4-(4-fluorophenyl)-1-(3-phenylpropyl)-5-(4-pyridyl)imidazole, |
| 3 | 5-(4-fluorophenyl)-1-(3-phenylpropyl)-4-(4-pyridyl)imidazole, |
| 4 | 4-(4-fluorophenyl)-2-iodo-1-(3-phenylpropyl)-5-(4-pyridyl)imidazole, |
| 5 | 4-(4-fluorophenyl)-2-(4-hydroxybutyn-1-yl)-1-(3-phenylpropyl)-5-(4-pyridyl)imidazole, |
| 6 | 4-(4-fluorophenyl)-5-(4-pyridyl)-1-[2-(trimethylsilyl)ethoxymethyl]-imidazole, |
| 7 | 5-(4-fluorophenyl)-4-(4-pyridyl)-1-[2-(trimethylsilyl)ethoxymethyl]-imidazole, |
| 8 | 5-(4-fluorophenyl)-2-iodo-4-(4-pyridyl)-1-[2-(trimethylsilyl)ethoxymethyl]-imidazole, |
| 9 | 5-(4-fluorophenyl)-4-(4-pyridyl)-2-(trimethylsilyl)ethinyl-1-[2-(trimethylsilyl)ethoxymethyl]-imidazole, |
| 10 | 2-(2-chlorovinyl)-5-(4-fluorophenyl)-4-(4-pyridyl)-imidazole, |
| 11 | 5-(4-fluorophenyl)-4-(4-pyridyl)-1-[2-(trimethylsilyl)ethoxymethyl]-imidazole-2-carboxaldehyde, |
| 12 | 2-[2,2-dibromoethylene-1-yl]-5-(4-fluorophenyl)-4-(4-pyridyl)-1-[2-(trimethylsilyl)ethoxymethyl]-imidazole-2-carboxaldehyde, |
| 13 | 5(4)-(4-fluorophenyl)-2-(3-hydroxy-3-phenyl-propyn-1-yl)-4(5)-(4-pyridyl)imidazole, |
| 14 | 5-(4-fluorophenyl)-4-(4-pyridyl)-1-[2-(trimethylsilyl)ethoxymethyl]-2-oximinoimidazole, |
| 15 | 5-(4-fluorophenyl)-4-(4-pyridyl)-2-imidazole oxime, |
| 16 | 2-(5-chloropentyn-1-yl)-4-(4-fluorophenyl)-1-(3-phenylpropyl)-5-(4-pyridyl)imidazole, |
| 17 | 4-(4-fluorophenyl)-2-(4-N-phenylcarbamoyloxybutyn-1-yl)1-(3-phenylpropyl)-5-(4-pyridyl)imidazole, |
| 17 | 2-(4-chlorobutyn-1-yl)-4-(4-fluorophenyl)-1-(3-phenylpropyl)-5-(4-pyridyl)imidazole, and |
| 18 | 2-(4-dimethylaminobutyn-1-yl)-4-(4-fluorophenyl)-1-(3-phenylpropyl)-5-(4-pyridyl)imidazole. |

An example of the invention includes a compound of Formula (I) wherein the compound is Compound 5 of the formula:

Compound 5

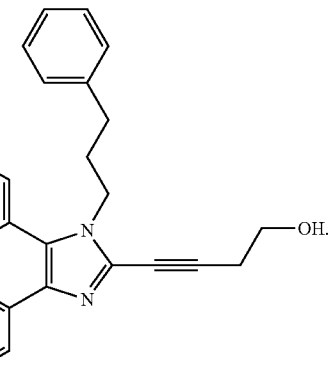

In one embodiment, the inhibitor of GSK-3B enzyme activity is a compound of the Formula (II):

Formula (II)

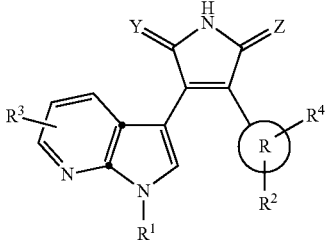

Wherein:

R is selected from the group consisting of $R_a$, —$C_{1-8}$ alkyl-$R_a$, —$C_{2-8}$alkenyl-$R_a$, —$C_{2-8}$alkynyl-$R_a$ and cyano;

$R_a$ is selected from the group consisting of cycloalkyl, heterocyclyl, aryl and heteroaryl;

$R^1$ is selected from the group consisting of hydrogen, —$C_{1-8}$alkyl-$R^5$, —$C_{2-8}$alkenyl-$R^5$, —$C_{2-8}$alkynyl-$R^5$, —C(O)—($C_{1-8}$)alkyl-$R^9$, —C(O)-aryl-$R^8$, —C(O)—O—($C_{1-8}$)alkyl-$R^9$, —C(O)—O-aryl-$R^8$, —C(O)—NH($C_{1-8}$alkyl-$R^9$), —C(O)—NH(aryl-$R^8$), —C(O)—N($C_{1-8}$alkyl-$R^9$)$_2$, —SO$_2$—($C_{1-8}$)alkyl-$R^9$, —SO$_2$-aryl-$R^8$, -cycloalkyl-$R^6$, -heterocyclyl-$R^6$, -aryl-$R^6$ and -heteroaryl-$R^6$; wherein heterocyclyl and heteroaryl are attached to the azaindole nitrogen atom in the one position via a heterocyclyl or heteroaryl ring carbon atom;

$R^5$ is 1 to 2 substituents independently selected from the group consisting of hydrogen, —O—($C_{1-8}$)alkyl, —O—($C_{1-8}$) alkyl-OH, —O—($C_{1-8}$)alkyl-O—($C_{1-8}$)alkyl, —O—($C_{1-8}$)alkyl-NH$_2$, —O—($C_{1-8}$)alkyl-NH($C_{1-8}$alkyl), —O—($C_{1-8}$)alkyl-N($C_{1-8}$alkyl)$_2$, —O—($C_{1-8}$)alkyl-S—($C_{1-8}$) alkyl, —O—($C_{1-8}$)alkyl-SO$_2$—($C_{1-8}$)alkyl, —O—($C_{1-8}$) alkyl-SO$_2$—NH$_2$, —O—($C_{1-8}$)alkyl-SO$_2$—NH($C_{1-8}$alkyl), —O—($C_{1-8}$)alkyl-SO$_2$—N($C_{1-8}$alkyl)$_2$, —O—C(O)H, —O—C(O)—($C_{1-8}$)alkyl, —O—C(O)—NH$_2$, —O—C(O)—NH($C_{1-8}$alkyl), —O—C(O)—N($C_{1-8}$alkyl)$_2$, —O—($C_{1-8}$)alkyl-C(O)H, —O—($C_{1-8}$)alkyl-C(O)—($C_{1-8}$)alkyl, —O—($C_{1-8}$)alkyl-CO$_2$H, —O—($C_{1-8}$)alkyl-C(O)—O—($C_{1-8}$)alkyl, —O—($C_{1-8}$)alkyl-C(O)—NH$_2$, —O—($C_{1-8}$) alkyl-C(O)—NH($C_{1-8}$alkyl), —O—($C_{1-8}$)alkyl-C(O)—N($C_{1-8}$alkyl)$_2$, —C(O)H, —C(O)—($C_{1-8}$)alkyl, —CO$_2$H, —C(O)—O—($C_{1-8}$)alkyl, —C(O)—NH$_2$, —C(NH)—NH$_2$, —C(O)—NH($C_{1-8}$alkyl), —C(O)—N($C_{1-8}$alkyl)$_2$, —SH, —S—($C_{1-8}$)alkyl, —S—($C_{1-8}$)alkyl-S—($C_{1-8}$)alkyl, —S—($C_{1-8}$)alkyl-O—($C_{1-8}$)alkyl, —S—($C_{1-8}$)alkyl-O—($C_{1-8}$) alkyl-OH, —S—($C_{1-8}$)alkyl-O—($C_{1-8}$)alkyl-NH$_2$, —S—($C_{1-8}$)alkyl-O—($C_{1-8}$)alkyl-NH($C_{1-8}$alkyl), —S—($C_{1-8}$) alkyl-O—($C_{1-8}$)alkyl-N($C_{1-8}$alkyl)$_2$, —S—($C_{1-8}$)alkyl-NH ($C_{1-8}$alkyl), —SO$_2$—($C_{1-8}$)alkyl, —SO$_2$—NH$_2$, —SO$_2$—NH($C_{1-8}$alkyl), —SO$_2$—N($C_{1-8}$alkyl)$_2$, —N—$R^7$, cyano, (halo)$_{1-3}$, hydroxy, nitro, oxo, -cycloalkyl-$R^6$, -heterocyclyl-$R^6$, -aryl-$R^6$ and -heteroaryl-$R^6$;

$R^6$ is 1 to 4 substituents attached to a carbon or nitrogen atom independently selected from the group consisting of hydrogen, —$C_{1-8}$alkyl, —$C_{2-8}$alkenyl, —$C_{2-8}$alkynyl, —C(O)H, —C(O)—($C_{1-8}$)alkyl, —CO$_2$H, —C(O)—O—($C_{1-8}$)alkyl, —C(O)—NH$_2$, —C(NH)—NH$_2$, —C(O)—NH($C_{1-8}$alkyl), —C(O)—N($C_{1-8}$alkyl)$_2$, —SO$_2$—($C_{1-8}$)alkyl, —SO$_2$—NH$_2$, —SO$_2$—NH($C_{1-8}$alkyl), —SO$_2$—N($C_{1-8}$ alkyl)$_2$, —($C_{1-8}$)alkyl-N—$R^7$, —($C_{1-8}$)alkyl-(halo)$_{1-3}$, —($C_{1-8}$)alkyl-OH, -aryl-$R^8$, —($C_{1-8}$)alkyl-aryl-$R^8$ and —($C_{1-8}$)alkyl-heteroaryl-$R^8$; with the proviso that, when $R^6$ is attached to a carbon atom, $R^6$ is further selected from the group consisting of —$C_{1-8}$alkoxy, —($C_{1-8}$)alkoxy-(halo)$_{1-3}$, —SH, —S—($C_{1-8}$)alkyl, —N—$R^7$, cyano, halo, hydroxy, nitro, oxo and -heteroaryl-$R^8$;

$R^7$ is 2 substituents independently selected from the group consisting of hydrogen, —$C_{1-8}$alkyl, —$C_{2-8}$alkenyl, —$C_{2-8}$ alkynyl, —($C_{1-8}$)alkyl-OH, —($C_{1-8}$)alkyl-O—($C_{1-8}$)alkyl, —($C_{1-8}$)alkyl-NH$_2$, —($C_{1-8}$)alkyl-NH($C_{1-8}$alkyl), —($C_{1-8}$) alkyl-N($C_{1-8}$alkyl)$_2$, —($C_{1-8}$)alkyl-S—($C_{1-8}$)alkyl, —C(O) H, —C(O)—($C_{1-8}$)alkyl, —C(O)—O—($C_{1-8}$)alkyl, —C(O)—NH$_2$, —C(O)—NH($C_{1-8}$alkyl), —C(O)—N($C_{1-8}$ alkyl)$_2$, —SO$_2$—($C_{1-8}$)alkyl, —SO$_2$—NH$_2$, —SO$_2$—NH ($C_{1-8}$alkyl), —SO$_2$—N($C_{1-8}$alkyl)$_2$, —C(N)—NH$_2$, -cycloalkyl-$R^8$, —($C_{1-8}$)alkyl-heterocyclyl-$R^8$, -aryl-$R^8$, —($C_{1-8}$)alkyl-aryl-$R^8$ and —($C_{1-8}$)alkyl-heteroaryl-$R^8$;

$R^8$ is 1 to 4 substituents attached to a carbon or nitrogen atom independently selected from the group consisting of hydrogen, —$C_{1-8}$alkyl, —($C_{1-8}$)alkyl-(halo)$_{1-3}$ and —($C_{1-8}$) alkyl-OH; with the proviso that, when $R^8$ is attached to a carbon atom, $R^8$ is further selected from the group consisting of —$C_{1-8}$alkoxy, —NH$_2$, —NH($C_{1-8}$alkyl), —N($C_{1-8}$ alkyl)$_2$, cyano, halo, —($C_{1-8}$)alkoxy-(halo)$_{1-3}$, hydroxy and nitro;

$R^9$ is 1 to 2 substituents independently selected from the group consisting of hydrogen, —$C_{1-8}$alkoxy, —NH$_2$, —NH ($C_{1-8}$alkyl), —N($C_{1-8}$alkyl)$_2$, cyano, (halo)$_{1-3}$, hydroxy and nitro;

$R^2$ is one substituent attached to a carbon or nitrogen atom selected from the group consisting of hydrogen, —$C_{1-8}$ alkyl-$R^5$, —$C_{2-8}$alkenyl-$R^5$, —$C_{2-8}$alkynyl-$R^5$, —C(O)H, —C(O)—($C_{1-8}$)alkyl-$R^9$, —C(O)—NH$_2$, —C(O)—NH ($C_{1-8}$ alkyl-$R^9$), —C(O)—N($C_{1-8}$alkyl-$R^9$)$_2$, —C(O)—NH (aryl-$R^8$), —C(O)-cycloalkyl-$R^8$, —C(O)-heterocyclyl-$R^8$, —C(O)-aryl-$R^8$, —C(O)-heteroaryl-$R^8$, —CO$_2$H, —C(O)—O—($C_{1-8}$)alkyl-$R^9$, —C(O)—O-aryl-$R^8$, —SO$_2$—($C_{1-8}$)alkyl-$R^9$, —SO$_2$-aryl-$R^8$, -cycloalkyl-$R^6$, -aryl-$R^6$ and —($C_{1-8}$)alkyl-N—$R^7$; with the proviso that, when $R^2$ is attached to a carbon atom, $R^2$ is further selected from the group consisting of —$C_{1-8}$alkoxy-$R^5$, —N—$R^7$, cyano, halogen, hydroxy, nitro, oxo, -heterocyclyl-$R^6$ and -heteroaryl-$R^6$;

$R^3$ is 1 to 3 substituents attached to a carbon atom independently selected from the group consisting of hydrogen, —$C_{1-8}$alkyl-$R^{10}$, —$C_{2-8}$alkenyl-$R^{10}$, —$C_{2-8}$alkynyl-$R^{10}$, —$C_{1-8}$alkoxy-$R^{10}$, —C(O)H, —C(O)—($C_{1-8}$)alkyl-$R^9$, —C(O)—NH$_2$, —C(O)—NH($C_{1-8}$alkyl-$R^9$), —C(O)—N ($C_{1-8}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—NH$_2$, —CO$_2$H, —C(O)—O—($C_{1-8}$)alkyl-$R^9$, —C(O)—O-aryl-$R^8$, —SO$_2$—($C_{1-8}$)alkyl-$R^9$, —SO$_2$-aryl-$R^8$, —N—$R^7$, cyano, halogen, hydroxy, nitro, -cycloalkyl-$R^8$, -heterocyclyl-$R^8$, -aryl-$R^8$ and -heteroaryl-$R^8$;

$R^4$ is 1 to 4 substituents attached to a carbon atom independently selected from the group consisting of hydrogen, —$C_{1-8}$alkyl-$R^{10}$, —$C_{2-8}$alkenyl-$R^{10}$, —$C_{2-8}$alkynyl-$R^{10}$, —$C_{1-8}$alkoxy-$R^{10}$, —C(O)H, —C(O)—($C_{1-8}$)alkyl-$R^9$, —C(O)—NH$_2$, —C(O)—NH($C_{1-8}$alkyl-$R^9$), —C(O)—N ($C_{1-8}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—NH$_2$, —CO$_2$H, —C(O)—O—($C_{1-8}$)alkyl-$R^9$, —C(O)—O-aryl-$R^8$, —SH, —S—($C_{1-8}$)alkyl-$R^{10}$, —SO$_2$—($C_{1-8}$)alkyl-$R^9$, —SO$_2$-aryl-$R^8$, —SO$_2$—NH$_2$, —SO$_2$—NH($C_{1-8}$alkyl-$R^9$), —SO$_2$—N($C_{1-8}$alkyl-$R^9$)$_2$, —N—$R^7$, cyano, halogen, hydroxy, nitro, -cycloalkyl-$R^8$, -heterocyclyl-$R^8$, -aryl-$R^8$ and -heteroaryl-$R^8$;

$R^{10}$ is 1 to 2 substituents independently selected from the group consisting of hydrogen, —NH$_2$, —NH($C_{1-8}$alkyl), —N($C_{1-8}$alkyl)$_2$, cyano, (halo)$_{1-3}$, hydroxy, nitro and oxo; and, Y and Z are independently selected from the group consisting of O, S, (H,OH) and (H,H); with the proviso that one of Y and Z is O and the other is selected from the group consisting of O, S, (H,OH) and (H,H); and pharmaceutically acceptable salts thereof.

Embodiments of the present invention include compounds of Formula (II) wherein, R is selected from the group consisting of $R_a$, —$C_{1-4}$alkyl-$R_a$, —$C_{2-4}$alkenyl-$R_a$, —$C_{2-4}$alkynyl-$R_a$ and cyano.

Embodiments of the present invention include compounds of Formula (II) wherein, $R_a$ is selected from the group consisting of heterocyclyl, aryl and heteroaryl.

In one embodiment, $R_a$ is selected from the group consisting of dihydro-pyranyl, phenyl, naphthyl, thienyl, pyrrolyl, imidazolyl, pyrazolyl, pyridinyl, azaindolyl, indazolyl, benzofuryl, benzothienyl, dibenzofuryl and dibenzothienyl.

Embodiments of the present invention include compounds of Formula (II) wherein, $R^1$ is selected from the group consisting of hydrogen, —$C_{1-4}$alkyl-$R^5$, —$C_{2-4}$alkenyl-$R^5$, —$C_{2-4}$alkynyl-$R^5$, —C(O)—($C_{1-4}$)alkyl-$R^9$, —C(O)-aryl-$R^8$, —C(O)—O—($C_{1-4}$)alkyl-$R^9$, —C(O)—O-aryl-$R^8$, —C(O)—NH($C_{1-4}$alkyl-$R^9$), —C(O)—NH(aryl-$R^8$), —C(O)—N($C_{1-4}$alkyl-$R^9$)$_2$, —SO$_2$—($C_{1-4}$)alkyl-$R^9$, —SO$_2$-aryl-$R^8$, -cycloalkyl-$R^6$, -heterocyclyl-$R^6$, -aryl-$R^6$ and -heteroaryl-$R^6$; wherein heterocyclyl and heteroaryl are attached to the azaindole nitrogen atom in the one position via a heterocyclyl or heteroaryl ring carbon atom.

In one embodiment, $R^1$ is selected from the group consisting of hydrogen, —$C_{1-4}$alkyl-$R^5$, -aryl-$R^6$ and -heteroaryl-$R^6$; wherein heteroaryl is attached to the azaindole nitrogen atom in the one position via a heteroaryl ring carbon atom.

In one embodiment, $R^1$ is selected from the group consisting of hydrogen, —$C_{1-4}$alkyl-$R^5$ and -naphthyl-$R^6$.

Embodiments of the present invention include compounds of Formula (II) wherein, $R^5$ is 1 to 2 substituents independently selected from the group consisting of hydrogen, —O—($C_{1-4}$alkyl, —O—($C_{1-4}$alkyl-OH, —O—($C_{1-4}$alkyl-O—($C_{1-4}$alkyl, —O—($C_{1-4}$alkyl-NH$_2$, —O—($C_{1-4}$alkyl-NH($C_{1-4}$alkyl), —O—($C_{1-4}$alkyl-N($C_{1-4}$alkyl)$_2$, —O—($C_{1-4}$alkyl-S—($C_{1-4}$)alkyl, —O—($C_{1-4}$)alkyl-SO$_2$—($C_{1-4}$)alkyl, —O—($C_{1-4}$alkyl-SO$_2$—NH$_2$, —O—($C_{1-4}$alkyl-SO$_2$—NH($C_{1-4}$alkyl), —O—($C_{1-4}$alkyl-SO$_2$—N($C_{1-4}$alkyl)$_2$, —O—C(O)H, —O—C(O)—($C_{1-4}$alkyl, —O—C(O)—NH$_2$, —O—C(O)—NH($C_{1-4}$alkyl), —O—C(O)—N($C_{1-4}$alkyl)$_2$, —O—($C_{1-4}$alkyl-C(O)H, —O—($C_{1-4}$alkyl-C(O)—($C_{1-4}$)alkyl, —O—($C_{1-4}$alkyl-CO$_2$H, —O—($C_{1-4}$alkyl-C(O)—O—($C_{1-4}$alkyl, —O—($C_{1-4}$)alkyl-C(O)—NH$_2$, —O—($C_{1-4}$alkyl-C(O)—NH($C_{1-4}$alkyl), —O—($C_{1-4}$alkyl-C(O)—N($C_{1-4}$alkyl)$_2$, —C(O)H, —C(O)—($C_{1-4}$alkyl, —CO$_2$H, —C(O)—O—($C_{1-4}$alkyl, —C(O)—NH$_2$, —C(NH)—NH$_2$, —C(O)—NH($C_{1-4}$alkyl), —C(O)—N($C_{1-4}$ alkyl)$_2$, —SH, —S—($C_{1-4}$alkyl, —S—($C_{1-4}$alkyl-S—($C_{1-4}$)alkyl, —S—($C_{1-4}$alkyl-O—($C_{1-4}$)alkyl, —S—($C_{1-4}$alkyl-O—($C_{1-4}$)alkyl-OH, —S—($C_{1-4}$alkyl-O—($C_{1-4}$)alkyl-NH$_2$, —S—($C_{1-4}$alkyl-O—($C_{1-4}$)alkyl-NH($C_{1-4}$alkyl), —S—($C_{1-4}$alkyl-O—($C_{1-4}$)alkyl-N($C_{1-4}$alkyl)$_2$, —S—($C_{1-4}$ alkyl-NH($C_{1-4}$alkyl), —SO$_2$—($C_{1-4}$alkyl, —SO$_2$—NH$_2$, —SO$_2$—NH($C_{1-4}$alkyl), —SO$_2$—N($C_{1-4}$alkyl)$_2$, —N—$R^7$, cyano, (halo)$_{1-3}$, hydroxy, nitro, oxo, -cycloalkyl-$R^6$, -heterocyclyl-$R^6$, -aryl-$R^6$ and -heteroaryl-$R^6$.

In one embodiment, $R^5$ is 1 to 2 substituents independently selected from the group consisting of hydrogen, —O—($C_{1-4}$alkyl, —N—$R^7$, hydroxy and -heteroaryl-$R^6$.

In one embodiment, $R^5$ is 1 to 2 substituents independently selected from the group consisting of hydrogen, —O—($C_{1-4}$alkyl, —N—$R^7$, hydroxy, -imidazolyl-$R^6$, -triazolyl-$R^6$ and -tetrazolyl-$R^6$.

Embodiments of the present invention include compounds of Formula (II) wherein, $R^6$ is 1 to 4 substituents attached to a carbon or nitrogen atom independently selected from the group consisting of hydrogen, —$C_{1-4}$alkyl, —$C_{2-4}$alkenyl, —$C_{2-4}$alkynyl, —C(O)H, —C(O)—($C_{1-4}$alkyl, —CO$_2$H, —C(O)—O—($C_{1-4}$alkyl, —C(O)—NH$_2$, —C(NH)—NH$_2$, —C(O)—NH($C_{1-4}$alkyl), —C(O)—N($C_{1-4}$)alkyl)$_2$, —SO$_2$—($C_{1-4}$alkyl, —SO$_2$—NH$_2$, —SO$_2$—NH($C_{1-4}$alkyl), —SO$_2$—N($C_{1-4}$alkyl)$_2$, —($C_{1-4}$)alkyl-N—$R^7$, —($C_{1-4}$)alkyl-(halo)$_{1-3}$, —($C_{1-4}$alkyl-OH, -aryl-$R^8$, —($C_{1-4}$)alkyl-aryl-$R^8$ and —($C_{1-4}$)alkyl-heteroaryl-$R^8$; with the proviso that, when $R^6$ is attached to a carbon atom, $R^6$ is further selected from the group consisting of —$C_{1-4}$ alkoxy, —($C_{1-4}$)alkoxy-(halo)$_{1-3}$, —SH, —S—($C_{1-4}$)alkyl, —N—$R^7$, cyano, halo, hydroxy, nitro, oxo and -heteroaryl-$R^8$.

In one embodiment, $R^6$ is hydrogen.

Embodiments of the present invention include compounds of Formula (II) wherein, $R^7$ is 2 substituents independently selected from the group consisting of hydrogen, —$C_{1-4}$alkyl, —$C_{2-4}$alkenyl, —$C_{2-4}$alkynyl, —($C_{1-4}$)alkyl-OH, —($C_{1-4}$)alkyl-O—($C_{1-4}$)alkyl, —($C_{1-4}$)alkyl-NH$_2$, —($C_{1-4}$)alkyl-NH($C_{1-4}$alkyl), —($C_{1-4}$)alkyl-N($C_{1-4}$alkyl)$_2$, —($C_{1-4}$)alkyl-S—($C_{1-4}$)alkyl, —C(O)H, —C(O)—($C_{1-4}$ alkyl, —C(O)—O—($C_{1-4}$alkyl, —C(O)—NH$_2$, —C(O)—NH($C_{1-4}$alkyl), —C(O)—N($C_{1-4}$alkyl)$_2$, —SO$_2$—($C_{1-4}$)alkyl, —SO$_2$—NH$_2$, —SO$_2$—NH($C_{1-4}$alkyl), —SO$_2$—N($C_{1-4}$alkyl)$_2$, —C(N)—NH$_2$, -cycloalkyl-$R^8$, —($C_{1-4}$)alkyl-heterocyclyl-$R^8$, -aryl-$R^8$, —($C_{1-4}$)alkyl-aryl-$R^8$ and —($C_{1-4}$)alkyl-heteroaryl-$R^8$.

In one embodiment $R^2$ is 2 substituents independently selected from the group consisting of hydrogen, —$C_{1-4}$alkyl, —C(O)H, —C(O)—($C_{1-4}$)alkyl, —C(O)—O—($C_{1-4}$)alkyl, —SO$_2$—NH$_2$, —SO$_2$—NH($C_{1-4}$alkyl) and —SO$_2$—N($C_{1-4}$alkyl)$_2$.

Embodiments of the present invention include compounds of Formula (II) wherein, $R^8$ is 1 to 4 substituents attached to a carbon or nitrogen atom independently selected from the group consisting of hydrogen, —$C_{1-4}$alkyl, —($C_{1-4}$) alkyl-(halo)$_{1-3}$ and —($C_{1-4}$)alkyl-OH; with the proviso that, when $R^8$ is attached to a carbon atom, $R^8$ is further selected from the group consisting of —$C_{1-4}$alkoxy, —NH$_2$, —NH($C_{1-4}$alkyl), —N($C_{1-4}$alkyl)$_2$, cyano, halo, —($C_{1-4}$) alkoxy-(halo)$_{1-3}$, hydroxy and nitro.

In one embodiment, $R^8$ is hydrogen.

Embodiments of the present invention include compounds of Formula (II) wherein, $R^9$ is 1 to 2 substituents independently selected from the group consisting of hydrogen, —$C_{1-4}$alkoxy, —NH$_2$, —NH($C_{1-4}$alkyl), —N($C_{1-4}$ alkyl)$_2$, cyano, (halo)$_{1-3}$, hydroxy and nitro.

In one embodiment, $R^9$ is hydrogen.

Embodiments of the present invention include compounds of Formula (II) wherein, $R^2$ is one substituent attached to a carbon or nitrogen atom selected from the group consisting of hydrogen, —$C_{1-4}$alkyl-$R^5$, —$C_{2-4}$alkenyl-$R^5$, —$C_{2-4}$alkynyl-$R^5$, —C(O)H, —C(O)—($C_{1-4}$alkyl-$R^9$, —C(O)—NH$_2$, —C(O)—NH($C_{1-4}$alkyl-$R^9$), —C(O)—N($C_{1-4}$alkyl-$R^9$)$_2$, —C(O)—NH(aryl-$R^8$), —C(O)-cycloalkyl-$R^8$, —C(O)-heterocyclyl-$R^8$, —C(O)-aryl-$R^8$, —C(O)-heteroaryl-$R^8$, —CO$_2$H, —C(O)—O—($C_{1-4}$alkyl-$R^9$, —C(O)—O-aryl-$R^8$, —SO$_2$—($C_{1-4}$alkyl-$R^9$, —SO$_2$-aryl-$R^8$, -cycloalkyl-$R^6$, -aryl-$R^6$ and —($C_{1-4}$)alkyl-N—$R^7$; with the proviso that, when $R^2$ is attached to a carbon atom, $R^2$ is further selected from the group consisting of —$C_{1-4}$alkoxy-$R^5$, —N—$R^2$, cyano, halogen, hydroxy, nitro, oxo, -heterocyclyl-$R^6$ and -heteroaryl-$R^6$.

In one embodiment, $R^2$ is one substituent attached to a carbon or nitrogen atom selected from the group consisting of hydrogen, —$C_{1-4}$alkyl-$R^5$, —$C_{2-4}$alkenyl-$R^5$, —$C_{2-4}$alkynyl-$R^5$, —$CO_2H$, —C(O)—O—($C_{1-4}$alkyl-$R^9$), -cycloalkyl-$R^6$, -aryl-$R^6$ and —($C_{1-4}$)alkyl-N—$R^7$; with the proviso that, when $R^2$ is attached to a nitrogen atom, a quaternium salt is not formed; and, with the proviso that, when $R^2$ is attached to a carbon atom, $R^2$ is further selected from the group consisting of —$C_{1-4}$alkoxy-$R^5$, —N—$R^7$, cyano, halogen, hydroxy, nitro, oxo, -heterocyclyl-$R^6$ and -heteroaryl-$R^6$.

In one embodiment, $R^2$ is one substituent attached to a carbon or nitrogen atom selected from the group consisting of hydrogen, —$C_{1-4}$alkyl-$R^5$ and -aryl-$R^6$; with the proviso that, when $R^2$ is attached to a nitrogen atom, a quaternium salt is not formed; and, with the proviso that when $R^2$ is attached to a carbon atom, $R^2$ is further selected from the group consisting of —N—$R^7$, halogen, hydroxy and -heteroaryl-$R^6$.

Embodiments of the present invention include compounds of Formula (II) wherein, $R^3$ is 1 to 3 substituents attached to a carbon atom independently selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —C(O)—($C_{1-4}$alkyl-$R^9$), —C(O)—$NH_2$, —C(O)—NH($C_{1-4}$alkyl-$R^9$), —C(O)—N($C_{1-4}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—$NH_2$, —$CO_2H$, —C(O)—O—($C_{1-4}$alkyl-$R^9$, —C(O)—O-aryl-$R^8$, —$SO_2$—($C_{1-8}$)alkyl-$R^9$, —$SO_2$-aryl-$R^8$, —N—$R^7$, —($C_{1-4}$)alkyl-N—$R^7$, cyano, halogen, hydroxy, nitro, -cycloalkyl-$R^8$, -heterocyclyl-$R^8$, -aryl-$R^8$ and -heteroaryl-$R^8$.

In one embodiment, $R^3$ is one substituent attached to a carbon atom selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —$CO_2H$, —$NH_2$, —NH($C_{1-4}$alkyl), —N($C_{1-4}$alkyl)$_2$, cyano, halogen, hydroxy and nitro.

In one embodiment, $R^3$ is one substituent attached to a carbon atom selected from the group consisting of hydrogen, —$C_{1-4}$alkyl-$R^{10}$, —$NH_2$, —NH($C_{1-4}$alkyl), —N($C_{1-4}$alkyl)$_2$, halogen and hydroxy.

Embodiments of the present invention include compounds of Formula (II) wherein, $R^4$ is 1 to 4 substituents attached to a carbon atom independently selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —C(O)—($C_{1-4}$alkyl-$R^9$), —C(O)—$NH_2$, —C(O)—NH($C_{1-4}$alkyl-$R^9$), —C(O)—N($C_{1-4}$alkyl-$R^9$)$_2$, —C(O)-cycloalkyl-$R^8$, —C(O)-heterocyclyl-$R^8$, —C(O)-aryl-$R^8$, —C(O)-heteroaryl-$R^8$, —C(NH)—$NH_2$, —$CO_2H$, —C(O)—O—($C_{1-4}$alkyl-$R^9$, —C(O)—O-aryl-$R^8$, —SH, —S—($C_{1-4}$alkyl-$R^{10}$, —$SO_2$—($C_{1-4}$alkyl-$R^9$, —$SO_2$-aryl-$R^8$, —$SO_2$—$NH_2$, —$SO_2$—NH($C_{1-4}$alkyl-$R^9$), —$SO_2$—N($C_{1-4}$alkyl-$R^9$)$_2$, —N—$R^7$, cyano, halogen, hydroxy, nitro, -cycloalkyl-$R^8$, -heterocyclyl-$R^8$, -aryl-$R^8$ and -heteroaryl-$R^8$.

In one embodiment, $R^4$ is 1 to 4 substituents attached to a carbon atom independently selected from the group consisting of hydrogen, —$C_{1-4}$alkyl-$R^{10}$, —$C_{2-4}$alkenyl-$R^{10}$, —$C_{2-4}$alkynyl-$R^{10}$, —$C_{1-4}$alkoxy-$R^{10}$, —C(O)H, —$CO_2H$, —$NH_2$, —NH($C_{1-4}$alkyl), —N($C_{1-4}$alkyl)$_2$, cyano, halogen, hydroxy, nitro, -cycloalkyl, -heterocyclyl, -aryl and -heteroaryl.

In one embodiment, $R^4$ is 1 to 4 substituents attached to a carbon atom independently selected from the group consisting of hydrogen, $C_{1-4}$alkyl-$R^{10}$, $C_{1-4}$alkoxy-$R^{10}$, —$NH_2$, —NH($C_{1-4}$alkyl), —N($C_{1-4}$alkyl)$_2$, halogen and hydroxy.

In one embodiment, $R^4$ is 1 to 4 substituents attached to a carbon atom independently selected from the group consisting of hydrogen, $C_{1-4}$alkyl-$R^{10}$, $C_{1-4}$alkoxy-$R^{10}$, —$NH_2$, —NH($C_{1-4}$alkyl), —N($C_{1-4}$alkyl)$_2$, chlorine, fluorine and hydroxy.

Embodiments of the present invention include compounds of Formula (II) wherein, $R^{10}$ is 1 to 2 substituents independently selected from the group consisting of hydrogen, —$NH_2$, —NH($C_{1-4}$alkyl), —N($C_{1-4}$alkyl)$_2$, cyano, (halo)$_{1-3}$, hydroxy, nitro and oxo.

In one embodiment, $R^{10}$ is 1 to 2 substituents independently selected from the group consisting of hydrogen and (halo)$_{1-3}$.

In one embodiment, $R^{10}$ is 1 to 2 substituents independently selected from the group consisting of hydrogen and (fluoro)$_3$.

Embodiments of the present invention include compounds of Formula (II) wherein, Y and Z are independently selected from the group consisting of O, S, (H,OH) and (H,H); with the proviso that one of Y and Z is O and the other is selected from the group consisting of O, S, (H,OH) and (H,H).

In one embodiment, Y and Z are independently selected from the group consisting of O and (H,H); with the proviso that one of Y and Z is O, and the other is selected from the group consisting of O and (H,H).

In one embodiment, Y and Z are independently selected from O.

Compounds of Formula (II) are disclosed in commonly assigned U.S. Pat. No. 7,125,878, the complete disclosure of which is herein incorporated by reference.

An example of the invention includes a compound of Formula (II) wherein the compound is selected from the group consisting of:

| Compound | Name |
|---|---|
| 1 | 3-(2-chlorophenyl)-4-[1-(3-hydroxypropyl)-1H-pyrrolo[2,3-b]pyridin-3-yl]-1H-pyrrole-2,5-dione, |
| 2 | 3-(2-chlorophenyl)-4-[1-[3-(dimethylamino)propyl]-1H-pyrrolo[2,3-b]pyridine-3-yl]-1H-pyrrole-2,5-dione, |
| 3 | 3-[1-(3-hydroxypropyl)-1H-pyrrolo[2,3-b]pyridin-3-yl]-4-(1-naphthalenyl)-1H-pyrrole-2,5-dione, |
| 4 | 3-[1-[3-(dimethylamino)propyl]-1H-pyrrolo[2,3-b]pyridin-3-yl]-4-(1-naphthalenyl)-1H-pyrrole-2,5-dione, |
| 5 | 3-(5-chlorobenzo[b]thien-3-yl)-4-[1-(3-hydroxypropyl)-1H-pyrrolo[2,3-b]pyridine-3-yl]-1H-pyrrole-2,5-dione, |
| 6 | 3-[1-(3-hydroxypropyl)-1H-pyrrolo[2,3-b]pyridin-3-yl]-4-(1H-indazol-3-yl)-1H-pyrrole-2,5-dione, |

-continued

| Compound | Name |
|---|---|
| 7 | 3-(1-ethyl-1H-pyrrolo[2,3-b]pyridin-3-yl)-4-[1-(3-hydroxypropyl)-1H-pyrrolo[2,3-b]pyridin-3-yl]-1H-pyrrole-2,5-dione, |
| 8 | 3-[1-(3-hydroxypropyl)-1H-pyrrolo[2,3-b]pyridin-3-yl]-4-(2-methoxyphenyl)-1H-pyrrole-2,5-dione, |
| 9 | 3-[1-(3-hydroxypropyl)-1H-pyrrolo[2,3-b]pyridin-3-yl]-4-(3-methoxyphenyl)-1H-pyrrole-2,5-dione, |
| 10 | 3-(2-chloro-4-fluorophenyl)-4-[1-(3-hydroxypropyl)-1H-pyrrolo[2,3-b]pyridine-3-yl]-1H-pyrrole-2,5-dione, |
| 11 | 3-[1-(3-hydroxypropyl)-1H-pyrrolo[2,3-b]pyridin-3-yl]-4-[2-(trifluoromethyl)phenyl]-1H-pyrrole-2,5-dione, |
| 12 | 3-[1-(3-hydroxypropyl)-1H-pyrrolo[2,3-b]pyridin-3-yl]-4-(2-pyridinyl)-1H-pyrrole-2,5-dione, |
| 13 | 3-[3-chloro-5-(trifluoromethyl)-2-pyridinyl]-4-[1-(3-hydroxypropyl)-1H-pyrrolo[2,3-b]pyridin-3-yl]-1H-pyrrole-2,5-dione, |
| 14 | 3-[1-(3-hydroxypropyl)-1H-pyrrolo[2,3-b]pyridin-3-yl]-4-(2-thienyl)-1H-pyrrole-2,5-dione, |
| 15 | 3-(2,5-dichloro-3-thienyl)-4-[1-(3-hydroxypropyl)-1H-pyrrolo[2,3-b]pyridin-3-yl]-1H-pyrrole-2,5-dione, |
| 16 | 3-[1-(3-hydroxypropyl)-1H-pyrazol-3-yl]-4-[1-(3-hydroxypropyl)-1H-pyrrolo[2,3-b]pyridin-3-yl]-1H-pyrrole-2,5-dione, |
| 17 | 3-[1-(3-hydroxypropyl)-1H-pyrrolo[2,3-b]pyridin-3-yl]-4-(1H-imidazol-2-yl)-1H-pyrrole-2,5-dione, |
| 18 | 3-[1-(3-hydroxypropyl)-1H-imidazol-4-yl]-4-[1-(3-hydroxypropyl)-1H-pyrrolo[2,3-b]pyridin-3-yl]-1H-pyrrole-2,5-dione, |
| 19 | 3-[1-(2-hydroxyethyl)-1H-imidazol-4-yl]-4-[1-(3-hydroxypropyl)-1H-pyrrolo[2,3-b]pyridin-3-yl]-1H-pyrrole-2,5-dione, |
| 20 | 3-[1-[3-(dimethylamino)propyl]-1H-indazol-3-yl]-4-[1-(2-naphthalenyl)-1H-pyrrolo[2,3-b]pyridin-3-yl]-1H-pyrrole-2,5-dione, |
| 21 | 3-[1-(3-hydroxypropyl)-1H-indazol-3-yl]-4-[1-(2-naphthalenyl)-1H-pyrrolo[2,3-b]pyridin-3-yl]-1H-pyrrole-2,5-dione, |
| 22 | 3-[(E)-2-(4-fluorophenyl)ethenyl]-4-[1-(3-hydroxypropyl)-1H-pyrrolo[2,3-b]pyridin-3-yl]-1H-pyrrole-2,5-dione, |
| 23 | 3-(3,4-dihydro-2H-pyran-6-yl)-4-[1-(3-hydroxypropyl)-1H-pyrrolo[2,3-b]pyridine-3-yl]-1H-pyrrole-2,5-dione, |
| 24 | 4-[1-(3-hydroxypropyl)-1H-pyrrolo[2,3-b]pyridin-3-yl]-[3,3'-bi-1H-pyrrole]-2,5-dione, |
| 25 | 3-(2-benzofuranyl)-4-[1-(3-hydroxypropyl)-1H-pyrrolo[2,3-b]pyridin-3-yl]-1H-pyrrole-2,5-dione, |
| 26 | 3-[1-(3-hydroxypropyl)-1H-pyrrolo[2,3-b]pyridin-3-yl]-4-(1-methyl-1H-pyrazol-3-yl)-1H-pyrrole-2,5-dione, |
| 27 | 2,5-dihydro-4-[1-(3-hydroxypropyl)-1H-pyrrolo[2,3-b]pyridin-3-yl]-2,5-dioxo-1H-pyrrole-3-carbonitrile, |
| 28 | 3-dibenzo[b,d]thien-4-yl-4-[1-(3-hydroxypropyl)-1H-pyrrolo[2,3-b]pyridine-3-yl]-1H-pyrrole-2,5-dione, |
| 29 | 3-(4-dibenzofuranyl)-4-[1-(3-hydroxypropyl)-1H-pyrrolo[2,3-b]pyridin-3-yl]-1H-pyrrole-2,5-dione, |
| 30 | 3-(2-hydroxyphenyl)-4-[1-(3-methoxypropyl)-1H-pyrrolo[2,3-b]pyridin-3-yl]-1H-pyrrole-2,5-dione, |
| 31 | 3-(3,4-dimethoxyphenyl)-4-[1-(3-methoxypropyl)-1H-pyrrolo[2,3-b]pyridine-3-yl]-1H-pyrrole-2,5-dione, |
| 32 | 3-(3,4-dihydroxyphenyl)-4-[1-(3-hydroxypropyl)-1H-pyrrolo[2,3-b]pyridine-3-yl]-1H-pyrrole-2,5-dione, |
| 33 | 3-(2-methoxyphenyl)-4-[1-(2-naphthalenyl)-1H-pyrrolo[2,3-b]pyridin-3-yl]-1H-pyrrole-2,5-dione, |
| 34 | [3-[3-[2,5-dihydro-4-(2-methoxyphenyl)-2,5-dioxo-1H-pyrrol-3-yl]-1H-pyrrolo[2,3-b]pyridin-1-yl]propyl]-carbamic acid 2-methylpropyl ester, |
| 35 | 3-[1-(3-aminopropyl)-1H-pyrrolo[2,3-b]pyridin-3-yl]-4-(2-methoxyphenyl)-1H-pyrrole-2,5-dione, |
| 36 | N-[3-[3-[2,5-dihydro-4-(2-methoxyphenyl)-2,5-dioxo-1H-pyrrol-3-yl]-1H-pyrrolo[2,3-b]pyridin-1-yl]propyl]-acetamide, |
| 37 | N-[3-[3-[2,5-dihydro-4-(2-methoxyphenyl)-2,5-dioxo-1H-pyrrol-3-yl]-1H-pyrrolo[2,3-b]pyridin-1-yl]propyl]-sulfamide, |
| 38 | 3-(2-methoxyphenyl)-4-[1-[3-(1H-tetrazol-1-yl)propyl]-1H-pyrrolo[2,3-b]pyridine-3-yl]-1H-pyrrole-2,5-dione, |
| 39 | 3-(2-methoxyphenyl)-4-[1-[3-(2H-tetrazol-2-yl)propyl]-1H-pyrrolo[2,3-b]pyridine-3-yl]-1H-pyrrole-2,5-dione, |
| 40 | 3-[1-(3-hydroxy-propyl)-1H-pyrrolo[2,3-b]pyridin-3-yl]-4-pyrazin-2-yl-pyrrole-2,5-dione, |
| 41 | 3-(2,4-dimethoxy-pyrimidin-5-yl)-4-[1-(3-hydroxy-propyl)-1H-pyrrolo[2,3-b]pyridin-3-yl]-pyrrole-2,5-dione, |

-continued

| Compound | Name |
|---|---|
| 42 | 4-{3-[4-(2,4-dimethoxy-pyrimidin-5-yl)-2,5-dioxo-2,5-dihydro-1H-pyrrol-3-yl]-pyrrolo[2,3-b]pyridin-1-yl}-butyronitrile, |
| 43 | 4-{3-[4-(1-methyl-1H-pyrazol-3-yl)-2,5-dioxo-2,5-dihydro-1H-pyrrol-3-yl]-pyrrolo[2,3-b]pyridin-1-yl}-butyronitrile, and |
| 44 | 3-(2,4-dimethoxy-pyrimidin-5-yl)-4-(1-phenethyl-1H-pyrrolo[2,3-b]pyridine-3-yl)-pyrrole-2,5-dione. |

An example of the invention includes a compound of Formula (II) wherein the compound is selected from the group consisting of:

Compound 11

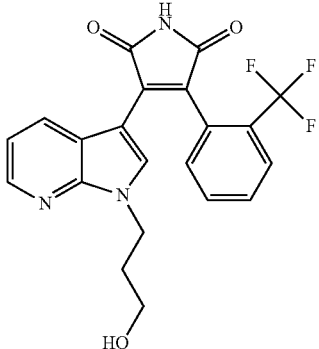

Compound 26

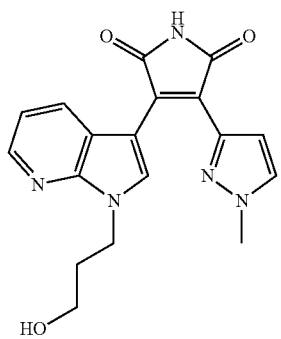

Compound 40

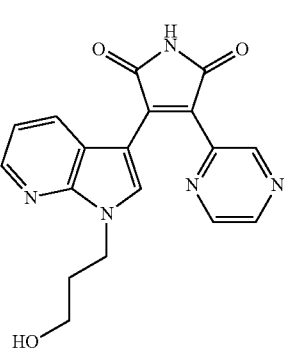

Compound 41

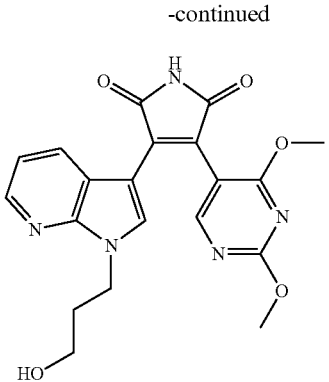

Compound 42

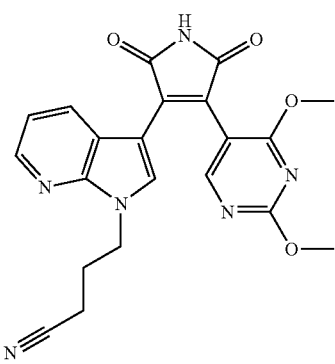

Compound 43

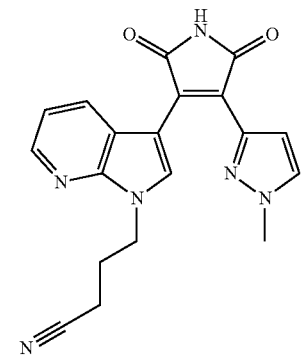

Compound 44

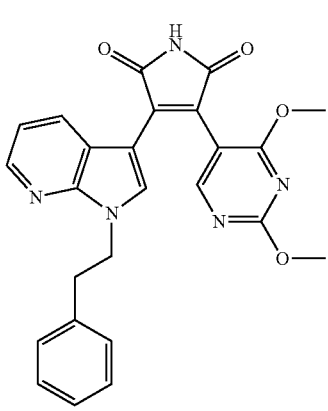

In one embodiment, the inhibitor of GSK-3B enzyme activity is a compound of the Formula (III):

Formula (III)

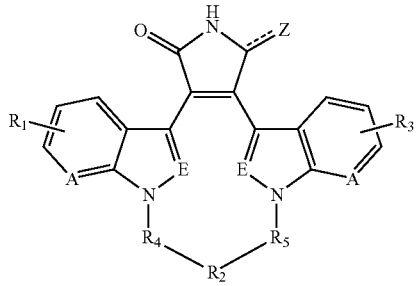

wherein

A and E are independently selected from the group consisting of a hydrogen substituted carbon atom and a nitrogen atom; wherein

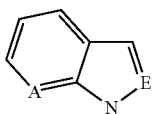

is independently selected from the group consisting of 1H-indole, 1H-pyrrolo[2,3-b]pyridine, 1H-pyrazolo[3,4-b]pyridine and 1H-indazole;

Z is selected from 0; alternatively, Z is selected from dihydro; wherein each hydrogen atom is attached by a single bond;

$R_4$ and $R_5$ are independently selected from $C_{1-8}$alkyl, $C_{2-8}$alkenyl and $C_{2-8}$alkynyl optionally substituted with oxo;

$R_2$ is selected from the group consisting of —$C_{1-8}$alkyl-, —$C_{2-8}$alkenyl-, —$C_{2-8}$alkynyl-, —O—($C_{1-8}$)alkyl-O—, —O—($C_{2-8}$)alkenyl-O—, —O—($C_{2-8}$)alkynyl-O—, —C(O)—($C_{1-8}$)alkyl-C(O)— (wherein any of the foregoing alkyl, alkenyl and alkynyl linking groups are straight carbon chains optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, —C(O)O—($C_{1-8}$)alkyl, —$C_{1-8}$alkyl-C(O)O—($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy, hydroxy($C_{1-8}$)alkyl and oxo; and, wherein any of the foregoing alkyl, alkenyl and alkynyl linking groups are optionally substituted with one to two substituents independently selected from the group consisting of heterocyclyl, aryl, heteroaryl, heterocyclyl($C_{1-8}$)alkyl, aryl($C_{1-8}$)alkyl, heteroaryl($C_{1-8}$)alkyl, spirocycloalkyl and spiroheterocyclyl (wherein any of the foregoing cycloalkyl, heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein any of the foregoing heterocyclyl substituents are optionally substituted with oxo)), cycloalkyl, heterocyclyl, aryl, heteroaryl (wherein cycloalkyl, heterocyclyl, aryl and heteroaryl are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein heterocyclyl is optionally substituted with oxo), —O—(CH$_2$)$_{1-6}$)$_{0-5}$—O—, —O—(CH$_2$)$_{1-6}$—O—(CH$_2$)$_{1-6}$—O—, —O—(CH$_2$)$_{1-6}$—O—(CH$_2$)$_{1-6}$—O—(CH$_2$)$_{1-6}$—O—, —(O—(CH$_2$)$_{1-6}$)$_{0-5}$—NR$_6$—, —O—(CH$_2$)$_{1-6}$—NR$_6$—(CH$_2$)$_{1-6}$—O—, —O—(CH$_2$)$_{1-6}$—O—(CH$_2$)$_{1-6}$—NR$_6$, —(O—(CH$_2$)$_{1-6}$)$_{0-5}$—S—, —O—(CH$_2$)$_{1-6}$—S—(CH$_2$)$_{1-6}$—O—, —O—(CH$_2$)$_{1-6}$—O—(CH$_2$)$_{1-6}$—S—, —NR$_6$—, —NR$_6$—NR$_7$—, —NR$_6$—(CH$_2$)$_{1-6}$—NR$_7$—, —NR$_6$—(CH$_2$)$_{1-6}$—NR$_7$—(CH$_2$)$_{1-6}$—NR$_8$—, —NR$_6$—C(O)—, —C(O)—NR$_6$—, —C(O)—(CH$_2$)$_{0-6}$—NR$_6$—(CH$_2$)$_{0-6}$—C(O)—, —NR$_6$—(CH$_2$)$_{0-6}$—C(O)—(CH$_2$)$_{1-6}$—C(O)—(CH$_2$)$_{0-6}$—NR$_7$—, —NR$_6$—C(O)—NR$_7$—, —NR$_6$—C(NR$_7$)—NR$_8$—, —O—(CH$_2$)$_{1-6}$—NR$_6$—(CH$_2$)$_{1-6}$—S—, —S—(CH$_2$)$_{1-6}$—NR$_6$—(CH$_2$)$_{1-6}$—O—, —S—(CH$_2$)$_{1-6}$—NR$_6$—(CH$_2$)$_{1-6}$—S—, —NR$_6$—(CH$_2$)$_{1-6}$—S—(CH$_2$)$_{1-6}$—NR$_7$— and —SO$_2$— (wherein $R_6$, $R_7$ and $R_8$ are independently selected from the group consisting of hydrogen, $C_{1-8}$alkyl, $C_{1-8}$alkoxy($C_{1-8}$)alkyl, carboxyl($C_{1-8}$)alkyl, amino($C_{1-8}$)alkyl (wherein amino is substituted with a substituent independently selected from the group consisting of hydrogen and $C_{1-4}$alkyl), hydroxy($C_{1-8}$)alkyl, heterocyclyl($C_{1-8}$)alkyl, aryl($C_{1-8}$)alkyl and heteroaryl($C_{1-8}$)alkyl (wherein the foregoing heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein heterocyclyl is optionally substituted with oxo)); with the proviso that, if A and E are selected from a hydrogen substituted carbon atom, then $R_2$ is selected from the group consisting of —$C_{2-8}$alkynyl-, —O—($C_{1-8}$)alkyl-O—, —O—($C_{2-8}$)alkenyl-O—, —O—($C_{2-8}$)alkynyl-O—, —C(O)—($C_{1-8}$)alkyl-C(O)— (wherein any of the foregoing alkyl, alkenyl and alkynyl linking groups are straight carbon chains optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, —C(O)O—($C_{1-8}$)alkyl, —$C_{1-8}$alkyl-C(O)O—($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy, hydroxy($C_{1-8}$)alkyl and oxo; and, wherein any of the foregoing alkyl, alkenyl and alkynyl linking groups are optionally substituted with one to two substituents independently selected from the group consisting of heterocyclyl, aryl, heteroaryl, heterocyclyl($C_{1-8}$)alkyl, aryl($C_{1-8}$)alkyl, heteroaryl($C_{1-8}$)alkyl, spirocycloalkyl and spiroheterocyclyl (wherein any of the foregoing cycloalkyl, heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein any of the foregoing heterocyclyl substituents are optionally substituted with oxo)), cycloalkyl (wherein cycloalkyl is optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl), —(O—($CH_2$)$_{1-6}$)$_{1-5}$—O—, —O—($CH_2$)$_{1-6}$—O—($CH_2$)$_{1-6}$—O—, —O—($CH_2$)$_{1-6}$—O—($CH_2$)$_{1-6}$—O—($CH_2$)$_{1-6}$—O—, —(O—($CH_2$)$_{1-6}$)$_{1-5}$—NR$_6$—, —O—($CH_2$)$_{1-6}$—NR$_6$—($CH_2$)$_{1-6}$—O—, —O—($CH_2$)$_{1-6}$—O—($CH_2$)$_{1-6}$—NR$_6$—, —(O—($CH_2$)$_{1-6}$)$_{0-5}$—S—, —O—($CH_2$)$_{1-6}$—S—($CH_2$)$_{1-6}$—O—, —O—($CH_2$)$_{1-6}$—O—($CH_2$)$_{1-6}$—S—, —NR$_6$—NR$_7$—, —NR$_6$—($CH_2$)$_{1-6}$—NR$_7$—, —NR$_6$—($CH_2$)$_{1-6}$—NR$_7$—($CH_2$)$_{1-6}$—NR$_8$—, —NR$_9$—C(O)—, —C(O)—NR$_9$—, —C(O)—($CH_2$)$_{0-6}$—NR$_6$—($CH_2$)$_{0-6}$—C(O)—, —NR$_6$—($CH_2$)$_{0-6}$—C(O)—($CH_2$)$_{1-6}$—C(O)—($CH_2$)$_{0-6}$—NR$_7$—, —NR$_6$—C(O)—NR$_7$—, —NR$_6$—C(NR$_7$)—NR$_8$—, —O—($CH_2$)$_{1-6}$—NR$_6$—($CH_2$)$_{1-6}$—S—, —S—($CH_2$)$_{1-6}$—NR$_6$—($CH_2$)$_{1-6}$—O—, —S—($CH_2$)$_{1-6}$—NR$_6$—($CH_2$)$_{1-6}$—S— and —NR$_6$—($CH_2$)$_{1-6}$—S—($CH_2$)$_{1-6}$—NR$_7$— (wherein $R_6$, $R_7$ and $R_8$ are independently selected from the group consisting of hydrogen, $C_{1-8}$alkyl, $C_{1-8}$alkoxy($C_{1-8}$)alkyl, carboxyl($C_{1-8}$)alkyl, amino($C_{1-8}$)alkyl (wherein amino is substituted with a substituent independently selected from the group consisting of hydrogen and $C_{1-4}$alkyl), hydroxy($C_{1-8}$)alkyl, heterocyclyl($C_{1-8}$)alkyl, aryl($C_{1-8}$)alkyl and heteroaryl($C_{1-8}$)alkyl (wherein the foregoing heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein heterocyclyl is optionally substituted with oxo); and, wherein $R_9$ is selected from the group consisting of $C_{1-8}$alkyl, $C_{1-8}$alkoxy($C_{1-8}$)alkyl, carboxyl($C_{1-8}$)alkyl, amino($C_{1-8}$)alkyl (wherein amino is substituted with a substituent independently selected from the group consisting of hydrogen and $C_{1-4}$alkyl), hydroxy($C_{1-8}$)alkyl, heterocyclyl($C_{1-8}$)alkyl, aryl($C_{1-8}$)alkyl and heteroaryl($C_{1-8}$)alkyl (wherein the foregoing heterocyclyl, aryl and heteroaryl substituents are optionally substituted with one to four substituents independently selected from the group consisting of $C_{1-8}$alkyl, $C_{1-8}$alkoxy, $C_{1-8}$alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl; and, wherein heterocyclyl is optionally substituted with oxo)); and, $R_1$ and $R_3$ are independently selected from the group consisting of hydrogen, $C_{1-8}$alkyl, $C_{2-8}$alkenyl, $C_{2-8}$alkynyl (wherein alkyl, alkenyl and alkynyl are optionally substituted with a substituent selected from the group consisting of $C_{1-8}$alkoxy, alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), (halo)$_{1-3}$, (halo)$_{1-3}$($C_{1-8}$)alkyl, (halo)$_{1-3}$($C_{1-8}$)alkoxy, hydroxy, hydroxy($C_{1-8}$)alkyl and oxo), $C_{1-8}$alkoxy, $C_{1-8}$alkoxycarbonyl, (halo)$_{1-3}$($C_{1-8}$)alkoxy, $C_{1-8}$alkylthio, aryl, heteroaryl (wherein aryl and heteroaryl are optionally substituted with a substituent selected from the group consisting of $C_{1-8}$alkyl, $C_{1-8}$alkoxy, alkoxy($C_{1-8}$)alkyl, carboxyl, carboxyl($C_{1-8}$)alkyl, amino (substituted with a substituent independently selected from the group consisting of hydrogen and $C_{1-4}$alkyl), amino($C_{1-8}$)alkyl (wherein amino is substituted with a substituent independently selected from the group consisting of hydrogen and $C_{1-4}$alkyl), halogen, (halo)$_{1-3}$($C_{1-8}$)alkyl, (halo)$_{1-3}$($C_{1-8}$)alkoxy, hydroxy and hydroxy($C_{1-8}$)alkyl), amino (substituted with a substituent independently selected from the group consisting of hydrogen and $C_{1-4}$alkyl), cyano, halogen, hydroxy and nitro; and pharmaceutically acceptable salts thereof.

In one embodiment, a compound of Formula (III) is a compound selected from the group consisting of:

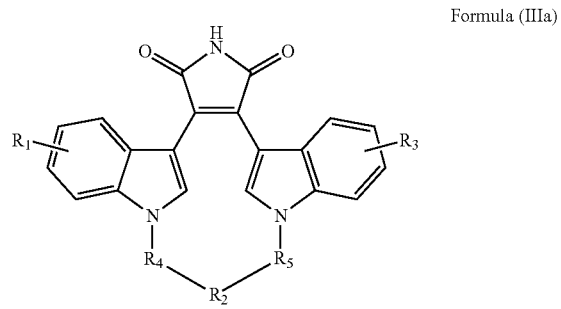

Formula (IIIa)

Formula (IIIb)
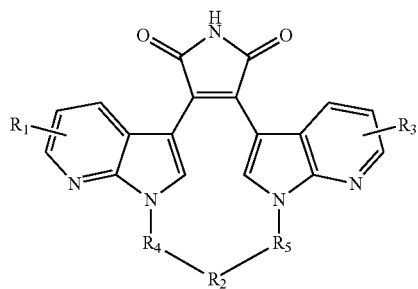
Formula (IIIc)
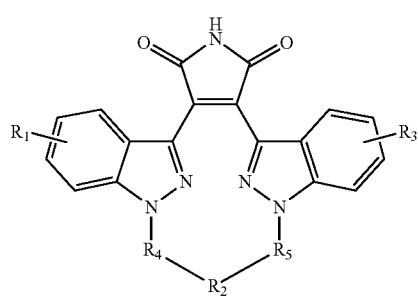
Formula (IIId)
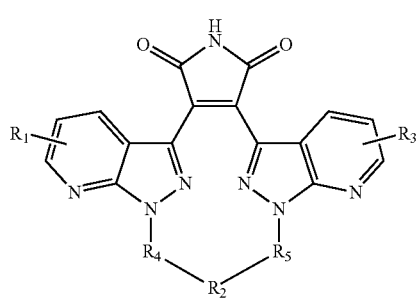
Formula (IIIe)
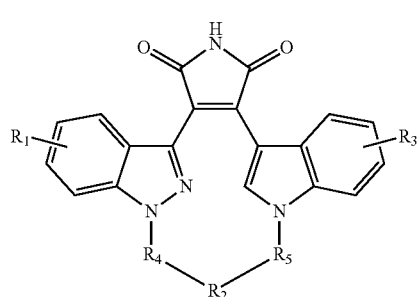
Formula (IIIf)
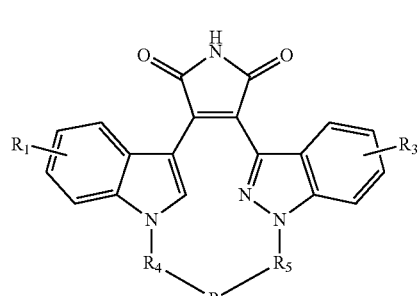
Formula (IIIg)
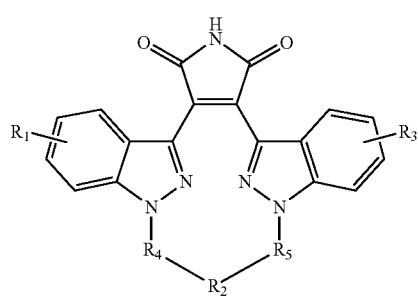
Formula (IIIh)
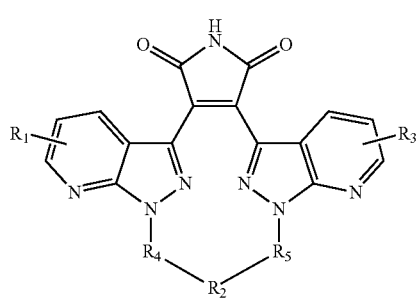
Formula (IIIi)
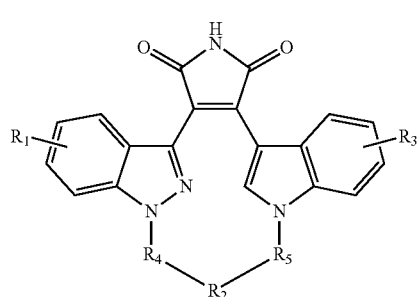
Formula (IIIj)
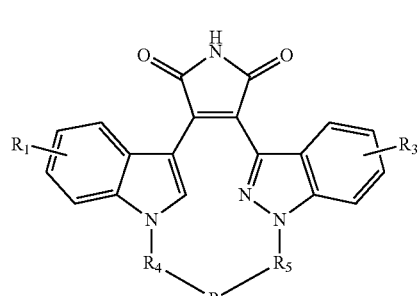
Formula (IIIk)
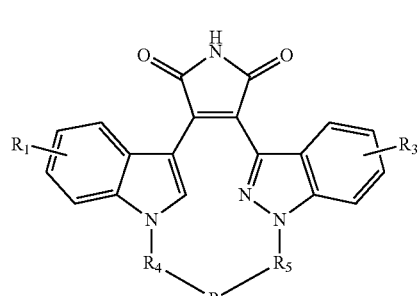

-continued

Formula (IIIi)

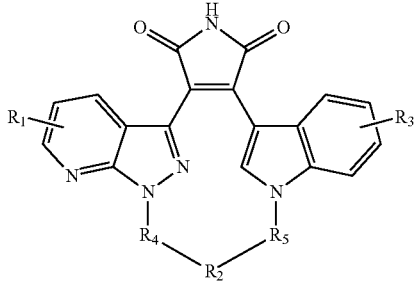

Formula (IIIm)

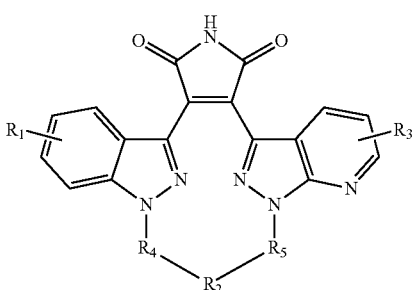

Formula (IIIn)

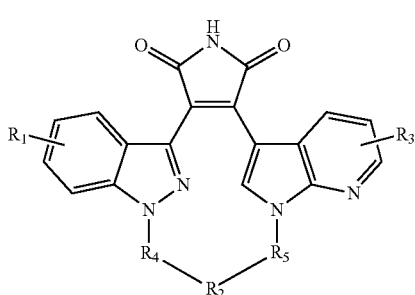

wherein all other variables are as previously defined; and, pharmaceutically acceptable salts thereof.

In one embodiment, a compound of Formula (III) is a compound selected from the group consisting of:

Formula (IIIa)

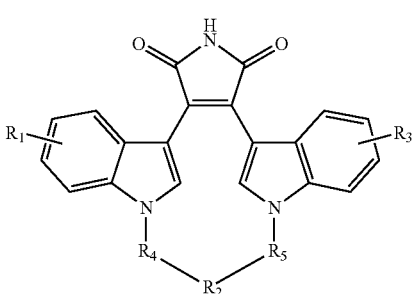

Formula (IIIb)

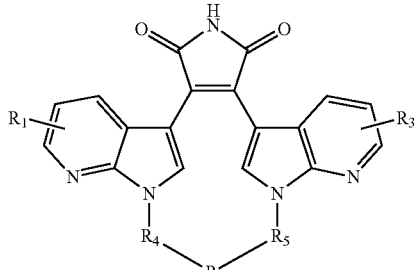

Formula (IIIf)

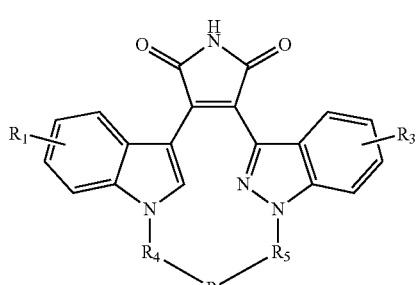

Formula (IIIi)

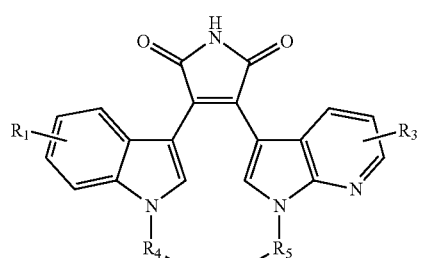

Formula (IIIj)

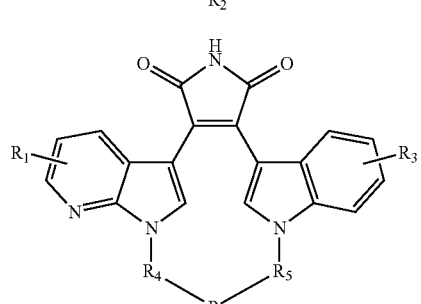

wherein all other variables are as previously defined; and, pharmaceutically acceptable salts thereof.

Compounds of Formula (III) are disclosed in commonly assigned U.S. Pat. No. 6,828,327, the complete disclosure of which is herein incorporated by reference.

An example of the invention includes a compound of Formula (III) wherein the compound is selected from the group consisting of:

| Compound | Name |
|---|---|
| 1 | 6,7,9,10,12,13,15,16-octahydro-23H-5,26: 17,22-dimetheno-5H-dipyrido[2,3-k: 3',2'-q]pyrrolo[3,4-n][1,4,7,10,19]trioxadiazacyclohenicosine-23,25(24H)-dione, |
| 2 | 10,11,13,14,16,17,19,20,22,23-decahydro-9,4: 24,29-dimetheno-1H-dipyrido[2,3-n: 3',2'-t]pyrrolo[3,4-q][1,4,7,10,13,22]tetraoxadiazacyclotetracosine-1,3(2H)-dione, |

| Compound | Name |
|---|---|
| 3 | 10,11,13,14,16,17,19,20,22,23,25,26-dodecahydro-9,4: 27,32-dimetheno-1H-dipyrido[2,3-q: 3',2'-w]pyrrolo[3,4-t][1,4,7,10,13,16,25]pentaoxadiazacycloheptacosine-1,3(2H)-dione, |
| 4 | 6,7,9,10,12,13-hexahydro-20H-5,23: 14,19-dimetheno-5H-dibenzo[h,n]pyrrolo[3,4-k][1,4,7,16]dioxadiazacyclooctadecine-20,22(21H)-dione, |
| 5 | 6,7,9,10,12,13,15,16-octahydro-23H-5,26: 17,22-dimetheno-5H-dibenzo[k,q]pyrrolo[3,4-n][1,4,7,10,19]trioxadiazacycloheneicosine-23,25(24H)-dione, |
| 6 | 10,11,13,14,16,17,19,20,22,23-decahydro-9,4: 24,29-dimetheno-1H-dibenzo[n,t]pyrrolo[3,4-q][1,4,7,10,13,22]tetraoxadiazacyclotetracosine-1,3(2H)-dione, |
| 7 | 10,11,13,14,16,17,19,20,22,23,25,26-dodecahydro-9,4: 27,32-dimetheno-1H-dibenzo[q,w]pyrrolo[3,4-t][1,4,7,10,13,16,25]pentaoxadiazacycloheptacosine-1,3(2H)-dione, |
| 8 | 12-hydro-6H,19H-5,22: 13,18: 7,11-trimethenopyrido[2,3-j]pyrrolo[3,4-m][1,9]benzodiazacycloheptadecine-19,21(20H)-dione, |
| 9 | 12-hydro-6H,19H-5,22: 13,18-dimetheno-7,11-nitrilopyrido[2,3-j]pyrrolo[3,4-m][1,9]benzodiazacycloheptadecine-19,21(20H)-dione, |
| 10 | 6,7,9,10,12,13-hexahydro-20H-5,23: 14,19-dimetheno-5H-pyrido[2,3-k]pyrrolo[3,4-n][4,7,1,10]benzodioxadiazacyclooctadecine-20,22(21H)-dione, |
| 11 | 6,7,9,10,12,13,15,16-octahydro-23H-5,26: 17,22-dimetheno-5H-pyrido[2,3-n]pyrrolo[3,4-q][4,7,10,1,13]benzotrioxadiazacycloheneicosine-23,25(24H)-dione, |
| 12 | 11-ethyl-6,7,10,11,12,13,15,16-octahydro-23H-5,26: 17,22-dimetheno-5H,9H-dibenzo[k,q]pyrrolo[3,4-n][1,7,4,10,19]dioxatriazacycloheneicosine-23,25(24H)-dione, |
| 13 | 6,7,10,11,12,13,15,16-octahydro-11-methyl-23H-5,26: 17,22-dimetheno-5H,9H-dibenzo[k,q]pyrrolo[3,4-n][1,7,4,10,19]dioxatriazacycloheneicosine-23,25(24H)-dione, |
| 14 | 6,7,10,11,12,13,15,16-octahydro-11-(1-methylethyl)-23H-5,26: 17,22-dimetheno-5H,9H-dibenzo[k,q]pyrrolo[3,4-n][1,7,4,10,19]dioxatriazacycloheneicosine-23,25(24H)-dione, |
| 15 | 7,8,9,10,11,12,13,14,15,16-decahydro-8,11,14-trimethyl-6H,23H-5,26: 17,22-dimethenodibenzo[n,t]pyrrolo[3,4-q][1,4,7,10,13]pentaazacycloheneicosine-23,25(24H)-dione, |
| 16 | 6,7,10,11,12,13,15,16-octahydro-11-methyl-23H-5,26-metheno-17,22-nitrilo-5H,9H-dibenzo[k,q]pyrrolo[3,4-n][1,7,4,10,19]dioxatriazacycloheneicosine-23,25(24H)-dione, |
| 17 | 11-ethyl-6,7,10,11,12,13,15,16-octahydro-23H-5,26-metheno-17,22-nitrilo-5H,9H-dibenzo[k,q]pyrrolo[3,4-n][1,7,4,10,19]dioxatriazacycloheneicosine-23,25(24H)-dione, |
| 18 | 11-ethyl-6,7,10,11,12,13,15,16-octahydro-23H-5,26: 17,22-dimetheno-5H,9H-dipyrido[2,3-k: 3',2'-q]pyrrolo[3,4-n][1,7,4,10,19]dioxatriazacycloheneicosine-23,25(24H)-dione, |
| 19 | 6,7,9,10,12,13,15,16-octahydro-23H-5,26: 17,22-dimetheno-5H-dipyrido[2,3-k: 3',2'-q]pyrrolo[3,4-n][1,7,4,10,19]dioxathiadiazacycloheneicosine-23,25(24H)-dione, |
| 20 | 7,8,9,10,11,12,13,14,15,16-decahydro-(6H,23H-5,26: 17,22-dimethenodipyrido[2,3-n: 3',2'-t]pyrrolo[3,4-q][1,7,13]triazacycloheneicosine-23,25(24H)-dione, |
| 21 | 11-ethyl-7,8,9,10,11,12,13,14,15,16-decahydro-6H,23H-5,26: 17,22-dimethenodipyrido[2,3-n: 3',2'-t]pyrrolo[3,4-q][1,7,13]triazacycloheneicosine-23,25(24H)-dione, |
| 22 | 6,7,8,9,10,11,12,13,14,15-decahydro-22H-5,25: 16,21-dimetheno-5H-dipyrido[2,3-m: 3',2'-s]pyrrolo[3,4-p][1,6,12]triazacycloeicosine-22,24(23H)-dione, |
| 23 | 10-ethyl-6,7,8,9,10,11,12,13,14,15-decahydro-22H-5,25: 16,21-dimetrieno-5H-dipyrido[2,3-m: 3',2'-s]pyrrolo[3,4-p][1,6,12]triazacycloeicosine-22,24(23H)-dione, |
| 24 | 7,8,9,15,16,17,18-heptahydro-6H,25H-5,28: 19,24-dimetheno-10,14-nitrilodipyrido[2,3-b: 3',2'-h]pyrrolo[3,4-e][1,10]diazacyclotricosine-25,27(26H)-dione, |
| 25 | 7,8,9,10,11,13,14,15,16-nonahydro-6H,23H-5,26: 17,22-dimetrienodipyrido[2,3-b: 3',2'-h]pyrrolo[3,4-e][1,10]diazacycloheneicosine-12,23,25(24H)-trione, |
| 26 | 7,8,9,11,12,13,14-heptahydro-6H,21H-5,24: 15,20-dimethenodipyrido[2,3-b: 3',2'-h]pyrrolo[3,4-e][1,10]diazacyclononadecine-10,21,23(22H)-trione, |
| 27 | 6,7,8,9,10,11,12,13,14,15-decahydro-7,14-dihydroxy-(7R,14R)-22H-5,25: 16,21-dimetheno-5H-dipyrido[2,3-b: 3',2'-h]pyrrolo[3,4-e][1,10]diazacycloeicosine-22,24(23H)-dione, |
| 28 | 6,7,9,10,12,13-hexahydro-20H-5,23: 14,19-dimetheno-5H-dipyrido[2,3-h: 3',2'-n]pyrrolo[3,4-k][1,4,7,16]dioxadiazacyclooctadecine-20,22(21H)-dione, |

| Compound | Name |
|---|---|
| 29 | 6,7,10,11,12,13,15,16-octahydro-11-(2-methoxyethyl)-23H-5,26-metheno-17,22-nitrilo-5H,9H-dibenzo[k,q]pyrrolo[3,4-n][1,7,4,10,19]dioxatriazacycloheneicosine-23,25(24H)-dione, |
| 30 | 6,7,10,11,12,13,15,16-octahydro-11-(2-hydroxyethyl)-23H-5,26: 17,22-dimetheno-5H,9H-dibenzo[k,q]pyrrolo[3,4-n][1,7,4,10,19]dioxatriazacycloheneicosine-23,25(24H)-dione, and |
| 31 | 6,7,9,10,12,13,14,15,16,17-decahydro-14-methyl-24H-5,27: 18,23-dimetheno-5H-dibenzo[l,r]pyrrolo[3,4-o][1,4,7,11,20]dioxatriazacyclodocosine-24,26(25H)-dione. |

An example of the invention includes a compound of Formula (III) wherein the compound is selected from the group consisting of:

Compound 1

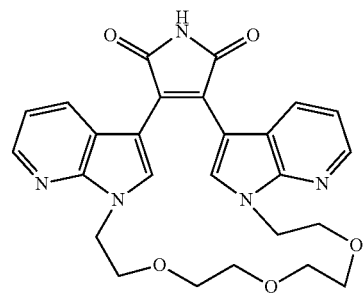

Compound 2

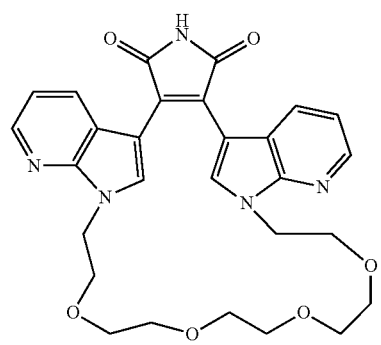

Compound 5

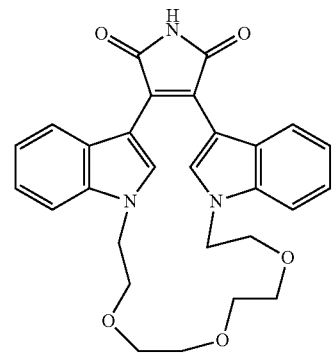

Compound 6

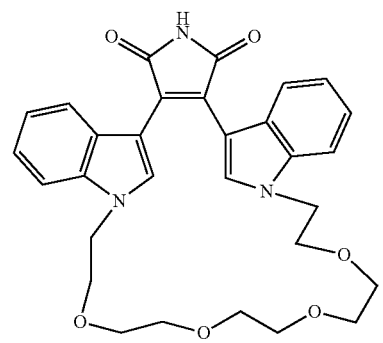

Other examples of the invention include a compound selected from the group consisting of:

| Compound | Name |
|---|---|
| 1a | To be provided |
| 2a | 3-[1-[3-[(2-hydroxyethyl)methylamino]propyl]-1H-indazol-3-yl]-4-[1-(3-pyridinyl)-1H-indol-3-yl]-1H-pyrrole-2,5-dione, |
| 3a | 3,5-dichloro-N-[3-chloro-4-[(3,4,12,12a-tetrahydro-1H-[1,4]thiazino[3,4-c][1,4]benzodiazepin-11(6H)-yl)carbonyl]phenyl]-benzamide, |
| 4a | 3-[1-(2-hydroxy-ethyl)-1H-indol-3-yl]-4-(1-pyridin-3-yl-1H-indol-3-yl)-pyrrole-2,5-dione, |
| 5a | 3-(2-methoxy-phenyl)-4-(1-pyridin-3-yl-1H-indol-3-yl)-pyrrole-2,5-dione, |

| Compound | Name |
| --- | --- |
| 6a | 6-[[2-[[4-(2,4-dichlorophenyl)-5-(4-methyl-1H-imidazol-2-yl)-2-pyrimidinyl]amino]ethyl]amino]-3-pyridinecarbonitrile, |
| 7a | 3-(5-chloro-1-methyl-1H-indol-3-yl)-4-[1-(3-imidazol-1-yl-propyl)-1H-indazol-3-yl]-pyrrole-2,5-dione, |
| 8a | 3-(5-chloro-1-methyl-1H-indol-3-yl)-4-[1-(3-[1,2,3 ]triazol-1-yl-propyl)-1H-indazol-3-yl]-pyrrole-2,5-dione, |
| 9a | 3-[1-(3-hydroxy-propyl)-1H-pyrrolo[2,3-b]pyridin-3-yl]-4-(1-methyl-1H-pyrazol-3-yl)-pyrrole-2,5-dione, |
| 10a | To be provided |
| 11a | 3-[1-(3-hydroxy-3-methyl-butyl)-1H-indazol-3-yl]-4-(1-pyridin-3-yl-1H-indol-3-yl)-pyrrole-2,5-dione, |
| 12a | 3-[1-(2-hydroxy-ethyl)-1H-indazol-3-yl]-4-(1-pyrimidin-5-yl-1H-indol-3-yl)-pyrrole-2,5-dione, |
| 13a | 3-[1-(2-hydroxy-ethyl)-1H-indol-3-yl]-4-(1-pyrimidin-5-yl-1H-indol-3-yl)-pyrrole-2,5-dione, |
| 14a | (11Z)-8,9,10,13,14,15-hexahydro-2,6: 17,21-di(metheno)pyrrolo[3,4-h][1,15,7] dioxazacyclotricosine-22,24(1H,23H)-dione, |
| 15a | 3-(5-chloro-1-pyridin-3-yl-1H-indol-3-yl)-4-[1-(3-hydroxy-propyl)-1H-indazol-3-yl]-pyrrole-2,5-dione, |
| 16a | 3-(2-methoxy-phenyl)-4-[1-(3-methoxy-propyl)-1H-pyrrolo[3,2-c]pyridin-3-yl]-pyrrole-2,5-dione, |
| 17a | 3-[1-(3-hydroxy-propyl)-1H-indazol-3-yl]-4-[1-(tetrahydro-pyran-4-yl)-1H-indol-3-yl]-pyrrole-2,5-dione, |
| 18a | 2-{3-[4-(5-chloro-1-methyl-1H-indol-3-yl)-2,5-dioxo-2,5-dihydro-1H-pyrrol-3-yl]-indazol-1-yl}-N-(2-hydroxy-ethyl)-acetamide, |
| 19a | 4-(3-chloro-phenyl)-6-(3-dimethylamino-propyl)-5,6-dihydro-4H-2,4,6-triaza-cyclopenta[c]fluorine-1,3-dione, |
| 20a | 14-ethyl-6,7,9,10,13,14,15,16-octahydro-12H,23H-5,26: 17,22-dimethenodibenzo[k,q]pyrrolo[3,4-n][1,4,7,10,19]dioxatriazacycloheneicosine-23,25(24H)-dione, |
| 21a | 14-benzyl-6,7,9,10,13,14,15,16-octahydro-12H,23H-5,26: 17,22-di(metheno)dibenzo[k,q]pyrrolo[3,4-n][1,4,7,10,19]dioxatriazacyclohenicosine-23,25(24H)-dione, |
| 22a | 3-(1-{2-[2-(2-hydroxy-ethoxy)-ethoxy]-ethyl}-1H-indol-3-yl)-4-[1-(2-hydroxy-ethyl)-1H-indol-3-yl]-pyrrole-2,5-dione, |
| 23a | 6,7,8,9,10,11,12,13-octahydro-8,11-dimethyl-5,23: 14,19-dimetheno-20H-dibenzo[k,q]pyrrolo[3,4-n][1,4,7,10]tetraazacyclooctadecine-20,22(21H)-dione, |
| 24a | 7,8,9,10,12,13,16,17,18,19-decahydro-8,17-dimethyl-15H,26H-5,29: 20,25-dimetheno-6H-dibenzo[k,q]pyrrolo[3,4-n][1,4,7,10,19,22]dioxatetraazacyclotetracosine-26,28(27H)-dione, |
| 25a | 14-(2-furylmethyl)-6,7,9,10,13,14,15,16-octahydro-12H,23H-5,26: 17,22-di(metheno)dibenzo[k,q]pyrrolo[3,4-n][1,4,7,10,19]dioxatriazacyclohenicosine-23,25(24H)-dione, |
| 26a | 14-(2-thienylmethyl)-6,7,9,10,13,14,15,16-octahydro-12H,23H-5,26: 17,22-di(metheno)dibenzo[k,q]pyrrolo[3,4-n][1,4,7,10,19]dioxatriazacyclohenicosine-23,25(24H)-dione, |
| 27a | 14-(1-naphthylmethyl)-6,7,9,10,13,14,15,16-octahydro-12H,23H-5,26: 17,22-di(metheno)dibenzo[k,q]pyrrolo[3,4-n][1,4,7,10,19]dioxatriazacyclohenicosine-23,25(24H)-dione, |
| 28a | 14-(pyridin-4-ylmethyl)-6,7,9,10,13,14,15,16-octahydro-12H,23H-5,26: 17,22-di(metheno)dibenzo[k,q]pyrrolo[3,4-n][1,4,7,10,19]dioxatriazacyclohenicosine-23,25(24H)-dione, |
| 29a | 3-[1-(2-{2-[2-(1,2,3,4-tetrahydro-naphthalen-1-ylamino)-ethoxy]-ethoxy}-ethyl)-1H-indol-3-yl]-4-{1-[2-(1,2,3,4-tetrahydro-naphthalen-1-ylamino)-ethyl]-1H-indol-3-yl}-pyrrole-2,5-dione, |
| 30a | 3-[1-(3-dimethylamino-phenyl)-1H-indol-3-yl]-4-[1-(2-hydroxy-ethyl)-1H-indazol-3-yl]-pyrrole-2,5-dione, |
| 31a | 3-[5-chloro-1-(6-dimethylamino-pyridin-3-yl)-1H-indol-3-yl]-4-[1-(2-hydroxy-ethyl)-1H-indazol-3-yl]-pyrrole-2,5-dione, and |
| 32a | 5-(5-chloro-3-{4-[1-(2-hydroxy-ethyl)-1H-indazol-3-yl]-2,5-dioxo-2,5-dihydro-1H-pyrrol-3-yl}-indol-1-yl)-nicotinic acid methyl ester. |

Other examples of the invention include a compound selected from the group consisting of:
Compound 1a
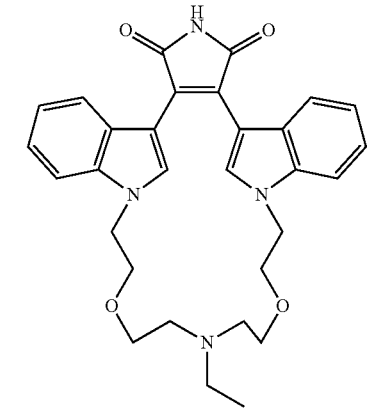
Compound 2a
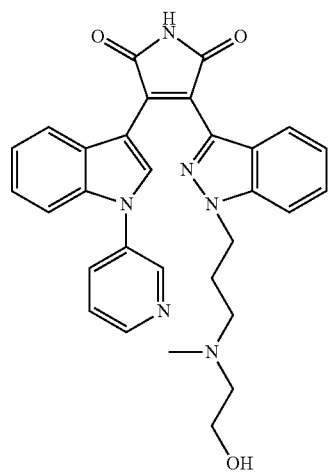
Compound 3a
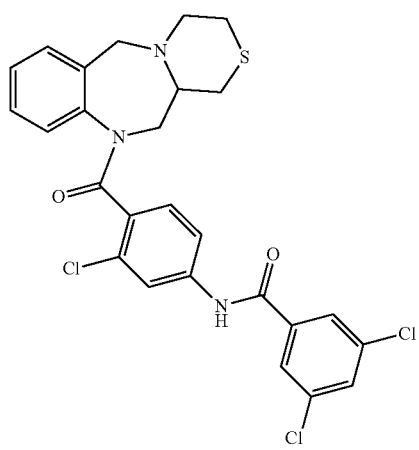
Compound 4a
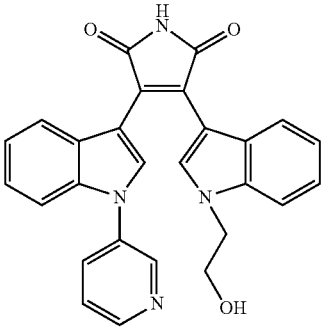
Compound 5a
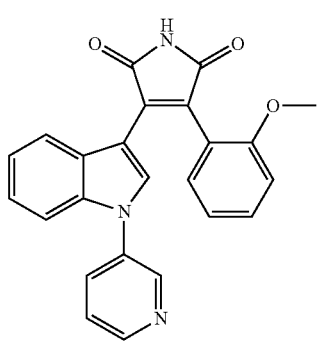
Compound 6a
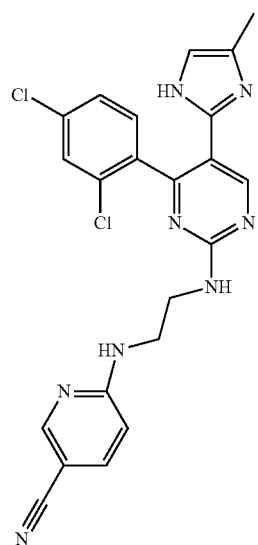
Compound 7a
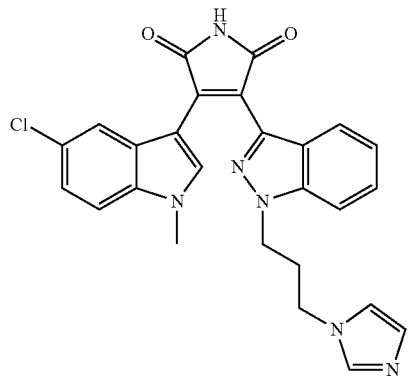

-continued

Compound 8a

Compound 9a

Compound 10a

Compound 11a

-continued

Compound 12a

Compound 13a

Compound 14a

Compound 15a

-continued
Compound 16a
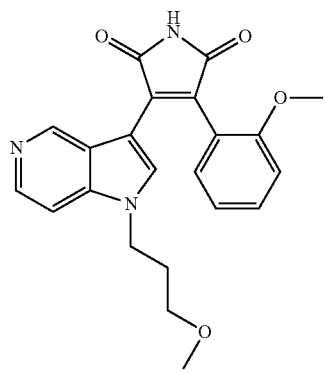
Compound 17a
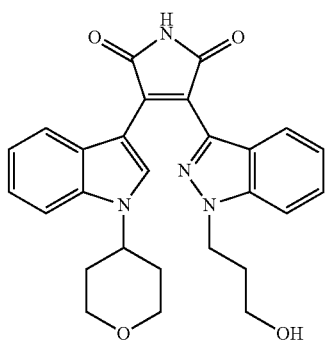
Compound 18a
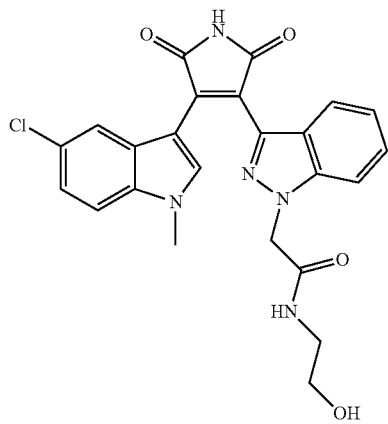
Compound 19a
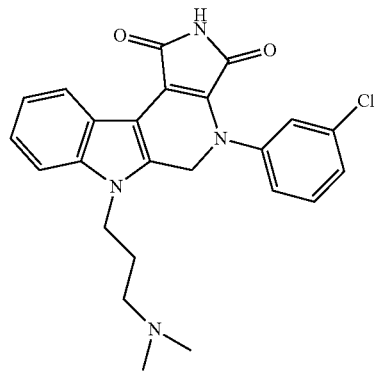
Compound 20a
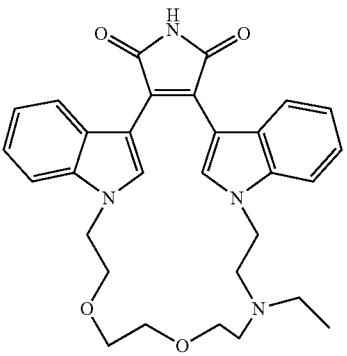
Compound 21a
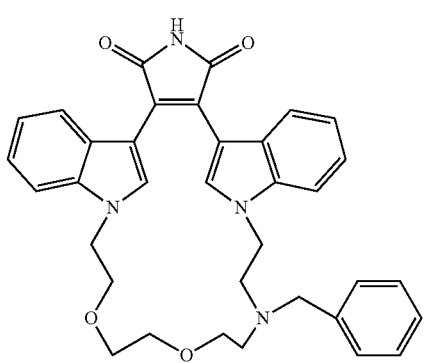
Compound 22a
Compound 23a Compound 24a
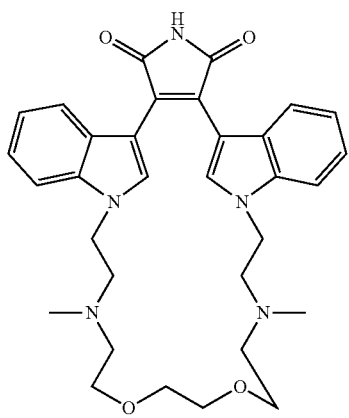
Compound 28a
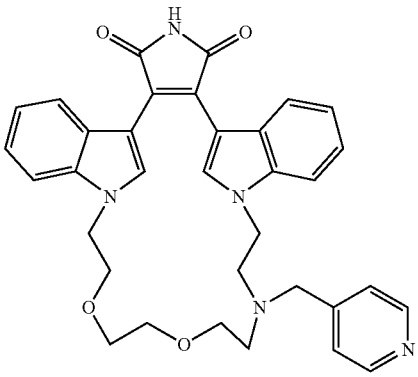
Compound 25a
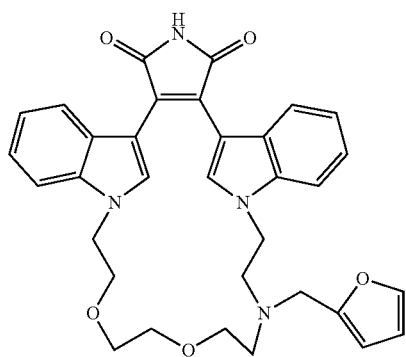
Compound 29a
Compound 26a
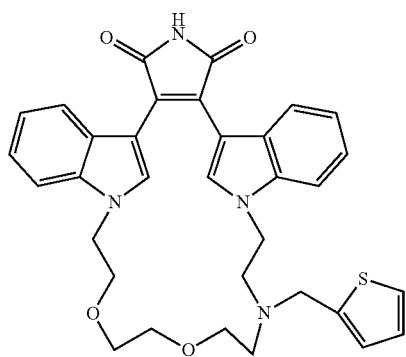
Compound 27a
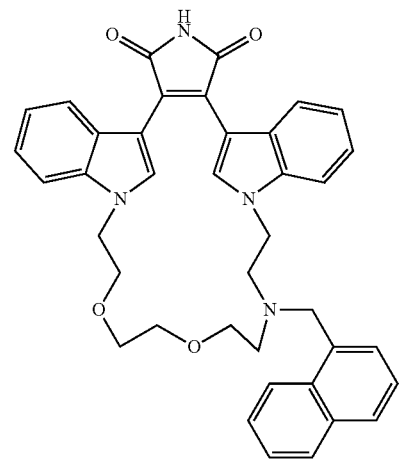
Compound 30a
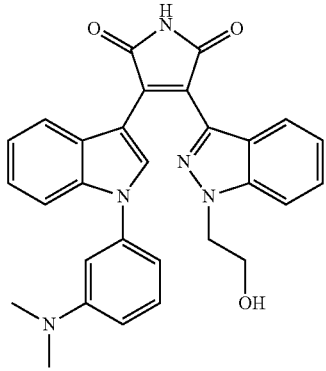

-continued

Compound 31a

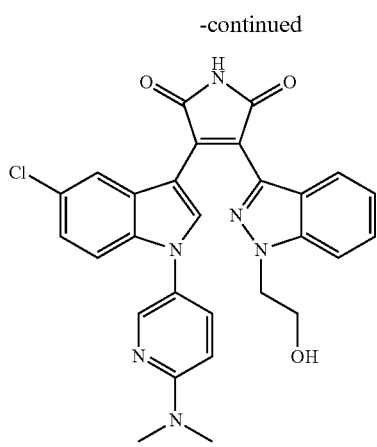

Compound 32a

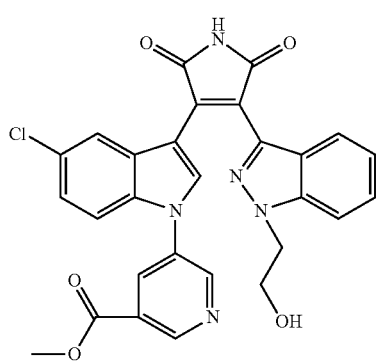

Cells Suitable for Treatment According to the Methods of the Present Invention

Pluripotent cells, suitable for use in the present invention express at least one of the following pluripotency markers selected from the group consisting of: ABCG2, cripto, FoxD3, Connexin43, Connexin45, Oct4, SOX-2, Nanog, hTERT, UTF-1, ZFP42, SSEA-3, SSEA-4, Tra1-60, and Tra1-81.

In one embodiment, the pluripotent cells are embryonic stem cells. In an alternate embodiment, the pluripotent cells are cells expressing pluripotency markers derived from embryonic stem cells. In one embodiment, the embryonic stem cells are human.

Isolation, Expansion and Culture of Human Embryonic Stem Cells

Characterization of Human Embryonic Stem Cells:

Human embryonic stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of human embryonic stem cells in vitro results in the loss of SSEA-4, Tra-1-60, and Tra-1-81 expression (if present) and increased expression of SSEA-1. Undifferentiated human embryonic stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated human embryonic stem cells is a potential to differentiate into cells of all three germinal layers: endoderm, mesoderm, and ectoderm tissues. Pluripotency of human embryonic stem cells can be confirmed, for example, by injecting cells into SCID mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated human embryonic stem cell lines may be karyotyped using a standard G-banding technique and compared to published karyotypes of the corresponding primate species. It is desirable to obtain cells that have a "normal karyotype", which means that the cells are euploid, wherein all human chromosomes are present and not noticeably altered.

Sources of Human Embryonic Stem Cells:

Types of human embryonic stem cells that may be used include established lines of human embryonic cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines H1, H7, and H9 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.).

In one embodiment, Human embryonic stem cells are prepared as described by Thomson et al. (U.S. Pat. No. 5,843,780; Science 282:1145, 1998; Curr. Top. Dev. Biol. 38:133 ff., 1998; Proc. Natl. Acad. Sci. U.S.A. 92:7844, 1995).

Culture of Human Embryonic Stem Cells:

In one embodiment, human embryonic stem cells are cultured in a culture system that is essentially free of feeder cells, but nonetheless supports proliferation of human embryonic stem cells without undergoing substantial differentiation. The growth of human embryonic stem cells in feeder-free culture without differentiation is supported using a medium conditioned by culturing previously with another cell type. Alternatively, the growth of human embryonic stem cells in feeder-free culture without differentiation is supported using a chemically defined medium.

In an alternate embodiment, human embryonic stem cells are initially cultured layer of feeder cells that support the human embryonic stem cells in various ways. The human embryonic are then transferred to a culture system that is essentially free of feeder cells, but nonetheless supports proliferation of human embryonic stem cells without undergoing substantial differentiation.

Examples of conditioned media suitable for use in the present invention are disclosed in US20020072117, U.S. Pat. No. 6,642,048, WO2005014799, and Xu et al (Stem Cells 22: 972-980, 2004).

An example of a chemically defined medium suitable for use in the present invention may be found in US20070010011.

Suitable culture media may be made from the following components, such as, for example, Dulbecco's modified Eagle's medium (DMEM), Gibco #11965-092; Knockout Dulbecco's modified Eagle's medium (KO DMEM), Gibco

10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029.

In one embodiment, the human embryonic stem cells are plated onto a suitable culture substrate that is treated prior to treatment according to the methods of the present invention. In one embodiment, the treatment is an extracellular matrix component, such as, for example, those derived from basement membrane or that may form part of adhesion molecule receptor-ligand couplings. In one embodiment, a the suitable culture substrate is Matrigel® (Becton Dickenson). Matrigel® is a soluble preparation from Engelbreth-Holm-Swarm tumor cells that gels at room temperature to form a reconstituted basement membrane.

Other extracellular matrix components and component mixtures are suitable as an alternative. This may include laminin, fibronectin, proteoglycan, entactin, heparan sulfate, and the like, alone or in various combinations.

The human embryonic stem cells are plated onto the substrate in a suitable distribution and in the presence of a medium that promotes cell survival, propagation, and retention of the desirable characteristics. All these characteristics benefit from careful attention to the seeding distribution and can readily be determined by one of skill in the art.

Isolation, Expansion and Culture of Cells Expressing Pluripotency Markers that are Derived from Human Embryonic Stem Cells In one embodiment, cells expressing pluripotency markers are derived from human embryonic stem cells by a method comprising the steps of:
a. Culturing human embryonic stem cells,
b. Differentiating the human embryonic stem cells into cells expressing markers characteristic of definitive endoderm cells, and
c. Removing the cells, and subsequently culturing them under hypoxic conditions, on a tissue culture substrate that is not pre-treated with a protein or an extracellular matrix prior to culturing the cells.

In one embodiment, cells expressing pluripotency markers are derived from human embryonic stem cells by a method comprising the steps of:
a. Culturing human embryonic stem cells, and
b. Removing the cells, and subsequently culturing them under hypoxic conditions, on a tissue culture substrate that is not pre-treated with a protein or an extracellular matrix.

Cell Culture Under Hypoxic Conditions on a Tissue Culture Substrate that is not Pre-Treated with a Protein or an Extracellular Matrix In one embodiment, the cells are cultured under hypoxic conditions, on a tissue culture substrate that is not coated with an extracellular matrix for about 1 to about 20 days. In an alternate embodiment, the cells are cultured under hypoxic conditions, on a tissue culture substrate that is not coated with an extracellular matrix for about 5 to about 20 days. In an alternate embodiment, the cells are cultured under hypoxic conditions, on a tissue culture substrate that is not coated with an extracellular matrix for about 15 days.

In one embodiment, the hypoxic condition is about 1% $O_2$ to about 20% $O_2$. In an alternate embodiment, the hypoxic condition is about 2% $O_2$ to about 10% $O_2$. In an alternate embodiment, the hypoxic condition is about 3% $O_2$.

The cells may be cultured, under hypoxic conditions on a tissue culture substrate that is not pre-treated with a protein or an extracellular matrix, in medium containing serum, activin A, and a Wnt ligand. Alternatively, the medium may also contain IGF-1.

The culture medium may have a serum concentration in the range of about 2% to about 5%. In an alternate embodiment, the serum concentration may be about 2%.

Activin A may be used at a concentration from about 1 pg/ml to about 100 µg/ml. In an alternate embodiment, the concentration may be about 1 pg/ml to about 1 µg/ml. In another alternate embodiment, the concentration may be about 1 pg/ml to about 100 ng/ml. In another alternate embodiment, the concentration may be about 50 ng/ml to about 100 ng/ml. In another alternate embodiment, the concentration may be about 100 ng/ml.

The Wnt ligand may be selected from the group consisting of Wnt-1, Wnt-3a, Wnt-5a and Wnt-7a. In one embodiment, the Wnt ligand is Wnt-1. In an alternate embodiment, the Wnt ligand is Wnt-3a.

The Wnt ligand may be used at a concentration of about 1 ng/ml to about 1000 ng/ml. In an alternate embodiment, the Wnt ligand may be used at a concentration of about 10 ng/ml to about 100 ng/ml. In one embodiment, the concentration of the Wnt ligand is about 20 ng/ml.

IGF-1 may be used at a concentration of about 1 ng/ml to about 100 ng/ml. In an alternate embodiment, the IGF-1 may be used at a concentration of about 10 ng/ml to about 100 ng/ml. In one embodiment, the concentration of IGF-1 is about 50 ng/ml.

The cells expressing pluripotency markers derived by the methods of the present invention are capable of expansion in culture under hypoxic conditions, on tissue culture substrate that is not pre-treated with a protein or an extracellular matrix.

The cells expressing pluripotency markers derived by the methods of the present invention express at least one of the following pluripotency markers selected from the group consisting of: ABCG2, cripto, FoxD3, Connexin43, Connexin45, Oct4, SOX-2, Nanog, hTERT, UTF-1, ZFP42, SSEA-3, SSEA-4, Tra1-60, and Tra1-81.

Further Differentiation of Cells Expressing Markers Characteristic of the Definitive Endoderm Lineage Cells expressing markers characteristic of the definitive endoderm lineage may be differentiated into cells expressing markers characteristic of the pancreatic endoderm lineage by any method in the art.

For example, cells expressing markers characteristic of the definitive endoderm lineage may be differentiated into cells expressing markers characteristic of the pancreatic endoderm lineage according to the methods disclosed in D'Amour et al, Nature Biotechnology 24, 1392-1401 (2006).

For example, cells expressing markers characteristic of the definitive endoderm lineage are further differentiated into cells expressing markers characteristic of the pancreatic endoderm lineage, by treating the cells expressing markers characteristic of the definitive endoderm lineage with a fibroblast growth factor and KAAD-cyclopamine, then removing the medium containing the fibroblast growth factor and KAAD-cyclopamine and subsequently culturing the cells in medium containing retinoic acid, a fibroblast growth factor and KAAD-cyclopamine. An example of this method is disclosed in D'Amour et al, Nature Biotechnology, 24: 1392-1401, (2006).

Markers characteristic of the pancreatic endoderm lineage are selected from the group consisting of Pdx1, HNF-1beta, PTF1a, HNF-6, HB9 and PROX1. Suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell.

Further Differentiation of Cells Expressing Markers Characteristic of the Pancreatic Endoderm Lineage Cells expressing markers characteristic of the pancreatic endoderm lineage may be differentiated into cells expressing markers characteristic of the pancreatic endocrine lineage by any method in the art.

For example, cells expressing markers characteristic of the pancreatic endoderm lineage may be differentiated into cells expressing markers characteristic of the pancreatic endocrine lineage according to the methods disclosed in D'Amour et al, Nature Biotechnology 24, 1392-1401 (2006).

Markers characteristic of the pancreatic endocrine lineage are selected from the group consisting of NGN-3, NeuroD, Islet-1, Pdx-1, NKX6.1, Pax-4, Ngn-3, and PTF-1 alpha. In one embodiment, a pancreatic endocrine cell is capable of expressing at least one of the following hormones: insulin, glucagon, somatostatin, and pancreatic polypeptide. Suitable for use in the present invention is a cell that expresses at least one of the markers characteristic of the pancreatic endocrine lineage. In one aspect of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In one aspect of the present invention, the pancreatic endocrine cell is a cell expressing markers characteristic of the β cell lineage. A cell expressing markers characteristic of the β cell lineage expresses Pdx1 and at least one of the following transcription factors: NGN-3, Nkx2.2, Nkx6.1, NeuroD, Is1-1, HNF-3 beta, MAFA, Pax4, and Pax6. In one aspect of the present invention, a cell expressing markers characteristic of the β cell lineage is a β cell.

Detection of Cells Expressing Markers Characteristic of the Definitive Endoderm Lineage Formation of cells expressing markers characteristic of the definitive endoderm lineage may be determined by testing for the presence of the markers before and after following a particular protocol. Pluripotent stem cells typically do not express such markers. Thus, differentiation of pluripotent cells is detected when cells begin to express them.

The efficiency of differentiation may be determined by exposing a treated cell population to an agent (such as an antibody) that specifically recognizes a protein marker expressed by cells expressing markers characteristic of the definitive endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

For example, characteristics of pluripotent stem cells are well known to those skilled in the art, and additional characteristics of pluripotent stem cells continue to be identified. Pluripotent stem cell markers include, for example, the expression of one or more of the following: ABCG2, cripto, FoxD3, Connexin43, Connexin45, Oct4, Sox2, Nanog, hTERT, UTF-1, ZFP42, SSEA-3, SSEA-4, Tra1-60, Tra1-81.

After treating pluripotent stem cells with the methods of the present invention, the differentiated cells may be purified by exposing a treated cell population to an agent (such as an antibody) that specifically recognizes a protein marker, such as CXCR4, expressed by cells expressing markers characteristic of the definitive endoderm lineage.

Detection of Cells Expressing Markers Characteristic of the Pancreatic Endoderm Lineage Markers characteristic of the pancreatic endoderm lineage are well known to those skilled in the art, and additional markers characteristic of the pancreatic endoderm lineage continue to be identified. These markers can be used to confirm that the cells treated in accordance with the present invention have differentiated to acquire the properties characteristic of the pancreatic endoderm lineage. Pancreatic endoderm lineage specific markers include the expression of one or more transcription factors such as, for example, Hlxb9, PTF-1a, PDX-1, HNF-6, HNF-1beta.

The efficiency of differentiation may be determined by exposing a treated cell population to an agent (such as an antibody) that specifically recognizes a protein marker expressed by cells expressing markers characteristic of the pancreatic endoderm lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

Detection of Cells Expressing Markers Characteristic of the Pancreatic Endocrine Lineage Markers characteristic of cells of the pancreatic endocrine lineage are well known to those skilled in the art, and additional markers characteristic of the pancreatic endocrine lineage continue to be identified. These markers can be used to confirm that the cells treated in accordance with the present invention have differentiated to acquire the properties characteristic of the pancreatic endocrine lineage. Pancreatic endocrine lineage specific markers include the expression of one or more transcription factors such as, for example, NGN-3, NeuroD, Islet-1.

Markers characteristic of cells of the β cell lineage are well known to those skilled in the art, and additional markers characteristic of the β cell lineage continue to be identified. These markers can be used to confirm that the cells treated in accordance with the present invention have differentiated to acquire the properties characteristic of the β-cell lineage. β cell lineage specific characteristics include the expression of one or more transcription factors such as, for example, Pdx1 (pancreatic and duodenal homeobox gene-1), Nkx2.2, Nkx6.1, Is11, Pax6, Pax4, NeuroD, Hnf1b, Hnf-6, Hnf-3beta, and MafA, among others. These transcription factors are well established in the art for identification of endocrine cells. See, e.g., Edlund (Nature Reviews Genetics 3: 524-632 (2002)).

The efficiency of differentiation may be determined by exposing a treated cell population to an agent (such as an antibody) that specifically recognizes a protein marker expressed by cells expressing markers characteristic of the pancreatic endoderm lineage. Alternatively, the efficiency of differentiation may be determined by exposing a treated cell population to an agent (such as an antibody) that specifically recognizes a protein marker expressed by cells expressing markers characteristic of the β cell lineage.

Methods for assessing expression of protein and nucleic acid markers in cultured or isolated cells are standard in the art. These include quantitative reverse transcriptase polymerase chain reaction (RT-PCR), Northern blots, in situ hybridization (see, e.g., Current Protocols in Molecular Biology (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, Using Antibodies: A Laboratory Manual, New York: Cold Spring Harbor Laboratory Press (1998)).

Examples of antibodies useful for detecting certain protein markers are listed in Table IA. It should be noted that alternate antibodies directed to the same markers that are recognized by the antibodies listed in Table IA are available, or can be readily developed. Such alternate antibodies can also be employed for assessing expression of markers in the cells isolated in accordance with the present invention.

The present invention is further illustrated, but not limited by, the following examples.

Example 1

Human Embryonic Stem Cell Culture

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

The human embryonic stem cell lines H1, H7 and H9 were obtained from WiCell Research Institute, Inc., (Madison, Wis.) and cultured according to instructions provided by the source institute. Briefly, cells were cultured on mouse embryonic fibroblast (MEF) feeder cells in ES cell medium consisting of DMEM/F12 (Invitrogen/GIBCO) supplemented with 20% knockout serum replacement, 100 nM MEM nonessential amino acids, 0.5 mM beta-mercaptoethanol, 2 mM L-glutamine with 4 ng/ml human basic fibroblast growth factor (bFGF) (all from Invitrogen/GIBCO). MEF cells, derived from E13 to 13.5 mouse embryos, were purchased from Charles River. MEF cells were expanded in DMEM medium supplemented with 10% FBS (Hyclone), 2 mM glutamine, and 100 mM MEM nonessential amino acids. Sub-confluent MEF cell cultures were treated with 10 µg/ml mitomycin C (Sigma, St. Louis, Mo.) for 3 h to arrest cell division, then trypsinized and plated at $2 \times 10^4/cm^2$ on 0.1% bovine gelatin-coated dishes. MEF cells from passage two through four were used as feeder layers. Human embryonic stem cells plated on MEF cell feeder layers were cultured at 37° C. in an atmosphere of 5% $CO_2$/within a humidified tissue culture incubator. When confluent (approximately 5-7 days after plating), human embryonic stem cells were treated with 1 mg/ml collagenase type IV (Invitrogen/GIBCO) for 5-10 min and then gently scraped off the surface using a 5-ml pipette. Cells were spun at 900 rpm for 5 min, and the pellet was resuspended and re-plated at a 1:3 to 1:4 ratio of cells in fresh culture medium.

In parallel, H1, H7, and H9 human embryonic stem cells were also seeded on plates coated with a 1:30 dilution of growth factor reduced MATRIGEL™ (BD Biosciences) and cultured in MEF-conditioned media supplemented with 8 ng/ml bFGF. The cells cultured on MATRIGEL™ were routinely passaged with collagenase IV (Invitrogen/GIBCO), Dispase (BD Biosciences) or Liberase enzyme (Source). Some of the human embryonic stem cell cultures were incubated under hypoxic conditions (approximately 3% $O_2$).

Example 2

Derivation and Culture of Cells Expressing Pluripotency Markers, Derived from Human Embryonic Stem Cells Cells from the human embryonic stem cell lines H1 and H9 various passages (Passage 30-54) were cultured under hypoxic conditions (approximately 3% $O_2$) for at least three passages. The cells were cultured in MEF-CM supplemented with 8 ng/ml of bFGF and plated on MATRIGEL coated plates according to Example 1.

Cells were then treated with DMEM/F12 medium supplemented with 0.5% FBS, 20 ng/ml WNT-3a (Catalog#1324-WN-002, R&D Systems, MN), and 100 ng/ml Activin-A (R&D Systems, MN) for two days followed by treatment with DMEM/F12 media supplemented with 2% FBS and 100 ng/ml Activin-A (AA) for an additional 3 to 4 days. This protocol resulted in significant upregulation of definitive endoderm markers.

The cells were then treated with TrypLE™ Express solution (Invitrogen, CA) for 5 mins. Released cells were resuspended in DMEM-F12+2% FBS medium, recovered by centrifugation, and counted using a hemocytometer. The released cells were seeded at 1000-10,000 cells/$cm^2$ on tissue culture polystyrene (TCPS) treated flasks and cultured in DMEM-F12+2% FBS+100 ng/ml activin-A+20 ng/ml WNT-3A under hypoxic conditions (approximately 3% $O_2$) at 37° C. in standard tissue culture incubator. The TCPS flaks were not coated with MATRIGEL or other extarcellular matrix proteins. The media was changed daily. In some cultures, the media was further supplemented with 10-50 ng/ml of IGF-I (insulin growth factor-I from R&D Systems, MN) or 1×ITS (Insulin, transferrin, and selenium from Invitrogen, Ca). In some of the culture conditions the basal media (DM-F12+2% FBS) was further supplemented with 0.1 mM mercaptoethanol (Invitrogen, CA) and non-essential amino acids (1×, NEAA from Invitrogen, CA).

Following 5 to 15 days of culturing, distinct cell colonies appeared surrounded by a large number of enlarged cells that appear to be in senescence. At approximately 50 to 60% confluency, the cultures were passaged by exposure to TrypLE™ Express solution for 5 mins at room temperature. The released cells were resuspended in DMEM-F12+2% FBS medium, recovered by centrifugation, and seeded at 10,000 cells/cm² on tissue culture polystyrene (TCPS) treated flasks in DMEM-F12+2% FBS+100 ng/ml activin-A+20 ng/ml WNT-3A+/−50 ng/ml of IGF-I. This media will be further referred to as the "growth media".

Example 3

Derivation of Cells Expressing Pluripotency Markers from a Single Cell Suspension of Human Embryonic Stem Cells Cells from the human embryonic stem cell lines H1 P33 and H9 P45 were cultured under hypoxic conditions (approximately 3% $O_2$) for at least three passages. The cells were cultured in MEF-CM supplemented with 8 ng/ml of bFGF and plated on MATRIGEL coated plates according to Example 1. At approximately 60% confluency, the cultures were exposed to TrypLE™ Express solution (Invitrogen, CA) for 5 mins. Released cells were resuspended in DMEM-F12+2% FBS medium, recovered by centrifugation, and counted using a hemocytometer. The released cells were seeded at 1000 to 10,000 cells/cm² on tissue culture polystyrene (TCPS) treated flasks and cultured in DM-F12+2% FBS+100 ng/ml activin-A+20 ng/ml WNT-3A+50 ng/ml of IGF-I+0.1 mM mercaptoethanol (Invitrogen, CA) and non-essential amino acids (1×, NEAA from Invitrogen, CA) under hypoxic conditions (approximately 3% $O_2$) at 37° C. in standard tissue culture incubator. The TCPS flasks were not coated with MATRIGEL or other extracellular matrix proteins. The media was changed daily. The first passage cells are referred to as P1.

Example 4

Various Growth Media Useful for Expansion of Cells Expressing Pluripotency Markers Derived from Human Embryonic Stem Cells Cells expressing pluripotency markers derived from human embryonic stem cells have been successfully cultured in the following media compositions for at least 2-30 passages:
1. DM-F12+2% FBS+100 ng/ml AA+20 ng/ml WNT-3A
2. DM-F12+2% FBS+100 ng/ml AA+20 ng/ml WNT-3A+50 ng/ml IGF-I
3. DM-F12+2% FBS+100 ng/ml AA+20 ng/ml WNT-3A+10 ng/ml IGF-I
4. DM-F12+2% FBS+50 ng/ml AA+20 ng/ml WNT-3A+50 ng/ml IGF-I
5. DM-F12+2% FBS+50 ng/ml AA+10 ng/ml WNT-3A+50 ng/ml IGF-I
6. DM-F12+2% FBS+50 ng/ml AA+20 ng/ml WNT-3A+10 ng/ml IGF-I
7. DM-F12+2% FBS+100 ng/ml AA+10 ng/ml WNT-3A+10 ng/ml IGF-I
8. HEScGRO defined media (Chemicon, CA)

The basal component of the above listed media may be replaced with similar media such as, RPMI, DMEM, CRML, Knockout™DMEM, and F12.

Example 4

Effects of Inhibitors of GSK-3β Enzyme Activity on the Viability of Cells Expressing Pluripotency Markers Derivation and maintenance of cells expressing pluripotency makers was conducted as has been described in Example 2. Cells were grown in DMEM:F12 supplemented with 2% FCS (Invitrogen), 100 ng/ml Activin A, 20 ng/ml Wnt-3a, and 50 ng/ml IGF (R&D Biosystems). Cells were seeded at a density of 10,000 cells/cm² on Falcon polystyrene flasks and grown in monolayer culture at 37° C., 5% $CO_2$, low oxygen. After reaching 60-70% confluence, cells were passed by washing the monolayer with PBS and incubating with TrypLE (Invitrogen) for 3-5 minutes to allow detachment and single cell dispersal.

Screening was conducted using test compounds from a proprietary library of small molecules selected for their ability to inhibit GSK-3B enzyme activity. Compounds from this library were made available as 1 mM stocks, in a 96-well plate format in 50 mM HEPES, 30% DMSO. For assay, cells expressing pluripotency markers were washed, counted, and plated in normal culture medium at a seeding density of 20,000 cells per well in 96-well clear-bottom, dark-well plates (Costar). This seeding density was previously determined to yield optimal monolayer formation in overnight culture. On the following day, culture medium was removed, cell monolayers were rinsed three times with PBS, and test compounds were added to the wells in 80 μl aliquots, each diluted into assay medium at a final assay concentration of 10 μM. On day 2 of the assay, medium was removed from each well and replaced with a fresh aliquot of test compounds diluted into assay medium. Assay medium on days 1 and 2 of culture consisted of DMEM:F12 supplemented with 0.5% FCS and 100 ng/ml Activin A. On days 3 and 4 of culture, medium was removed from each well and replaced with DMEM:F12 supplemented with 2% FCS and 100 ng/ml Activin A (no test compound). On day 4 of assay, 15 μl of MTS (Promega) was added to each well and plates were incubated at 37° C. for 1.5 to 4 hours prior to reading optical density at 490 nm on a SpectraMax (Molecular Devices) instrument. Statistical measures consisting of mean, standard deviation, and coefficient of variation were calculated for each duplicate set. Toxicity was calculated for each test well relative to a positive control (wells treated with Activin A and Wnt3a on days 1 and 2 of culture).

Table II is a compilation of all screening results. Cells expressing pluripotency markers were plated initially as a confluent monolayer in this assay; hence, the results are representative of a toxicity measure over the four-day culture period. Results are expressed as percentage viability of control, and demonstrate variable toxicity for some compounds at the 10 μM screening concentration used. A larger proportion of the compounds have minimal or no measurable toxicity in this cell-based assay.

A small panel of select compounds was repeat tested over a narrow dose titration range, again using cells expressing pluripotency markers in a similar assay as described above. Table III is a summary of these results, demonstrating variable dose titration effects for a range of toxic and non-toxic compounds.

Example 5

Effects of Inhibitors of GSK-3β Enzyme Activity on the Differentiation and Proliferation of Human Embryonic Stem Cells Determined Using a High Content Screening Assay Maintenance of human embryonic stem cells (H9 line) was conducted as described in Example 1. Colonies of cells were maintained in an undifferentiated, pluripotent state with passage on average every four days. Passage was performed by exposing cell cultures to a solution of collagenase (1 mg/ml; Sigma-Aldrich) for 10 to 30 minutes at 37° C. followed by gentle scraping with a pipette tip to recover cell clusters. Clusters were allowed to sediment by gravity, followed by washing to remove residual collagenase. Cell clusters were split at a 1:3 ratio for routine maintenance culture or a 1:1 ratio for immediate assay. The human embryonic stem cell lines used were maintained at passage numbers less than passage 50 and routinely evaluated for normal karyotypic phenotype and absence of mycoplasma contamination.

Cell clusters used in the assay were evenly resuspended in normal culture medium and plated onto MATRIGEL-coated 96-well Packard VIEWPLATES (PerkinElmer) in volumes of 100 µl/well. MEF conditioned medium supplemented with 8 ng/ml bFGF was used for initial plating and recovery. Daily feeding was conducted by aspirating spent culture medium from each well and replacing with an equal volume of fresh medium. Plates were maintained at 37° C., 5% $CO_2$ in a humidified box throughout the duration of assay.

Screening was conducted using test compounds from a proprietary library of small molecules selected for their ability to inhibit GSK-3B enzyme activity. Compounds from this library were made available as 1 mM stocks, in a 96-well plate format in 50 mM HEPES, 30% DMSO. Screening compounds were tested in triplicate or duplicate sets. Primary screening assays were initiated by aspirating culture medium from each well followed by three washes in PBS to remove residual growth factors and serum. Test volumes of 80 to 100 µl per well were added back containing DMEM:F12 base medium (Invitrogen) supplemented with 0.5% FCS (HyClone) and 100 ng/ml activin A (R&D Biosystems) plus 101.1M test compound. Positive control wells contained the same base medium, substituting 10-20 ng/ml Wnt3a (R&D Biosystems) for the test compound. Negative control wells contained base medium with 0.5% FCS and activin A alone (AA only) or alternatively, 0.5% FCS without activin A or Wnt3a (no treatment). Wells were aspirated and fed again with identical solutions on day 2 of assay. On days 3 and 4, all assay wells were aspirated and converted to DMEM:F12 supplemented with 2% FCS and 100 ng/ml activin A (without test compound or Wnt3a); parallel negative control wells were maintained in DMEM:F12 base medium with 2% FCS and activin A (AA only) or alternatively, 2% FCS without activin A (no treatment).

At the end of culture, cells in 96-well plates were fixed with 4% paraformaldehyde at room temperature for 20 minutes, washed three times with PBS, and then permeabilized with 0.5% Triton X-100 for 20 minutes at room temperature. Alternatively, cells were fixed with ice cold 70% ethanol overnight at −20° C., washed three times with PBS, and then permeabilized with Triton X-100 for 5 minutes at 4° C. After fixing and permeabilizing, cells were washed again three times with PBS and then blocked with 4% chicken serum (Invitrogen) in PBS for 30 minutes at room temperature. Primary antibodies (goat anti-human Sox17 and goat anti-human HNF-3beta; R&D Systems) were diluted 1:100 in 4% chicken serum and added to cells for one hour at room temperature. Alexa Fluor 488 conjugated secondary antibody (chicken anti-goat IgG; Molecular Probes) was diluted 1:200 in PBS and added after washing the cells three times with PBS. To counterstain nuclei, 5 mM Draq5 (Alexis Biochemicals) was added for five minutes at room temperature. Cells were washed once with PBS and left in 100 ml/well PBS for imaging.

Cells were imaged using an IN Cell Analyzer 1000 (GE Healthcare) utilizing the 51008bs dichroic for cells stained with Draq5 and Alexa Fluor 488. Exposure times were optimized using a positive control wells and wells with secondary only for untreated negative controls. Twelve fields per well were obtained to compensate for any cell loss during the treatment and staining procedures. Total cell numbers and total cell intensity for Sox-17 and HNF-3beta were measured using the IN Cell Developer Toolbox 1.6 (GE Healthcare) software. Segmentation for the nuclei was determined based on grey-scale levels (baseline range 100-300) and nuclear size. Averages and standard deviations were calculated for replicates. Total protein expression was reported as total intensity or integrated intensity, defined as total fluorescence of the cell times area of the cell. Background was eliminated based on acceptance criteria of grey-scale ranges between 300 to 3000 and form factors greater than or equal to 0.4. Total intensity data were normalized by dividing the total intensities for each well by the average total intensity for the Wnt3a/Activin A positive control. Normalized data was calculated for averages and standard deviation for each replicate set.

Table IV is a representative summary of all screening results. Table V is a list of hits from this screening. Strong hits are defined as greater than or equal to 120% of control values; moderate hits are defined as falling within the interval of 60-120% of control values. A significant number of compounds induce both a proliferative response in this assay. In parallel, a significant number of compounds induce differentiation in this assay, as measured by the protein expression of Sox17 and Hnf-3b transcription factors.

Example 6

Effects of Inhibitors of GSK-3β Enzyme Activity on the Proliferation of Human Embryonic Stem Cells Determined Using a Plate Reader Assay Maintenance of human embryonic stem cells (H9 or H1 lines) was conducted as described in Example 1. Colonies of cells were maintained in an undifferentiated, pluripotent state with passage on average every four days. Passage was performed by exposing cell cultures to a solution of collagenase (1 mg/ml; Sigma-Aldrich) for 10 to 30 minutes at 37° C. followed by gentle scraping with a pipette tip to recover cell clusters. Clusters were allowed to sediment and washed to remove residual collagenase. Cell clusters were split at a ratio of 1:3 monolayer area for routine culture or a 1:1 ratio for immediate assay. The human embryonis stem cell lines used for these examples were maintained at passage numbers less than 50 and routinely evaluated for normal karyotypic phenotype as well as absence of mycoplasm contamination.

Cell clusters used in assay were evenly resuspended in normal culture medium and plated into MATRIGEL-coated 96-well Packard VIEWPLATES (PerkinElmer) in volumes of 100 µl/well. MEF conditioned medium supplemented with 8 ng/ml bFGF) was used for initial plating and recovery. Daily feeding was conducted by aspirating spent culture medium from each well and replacing with an equal volume of fresh medium. Plates were maintained at 37° C. in a humidified box, 5% $CO_2$ throughout the duration of assay.

Primary screening assays were initiated by aspirating culture medium from each well followed by three washes in PBS to remove residual growth factors and serum. Test volumes of 80-100 μl per well were added back containing DMEM:F12 base medium (Invitrogen) supplemented with 0.5% FCS (HyClone) and 100 ng/ml activin A (R&D Biosystems) and 10 μM test compound. Positive control wells contained the same medium substituting 10-20 ng/ml Wnt3a (R&D Biosystems). Negative control wells contained base medium with 0.5% FCS without activin A or Wnt3a. Screening compounds were tested in triplicate. Wells were aspirated and fed again with identical solutions on day 2 of the assay. On days 3 and 4, all assay wells were aspirated and converted to DMEM:F12 supplemented with 2% FCS and 100 ng/ml activin A with the exception of negative control wells which were maintained in DMEM:F12 base medium with 2% FCS.

On day 4 of assay, 15-20111 of MTS (Promega) was added to each well and plates were incubated at 37° C. for 1.5 to 4 hours. Densitometric readings at OD490 were determined using a Molecular Devices spectrophotometer plate reader. Average readings for replicate sets were calculated along with standard deviation and coefficient of variation. Experimental wells were compared to the Activin A/Wnt3a positive control to calculate a percent control value as a measure of proliferation.

Table VI is a representative summary of all screening results. Table VII is a list of hits from this screening. Strong hits are defined as greater than or equal to 120% of control values; moderate hits are defined as falling within the interval of 60-120% of control values. A significant number of compounds induce a proliferative response in this assay.

Example 7

Effects of GSK-3β Enzyme Inhibitors on the Differentiation and Proliferation of Human Embryonic Stem Cells: Dose Titration of Lead Compounds It was important to confirm the activity of hits identified from primary screening and further analyze the range of activity by dose titration. New samples of a selective subset of primary screening hits were obtained as dry powders, solubilized to make fresh stock reagents, and diluted into secondary confirmation assays to evaluate effects on human embryonic stem cells.

Culture of two human embryonic stem cells (H1 and H9) was conducted as described in Example 1. Colonies of cells were maintained in an undifferentiated, pluripotent state on Matrigel™ (Invitrogen) coated polystyrene plastic, using a 1:30 dilution of Matrigel™ in DMEM:F12 to coat the surface. Cells were split by enzymatic passage every four days on average. Passage was performed by exposing cell monolayers to a solution of collagenase (1 mg/ml; Sigma-Aldrich) for 10 to 60 minutes at 37° C. followed by gentle scraping with a pipette tip to recover cell clusters. Clusters were allowed to sediment by gravity, then washed to remove residual collagenase. Cell clusters were split at a 1:3 ratio for maintenance culture or a 1:1 ratio for subsequent assay. The human embryonic stem cell lines were maintained at less than passage 50 and routinely evaluated for normal karyotypic phenotype and absence of mycoplasma contamination.

Preparation of Cells for Assay:

Cell clusters of the H1 or H9 human embryonic stem cell lines used in the assay were evenly resuspended in culture medium and plated onto Matrigel™-coated 96-well Packard VIEWPLATES (PerkinElmer) in volumes of 100 μl/well. MEF conditioned medium supplemented with 8 ng/ml bFGF was used for initial plating and expansion. Daily feeding was conducted by aspirating spent culture medium from each well and replacing with an equal volume of fresh medium. Cultures were allowed to expand one to three days after plating prior to initiating assay. Plates were maintained at 37° C., 5% $CO_2$ in a humidified box for the duration of assay.

Preparation of Compounds and Assay Medium:

A subset of hits resulting from primary screening was used for follow-up study and subsequent secondary assays. Twenty compounds available as dry powders were solubilized as 10 mM stocks in DMSO and stored dessicated at −20° C. until use Immediately prior to assay, compound stocks were diluted 1:1000 to make 10 μM test compound in DMEM:F12 base medium (Invitrogen) supplemented with 0.5% FCS (HyClone) and 100 ng/ml Activin A (R&D Biosystems). This was further diluted two-fold in series to make a seven point dilution curve for each compound, also in DMEM:F12 base medium with 0.5% FCS and 100 ng/ml Activin A.

Secondary Screening Assay:

Assay was initiated by aspirating culture medium from cell monolayers in each well followed by three washes in PBS to remove residual growth factors and serum. Test volumes of 100 μl per well were added back containing medium with 0.5% FCS and different concentrations of inhibitor compounds with 100 ng/ml Activin A, without Wnt3a. Positive control wells contained the same base medium with 0.5% FCS and with 20 ng/ml Wnt3a (R&D Biosystems) in the absence of test compound. Negative control wells contained the same base medium with 0.5% FCS, in the absence of Activin A, Wnt3a, or test compound. Assay wells were aspirated and fed again with identical concentrations of test compound or control solutions on day 2 of assay. On days 3 and 4, all assay wells were aspirated and fed with DMEM:F12 supplemented with 2% FCS and 100 ng/ml Activin A in the absence of both test compound or Wnt3a. Parallel negative control wells were maintained on days 3 and 4 in DMEM:F12 base medium with 2% FCS.

Assay Evaluation:

At the end of culture, cells in 96-well plates were washed twice with PBS then fixed with 4% paraformaldehyde at room temperature for 20 minutes, washed three times more with PBS, and then permeabilized with 0.5% Triton X-100 for 20 minutes at room temperature. After fixing and permeabilizing, cells were washed again three times with PBS and then blocked with 4% chicken serum (Invitrogen) in PBS for 30 minutes at room temperature. Primary antibodies (goat anti-human Sox17; R&D Systems) were diluted 1:100 in 4% chicken serum and added to the cells for one hour at room temperature. Alexa Fluor 488 conjugated secondary antibody (chicken anti-goat IgG; Molecular Probes) was diluted 1:200 in PBS and added to each well after washing the cells three times with PBS. To counterstain nuclei, 2 μg/ml Hoechst 33342 (Invitrogen) was added for ten minutes at room temperature. Cells were washed once with PBS and left in 100 μl/well PBS for imaging.

Cells were imaged using an IN Cell Analyzer 1000 (GE Healthcare) utilizing the 51008bs dichroic for cells stained with Hoechst 33342 and Alexa Fluor 488. Exposure times were optimized using positive control wells and wells stained with secondary antibody alone as an untreated negative control. Images from 15 fields per well were acquired to compensate for any cell loss during the treatment and staining procedures. Measurements for total cell number and total Sox-17 intensity were obtained for each well using IN Cell Developer Toolbox 1.7 (GE Healthcare) software. Segmentation for the nuclei was determined based on grey-scale levels (baseline range 100-300) and nuclear size. Averages and standard deviations were calculated for each replicate data set. Total Sox17 protein expression was reported as total intensity or integrated intensity, defined as total fluorescence of the cell times area of the cell. Background was eliminated based on acceptance criteria of grey-scale ranges between 300 to 3000 and form factors greater than or equal to 0.4. Total intensity data were normalized by dividing the total intensities for each well by the average total intensity for the Wnt3a/Activin A positive control. Normalized data were calculated for averages and standard deviations for each replicate set.

Results

Results are shown for eight GSK-3B enzyme inhibitors where activity was confirmed and potency was determined by titration in this secondary assay. Data presented show compound effects on cell number and Sox17 intensity where respective data points were averaged from a duplicate set and mined for each parameter from identical fields and wells. In this example, Sox17 expression is indicative of definitive endoderm differentiation. Results for cell number and Sox17 intensity, respectively, using the H1 human embryonic stem cell line are shown in Tables VIII and IX. Results for the H9 human embryonic stem cell line are shown in Tables X and XI. Positive control values were normalized to 1.000 for cell number and Sox17 intensity. Negative control values were less-than 0.388 for cell number and less-than 0.065 for Sox17 intensity with both cell lines. A graphic portrayal of these data, comparing both human embryonic stem cell lines and including a dose titration of each compound, is provided in FIGS. 1 to 8. Cell number is presented in panel A; Sox 17 intensity is shown in panel B. These data confirm that each compound can promote hES cell proliferation and definitive endoderm differentiation and identify an optimal range of activity.

Example 8

Effects of GSK-3β Enzyme Inhibitors on the Expression of Additional Markers Associated with Definitive Endoderm It was important to demonstrate that lead compounds could also induce other markers indicative of definitive endoderm differentiation, in addition to the transcription factor Sox17. A select subset of hits was tested for their ability to promote expression of CXCR4, a surface receptor protein, and HNF-3 beta, a transcription factor also associated with definitive endoderm differentiation.

Preparation of Cells for Assay:

Cell clusters from the H1 human embryonis stem cell line used in the assay were evenly resuspended in culture medium and plated onto MATRIGEL™-coated (1:30 dilution) 6-well plates (Corning) in volumes of 2 ml/well. MEF conditioned medium supplemented with 8 ng/ml bFGF was used for initial plating and expansion. Daily feeding was conducted by aspirating spent culture medium from each well and replacing with an equal volume of fresh medium. Cultures were allowed to expand one to three days after plating prior to initiating assay. Plates were maintained at 37° C., 5% $CO_2$ for the duration of assay.

Preparation of Compounds and Assay Medium:

A subset of seven hits resulting from primary screening was used for follow-up study and subsequent secondary assays. Neat compounds were solubilized as 10 mM stocks in DMSO and stored dessicated at −20° C. until use. Immediately prior to assay, compound stocks were diluted to a final concentration ranging between 1 μM and 5 μM in DMEM:F12 base medium (Invitrogen) supplemented with 0.5% FCS (HyClone) and 100 ng/ml Activin A (R&D Biosystems).

Assay:

The assay was initiated by aspirating culture medium from cell monolayers in each well followed by three washes in PBS to remove residual growth factors and serum. Test volumes of 2 ml per well were added back containing medium with 0.5% FCS and different concentrations of inhibitor compounds with 100 ng/ml Activin A, without Wnt3a. Positive control wells contained the same base medium and 0.5% FCS with 100 ng/ml Activin A and 20 ng/ml Wnt3a (R&D Biosystems) in the absence of test compound. Negative control wells contained base medium with 0.5% FCS, in the absence of Activin A, Wnt3a, or test compound. Assay wells were aspirated and fed again with identical concentrations of test compound or control solutions on day 2 of assay. On days 3 and 4, all assay wells were aspirated and fed with DMEM:F12 supplemented with 2% FCS and 100 ng/ml Activin A in the absence of both test compound or Wnt3a. Parallel negative control wells were maintained on days 3 and 4 in DMEM:F12 base medium with 2% FCS.

Assay Evaluation:

At the end of culture, cell monolayers were washed with PBS and harvested from culture plates by incubating 5 minutes with TrypLE™ Express solution (Invitrogen, CA). Cells were resuspended in MEF conditioned medium and split into two equal samples. One set of samples was further stained with various fluorescent labeled antibodies and subjected to flow cytometric (FACS) analysis. A second parallel set of samples was subjected to quantitative PCR.

Cells for FACS analysis were washed into PBS and blocked for 15 minutes at 4° C. in 0. 125% human gamma-globulin (Sigma cat# G-4386) diluted in PBS and BD FACS staining buffer. Aliquots of cells (approximately $10^5$ cells each) were stained for 30 minutes at 4° C. with antibodies directly conjugated to a fluorescent tag and having specificity for CD9 PE (BD#555372), CD99 PE (Caltag#MHCD9904), or CXCR-4 APC (R&D Systems cat# FAB173A). After a series of washes in BD FACS staining buffer, cells were stained with 7-AAD (BD#559925) to assess viability and analyzed on a BD FACS Array instrument (BD Biosciences), collecting at least 10,000 events. Mouse $IgG_1k$ isotype control antibodies for both PE and APC were used to gate percent positive cells.

Cells for quantitative PCR were processed for RNA extraction, purification, and cDNA synthesis. RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, Inc.), and high-quality RNA was eluted in water. Yield and purity were assessed by A260 and A280 readings on a spectrophotometer. cDNA copies were made from purified RNA using an Applied Biosystems, Inc. (ABI, CA) high capacity cDNA archive kit.

Unless otherwise stated, all reagents for real-time PCR amplification and quantitation were purchased from ABI. Real-time PCR reactions were performed using the ABI PRISM 7900 Sequence Detection System. TAQMAN UNIVERSAL PCR MASTER MIX (ABI, CA) was used with 20 ng of reverse transcribed RNA in a total reaction volume of 20 µl. Each cDNA sample was run in duplicate to correct for pipetting errors. Primers and FAM-labeled TAQMAN probes were used at concentrations of 200 nM. The level of expression for each target gene was normalized using a human glyceraldehyde-3-phosphate dehydrogenase (GAPDH) endogenous control previously developed by ABI. Primer and probe sets are listed as follows: CXCR4 (Hs00237052), GAPDH (4310884E), HNF3b (Hs00232764), SOX17 (probe part #450025, forward and reverse part #4304971).

After an initial incubation at 50° C. for 2 min followed by 95° C. for 10 min, samples were cycled 40 times in two stages, a denaturation step at 95° C. for 15 sec followed by an annealing/extension step at 60° C. for 1 min. Data analysis was carried out using GENEAMP 7000 Sequence Detection System software. For each primer/probe set, a Ct value was determined as the cycle number at which the fluorescence intensity reached a specific value in the middle of the exponential region of amplification. Relative gene expression levels were calculated using the comparative Ct method. Briefly, for each cDNA sample, the endogenous control Ct value was subtracted from the gene of interest Ct to give the delta Ct value ($\Delta$Ct). The normalized amount of target was calculated as 2-$\Delta$Ct, assuming amplification to be 100% efficiency. Final data were expressed relative to a calibrator sample.

Results

Figure 9:
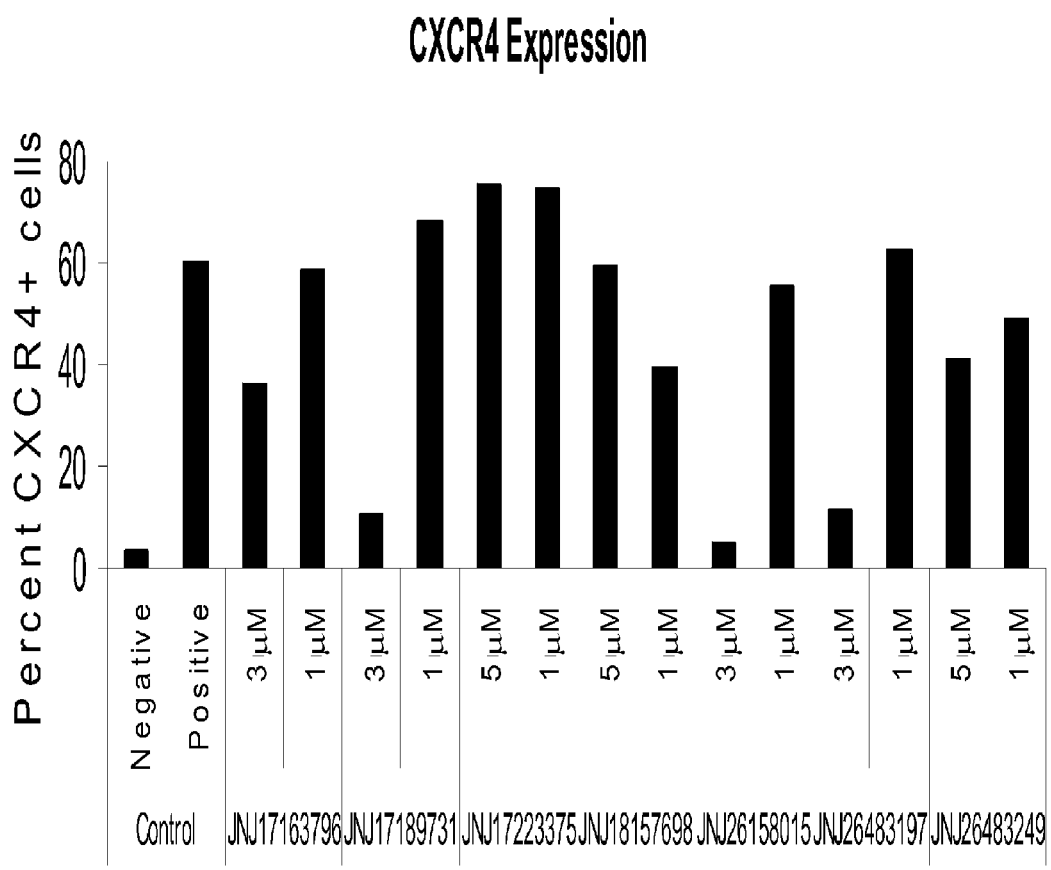
FIG. 9 shows the expression of CXCR4 on the surface of cells, as determined by immunofluorescent staining and flow cytometric analysis, on cells treated with the compounds shown, according to the methods described in Example 8.

FIG. 9 displays the FACS analysis of percent positive cells expressing CXCR4 surface receptor after treatment with various GSK3 inhibitors. Two concentrations of each compound, ranging between 1 µM and 5 µM, are shown relative to an untreated population of cells (negative control) or cells treated with Activin A and Wnt3 (positive control). FIG. 10 panels a, b, and c show real-time PCR data for CXCR4, Sox17, and HNF3beta, which are also considered to be markers of definitive endoderm. Both FACS and real-time PCR analysis demonstrate a significant increase in each of these markers observed in differentiated cells relative to untreated control cells. Expression levels of these definitive endoderm markers were equivalent in some cases to the positive control, demonstrating that a GSK3 inhibitor can substitute for Wnt3a at this stage of differentiation.

Example 9

Effects of GSK-3$\beta$ Enzyme Inhibitors on the Formation of Pancreatic Endoderm It was important to demonstrate that treatment with GSK3$\beta$ inhibitors during induction of definitive endoderm did not prevent the subsequent differentiation of other cell types, such as pancreatic endoderm, for example. A select subset of hits was tested for their ability to promote expression of PDX1 and HNF6, key transcription factors associated with pancreatic endoderm.

Maintenance of human embryonic stem cells (H1 and H9 lines) was conducted as described in Example 1. Colonies of cells were maintained in an undifferentiated, pluripotent state with passage on average every four days. Passage was performed by exposing cell cultures to a solution of collagenase (1 mg/ml; Sigma-Aldrich) for 10 to 30 minutes at 37° C., followed by gentle scraping with a pipette tip to recover cell clusters. Clusters were allowed to sediment by gravity, followed by washing to remove residual collagenase. Cell clusters were split at a 1:3 ratio for routine maintenance culture or a 1:1 ratio for subsequent assay. The human embryonic stem cell lines used were maintained at less than passage 50 and routinely evaluated for normal karyotypic phenotype and absence of mycoplasma contamination.

Cell Preparation of Assay:

Cell clusters of the H1 human embryonis stem cell line used in the assay were evenly resuspended in culture medium and plated onto MATRIGEL™-coated (1:30 dilution) 24-well plates (black well; Arctic White) in volumes of 1 ml/well. MEF conditioned medium supplemented with 8 ng/ml bFGF was used for initial plating and expansion. In a second experiment, clusters of hES cells from the H9 line were plated in 96-well plates on mouse embryonic feeder (MEF) layers, previously inactivated by treating with mitomycin C (Sigma Chemical Co). Culture medium for hES cells on MEF monolayers consisted of DMEM:F12 with 20% Knockout Serum Replacer (Invitrogen) supplemented with minimal essential amino acids (Invitrogen), L-glutamine, and 2-mercaptoethanol. Daily feeding was conducted by aspirating spent culture medium from each well and replacing with an equal volume of fresh medium. Cultures were allowed to expand one to three days after plating prior to initiating assay. Plates were maintained at 37° C., 5% $CO_2$ for the duration of assay.

Preparation of Compounds and Assay Medium:

A subset of eight hits resulting from primary screening was used for follow-up study and subsequent secondary assays. Neat compounds were solubilized as 10 mM stocks in DMSO and stored dessicated at –20° C. until use. Immediately prior to assay, compound stocks were diluted to a final concentration ranging between 1 µM and 5 µM in base medium with additives.

Assay:

In this assay, GSK3 inhibitors were included only on days 1 and 2 of the definitive endoderm differentiation step, substituting for Wnt3a. Embryonic stem cell cultures on MATRIGEL™ were initiated as described in Examples 7 and 8 above by aspirating culture medium from cell monolayers in each well followed by three washes in PBS to remove residual growth factors and serum. For differentiation to definitive endoderm, test volumes (0.5 ml per well for 24-well plates, 100 ill per well for 96-well plates) were added containing DMEM:F12 medium with) 0.5% FCS and different concentrations of inhibitor compounds with 100 ng/ml Activin A, without Wnt3a. Positive control wells contained the same base medium with 0.5% FCS and with 100 ng/ml Activin A and 20 ng/ml Wnt3a (R&D Biosystems) in the absence of test compound. Negative control wells contained the same base medium with 0.5% FCS, in the absence of Activin A, Wnt3a, or test compound. Assay wells were aspirated and fed again with identical concentrations of test compound or control solutions on day 2 of assay. On days 3 and 4, all assay wells were aspirated and fed with DMEM:F12 supplemented with 2% FCS and 100 ng/ml Activin A in the absence of both test compound or Wnt3a. Parallel negative control wells were maintained on days 3 and 4 in DMEM:F12 base medium with 2% FCS. For differentiation to pancreatic endoderm, cells were treated for three days, feeding daily with DMEM:F12 base medium containing 2% FCS with 0.2511M KAAD cyclopamine (EMD Biosciences) and 20 ng/ml FGF7 (R&D Biosystems).

Cells were then treated for an additional four days, feeding daily with DMEM:F12 containing 1% B27 (Invitrogen), 0.2511M KAAD cyclopamine, 2 µM Retinoic Acid (RA; Sigma-Aldrich) and 20 ng/ml FGF7. Parallel negative control wells were maintained throughout in DMEM:F12 base medium with 2% FCS (stage 2) or 1% B27 (stage 3) and without any other additives.

Parallel cultures of H9 human embryonic cells were grown on MEF feeder layers, and differentiated to pancreatic endoderm. Definitive endoderm differentiation was achieved by culturing the cells in medium consisting of RPMI-1640 (Invitrogen) containing no serum on day 1 and 0.2% FCS on days 2 and 3 along with different concentrations of inhibitor compounds and 100 ng/ml Activin A. Positive control wells contained the same base medium (with or without serum) with 100 ng/ml Activin A and 20 ng/ml Wnt3a (R&D Biosystems) in the absence of test compound. Negative control wells contained the same base medium with or without serum, in the absence of Activin A, Wnt3a, or test compound. Assay wells were aspirated and fed again with identical concentrations of test compound or control solutions on day 2 of assay. On day 3, all assay wells were aspirated and fed with RPMI-1640 supplemented with 2% FCS and 100 ng/ml Activin A in the absence of both test compound and Wnt3a. Parallel negative control wells were maintained on day 3 in RPMI-1640 base medium with 2% FCS. Cells were differentiated into pancreatic endoderm by treating the cells for four days, feeding daily with RPMI-1640 base medium containing 2% FCS with 0.25 mM KAAD cyclopamine (EMD Biosciences) and 50 ng/ml FGF10 (R&D Biosystems). Subsequently, cells were treated for three days duration, feeding daily with RPMI-1640 containing 1% B27 (Invitrogen), 0.25 mM KAAD cyclopamine, 2 mM Retinoic Acid (RA; Sigma-Aldrich) and 50 ng/ml FGF10. Parallel negative control wells were maintained throughout in RPMI-1640 base medium with 2% FCS (stage 2) or 1% B27 (stage 3) and without any other additives.

Assay Evaluation:

At the end the differentiation, cells were examined as described in Example 8 for gene expression by real-time PCR. For high content fluorescence staining, cells in 96-well plates were washed twice with PBS then fixed with 4% paraformaldehyde at room temperature for 20 minutes, washed three times more with PBS, and then permeabilized with 0.5% Triton X-100 for 20 minutes at room temperature. After fixing and permeabilizing, cells were washed again three times with PBS and blocked with 4% chicken serum (Invitrogen) in PBS for 30 minutes at room temperature. Primary antibody (goat anti-human Pdx1; Santa Cruz) was diluted 1:100 in 4% chicken serum and added to cells for two hours at room temperature. Alexa Fluor 488 conjugated secondary antibody (chicken anti-goat IgG; Molecular Probes) was diluted 1:200 in PBS and added to each well after washing the cells three times with PBS. To counterstain nuclei, 2 µg/ml Hoechst 33342 (Invitrogen) was added for ten minutes at room temperature. Cells were washed once with PBS and left in 100 µl/well PBS for imaging.

Cells were imaged using an IN Cell Analyzer 1000 (GE Healthcare) utilizing the 51008bs dichroic for cells stained with Hoechst 33342 and Alexa Fluor 488. Exposure times were optimized using positive control wells and wells stained with secondary antibody alone. Images from 15 fields per well were acquired to compensate for any cell loss during the treatment and staining procedures. Measurements for total cell number and total Pdx1 intensity were obtained for each well using IN Cell Developer Toolbox 1.7 (GE Healthcare) software. Segmentation for the nuclei was determined based on grey-scale levels (baseline range 100-300) and nuclear size. Averages and standard deviations were calculated for each replicate data set. Total Pdx1 protein expression was reported as total intensity or integrated intensity, defined as total fluorescence of the cell times area of the cell. Background was eliminated based on acceptance criteria of grey-scale ranges between 300 to 3000. Total intensity data were normalized by dividing the total intensities for each well by the average total intensity for the Wnt3a/Activin A positive control. Normalized data were calculated for averages and standard deviations for each replicate set.

Cells for quantitative PCR were lysed in RLT buffer (Qiagen) and then processed for RNA extraction, purification, and cDNA synthesis. RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, Inc.), and high-quality RNA was then eluted in water. Yield and purity were assessed by A260 and A280 readings on a spectrophotometer. cDNA copies were made from purified RNA using an Applied Biosystems, Inc. (ABI, CA) high capacity cDNA archive kit.

Unless otherwise stated, all reagents for real-time PCR amplification and quantitation were purchased from ABI. Real-time PCR reactions were performed using the ABI PRISM 7900 Sequence Detection System. TAQMAN UNIVERSAL PCR MASTER MIX was used with 20 ng of reverse transcribed RNA in a total reaction volume of 20 µl. Each cDNA sample was run in duplicate to correct for pipetting errors. Primers and FAM-labeled TAQMAN probes were used at concentrations of 200 nM. The level of expression for each target gene was normalized using a human glyceraldehyde-3-phosphate dehydrogenase (GAPDH) endogenous control previously developed by ABI. Primer and probe sets are listed as follows: PDX1 (Hs00236830_m1), GAPDH (4310884E), and HNF6 (Hs00413554_m1).

After an initial incubation at 50° C. for 2 min followed by 95° C. for 10 min, samples were cycled 40 times in two stages, a denaturation step at 95° C. for 15 sec followed by an annealing/extension step at 60° C. for 1 min. Data analysis was carried out using GENEAMPÒ7000 Sequence Detection System software. For each primer/probe set, a Ct value was determined as the cycle number at which the fluorescence intensity reached a specific value in the middle of the exponential region of amplification. Relative gene expression levels were calculated using the comparative Ct method. Briefly, for each cDNA sample, the endogenous control Ct value was subtracted from the gene of interest Ct to give the delta Ct value (ΔCt). The normalized amount of target was calculated as 2-ΔCt, assuming amplification to be 100% efficiency. Final data were expressed relative to a calibrator sample.

Results

Figure 12:
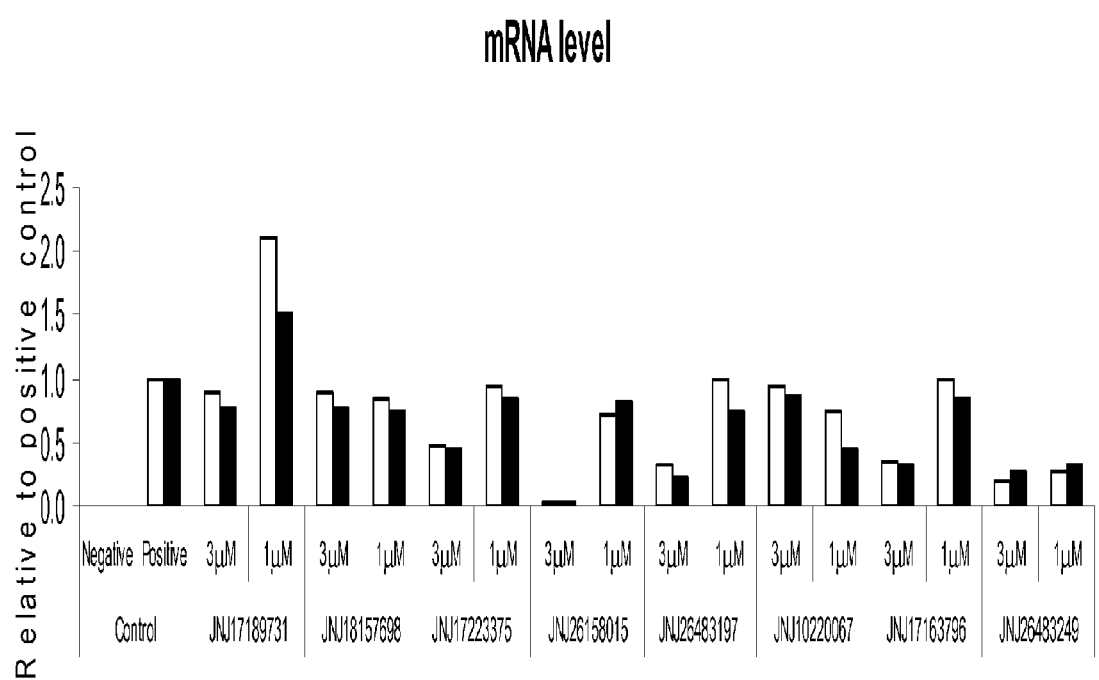
FIG. 12 shows the effect of a range of concentrations of the compounds shown on Pdx-1 expression (white bars) and HNF-6 (black bars), as determined by real-time PCR. Cells were treated according to the methods described in Example 9.

Results are shown for eight GSK-3β enzyme inhibitors. Data presented in FIG. 11 from high content analysis show effects on cell number (panel A) and Pdx1 intensity (panel B) for the H1 hES cell line, where respective data points were averaged from a duplicate sample set and mined for each parameter from identical fields and wells. Data presented in FIG. 12 from real-time PCR show effects of these small molecule inhibitors on induced expression of two transcription factors, Pdx1 and HNF6. In these examples, Pdx1 and HNF6 expression are indicative of pancreatic endoderm differentiation. GSK3β inhibitor compounds in these assays can substitute for Wnt3a during early stages of cell lineage commitment; resulting cells sustain a capacity to form pancreatic endoderm during later sequential stages of differentiation.

Example 10

Effects of GSK-3β Enzyme Inhibitors on the Formation of Pancreatic Endocrine Cells It was important to demonstrate that treatment with GSK3 inhibitors during induction of definitive endoderm did not prevent the subsequent differentiation of other cell types, such as pancreatic endocrine cells, or insulin producing cells, for example. A select subset of hits was tested for their ability to promote expression of pancreatic hormones.

Cell Preparation for Assay:

Pancreatic endoderm cells obtained according to the methods described in Example 9 (cultured on 96-wellplates and 24-well plates) were subsequently subjected to agents that cause the cells to differentiate into pancreatic hormone expressing cells.

Assay for cultures of the H1 human embryonic stem cell line on MATRIGEL™ was initiated as described in Examples 7-9 above by aspirating culture medium from cell monolayers in each well followed by three washes in PBS to remove residual growth factors and serum. For differentiation to definitive endoderm, test volumes (0.5 ml per well for 24-well plates, 100 μl per well for 96-well plates) were added containing medium with 0.5% FCS and different concentrations of inhibitor compounds with 100 ng/ml Activin A, without Wnt3a. Positive control wells contained the same base medium and 0.5% FCS with 100 ng/ml Activin A and 20 ng/ml Wnt3a (R&D Biosystems) in the absence of test compound. Negative control wells contained the same base medium with 0.5% FCS, in the absence of Activin A, Wnt3a, or test compound. Assay wells were aspirated and fed again with identical concentrations of test compound or control solutions on day 2 of assay. On days 3, 4, and 5, all assay wells were aspirated and fed with DMEM:F12 supplemented with 2% FCS and 100 ng/ml Activin A in the absence of both test compound or Wnt3a. Parallel negative control wells were maintained on days 3, 4, and 5 in DMEM:F12 base medium with 2% FCS. For differentiation to pancreatic endoderm, cells were treated for three days, feeding daily with DMEM:F12 base medium containing 2% FCS with 0.25 μM KAAD cyclopamine (EMD Biosciences) and 20 ng/ml FGF7 (R&D Biosystems). Cells were subsequently treated for four days, feeding daily with DMEM:F12 containing 1% B27 (Invitrogen), 0.25 μM KAAD cyclopamine, 2 μM Retinoic Acid (RA; Sigma-Aldrich) and 20 ng/ml FGF7. Parallel negative control wells during stages 2 and 3 were maintained throughout in DMEM:F12 base medium with 2% FCS or 1% B27 and without any other additives. After formation of pancreatic endoderm, cells were treated further for six days duration, feeding daily with DMEM:F12 base medium containing 1% B27 with 1 μM DAPT (gamma secretase inhibitor: EMD Biosciences) and 50 ng/ml Exendin 4 (Sigma-Aldrich). Cells were then treated for another three days duration, feeding daily with DMEM:F12 base medium containing 1% B27, 50 ng/ml Exendin 4, 50 ng/ml IGF (R&D Biosystems) and 50 ng/ml HGF (R&D Biosystems). Parallel negative control wells were maintained throughout in DMEM:F12 base medium with 1% B27 and without any other additives.

Assay Evaluation:

At the end of culture, cells were treated as in Examples 7 and 8 above for evaluation by high content analysis or real-time PCR.

For high content fluorescence staining, cells in 96-well plates were washed twice with PBS then fixed with 4% paraformaldehyde at room temperature for 20 minutes, washed three times more with PBS, and then permeabilized with 0.5% Triton X-100 for 20 minutes at room temperature. After fixing and permeabilizing, cells were washed again three times with PBS and blocked with 4% chicken serum (Invitrogen) in PBS for 30 minutes at room temperature. Primary antibody (guinea pig anti-swine insulin, cross-reactive with human insulin; DakoCytomation) was diluted 1:500 in 4% goat serum and added to cells for one hour at room temperature. Cells were washed three times with PBS and then stained with Alexa Fluor 488 conjugated secondary antibody (goat anti-guinea pig IgG; Molecular Probes) diluted 1:100 in 4% goat serum. To counterstain nuclei, 2 μg/ml Hoechst 33342 (Invitrogen) was added for ten minutes at room temperature. Cells were washed once with PBS and left in 100 μl/well PBS for imaging.

Cells were imaged using an IN Cell Analyzer 1000 (GE Healthcare) utilizing the 51008bs dichroic for cells stained with Hoechst 33342 and Alexa Fluor 488. Exposure times were optimized using positive control wells and wells stained with secondary antibody alone. Images from 15 fields per well were acquired to compensate for any cell loss during the treatment and staining procedures. Measurements for total cell number and total insulin intensity were obtained for each well using IN Cell Developer Toolbox 1.7 (GE Healthcare) software. Segmentation for the nuclei was determined based on grey-scale levels (baseline range 100-300) and nuclear size. Averages and standard deviations were calculated for each replicate data set. Total insulin protein expression was reported as total intensity or integrated intensity, defined as total fluorescence of the cell times area of the cell. Background was eliminated based on acceptance criteria of grey-scale ranges between 300 to 3000. Total intensity data were normalized by dividing the total intensities for each well by the average total intensity for the Wnt3a/Activin A positive control. Normalized data were calculated for averages and standard deviations for each triplicate set.

Cells for quantitative PCR were lysed in RLT buffer (Qiagen) and then processed for RNA extraction, purification, and cDNA synthesis. RNA samples were purified by binding to a silica-gel membrane (Rneasy Mini Kit, Qiagen, CA) in the presence of an ethanol-containing, high-salt buffer followed by washing to remove contaminants. The RNA was further purified using a TURBO DNA-free kit (Ambion, INC), and high-quality RNA was eluted in water. Yield and purity were assessed by A260 and A280 readings on a spectrophotometer. cDNA copies were made from purified RNA using an Applied Biosystems, Inc. (ABI, CA) high capacity cDNA archive kit.

Unless otherwise stated, all reagents for real-time PCR amplification and quantitation were purchased from ABI. Real-time PCR reactions were performed using the ABI PRISM® 7900 Sequence Detection System. TAQMAN® UNIVERSAL PCR MASTER MIX® (ABI, CA) was used with 20 ng of reverse transcribed RNA in a total reaction volume of 20 μl. Each cDNA sample was run in duplicate to correct for pipetting errors. Primers and FAM-labeled TAQMAN®probes were used at concentrations of 200 nM.

The level of expression for each target gene was normalized using a human glyceraldehyde-3-phosphate dehydrogenase (GAPDH) endogenous control previously developed by ABI. Primer and probe sets are listed as follows: PDX1 (Hs00236830_ml), Insulin (Hs00355773), and GAPDH (4310884E).

After an initial incubation at 50° C. for 2 min followed by 95° C. for 10 min, samples were cycled 40 times in two stages, a denaturation step at 95° C. for 15 sec followed by an annealing/extension step at 60° C. for 1 min. Data analysis was carried out using GENEAMP®7000 Sequence Detection System software. For each primer/probe set, a $C_t$ value was determined as the cycle number at which the fluorescence intensity reached a specific value in the middle of the exponential region of amplification. Relative gene expression levels were calculated using the comparative $C_t$ method. Briefly, for each cDNA sample, the endogenous control $C_t$ value was subtracted from the gene of interest $C_t$ to give the delta $C_t$ value ($\Delta C_t$). The normalized amount of target was calculated as $2^{-\Delta Ct}$, assuming amplification to be 100% efficiency. Final data were expressed relative to a calibrator sample.

Results

Figure 14:
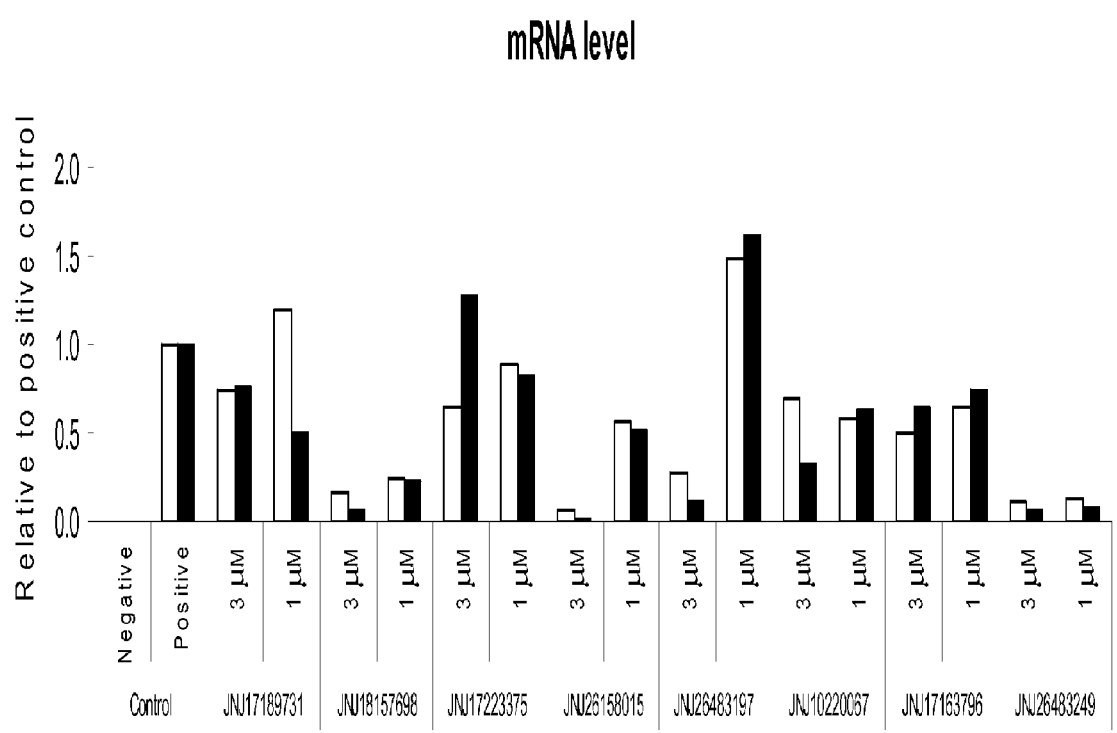
FIG. 14 shows effect of a range of concentrations of the compounds shown on Pdx-1 expression (white bars) and insulin (black bars), as determined by real-time PCR. Cells were treated according to the methods described in Example 10.

Results are shown for eight GSK-3B enzyme inhibitors. Data presented in FIG. 13 from high content analysis show compound effects on cell number (panel A) and insulin intensity (panel B) for the H1 hES cell line where respective data points were averaged from a triplicate set and mined for each parameter from identical fields and wells. Data presented in FIG. 14 from real-time PCR show compound effects for Pdx1 and insulin. In these examples, Pdx1 and insulin expression are indicative of pancreatic endoderm differentiation and generation of hormonal positive cells. Selective GSK3β inhibitor compounds in these assays can substitute for Wnt3a during early stages of cell lineage commitment and can induce and sustain pancreatic beta cell formation during later sequential stages of differentiation, as evident from both insulin immunostaining and real-time PCR.

Example 11

Additive Effects of GSK-3β Enzyme Inhibitors on the Formation of Pancreatic Endocrine Cells It was important to demonstrate that treatment with GSK3β inhibitors could improve pancreatic beta cell differentiation if added during multiple phases of cell fate commitment. A select subset of hits was tested by sequential timed addition to enhance insulin expression associated with pancreatic hormonal positive cells.

Preparation of Cells for Assay: Cell Preparation for Assay:

Pancreatic endoderm cells obtained according to the methods described in Example 9 and 10 (cultured on 96-wellplates) were subsequently subjected to agents that cause the cells to differentiate into pancreatic hormone expressing cells.

Assay for cultures of the H1 human embryonic stem cell line on MATRIGEL™ was initiated as described in Examples 7-9 above by aspirating culture medium from cell monolayers in each well followed by three washes in PBS to remove residual growth factors and serum. For differentiation to definitive endoderm, test volumes (100 μl per well for 96-well plates) were added containing medium with 0.5% FCS and different concentrations of inhibitor compounds with 100 ng/ml Activin A, without Wnt3a. Positive control wells contained the same base medium and 0.5% FCS with 100 ng/ml Activin A and 20 ng/ml Wnt3a (R&D Biosystems) in the absence of test compound. Negative control wells contained the same base medium with 0.5% FCS, in the absence of Activin A, Wnt3a, or test compound. Assay wells were aspirated and fed again with identical concentrations of test compound or control solutions on day 2 of assay. On days 3, 4, and 5, all assay wells were aspirated and fed with DMEM:F12 supplemented with 2% FCS and 100 ng/ml Activin A in the absence of both test compound or Wnt3a. Parallel negative control wells were maintained on days 3, 4, and 5 in DMEM:F12 base medium with 2% FCS. For differentiation to pancreatic endoderm, cells were treated for three days, feeding daily with DMEM:F12 base medium containing 2% FCS with 0.25 μM KAAD cyclopamine (EMD Biosciences) and 20 ng/ml FGF7 (R&D Biosystems). Cells were subsequently treated for four days, feeding daily with DMEM:F12 containing 1% B27 (Invitrogen), 0.25 μM KAAD cyclopamine, 2 μM Retinoic Acid (RA; Sigma-Aldrich) and 20 ng/ml FGF7. Parallel negative control wells were maintained throughout in DMEM:F12 base medium with 2% FCS or 1% B27 and without any other additives. After formation of pancreatic endoderm, cells were treated further for six days duration, feeding alternating days with DMEM:F12 base medium containing 1% B27 with 1 μM DAPT (gamma secretase inhibitor: EMD Biosciences) and 50 ng/ml Exendin 4 (Sigma-Aldrich) and 1 μM TGFbeta R1 inhibitor II (ALK5 inhibitor; EMD Biosciences). During this six day period, GSK3β inhibitors were added back to respective wells, using the same concentration as previous treatment at the initiation of differentiation. Cells were then treated for another three days duration, feeding alternating days with DMEM:F12 base medium containing 1% B27, 50 ng/ml Exendin 4, 50 ng/ml IGF (R&D Biosystems) and 50 ng/ml HGF (R&D Biosystems), and 1 μM TGFbeta R1 inhibitor II (ALK5 inhibitor; EMD Biosciences). During this three day period, GSK3β inhibitors were added back to respective wells, using the same concentration as previous treatment at the initiation of differentiation. Parallel sets of positive control wells were treated in the presence or absence of 20 ng/ml Wnt3a. Parallel negative control wells were maintained throughout in DMEM:F12 base medium with 1% B27 and without any other additives.

Assay Evaluation:

At the end of culture, cells were treated as in Examples 10 above for evaluation by high content analysis.

For high content fluorescence staining, cells in 96-well plates were washed twice with PBS then fixed with 4% paraformaldehyde at room temperature for 20 minutes, washed three times more with PBS, and then permeabilized with 0.5% Triton X-100 for 20 minutes at room temperature. After fixing and permeabilizing, cells were washed again three times with PBS and blocked with 4% chicken serum (Invitrogen) in PBS for 30 minutes at room temperature. Primary antibody (guinea pig anti-swine insulin, cross-reactive with human insulin; DakoCytomation) was diluted 1:500 in 4% goat serum and added to cells for one hour at room temperature. Cells were washed three times with PBS and then stained with Alexa Fluor 488 conjugated secondary antibody (goat anti-guinea pig IgG; Molecular Probes) diluted 1:100 in 4% goat serum. To counterstain nuclei, 2 μg/ml Hoechst 33342 (Invitrogen) was added for ten minutes at room temperature. Cells were washed once with PBS and left in 100 μl/well PBS for imaging.

Cells were imaged using an IN Cell Analyzer 1000 (GE Healthcare) utilizing the 51008bs dichroic for cells stained with Hoechst 33342 and Alexa Fluor 488. Exposure times were optimized using positive control wells and wells stained with secondary antibody alone. Images from 15 fields per well were acquired to compensate for any cell loss during the treatment and staining procedures. Measurements for total cell number and total insulin intensity were obtained for each well using IN Cell Developer Toolbox 1.7 (GE Healthcare) software. Segmentation for the nuclei was determined based on grey-scale levels (baseline range 100-300) and nuclear size. Averages and standard deviations were calculated for each replicate data set. Total insulin protein expression was reported as total intensity or integrated intensity, defined as total fluorescence of the cell times area of the cell. Background was eliminated based on acceptance criteria of grey-scale ranges between 300 to 3000. Total intensity data were normalized by dividing the total intensities for each well by the average total intensity for the Wnt3a/Activin A positive control. Normalized data were calculated for averages and standard deviations for each triplicate set.

Results

Results are shown for eight GSK-3B enzyme inhibitors. Data presented in FIG. 15 from high content analysis show compound effects on cell number (panel A) and insulin intensity (panel B) for the H1 hES cell line, where respective data points were averaged from a triplicate set and mined for each parameter from identical fields and wells. In this example, insulin expression is indicative of differentiation to hormonal positive pancreatic cells. Selective GSK3β inhibitor compounds in these assays can substitute for Wnt3a during early stages of cell lineage commitment and, when added at later stages of differentiation, appear to promote enhanced insulin expression relative to a positive control sample.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

TABLE IA

LIST OF PRIMARY ANTIBODIES USED FOR FACS AND IMMUNOSTAININGANALYSIS.

| Antibody | Supplier | Isotype | Clone |
|---|---|---|---|
| SSEA-1 | Chemicon (CA) | Mouse IgM | MC-480 |
| SSEA-3 | Chemicon (CA) | Mouse IgG3 | MC-631 |
| SSEA-4 | Chemicon (CA) | Rat IgM | MC-813-70 |
| TRA 1-60 | Chemicon (CA) | Mouse IgM | TRA 1-60 |
| TRA 1-81 | Chemicon (CA) | Mouse IgM | TRA 1-81 |
| TRA 1-85 | Chemicon (CA) | Mouse IgG1 | TRA 1-85 |
| AP | R&D Systems | Mouse IgG1 | B4-78 |
| HNF3β | R&D Systems | Goat IgG | |
| PDX1 | Santa Cruz Biotechnology, INC | Goat IgG | A-17 |
| GATA4 | R&D Systems | Goat IgG | |
| Sox 17 | R&D Systems | Goat IgG | |
| CD 9 | BD | Mouse IgG1 | M-L13 |

TABLE IB

LIST OF SECONDARY CONJUGATED ANTIBODIES USED FOR FACS AND IMMUNOSTAININGANALYSIS.

| Secondary Conjugated Antibody | Supplier | Dilution |
|---|---|---|
| Goat Anti-Mouse IgG APC conjugated | Jackson ImmunoResearch (PA) | 1:200 |
| Goat Anti-Mouse IgG PE conjugated | Jackson ImmunoResearch (PA) | 1:200 |
| Donkey anti-rabbit PE or - APC conjugated | Jackson ImmunoResearch (PA) | 1:200 |
| Donkey anti-goat PE or - APC conjugated | Jackson ImmunoResearch (PA) | 1:200 |
| Goat anti-mouse IgM PE | SouthernBiotech (AL) | 1:200 |
| Goat anti-Rat IgM PE | SouthernBiotech (AL) | 1:200 |
| Goat anti-mouse IgG3 PE | SouthernBiotech (AL) | 1:200 |

TABLE II

EFFECTS OF INHIBITORS OF GSK-3B ENZYME ACTIVITY ON THE VIABILITY OF CELLS EXPRESSING PLURIPOTENCY MARKERS.

| | Raw data (duplicate) | | Average | S.D. | % CV | % Control |
|---|---|---|---|---|---|---|
| JNJ5226780 | 0.785 | 0.790 | 0.788 | 0.00382 | 0.48 | 94.0 |
| JNJ10179026 | 0.148 | 0.152 | 0.150 | 0.00247 | 1.65 | 4.8 |
| JNJ17154215 | 0.427 | 0.462 | 0.444 | 0.02496 | 5.62 | 46.0 |
| JNJ17205955 | 0.643 | 0.638 | 0.641 | 0.00368 | 0.57 | 73.5 |
| JNJ180125 | 0.762 | 0.762 | 0.762 | 0.00007 | 0.01 | 90.4 |
| JNJ18157646 | 0.850 | 0.824 | 0.837 | 0.01824 | 2.18 | 101.0 |
| JNJ19370026 | 0.911 | 0.884 | 0.898 | 0.01881 | 2.10 | 109.5 |
| JNJ19567340 | 0.723 | 0.743 | 0.733 | 0.01421 | 1.94 | 86.4 |
| JNJ7830433 | 0.161 | 0.169 | 0.165 | 0.00559 | 3.39 | 6.9 |
| JNJ10179130 | 0.767 | 0.789 | 0.778 | 0.01556 | 2.00 | 92.6 |
| JNJ17154215 | 0.512 | 0.555 | 0.533 | 0.03048 | 5.72 | 58.4 |
| JNJ17205955 | 0.282 | 0.293 | 0.288 | 0.00792 | 2.75 | 24.1 |
| JNJ18014061 | 0.764 | 0.723 | 0.743 | 0.02892 | 3.89 | 87.9 |
| JNJ18157698 | 0.853 | 0.858 | 0.855 | 0.00382 | 0.45 | 103.5 |
| JNJ19376240 | 0.832 | 0.837 | 0.834 | 0.00361 | 0.43 | 100.6 |
| JNJ19567405 | 0.726 | 0.725 | 0.725 | 0.00042 | 0.06 | 85.3 |
| JNJ8706646 | 0.132 | 0.137 | 0.134 | 0.00368 | 2.74 | 2.6 |
| JNJ10182562 | 0.797 | 0.793 | 0.795 | 0.00346 | 0.44 | 95.1 |
| JNJ17157659 | 0.776 | 0.787 | 0.782 | 0.00792 | 1.01 | 93.2 |
| JNJ17205994 | 0.164 | 0.148 | 0.156 | 0.01131 | 7.24 | 5.6 |
| JNJ18014074 | 0.475 | 0.383 | 0.429 | 0.06548 | 15.26 | 43.8 |
| JNJ18157698 | 0.823 | 0.774 | 0.798 | 0.03444 | 4.31 | 95.6 |
| JNJ19386042 | 0.781 | 0.729 | 0.755 | 0.03649 | 4.83 | 89.5 |
| JNJ19573541 | 0.143 | 0.149 | 0.146 | 0.00396 | 2.72 | 4.2 |
| JNJ8710481 | 0.716 | 0.716 | 0.716 | 0.00014 | 0.02 | 84.1 |
| JNJ10182562 | 0.804 | 0.802 | 0.803 | 0.00148 | 0.18 | 96.2 |
| JNJ17163042 | 0.900 | 0.877 | 0.888 | 0.01626 | 1.83 | 108.2 |
| JNJ17226703 | 0.824 | 0.799 | 0.812 | 0.01725 | 2.13 | 97.4 |
| JNJ18018338 | 0.744 | 0.819 | 0.781 | 0.05261 | 6.73 | 93.2 |
| JNJ18157711 | 0.952 | 0.966 | 0.959 | 0.00933 | 0.97 | 118.1 |
| JNJ19410833 | 0.952 | 0.919 | 0.935 | 0.02277 | 2.43 | 114.8 |
| JNJ19574867 | 0.776 | 0.777 | 0.777 | 0.00042 | 0.05 | 92.5 |
| JNJ8710481 | 0.691 | 0.617 | 0.654 | 0.05254 | 8.03 | 75.4 |
| JNJ10184655 | 0.162 | 0.134 | 0.148 | 0.02022 | 13.66 | 4.5 |
| JNJ10166565 | 0.791 | 0.608 | 0.700 | 0.12947 | 18.50 | 81.8 |
| JNJ17982133 | 0.153 | 0.129 | 0.141 | 0.01676 | 11.87 | 3.5 |
| JNJ18018351 | 0.731 | 0.585 | 0.658 | 0.10317 | 15.68 | 75.9 |
| DMSO | 0.789 | 0.700 | 0.744 | 0.06279 | 8.44 | 88.0 |
| JNJ19410859 | 0.909 | 0.675 | 0.792 | 0.16546 | 20.88 | 94.7 |
| JNJ19574880 | 0.164 | 0.151 | 0.157 | 0.00926 | 5.89 | 5.8 |
| JNJ10148307 | 0.706 | 0.672 | 0.689 | 0.02404 | 3.49 | 83.9 |
| JNJ10222784 | 0.641 | 0.601 | 0.621 | 0.02878 | 4.63 | 73.7 |
| JNJ17174664 | 0.882 | 0.748 | 0.815 | 0.09504 | 11.66 | 102.5 |
| JNJ17989049 | 0.822 | 0.802 | 0.812 | 0.01400 | 1.72 | 102.1 |
| JNJ18047991 | 0.777 | 0.764 | 0.771 | 0.00919 | 1.19 | 95.9 |
| DMSO | 0.798 | 0.771 | 0.785 | 0.01916 | 2.44 | 98.0 |
| JNJ19410872 | 0.791 | 0.789 | 0.790 | 0.00134 | 0.17 | 98.7 |
| JNJ20948798 | 0.628 | 0.640 | 0.634 | 0.00806 | 1.27 | 75.6 |
| JNJ10164830 | 0.149 | 0.135 | 0.142 | 0.00969 | 6.81 | 2.7 |
| JNJ10222927 | 0.803 | 0.782 | 0.792 | 0.01492 | 1.88 | 99.1 |

TABLE II-continued

EFFECTS OF INHIBITORS OF GSK-3B ENZYME ACTIVITY ON THE VIABILITY OF CELLS EXPRESSING PLURIPOTENCY MARKERS.

| | Raw data (duplicate) | | Average | S.D. | % CV | % Control |
|---|---|---|---|---|---|---|
| JNJ17187027 | 0.125 | 0.129 | 0.127 | 0.00318 | 2.51 | 0.4 |
| JNJ17994873 | 0.315 | 0.542 | 0.428 | 0.15995 | 37.34 | 45.2 |
| JNJ18055726 | 0.820 | 0.748 | 0.784 | 0.05091 | 6.49 | 97.9 |
| JNJ18157711 | 0.154 | 0.165 | 0.160 | 0.00806 | 5.05 | 5.3 |
| JNJ19558929 | 0.737 | 0.730 | 0.734 | 0.00481 | 0.66 | 90.4 |
| JNJ21192730 | 0.659 | 0.647 | 0.653 | 0.00813 | 1.25 | 78.5 |
| JNJ10164895 | 0.165 | 0.154 | 0.159 | 0.00785 | 4.93 | 5.2 |
| JNJ10231273 | 0.637 | 0.554 | 0.595 | 0.05876 | 9.87 | 69.9 |
| JNJ17187053 | 0.684 | 0.588 | 0.636 | 0.06809 | 10.71 | 76.0 |
| JNJ17994899 | 0.750 | 0.624 | 0.687 | 0.08945 | 13.02 | 83.5 |
| JNJ18077800 | 0.678 | 0.618 | 0.648 | 0.04285 | 6.61 | 77.8 |
| JNJ19363357 | 0.777 | 0.667 | 0.722 | 0.07757 | 10.74 | 88.7 |
| DMSO | 0.799 | 0.649 | 0.724 | 0.10564 | 14.59 | 89.0 |
| JNJ21194667 | 0.648 | 0.625 | 0.636 | 0.01662 | 2.61 | 76.0 |
| JNJ10172058 | 0.601 | 0.620 | 0.611 | 0.01308 | 2.14 | 72.2 |
| JNJ10259847 | 0.695 | 0.702 | 0.698 | 0.00552 | 0.79 | 85.2 |
| JNJ17193774 | 0.568 | 0.709 | 0.639 | 0.09956 | 15.59 | 76.4 |
| JNJ17994912 | 0.623 | 0.765 | 0.694 | 0.10041 | 14.46 | 84.6 |
| JNJ18157074 | 0.758 | 0.762 | 0.760 | 0.00297 | 0.39 | 94.3 |
| JNJ19369233 | 0.487 | 0.434 | 0.461 | 0.03769 | 8.18 | 49.9 |
| JNJ19567314 | 0.690 | 0.686 | 0.688 | 0.00262 | 0.38 | 83.7 |
| JNJ21196227 | 0.535 | 0.550 | 0.543 | 0.01089 | 2.01 | 62.1 |
| JNJ10178727 | 0.743 | 0.638 | 0.691 | 0.07446 | 10.78 | 84.1 |
| JNJ10259847 | 0.694 | 0.603 | 0.649 | 0.06449 | 9.94 | 77.8 |
| JNJ17200976 | 0.160 | 0.186 | 0.173 | 0.01824 | 10.56 | 7.2 |
| JNJ17994925 | 0.662 | 0.566 | 0.614 | 0.06788 | 11.05 | 72.7 |
| JNJ18157087 | 0.600 | 0.514 | 0.557 | 0.06102 | 10.96 | 64.2 |
| JNJ19369246 | 0.685 | 0.524 | 0.605 | 0.11427 | 18.90 | 71.3 |
| JNJ19567327 | 0.731 | 0.525 | 0.628 | 0.14552 | 23.18 | 74.7 |
| JNJ24843611 | 0.715 | 0.596 | 0.655 | 0.08436 | 12.87 | 78.8 |
| JNJ24843611 | 0.592 | 0.572 | 0.582 | 0.01393 | 2.39 | 70.0 |
| JNJ25758785 | 0.614 | 0.611 | 0.613 | 0.00177 | 0.29 | 74.6 |
| JNJ26064571 | 0.766 | 0.849 | 0.807 | 0.05869 | 7.27 | 104.3 |
| JNJ26130403 | 0.830 | 0.813 | 0.822 | 0.01195 | 1.45 | 106.5 |
| JNJ26170794 | 0.727 | 0.730 | 0.728 | 0.00198 | 0.27 | 92.2 |
| JNJ26241774 | 0.713 | 0.836 | 0.774 | 0.08733 | 11.28 | 99.3 |
| JNJ26367991 | 0.726 | 0.719 | 0.722 | 0.00523 | 0.72 | 91.3 |
| JNJ26483310 | 0.646 | 0.681 | 0.663 | 0.02510 | 3.78 | 82.4 |
| JNJ24326185 | 0.651 | 0.649 | 0.650 | 0.00120 | 0.19 | 80.3 |
| JNJ25758850 | 0.642 | 0.622 | 0.632 | 0.01407 | 2.23 | 77.5 |
| JNJ26067626 | 0.843 | 0.672 | 0.758 | 0.12099 | 15.97 | 96.7 |
| JNJ26134771 | 0.734 | 0.815 | 0.774 | 0.05728 | 7.40 | 99.3 |
| JNJ26170820 | 0.823 | 0.743 | 0.783 | 0.05699 | 7.28 | 100.6 |
| JNJ26241917 | 0.871 | 0.874 | 0.872 | 0.00219 | 0.25 | 114.2 |
| JNJ26714220 | 0.652 | 0.642 | 0.647 | 0.00721 | 1.12 | 79.8 |
| JNJ26483223 | 0.617 | 0.633 | 0.625 | 0.01174 | 1.88 | 76.5 |
| JNJ24843572 | 0.657 | 0.655 | 0.656 | 0.00134 | 0.20 | 81.2 |
| JNJ25758863 | 0.684 | 0.809 | 0.746 | 0.08803 | 11.80 | 95.0 |
| JNJ26067652 | 0.901 | 0.735 | 0.818 | 0.11731 | 14.34 | 106.0 |
| JNJ26150202 | 0.791 | 0.768 | 0.779 | 0.01591 | 2.04 | 100.1 |
| JNJ26170833 | 0.948 | 0.764 | 0.856 | 0.12982 | 15.17 | 111.7 |
| JNJ26243204 | 0.821 | 0.608 | 0.714 | 0.15033 | 21.05 | 90.1 |
| JNJ26399906 | 0.745 | 0.685 | 0.715 | 0.04243 | 5.94 | 90.2 |
| JNJ26483236 | 0.624 | 0.618 | 0.621 | 0.00417 | 0.67 | 76.0 |
| JNJ24843585 | 0.652 | 0.624 | 0.638 | 0.01916 | 3.00 | 78.5 |
| JNJ25873419 | 0.773 | 0.662 | 0.718 | 0.07792 | 10.86 | 90.6 |
| JNJ26069901 | 0.856 | 0.834 | 0.845 | 0.01570 | 1.86 | 110.1 |
| JNJ26153647 | 0.828 | 0.800 | 0.814 | 0.02008 | 2.47 | 105.4 |
| JNJ26177086 | 0.821 | 0.841 | 0.831 | 0.01421 | 1.71 | 108.0 |
| JNJ26247143 | 0.816 | 0.787 | 0.802 | 0.02072 | 2.58 | 103.5 |
| JNJ26399906 | 0.744 | 0.737 | 0.741 | 0.00453 | 0.61 | 94.1 |
| JNJ26483249 | 0.699 | 0.679 | 0.689 | 0.01464 | 2.12 | 86.3 |
| JNJ25753520 | 0.186 | 0.208 | 0.197 | 0.01541 | 7.83 | 11.3 |
| JNJ25887537 | 0.665 | 0.699 | 0.682 | 0.02432 | 3.57 | 85.2 |
| JNJ26077883 | 0.810 | 0.683 | 0.746 | 0.09030 | 12.10 | 95.0 |
| JNJ26158015 | 0.141 | 0.162 | 0.151 | 0.01506 | 9.95 | 4.3 |
| DMSO | 0.784 | 0.605 | 0.695 | 0.12671 | 18.25 | 87.1 |
| JNJ26248729 | 0.726 | 0.590 | 0.658 | 0.09624 | 14.63 | 81.5 |
| JNJ26399945 | 0.635 | 0.620 | 0.628 | 0.01068 | 1.70 | 76.9 |
| JNJ26483249 | 0.697 | 0.695 | 0.696 | 0.00113 | 0.16 | 87.3 |
| JNJ25753403 | 0.154 | 0.153 | 0.154 | 0.00042 | 0.28 | 4.5 |
| JNJ25900641 | 0.616 | 0.645 | 0.630 | 0.02072 | 3.29 | 82.1 |
| JNJ22791671 | 0.909 | 0.830 | 0.869 | 0.05614 | 6.46 | 121.0 |
| JNJ26158054 | 0.150 | 0.150 | 0.150 | 0.00028 | 0.19 | 3.9 |
| JNJ26177762 | 0.981 | 1.056 | 1.018 | 0.05303 | 5.21 | 145.3 |
| JNJ26261105 | 0.166 | 0.189 | 0.177 | 0.01626 | 9.19 | 8.3 |
| JNJ26399971 | 0.718 | 0.451 | 0.584 | 0.18887 | 32.34 | 74.6 |
| JNJ26483262 | 0.652 | 0.647 | 0.649 | 0.00389 | 0.60 | 85.2 |
| JNJ25757173 | 0.503 | 0.529 | 0.516 | 0.01860 | 3.61 | 63.5 |
| JNJ25900654 | 0.603 | 0.609 | 0.606 | 0.00424 | 0.70 | 78.1 |
| JNJ26116922 | 0.856 | 0.793 | 0.824 | 0.04419 | 5.36 | 113.7 |
| JNJ26893438 | 0.883 | 0.848 | 0.866 | 0.02503 | 2.89 | 120.5 |
| JNJ26184457 | 0.779 | 0.784 | 0.781 | 0.00368 | 0.47 | 106.7 |
| JNJ26361712 | 0.892 | 0.914 | 0.903 | 0.01591 | 1.76 | 126.6 |
| JNJ26399984 | 0.544 | 0.537 | 0.540 | 0.00460 | 0.85 | 67.5 |
| JNJ26511901 | 0.532 | 0.682 | 0.607 | 0.10543 | 17.37 | 78.3 |
| JNJ25757173 | 0.665 | 0.645 | 0.655 | 0.01400 | 2.14 | 86.1 |
| JNJ25900706 | 0.676 | 0.677 | 0.677 | 0.00035 | 0.05 | 89.7 |
| JNJ26120601 | 0.935 | 0.807 | 0.871 | 0.09115 | 10.47 | 121.3 |
| JNJ26158093 | 0.916 | 0.859 | 0.887 | 0.03981 | 4.49 | 124.0 |
| JNJ26219050 | 0.907 | 0.891 | 0.899 | 0.01124 | 1.25 | 125.9 |
| JNJ26361725 | 0.909 | 0.896 | 0.902 | 0.00919 | 1.02 | 126.4 |
| JNJ26399997 | 0.682 | 0.797 | 0.740 | 0.08118 | 10.98 | 99.9 |
| JNJ26511927 | 0.679 | 0.644 | 0.661 | 0.02510 | 3.80 | 87.2 |
| JNJ25757238 | 0.300 | 0.223 | 0.261 | 0.05452 | 20.88 | 22.0 |
| JNJ26047723 | 0.183 | 0.175 | 0.179 | 0.00573 | 3.20 | 8.6 |
| JNJ26120614 | 0.741 | 0.728 | 0.734 | 0.00884 | 1.20 | 99.1 |
| JNJ26158106 | 0.935 | 0.906 | 0.921 | 0.02051 | 2.23 | 129.4 |
| JNJ26219063 | 0.131 | 0.128 | 0.129 | 0.00212 | 1.64 | 0.5 |
| JNJ26366730 | 0.138 | 0.137 | 0.138 | 0.00092 | 0.67 | 1.9 |
| JNJ26400049 | 0.241 | 0.227 | 0.234 | 0.01032 | 4.41 | 17.6 |
| JNJ26941226 | 0.604 | 0.639 | 0.622 | 0.02475 | 3.98 | 80.7 |
| JNJ25758707 | 0.247 | 0.182 | 0.215 | 0.04617 | 21.52 | 14.4 |
| JNJ26054912 | 0.659 | 0.634 | 0.647 | 0.01718 | 2.66 | 84.8 |
| JNJ26128726 | 0.758 | 0.575 | 0.667 | 0.12961 | 19.44 | 88.1 |
| JNJ26161343 | 0.166 | 0.170 | 0.168 | 0.00276 | 1.64 | 6.9 |
| JNJ26220454 | 0.651 | 0.559 | 0.605 | 0.06541 | 10.81 | 78.0 |
| JNJ26367991 | 0.803 | 0.694 | 0.748 | 0.07693 | 10.28 | 101.3 |
| JNJ26483197 | 0.823 | 0.634 | 0.728 | 0.13378 | 18.37 | 98.1 |
| JNJ26511953 | 0.624 | 0.618 | 0.621 | 0.00431 | 0.69 | 80.6 |
| RWJ351001 | 0.639 | 0.603 | 0.621 | 0.02553 | 4.11 | 73.6 |
| RWJ382867 | 0.143 | 0.149 | 0.146 | 0.00403 | 2.76 | 2.9 |
| RWJ682205 | 0.817 | 0.818 | 0.818 | 0.00071 | 0.09 | 102.8 |
| RWJ665862 | 0.742 | 0.752 | 0.747 | 0.00679 | 0.91 | 92.2 |
| RWJ670804 | 0.856 | 0.905 | 0.881 | 0.03479 | 3.95 | 112.1 |
| RWJ673829 | 0.650 | 0.576 | 0.613 | 0.05268 | 8.59 | 72.4 |
| RWJ675260 | 0.768 | 0.724 | 0.746 | 0.03097 | 4.15 | 92.2 |
| RWJ675946 | 0.556 | 0.549 | 0.553 | 0.00537 | 0.97 | 63.4 |
| RWJ351958 | 0.227 | 0.242 | 0.235 | 0.01103 | 4.70 | 16.1 |
| RWJ395477 | 0.634 | 0.663 | 0.649 | 0.02044 | 3.15 | 77.7 |
| RWJ447228 | 0.141 | 0.128 | 0.135 | 0.00919 | 6.83 | 1.3 |
| RWJ666167 | 0.847 | 0.832 | 0.840 | 0.01110 | 1.32 | 106.0 |
| RWJ670908 | 0.803 | 0.845 | 0.824 | 0.02998 | 3.64 | 103.7 |
| RWJ673830 | 0.860 | 0.860 | 0.860 | 0.00035 | 0.04 | 109.1 |
| RWJ675261 | 0.528 | 0.497 | 0.513 | 0.02227 | 4.34 | 57.5 |
| RWJ675948 | 0.683 | 0.688 | 0.686 | 0.00332 | 0.48 | 83.1 |
| RWJ447228 | 0.611 | 0.628 | 0.620 | 0.01202 | 1.94 | 73.3 |
| RWJ414342 | 0.719 | 0.749 | 0.734 | 0.02143 | 2.92 | 90.3 |
| RWJ553709 | 0.916 | 0.838 | 0.877 | 0.05487 | 6.26 | 111.6 |
| RWJ666168 | 0.771 | 0.740 | 0.755 | 0.02178 | 2.88 | 93.5 |
| RWJ670984 | 0.820 | 0.852 | 0.836 | 0.02305 | 2.76 | 105.5 |
| RWJ674239 | 0.971 | 0.913 | 0.942 | 0.04137 | 4.39 | 121.2 |
| RWJ675430 | 0.839 | 0.743 | 0.791 | 0.06746 | 8.53 | 98.8 |
| RWJ676061 | 0.562 | 0.527 | 0.544 | 0.02440 | 4.48 | 62.2 |
| RWJ352190 | 0.678 | 0.661 | 0.670 | 0.01195 | 1.78 | 80.8 |
| RWJ414984 | 0.722 | 0.713 | 0.717 | 0.00658 | 0.92 | 87.9 |
| RWJ659780 | 0.802 | 0.801 | 0.802 | 0.00106 | 0.13 | 100.4 |
| RWJ666205 | 0.854 | 0.857 | 0.855 | 0.00205 | 0.24 | 108.4 |
| RWJ671232 | 0.767 | 0.798 | 0.782 | 0.02157 | 2.76 | 97.5 |
| RWJ674240 | 0.789 | 0.776 | 0.782 | 0.00870 | 1.11 | 97.5 |
| RWJ675266 | 0.720 | 0.709 | 0.714 | 0.00764 | 1.07 | 87.4 |
| RWJ676085 | 0.641 | 0.618 | 0.630 | 0.01619 | 2.57 | 74.9 |
| RWJ352244 | 0.603 | 0.584 | 0.593 | 0.01372 | 2.31 | 69.4 |
| RWJ425264 | 0.135 | 0.158 | 0.146 | 0.01633 | 11.18 | 3.0 |
| RWJ662440 | 0.792 | 0.572 | 0.682 | 0.15563 | 22.83 | 82.6 |
| RWJ666213 | 0.752 | 0.593 | 0.673 | 0.11292 | 16.79 | 81.2 |

TABLE II-continued

EFFECTS OF INHIBITORS OF GSK-3B ENZYME ACTIVITY ON THE VIABILITY OF CELLS EXPRESSING PLURIPOTENCY MARKERS.

|  | Raw data (duplicate) | | Average | S.D. | % CV | % Control |
|---|---|---|---|---|---|---|
| RWJ672667 | 0.805 | 0.598 | 0.702 | 0.14644 | 20.87 | 85.5 |
| RWJ674241 | 0.599 | 0.504 | 0.552 | 0.06682 | 12.11 | 63.2 |
| RWJ675366 | 0.714 | 0.593 | 0.654 | 0.08549 | 13.08 | 78.4 |
| RWJ676137 | 0.699 | 0.698 | 0.698 | 0.00099 | 0.14 | 85.0 |
| RWJ352628 | 0.690 | 0.674 | 0.682 | 0.01131 | 1.66 | 83.3 |
| RWJ425268 | 0.616 | 0.634 | 0.625 | 0.01301 | 2.08 | 74.8 |
| RWJ663860 | 0.809 | 0.817 | 0.813 | 0.00552 | 0.68 | 103.0 |
| RWJ667045 | 0.128 | 0.133 | 0.131 | 0.00361 | 2.76 | 0.7 |
| RWJ672932 | 0.821 | 0.811 | 0.816 | 0.00721 | 0.88 | 103.4 |
| RWJ674320 | 0.456 | 0.474 | 0.465 | 0.01223 | 2.63 | 50.8 |
| RWJ675369 | 0.762 | 0.766 | 0.764 | 0.00304 | 0.40 | 95.7 |
| RWJ676139 | 0.680 | 0.663 | 0.671 | 0.01195 | 1.78 | 81.8 |
| RWJ353258 | 0.615 | 0.635 | 0.625 | 0.01400 | 2.24 | 74.8 |
| RWJ355923 | 0.681 | 0.698 | 0.689 | 0.01266 | 1.84 | 84.5 |
| RWJ664545 | 0.830 | 0.807 | 0.818 | 0.01584 | 1.94 | 103.8 |
| RWJ667046 | 0.869 | 0.849 | 0.859 | 0.01442 | 1.68 | 109.9 |
| RWJ672934 | 0.821 | 0.841 | 0.831 | 0.01428 | 1.72 | 105.7 |
| RWJ674817 | 0.819 | 0.840 | 0.830 | 0.01485 | 1.79 | 105.5 |
| RWJ675430 | 0.795 | 0.793 | 0.794 | 0.00078 | 0.10 | 100.1 |
| RWJ676431 | 0.640 | 0.636 | 0.638 | 0.00283 | 0.44 | 76.7 |
| RWJ355131 | 0.610 | 0.628 | 0.619 | 0.01266 | 2.05 | 73.9 |
| RWJ425271 | 0.143 | 0.144 | 0.144 | 0.00035 | 0.25 | 2.6 |
| RWJ353709 | 0.804 | 0.903 | 0.853 | 0.07000 | 8.20 | 109.0 |
| RWJ667069 | 0.918 | 0.854 | 0.886 | 0.04483 | 5.06 | 113.9 |
| RWJ673313 | 0.105 | 1.080 | 0.593 | 0.68971 | 116.37 | 70.0 |
| RWJ674855 | 0.877 | 0.860 | 0.868 | 0.01209 | 1.39 | 111.3 |
| RWJ675578 | 0.808 | 0.695 | 0.751 | 0.07941 | 10.57 | 93.8 |
| RWJ676432 | 0.720 | 0.697 | 0.709 | 0.01648 | 2.33 | 87.3 |
| RWJ355923 | 0.636 | 0.621 | 0.629 | 0.01054 | 1.68 | 75.4 |
| RWJ425348 | 0.640 | 0.634 | 0.637 | 0.00474 | 0.74 | 76.6 |
| RWJ665436 | 0.833 | 0.833 | 0.833 | 0.00000 | 0.00 | 106.0 |
| RWJ669182 | 0.887 | 0.846 | 0.866 | 0.02934 | 3.39 | 111.0 |
| RWJ673515 | 0.845 | 0.877 | 0.861 | 0.02326 | 2.70 | 110.2 |
| RWJ674855 | 0.794 | 0.784 | 0.789 | 0.00686 | 0.87 | 99.4 |
| RWJ675605 | 0.770 | 0.786 | 0.778 | 0.01138 | 1.46 | 97.8 |
| RWJ67657 | 0.629 | 0.659 | 0.644 | 0.02128 | 3.30 | 77.7 |
| RWJ356205 | 0.584 | 0.558 | 0.571 | 0.01817 | 3.18 | 66.8 |
| RWJ445224 | 0.707 | 0.679 | 0.693 | 0.01987 | 2.87 | 85.0 |
| RWJ665588 | 0.727 | 0.578 | 0.652 | 0.10536 | 16.15 | 78.9 |
| RWJ669327 | 0.742 | 0.629 | 0.685 | 0.07969 | 11.63 | 83.8 |
| DMSO | 0.653 | 0.507 | 0.580 | 0.10310 | 17.78 | 68.0 |
| RWJ675104 | 0.722 | 0.568 | 0.645 | 0.10904 | 16.90 | 77.9 |
| RWJ675881 | 0.643 | 0.581 | 0.612 | 0.04384 | 7.16 | 72.9 |
| RWJ676639 | 0.608 | 0.590 | 0.599 | 0.01245 | 2.08 | 70.9 |
| JNJ26511966 | 0.597 | 0.610 | 0.603 | 0.00926 | 1.54 | 71.2 |
| JNJ26511979 | 0.687 | 0.668 | 0.677 | 0.01336 | 1.97 | 82.4 |
| JNJ26512005 | 0.840 | 0.832 | 0.836 | 0.00594 | 0.71 | 106.1 |
| JNJ26533065 | 0.831 | 0.822 | 0.826 | 0.00587 | 0.71 | 104.7 |
| JNJ26533091 | 0.863 | 0.856 | 0.860 | 0.00509 | 0.59 | 109.7 |
| JNJ26533104 | 0.886 | 0.802 | 0.844 | 0.05954 | 7.05 | 107.3 |
| JNJ26533156 | 0.753 | 0.687 | 0.720 | 0.04660 | 6.47 | 88.8 |
| JNJ26714181 | 0.455 | 0.463 | 0.459 | 0.00587 | 1.28 | 49.6 |
| JNJ26714194 | 0.668 | 0.678 | 0.673 | 0.00764 | 1.13 | 81.7 |
| JNJ26714207 | 0.181 | 0.171 | 0.176 | 0.00658 | 3.74 | 7.2 |
| JNJ26714220 | 0.832 | 0.842 | 0.837 | 0.00658 | 0.79 | 106.3 |
| JNJ26875563 | 0.795 | 0.802 | 0.798 | 0.00445 | 0.56 | 100.5 |
| JNJ22791671 | 0.157 | 0.140 | 0.148 | 0.01202 | 8.11 | 3.0 |
| JNJ26893438 | 0.153 | 0.153 | 0.153 | 0.00035 | 0.23 | 3.7 |
| JNJ26941226 | 0.168 | 0.154 | 0.161 | 0.00969 | 6.02 | 4.9 |
| JNJ28572128 | 0.670 | 0.641 | 0.655 | 0.02079 | 3.17 | 79.1 |
| RWJ67694 | 0.706 | 0.679 | 0.693 | 0.01888 | 2.73 | 84.7 |
| RWJ676940 | 0.788 | 0.666 | 0.727 | 0.08627 | 11.86 | 89.8 |
| RWJ677545 | 0.879 | 0.785 | 0.832 | 0.06640 | 7.98 | 105.6 |
| RWJ678986 | 0.168 | 0.176 | 0.172 | 0.00537 | 3.13 | 6.6 |
| RWJ680665 | 0.946 | 0.848 | 0.897 | 0.06972 | 7.77 | 115.3 |
| RWJ680667 | 0.187 | 0.202 | 0.194 | 0.01089 | 5.61 | 9.9 |
| RWJ680668 | 0.906 | 0.688 | 0.797 | 0.15394 | 19.31 | 100.3 |
| RWJ680669 | 0.715 | 0.674 | 0.694 | 0.02850 | 4.10 | 84.9 |
| RWJ680858 | 0.695 | 0.700 | 0.697 | 0.00339 | 0.49 | 85.3 |
| RWJ680858 | 0.665 | 0.631 | 0.648 | 0.02369 | 3.66 | 78.0 |
| RWJ680879 | 0.590 | 0.613 | 0.601 | 0.01655 | 2.75 | 71.0 |
| RWJ680885 | 0.681 | 0.687 | 0.684 | 0.00382 | 0.56 | 83.3 |
| RWJ680991 | 0.829 | 0.821 | 0.825 | 0.00530 | 0.64 | 104.5 |
| RWJ680992 | 0.822 | 0.790 | 0.806 | 0.02270 | 2.82 | 101.6 |
| RWJ680993 | 0.671 | 0.684 | 0.677 | 0.00912 | 1.35 | 82.3 |
| RWJ681140 | 0.686 | 0.668 | 0.677 | 0.01266 | 1.87 | 82.3 |
| RWJ681142 | 0.212 | 0.197 | 0.204 | 0.01047 | 5.12 | 11.5 |
| RWJ681146 | 0.666 | 0.666 | 0.666 | 0.00007 | 0.01 | 80.7 |
| RWJ681945 | 0.736 | 0.656 | 0.696 | 0.05643 | 8.11 | 85.1 |
| RWJ68198 | 0.726 | 0.610 | 0.668 | 0.08217 | 12.30 | 81.0 |
| JNJ28850601 | 0.303 | 0.310 | 0.306 | 0.00488 | 1.59 | 26.7 |
| DMSO | 0.786 | 0.659 | 0.722 | 0.09001 | 12.46 | 89.1 |
| DMSO | 0.673 | 0.649 | 0.661 | 0.01676 | 2.53 | 79.9 |
| DMSO | 0.701 | 0.686 | 0.693 | 0.01011 | 1.46 | 84.8 |

TABLE III

EFFECTS OF INHIBITORS OF GSK-3B ENZYME ACTIVITY ON THE VIABILITY OF CELLS EXPRESSING PLURIPOTENCY MARKERS.

|  | cmpd conc (uM) | Raw data (duplicate) | | Average | S.D. | % CV | % Control |
|---|---|---|---|---|---|---|---|
| EXPRES 01 medium |  | 0.6379 | 0.6180 | 0.6280 | 0.0141 | 2.2 | 74.6 |
| no treatment |  | 0.7412 | 0.7038 | 0.7225 | 0.0264 | 3.7 | 88.7 |
| AA only |  | 0.7674 | 0.8047 | 0.7861 | 0.0264 | 3.4 | 98.3 |
| AA + Wnt3a |  | 0.7754 | 0.8200 | 0.7977 | 0.0315 | 4.0 | 100.0 |
| JNJ26512005 | 10 | 0.1412 | 0.1515 | 0.1464 | 0.0073 | 5.0 | 2.4 |
| JNJ26512005 | 5 | 0.1501 | 0.1444 | 0.1473 | 0.0040 | 2.7 | 2.5 |
| JNJ26512005 | 2.5 | 0.1541 | 0.4254 | 0.2898 | 0.1918 | 66.2 | 23.9 |
| JNJ26533065 | 10 | 0.1272 | 0.1282 | 0.1277 | 0.0007 | 0.6 | −0.4 |
| JNJ26533065 | 5 | 0.5862 | 0.5880 | 0.5871 | 0.0013 | 0.2 | 68.4 |
| JNJ26533065 | 2.5 | 0.7613 | 0.7603 | 0.7608 | 0.0007 | 0.1 | 94.5 |
| JNJ26533156 | 10 | 0.1481 | 0.1592 | 0.1537 | 0.0078 | 5.1 | 3.5 |
| JNJ26533156 | 5 | 0.1479 | 0.1639 | 0.1559 | 0.0113 | 7.3 | 3.8 |
| JNJ26533156 | 2.5 | 0.2861 | 0.2477 | 0.2669 | 0.0272 | 10.2 | 20.4 |
| JNJ26714194 | 10 | 0.2092 | 0.2426 | 0.2259 | 0.0236 | 10.5 | 14.3 |
| JNJ26714194 | 5 | 0.6815 | 0.7128 | 0.6972 | 0.0221 | 3.2 | 84.9 |
| JNJ26714194 | 2.5 | 0.7389 | 0.7870 | 0.7630 | 0.0340 | 4.5 | 94.8 |
| JNJ26150202 | 10 | 0.1381 | 0.1398 | 0.1390 | 0.0012 | 0.9 | 1.3 |
| JNJ26150202 | 5 | 0.7826 | 0.7578 | 0.7702 | 0.0175 | 2.3 | 95.9 |
| JNJ26150202 | 2.5 | 0.8231 | 0.7742 | 0.7987 | 0.0346 | 4.3 | 100.1 |

TABLE III-continued

EFFECTS OF INHIBITORS OF GSK-3B ENZYME ACTIVITY ON
THE VIABILITY OF CELLS EXPRESSING PLURIPOTENCY MARKERS.

|  | cmpd conc (uM) | Raw data (duplicate) | | Average | S.D. | % CV | % Control |
|---|---|---|---|---|---|---|---|
| JNJ26158015 | 10 | 0.1352 | 0.1326 | 0.1339 | 0.0018 | 1.4 | 0.5 |
| JNJ26158015 | 5 | 0.2632 | 0.2604 | 0.2618 | 0.0020 | 0.8 | 19.7 |
| JNJ26158015 | 2.5 | 0.4160 | 0.5314 | 0.4737 | 0.0816 | 17.2 | 51.4 |
| RWJ670804 | 10 | 0.4447 | 0.4791 | 0.4619 | 0.0243 | 5.3 | 49.7 |
| RWJ670804 | 5 | 0.6902 | 0.6884 | 0.6893 | 0.0013 | 0.2 | 83.8 |
| RWJ670804 | 2.5 | 0.7476 | 0.7483 | 0.7480 | 0.0005 | 0.1 | 92.5 |
| JNJ26170833 | 10 | 0.6790 | 0.6704 | 0.6747 | 0.0061 | 0.9 | 81.6 |
| JNJ26170833 | 5 | 0.7833 | 0.7924 | 0.7879 | 0.0064 | 0.8 | 98.5 |
| JNJ26170833 | 2.5 | 0.8155 | 0.8389 | 0.8272 | 0.0165 | 2.0 | 104.4 |
| JNJ26177086 | 10 | 0.6533 | 0.6884 | 0.6709 | 0.0248 | 3.7 | 81.0 |
| JNJ26177086 | 5 | 0.7697 | 0.7738 | 0.7718 | 0.0029 | 0.4 | 96.1 |
| JNJ26177086 | 2.5 | 0.8119 | 0.8219 | 0.8169 | 0.0071 | 0.9 | 102.9 |
| JNJ26177762 | 10 | 0.1242 | 0.1323 | 0.1283 | 0.0057 | 4.5 | −0.4 |
| JNJ26177762 | 5 | 0.1263 | 0.1303 | 0.1283 | 0.0028 | 2.2 | −0.3 |
| JNJ26177762 | 2.5 | 0.8480 | 0.7725 | 0.8103 | 0.0534 | 6.6 | 101.9 |
| RWJ673515 | 10 | 0.1695 | 0.1890 | 0.1793 | 0.0138 | 7.7 | 7.3 |
| RWJ673515 | 5 | 0.7217 | 0.7435 | 0.7326 | 0.0154 | 2.1 | 90.2 |
| RWJ673515 | 2.5 | 0.7812 | 0.7221 | 0.7517 | 0.0418 | 5.6 | 93.1 |
| EXPRES 01 medium | | 0.6294 | 0.6363 | 0.6329 | 0.0049 | 0.8 | 70.3 |
| no treatment | | 0.7156 | 0.7356 | 0.7256 | 0.0141 | 1.9 | 83.3 |
| AA only | | 0.8732 | 0.9046 | 0.8889 | 0.0222 | 2.5 | 106.0 |
| AA + Wnt3a | | 0.8415 | 0.8500 | 0.8458 | 0.0060 | 0.7 | 100.0 |
| JNJ19370026 | 10 | 0.1403 | 0.1493 | 0.1448 | 0.0064 | 4.4 | 2.3 |
| JNJ19370026 | 5 | 0.4434 | 0.3878 | 0.4156 | 0.0393 | 9.5 | 40.1 |
| JNJ19370026 | 2.5 | 0.7734 | 0.8038 | 0.7886 | 0.0215 | 2.7 | 92.0 |
| JNJ26483197 | 10 | 0.2993 | 0.3026 | 0.3010 | 0.0023 | 0.8 | 24.1 |
| JNJ26483197 | 5 | 0.7023 | 0.6299 | 0.6661 | 0.0512 | 7.7 | 75.0 |
| JNJ26483197 | 2.5 | 0.7835 | 0.8043 | 0.7939 | 0.0147 | 1.9 | 92.8 |
| RWJ675605 | 10 | 0.7205 | 0.7369 | 0.7287 | 0.0116 | 1.6 | 83.7 |
| RWJ675605 | 5 | 0.7769 | 0.8272 | 0.8021 | 0.0356 | 4.4 | 93.9 |
| RWJ675605 | 2.5 | 0.8214 | 0.8640 | 0.8427 | 0.0301 | 3.6 | 99.6 |
| RWJ675430 | 10 | 0.6275 | 0.5980 | 0.6128 | 0.0209 | 3.4 | 67.5 |
| RWJ675430 | 5 | 0.7159 | 0.7222 | 0.7191 | 0.0045 | 0.6 | 82.3 |
| RWJ675430 | 2.5 | 0.9245 | 0.9403 | 0.9324 | 0.0112 | 1.2 | 112.1 |
| RWJ675948 | 10 | 0.7220 | 0.6670 | 0.6945 | 0.0389 | 5.6 | 78.9 |
| RWJ675948 | 5 | 0.7526 | 0.7486 | 0.7506 | 0.0028 | 0.4 | 86.7 |
| RWJ675948 | 2.5 | 0.7557 | 0.7390 | 0.7474 | 0.0118 | 1.6 | 86.3 |
| JNJ26483249 | 10 | 0.8214 | 0.8636 | 0.8425 | 0.0298 | 3.5 | 99.5 |
| JNJ26483249 | 5 | 0.7996 | 0.7873 | 0.7935 | 0.0087 | 1.1 | 92.7 |
| JNJ26483249 | 2.5 | 0.8669 | 0.8195 | 0.8432 | 0.0335 | 4.0 | 99.6 |
| RWJ67657 | 10 | 0.6195 | 0.5908 | 0.6052 | 0.0203 | 3.4 | 66.5 |
| RWJ67657 | 5 | 0.8047 | 0.8319 | 0.8183 | 0.0192 | 2.4 | 96.2 |
| RWJ67657 | 2.5 | 0.8041 | 0.7900 | 0.7971 | 0.0100 | 1.3 | 93.2 |
| RWJ676639 | 10 | 0.1261 | 0.1520 | 0.1391 | 0.0183 | 13.2 | 1.5 |
| RWJ676639 | 5 | 0.1303 | 0.1263 | 0.1283 | 0.0028 | 2.2 | 0.0 |
| RWJ676639 | 2.5 | 0.4482 | 0.4051 | 0.4267 | 0.0305 | 7.1 | 41.6 |

TABLE IV

EFFECTS OF INHIBITORS OF GSK-3B ENZYME ACTIVITY ON THE DIFFERENTIATION AND
PROLIFERATION OF HUMAN EMBRYONIC STEM CELLS.

| | Proliferative Response | | SOX-17 Expression | | Proliferative Response | | HNF-3b Expression | |
|---|---|---|---|---|---|---|---|---|
| Compound name | Total cells | Fold over Wnt 3a/AA control | Total Intensity | Fold over Wnt 3a/AA control | Total cells | Fold over Wnt 3a/AA control | Total Intensity | Fold over Wnt 3a/AA control |
| JNJ26511966 | 1723 | 0.11244207 | 68870409 | 0.0708 | 1645 | 0.10460717 | 50143628 | 0.0453 |
| JNJ26511979 | 1110 | 0.07245904 | 42978557 | 0.0442 | 94 | 0.00597755 | 0 | 0.0000 |
| JNJ26512005 | 7990 | 0.52154188 | 339840000 | 0.3494 | 6833 | 0.43448539 | 231745000 | 0.2092 |
| JNJ26533065 | 4914 | 0.32074548 | 238555000 | 0.2453 | 2907 | 0.18485899 | 82808745 | 0.0747 |
| JNJ26533091 | 3056 | 0.19945819 | 153145000 | 0.1575 | 2643 | 0.16807097 | 122246784 | 0.1103 |
| JNJ26533104 | 3960 | 0.25850251 | 47669463 | 0.0490 | 4641 | 0.29512575 | 210730000 | 0.1902 |
| JNJ26533156 | 12243 | 0.79917096 | 699160000 | 0.7189 | 6536 | 0.41559887 | 248855000 | 0.2246 |
| JNJ26714181 | 401 | 0.02614400 | 25580022 | 0.0263 | 27 | 0.00168516 | 0 | 0.0000 |
| JNJ26714194 | 7958 | 0.51948561 | 351070000 | 0.3610 | 6992 | 0.44459636 | 288075000 | 0.2600 |
| JNJ26714207 | 277 | 0.01808212 | 6558563 | 0.0067 | 12 | 0.00073130 | 535481 | 0.0005 |
| JNJ26714220 | 1327 | 0.08662445 | 69037756 | 0.0710 | 1194 | 0.07589584 | 40478497 | 0.0365 |
| JNJ26875563 | 791 | 0.05160259 | 24732475 | 0.0254 | 64 | 0.00406982 | 1092011 | 0.0010 |
| JNJ22791671 | 0 | 0.00000000 | 0 | 0.0000 | 3 | 0.00019077 | 95784 | 0.0001 |
| JNJ26893438 | 2 | 0.00013056 | 0 | 0.0000 | 0 | 0.00000000 | 0 | 0.0000 |

TABLE IV-continued

EFFECTS OF INHIBITORS OF GSK-3B ENZYME ACTIVITY ON THE DIFFERENTIATION AND PROLIFERATION OF HUMAN EMBRYONIC STEM CELLS.

| Compound name | Proliferative Response | | SOX-17 Expression | | Proliferative Response | | HNF-3b Expression | |
|---|---|---|---|---|---|---|---|---|
| | Total cells | Fold over Wnt 3a/AA control | Total Intensity | Fold over Wnt 3a/AA control | Total cells | Fold over Wnt 3a/AA control | Total Intensity | Fold over Wnt 3a/AA control |
| JNJ26941226 | 6 | 0.00035903 | 1092432 | 0.0011 | 2 | 0.00009539 | 150222 | 0.0001 |
| JNJ28572128 | 2742 | 0.17899341 | 122926199 | 0.1264 | 3166 | 0.20132905 | 120729987 | 0.1090 |
| JNJ28850601 | 33 | 0.00212155 | 3855900 | 0.0040 | 8 | 0.00050873 | 208129 | 0.0002 |
| RWJ674817 | 2000 | 0.13055682 | 110080123 | 0.1132 | 116 | 0.00737655 | 4290889 | 0.0039 |
| RWJ674855 | 3495 | 0.22814805 | 110559816 | 0.1137 | 438 | 0.02782105 | 24450647 | 0.0221 |
| RWJ674855 | 3107 | 0.20278739 | 120998421 | 0.1244 | 6177 | 0.39276971 | 273965000 | 0.2473 |
| RWJ675104 | 658 | 0.04295320 | 37841044 | 0.0389 | 646 | 0.04107977 | 31352380 | 0.0283 |
| RWJ675260 | 5991 | 0.39108297 | 252690000 | 0.2598 | 8479 | 0.53915615 | 306520000 | 0.2767 |
| RWJ675261 | 1953 | 0.12745610 | 88653625 | 0.0912 | 641 | 0.04076182 | 18162585 | 0.0164 |
| RWJ675266 | 2024 | 0.13209087 | 128395000 | 0.1320 | 4923 | 0.31302661 | 232020000 | 0.2094 |
| RWJ675366 | 2979 | 0.19446439 | 93454696 | 0.0961 | 3582 | 0.22775110 | 137054653 | 0.1237 |
| RWJ675369 | 3703 | 0.24169332 | 138180000 | 0.1421 | 3980 | 0.25306032 | 139550000 | 0.1260 |
| RWJ675430 | 21070 | 1.37538351 | 1089750000 | 1.1205 | 21203 | 1.34831961 | 1281000000 | 1.1562 |
| RWJ675578 | 1297 | 0.08466610 | 47445962 | 0.0488 | 30 | 0.00190773 | 0 | 0.0000 |
| RWJ675605 | 14529 | 0.94839741 | 1013360000 | 1.0419 | 9871 | 0.62767480 | 540725000 | 0.4881 |
| RWJ675881 | 4063 | 0.26522619 | 207891758 | 0.2137 | 3973 | 0.25264697 | 177190000 | 0.1599 |
| RWJ675946 | 1 | 0.00006528 | 0 | 0.0000 | 7 | 0.00041334 | 0 | 0.0000 |
| RWJ675948 | 9716 | 0.63421242 | 572520000 | 0.5887 | 7650 | 0.48643922 | 329425000 | 0.2973 |
| RWJ676061 | 916 | 0.05979503 | 0 | 0.0000 | 1076 | 0.06839210 | 40211776 | 0.0363 |
| RWJ676085 | 738 | 0.04817547 | 30943000 | 0.0318 | 503 | 0.03198626 | 0 | 0.0000 |
| RWJ676137 | 8367 | 0.54618448 | 373185000 | 0.3837 | 7976 | 0.50720168 | 260000000 | 0.2347 |
| RWJ676139 | 20079 | 1.31069260 | 1104750000 | 1.1359 | 16884 | 1.07363836 | 1052345000 | 0.9499 |
| RWJ676431 | 13789 | 0.90012403 | 789085000 | 0.8113 | 11369 | 0.72296588 | 547055000 | 0.4938 |
| RWJ676432 | 16652 | 1.08698348 | 1045395000 | 1.0749 | 14950 | 0.95065340 | 854325000 | 0.7711 |
| RWJ676657 | 6376 | 0.41618252 | 324450000 | 0.3336 | 6058 | 0.38523417 | 269025000 | 0.2428 |
| RWJ676639 | 6470 | 0.42231869 | 327055000 | 0.3363 | 4357 | 0.27706591 | 109160000 | 0.0985 |
| RWJ674817 | 2000 | 0.13055682 | 110080123 | 0.1132 | 116 | 0.00737655 | 4290889 | 0.0039 |
| RWJ674855 | 3495 | 0.22814805 | 110559816 | 0.1137 | 438 | 0.02782105 | 24450647 | 0.0221 |
| RWJ674855 | 3107 | 0.20278739 | 120998421 | 0.1244 | 6177 | 0.39276971 | 273965000 | 0.2473 |
| RWJ675104 | 658 | 0.04295320 | 37841044 | 0.0389 | 646 | 0.04107977 | 31352380 | 0.0283 |
| RWJ675260 | 5991 | 0.39108297 | 252690000 | 0.2598 | 8479 | 0.53915615 | 306520000 | 0.2767 |
| RWJ675261 | 1953 | 0.12745610 | 88653625 | 0.0912 | 641 | 0.04076182 | 18162585 | 0.0164 |
| RWJ675266 | 2024 | 0.13209087 | 128395000 | 0.1320 | 4923 | 0.31302661 | 232020000 | 0.2094 |
| RWJ675366 | 2979 | 0.19446439 | 93454696 | 0.0961 | 3582 | 0.22775110 | 137054653 | 0.1237 |
| RWJ675369 | 3703 | 0.24169332 | 138180000 | 0.1421 | 3980 | 0.25306032 | 139550000 | 0.1260 |
| RWJ675430 | 21070 | 1.37538351 | 1089750000 | 1.1205 | 21203 | 1.34831961 | 1281000000 | 1.1562 |
| RWJ675578 | 1297 | 0.08466610 | 47445962 | 0.0488 | 30 | 0.00190773 | 0 | 0.0000 |
| RWJ675605 | 14529 | 0.94839741 | 1013360000 | 1.0419 | 9871 | 0.62767480 | 540725000 | 0.4881 |
| RWJ675881 | 4063 | 0.26522619 | 207891758 | 0.2137 | 3973 | 0.25264697 | 177190000 | 0.1599 |
| RWJ675946 | 1 | 0.00006528 | 0 | 0.0000 | 7 | 0.00041334 | 0 | 0.0000 |
| RWJ675948 | 9716 | 0.63421242 | 572520000 | 0.5887 | 7650 | 0.48643922 | 329425000 | 0.2973 |
| RWJ676061 | 916 | 0.05979503 | 0 | 0.0000 | 1076 | 0.06839210 | 40211776 | 0.0363 |
| RWJ676085 | 738 | 0.04817547 | 30943000 | 0.0318 | 503 | 0.03198626 | 0 | 0.0000 |
| RWJ676137 | 8367 | 0.54618448 | 373185000 | 0.3837 | 7976 | 0.50720168 | 260000000 | 0.2347 |
| RWJ676139 | 20079 | 1.31069260 | 1104750000 | 1.1359 | 16884 | 1.07363836 | 1052345000 | 0.9499 |
| RWJ676431 | 13789 | 0.90012403 | 789085000 | 0.8113 | 11369 | 0.72296588 | 547055000 | 0.4938 |
| RWJ676432 | 16652 | 1.08698348 | 1045395000 | 1.0749 | 14950 | 0.95065340 | 854325000 | 0.7711 |
| RWJ67657 | 6376 | 0.41618252 | 324450000 | 0.3336 | 6058 | 0.38523417 | 269025000 | 0.2428 |
| RWJ676639 | 6470 | 0.42231869 | 327055000 | 0.3363 | 4357 | 0.27706591 | 109160000 | 0.0985 |
| No treatment | 3891 | 0.25396566 | 97657703 | 0.1004 | 6091 | 0.38733268 | 109336609 | 0.0987 |
| AA | 4348 | 0.28379790 | 104735084 | 0.1077 | 122 | 0.00775810 | 5341271 | 0.0048 |
| AA/3a | 15319 | 1.00000000 | 972595000 | 1.0000 | 15726 | 1.00000000 | 1107900000 | 1.0000 |
| RWJ351001 | 738 | 0.44211577 | 0 | 0.0000 | 0 | 0.00000000 | 0 | 0.0000 |
| RWJ351958 | 0 | 0.00000000 | 0 | 0.0000 | 0 | 0.00000000 | 0 | 0.0000 |
| DMSO | 56 | 0.03353293 | 454796 | 0.0148 | 211 | 0.16644754 | 4455058 | 0.1626 |
| RWJ352190 | 1313 | 0.78642715 | 28506437 | 0.9266 | 5485 | 4.32684722 | 85245671 | 3.1115 |
| RWJ352244 | 12 | 0.00738523 | 85949 | 0.0028 | 67 | 0.05259006 | 1300640 | 0.0475 |
| RWJ352628 | 2899 | 1.73612774 | 32703235 | 1.0630 | 7460 | 5.88456482 | 149772525 | 5.4668 |
| RWJ353258 | 562 | 0.33632735 | 11388240 | 0.3702 | 787 | 0.62108861 | 10743082 | 0.3921 |
| RWJ355131 | 118 | 0.07045908 | 2574279 | 0.0837 | 57 | 0.04522745 | 2584708 | 0.0943 |
| RWJ355923 | 136 | 0.08163673 | 410648 | 0.0133 | 0 | 0.00000000 | 0 | 0.0000 |
| RWJ356205 | 19 | 0.01137725 | 0 | 0.0000 | 0 | 0.00000000 | 0 | 0.0000 |
| RWJ382867 | 3 | 0.00159681 | 431883 | 0.0140 | 31 | 0.02419143 | 847186 | 0.0309 |
| RWJ395477 | 33 | 0.01976048 | 0 | 0.0000 | 225 | 0.17749145 | 5223879 | 0.1907 |
| RWJ414342 | 16 | 0.00978044 | 0 | 0.0000 | 496 | 0.39127005 | 8966327 | 0.3273 |
| RWJ414984 | 26 | 0.01556886 | 459801 | 0.0149 | 189 | 0.14935577 | 1819533 | 0.0664 |
| RWJ425264 | 1 | 0.00039920 | 0 | 0.0000 | 42 | 0.03339469 | 1605538 | 0.0586 |
| RWJ425268 | 22 | 0.01297405 | 82062 | 0.0027 | 311 | 0.24506968 | 5749996 | 0.2099 |
| RWJ425271 | 0 | 0.00000000 | 0 | 0.0000 | 0 | 0.00000000 | 0 | 0.0000 |
| RWJ425348 | 26 | 0.01556886 | 0 | 0.0000 | 0 | 0.00000000 | 0 | 0.0000 |
| RWJ445224 | 202 | 0.12095808 | 627280 | 0.0204 | 1079 | 0.85143308 | 14326715 | 0.5229 |
| RWJ447228 | 3 | 0.00179641 | 0 | 0.0000 | 4 | 0.00315540 | 101114 | 0.0037 |

TABLE IV-continued

EFFECTS OF INHIBITORS OF GSK-3B ENZYME ACTIVITY ON THE DIFFERENTIATION AND PROLIFERATION OF HUMAN EMBRYONIC STEM CELLS.

| | Proliferative Response | | SOX-17 Expression | | Proliferative Response | | HNF-3b Expression | |
|---|---|---|---|---|---|---|---|---|
| Compound name | Total cells | Fold over Wnt 3a/AA control | Total Intensity | Fold over Wnt 3a/AA control | Total cells | Fold over Wnt 3a/AA control | Total Intensity | Fold over Wnt 3a/AA control |
| RWJ553709 | 1310 | 0.78423154 | 24382455 | 0.7926 | 3249 | 2.56323955 | 75834631 | 2.7680 |
| RWJ659780 | 20 | 0.01177645 | 0 | 0.0000 | 425 | 0.33526164 | 8880858 | 0.3242 |
| RWJ663860 | 9 | 0.00538922 | 37140 | 0.0012 | 134 | 0.10570602 | 2144545 | 0.0783 |
| RWJ662440 | 7 | 0.00419162 | 48154 | 0.0016 | 5 | 0.00420720 | 170177 | 0.0062 |
| RWJ664545 | 70 | 0.04191617 | 589594 | 0.0192 | 0 | 0.00000000 | 0 | 0.0000 |
| RWJ665436 | 1215 | 0.72774451 | 7568849 | 0.2460 | 0 | 0.00000000 | 0 | 0.0000 |
| no Treatment | 1145 | 0.68542914 | 6979814 | 0.2269 | not done | | | |
| AA | 100 | 0.05988024 | 1264807 | 0.0411 | 51 | 0.04049435 | 923625 | 0.0337 |
| AA/3a | 1670 | 1.00000000 | 30764293 | 1.0000 | 1268 | 1.00000000 | 27396787 | 1.0000 |
| RWJ665588 | 43 | 0.00510815 | 706614 | 0.0055 | 0 | 0.00000000 | 0 | 0.0000 |
| RWJ665862 | 7 | 0.00079815 | 102445 | 0.0008 | 0 | 0.00000000 | 0 | 0.0000 |
| RWJ666167 | 46 | 0.00546732 | 0 | 0.0000 | 46 | 0.00548446 | 818478 | 0.0044 |
| RWJ666168 | 5 | 0.00059861 | 284777 | 0.0022 | 32 | 0.00385502 | 2309043 | 0.0124 |
| RWJ666205 | 258 | 0.03092825 | 4009395 | 0.0312 | 391 | 0.04665766 | 14340307 | 0.0769 |
| RWJ666213 | 62 | 0.00742278 | 782261 | 0.0061 | 112 | 0.01335347 | 2792473 | 0.0150 |
| RWJ667045 | 36 | 0.00431000 | 312039 | 0.0024 | 2 | 0.00027820 | 1731575 | 0.0093 |
| RWJ667046 | 59 | 0.00702371 | 397711 | 0.0031 | 103 | 0.01232017 | 3561761 | 0.0191 |
| RWJ667069 | 22 | 0.00267380 | 770128 | 0.0060 | 0 | 0.00000000 | 0 | 0.0000 |
| RWJ669182 | 77 | 0.00925852 | 1631067 | 0.0127 | 0 | 0.00000000 | 0 | 0.0000 |
| RWJ669327 | 129 | 0.01540426 | 997629 | 0.0078 | 98 | 0.01164454 | 4138261 | 0.0222 |
| RWJ670804 | 2386 | 0.28565728 | 20866647 | 0.1625 | 2594 | 0.30931563 | 61161468 | 0.3280 |
| RWJ670908 | 172 | 0.02063213 | 625299 | 0.0049 | 133 | 0.01589699 | 3578458 | 0.0192 |
| RWJ670984 | 8 | 0.00099769 | 394948 | 0.0031 | 530 | 0.06319053 | 16678849 | 0.0894 |
| RWJ671232 | 17 | 0.00207519 | 0 | 0.0000 | 53 | 0.00627931 | 2270954 | 0.0122 |
| RWJ672667 | 11 | 0.00127704 | 0 | 0.0000 | 36 | 0.00433193 | 2287281 | 0.0123 |
| RWJ672932 | 2 | 0.00023944 | 0 | 0.0000 | 0 | 0.00000000 | 0 | 0.0000 |
| RWJ672934 | 174 | 0.02087158 | 1451727 | 0.0113 | 0 | 0.00000000 | 0 | 0.0000 |
| RWJ673313 | 80 | 0.00961769 | 940367 | 0.0073 | 333 | 0.03970273 | 5586343 | 0.0300 |
| RWJ673515 | 11886 | 1.42305850 | 223646667 | 1.7415 | 10331 | 1.23173834 | 309900000 | 1.6618 |
| RWJ673829 | 545 | 0.06524862 | 5849381 | 0.0455 | 404 | 0.04820761 | 6738305 | 0.0361 |
| RWJ673830 | 10 | 0.00115732 | 315367 | 0.0025 | 35 | 0.00421270 | 3072013 | 0.0165 |
| RWJ674239 | 2473 | 0.29603320 | 80676667 | 0.6282 | 4209 | 0.50182815 | 143916667 | 0.7718 |
| RWJ674240 | 8 | 0.00091787 | 233687 | 0.0018 | 6 | 0.00071536 | 0 | 0.0000 |
| RWJ674241 | 1 | 0.00007981 | 1309298 | 0.0102 | 0 | 0.00000000 | 0 | 0.0000 |
| RWJ674320 | 0 | 0.00003991 | 0 | 0.0000 | 0 | 0.00000000 | 0 | 0.0000 |
| No treatment | 7653 | 0.91619443 | 26272707 | 0.2046 | 12050 | 1.43665050 | 74453588 | 0.3993 |
| AA | 15 | 0.00175593 | 0 | 0.0000 | 210 | 0.02503776 | 3777945 | 0.0203 |
| AA/3a | 8353 | 1.00000000 | 128424304 | 1.0000 | 8387 | 1.00000000 | 186480000 | 1.0000 |
| RWJ355923 | 7319 | 0.91843393 | 387695000 | 1.0342 | 5436 | 1.07644321 | 437495000 | 0.9520 |
| RWJ664545 | 6620 | 0.83065629 | 333205000 | 0.8889 | 4767 | 0.94395485 | 397435000 | 0.8649 |
| RWJ353709 | 6217 | 0.78014807 | 337920000 | 0.9014 | 5013 | 0.99277156 | 437235000 | 0.9515 |
| reference cmpd | 5934 | 0.74463546 | 363935000 | 0.9708 | 4122 | 0.81621943 | 348135000 | 0.7576 |
| JNJ18157698 | 10447 | 1.31089221 | 382680000 | 1.0208 | 6908 | 1.36805624 | 560475000 | 1.2196 |
| JNJ5226780 | 10963 | 1.37570586 | 296920000 | 0.7921 | 5679 | 1.12456679 | 463525000 | 1.0087 |
| JNJ7830433 | 1766 | 0.22160873 | 162790000 | 0.4343 | 2184 | 0.43241905 | 189875000 | 0.4132 |
| JNJ8706646 | 2914 | 0.36566696 | 230965000 | 0.6161 | 2776 | 0.54975740 | 125125000 | 0.2723 |
| JNJ8710481 | 3600 | 0.45175053 | 276080000 | 0.7365 | 4121 | 0.81612041 | 294665000 | 0.6412 |
| JNJ8710481 | 1977 | 0.24808633 | 164760000 | 0.4395 | 2266 | 0.44865828 | 152060000 | 0.3309 |
| JNJ10148307 | 9964.5 | 1.25040783 | 363855000 | 0.9706 | 9728 | 1.92642836 | 635655000 | 1.3832 |
| JNJ10164830 | 2536.5 | 0.31829590 | 179185000 | 0.4780 | 2397 | 0.47460145 | 150660000 | 0.3277 |
| JNJ10164895 | 5706.5 | 0.71608734 | 319930000 | 0.8534 | 5096 | 1.00920883 | 341360000 | 0.7428 |
| JNJ10172058 | 4645.5 | 0.58294642 | 257295000 | 0.6864 | 4507 | 0.89256362 | 312605000 | 0.6803 |
| JNJ10178727 | 2892.5 | 0.36296900 | 213165000 | 0.5686 | 3043 | 0.60253490 | 269570000 | 0.5866 |
| JNJ10179026 | 2460.5 | 0.30875894 | 203350000 | 0.5425 | 2410 | 0.47727498 | 209795000 | 0.4565 |
| JNJ10179130 | 4783 | 0.60020078 | 306085000 | 0.8165 | 4556 | 0.90226755 | 326475000 | 0.7104 |
| JNJ10182562 | 6916.5 | 0.86792571 | 377885000 | 1.0080 | 4504 | 0.89196950 | 365090000 | 0.7945 |
| JNJ10182562 | 7370.5 | 0.92489647 | 365075000 | 0.9739 | 5300 | 1.04950985 | 399265000 | 0.8688 |
| JNJ10184655 | 10533 | 1.32174677 | 475250000 | 1.2678 | 5186 | 1.02693336 | 404710000 | 0.8807 |
| JNJ10222784 | 3513 | 0.44083323 | 242750000 | 0.6476 | 2522 | 0.49945539 | 214575000 | 0.4669 |
| No Treatment | not done | | | | not done | | | |
| AA | not done | | | | not done | | | |
| AA/3a | 7969 | 1.00000000 | 374870000 | 1.0000 | 5050 | 1.00000000 | 459540000 | 1.0000 |
| JNJ10222784 | 563 | 0.31250000 | 57351132 | 0.3295 | 1744 | 0.03386884 | 165365000 | 1.1010 |
| JNJ10222927 | 158 | 0.08777778 | 14786632 | 0.0850 | 83 | 0.00161234 | 14201404 | 0.0946 |
| JNJ10231273 | 3 | 0.00166667 | 0 | 0.0000 | 4 | 0.00007770 | 28439 | 0.0002 |
| JNJ10259847 | 5 | 0.00277778 | 0 | 0.0000 | 10 | 0.00019426 | 0 | 0.0000 |
| JNJ10259847 | 15 | 0.00805556 | 548982 | 0.0032 | 0 | 0.00000000 | 0 | 0.0000 |
| JNJ17154215 | 24 | 0.01305556 | 689535 | 0.0040 | 11 | 0.00021368 | 0 | 0.0000 |
| JNJ17154215 | 94 | 0.05194444 | 11142426 | 0.0640 | 12 | 0.00022340 | 1767033 | 0.0118 |
| JNJ17157659 | 15 | 0.00805556 | 0 | 0.0000 | 21 | 0.00039823 | 4567590 | 0.0304 |
| JNJ17163042 | 33 | 0.01805556 | 2188847 | 0.0126 | 69 | 0.00134038 | 13689421 | 0.0911 |
| JNJ10166565 | 4 | 0.00194444 | 0 | 0.0000 | 3 | 0.00005828 | 291660 | 0.0019 |

TABLE IV-continued

EFFECTS OF INHIBITORS OF GSK-3B ENZYME ACTIVITY ON THE DIFFERENTIATION AND PROLIFERATION OF HUMAN EMBRYONIC STEM CELLS.

| Compound name | Proliferative Response | | SOX-17 Expression | | Proliferative Response | | HNF-3b Expression | |
|---|---|---|---|---|---|---|---|---|
| | Total cells | Fold over Wnt 3a/AA control | Total Intensity | Fold over Wnt 3a/AA control | Total cells | Fold over Wnt 3a/AA control | Total Intensity | Fold over Wnt 3a/AA control |
| JNJ17174664 | 88 | 0.04888889 | 7121122 | 0.0409 | 399 | 0.00774117 | 65100086 | 0.4335 |
| JNJ17187027 | 11 | 0.00583333 | 1073763 | 0.0062 | 5 | 0.00008742 | 0 | 0.0000 |
| JNJ17187053 | 8 | 0.00444444 | 0 | 0.0000 | 9 | 0.00016512 | 0 | 0.0000 |
| JNJ17193774 | 109 | 0.06027778 | 15714170 | 0.0903 | 136 | 0.00263219 | 15725984 | 0.1047 |
| JNJ17200976 | 5 | 0.00250000 | 125443 | 0.0007 | 5 | 0.00009713 | 0 | 0.0000 |
| JNJ17205955 | 20 | 0.01083333 | 3135653 | 0.0180 | 8 | 0.00015541 | 0 | 0.0000 |
| JNJ17205955 | 9 | 0.00472222 | 72387 | 0.0004 | 17 | 0.00033024 | 736311 | 0.0049 |
| JNJ17205994 | 6 | 0.00305556 | 644015 | 0.0037 | 4 | 0.00007770 | 0 | 0.0000 |
| JNJ17226703 | 77 | 0.04277778 | 12632849 | 0.0726 | 28 | 0.00054392 | 9312311 | 0.0620 |
| JNJ17982133 | 14 | 0.00750000 | 887585 | 0.0051 | 1 | 0.00001943 | 52047 | 0.0003 |
| JNJ17989049 | 23 | 0.01277778 | 2117429 | 0.0122 | 13 | 0.00024282 | 0 | 0.0000 |
| No Treatment | not done | | | | 432 | 0.00838222 | 42987388 | 0.2862 |
| AA | 147 | 0.08138889 | 20330009 | 0.1168 | 8 | 0.00014569 | 87206 | 0.0006 |
| AA/3a | 1800 | 1.00000000 | 174052346 | 1.0000 | 1478 | 0.02870158 | 150190000 | 1.0000 |

TABLE V

EFFECTS OF INHIBITORS OF GSK-3B ENZYME ACTIVITY ON THE DIFFERENTIATION AND PROLIFERATION OF HUMAN EMBRYONIC STEM CELLS.

| Compound name | Fold over Wnt 3a/AA control |
|---|---|
| Proliferative Response - Strong Hits | |
| RWJ352628 | 5.8846 |
| RWJ352190 | 4.3268 |
| RWJ553709 | 2.5632 |
| JNJ10148307 | 1.9264 |
| RWJ673515 | 1.4231 |
| JNJ5226780 | 1.3757 |
| RWJ675430 | 1.3754 |
| JNJ18157698 | 1.3681 |
| JNJ10184655 | 1.3217 |
| RWJ676139 | 1.3107 |
| Proliferative Response - Moderate Hits | |
| JNJ5226780 | 1.1246 |
| RWJ676432 | 1.0870 |
| RWJ355923 | 1.0764 |
| RWJ676139 | 1.0736 |
| JNJ10182562 | 1.0495 |
| JNJ10184655 | 1.0269 |
| JNJ10164895 | 1.0092 |
| RWJ353709 | 0.9928 |
| RWJ675605 | 0.9484 |
| RWJ664545 | 0.9440 |
| JNJ10182562 | 0.9249 |
| JNJ10179130 | 0.9023 |
| RWJ676431 | 0.9001 |
| JNJ10172058 | 0.8926 |
| RWJ445224 | 0.8514 |
| reference cmpd | 0.8162 |
| JNJ8710481 | 0.8161 |
| JNJ26533156 | 0.7992 |
| RWJ352190 | 0.7864 |
| RWJ553709 | 0.7842 |
| RWJ665436 | 0.7277 |
| RWJ675948 | 0.6342 |
| RWJ353258 | 0.6211 |
| JNJ10173727 | 0.6025 |
| SOX17 Expression - Strong Hits | |
| RWJ673515 | 1.7415 |
| JNJ10184655 | 1.2678 |
| SOX17 Expression - Moderate Hits | |
| RWJ676139 | 1.1359 |
| RWJ675430 | 1.1205 |
| RWJ676432 | 1.0749 |
| RWJ352628 | 1.0630 |
| RWJ675605 | 1.0419 |
| RWJ355923 | 1.0342 |
| JNJ18157698 | 1.0208 |
| JNJ10182562 | 1.0030 |
| reference cmpd | 0.9708 |
| JNJ10148307 | 0.9706 |
| RWJ352190 | 0.9266 |
| RWJ353709 | 0.9014 |
| RWJ664545 | 0.8889 |
| JNJ10164895 | 0.8534 |
| JNJ10179130 | 0.8165 |
| RWJ676431 | 0.8113 |
| RWJ553709 | 0.7926 |
| JNJ5226780 | 0.7921 |
| JNJ8710481 | 0.7365 |
| JNJ26533156 | 0.7189 |
| JNJ10172058 | 0.6864 |
| JNJ10222784 | 0.6476 |
| RWJ674239 | 0.6282 |
| JNJ8706646 | 0.6161 |
| RWJ675948 | 0.5887 |
| JNJ10178727 | 0.5686 |
| HNF3β Expression - Strong Hits | |
| RWJ352628 | 5.4668 |
| RWJ352190 | 3.1115 |
| RWJ553709 | 2.7680 |
| RWJ673515 | 1.6618 |
| JNJ10148307 | 1.3832 |
| JNJ18157698 | 1.2196 |
| HNF3b Expression - Moderate Hits | |
| RWJ675430 | 1.1562 |
| JNJ10222784 | 1.1010 |
| JNJ5226780 | 1.0087 |
| RWJ355923 | 0.9520 |
| RWJ353709 | 0.9515 |
| RWJ676139 | 0.9499 |
| JNJ10184655 | 0.8807 |
| JNJ10182562 | 0.8683 |
| RWJ664545 | 0.8649 |
| RWJ674239 | 0.7718 |
| RWJ676432 | 0.7711 |
| reference cmpd | 0.7576 |

TABLE V-continued

EFFECTS OF INHIBITORS OF GSK-3B ENZYME ACTIVITY ON THE DIFFERENTIATION AND PROLIFERATION OF HUMAN EMBRYONIC STEM CELLS.

| Compound name | Fold over Wnt 3a/AA control |
|---|---|
| JNJ10164895 | 0.7428 |
| JNJ10179130 | 0.7104 |
| JNJ10172058 | 0.6803 |
| JNJ8710481 | 0.6412 |
| JNJ10178727 | 0.5866 |

TABLE VI

EFFECTS OF INHIBITORS OF GSK-3B ENZYME ACTIVITY ON THE PROLIFERATION OF HUMAN EMBRYONIC STEM CELLS.

| JNJ number | Raw Data | | | Average | S.D. | % CV | % Control |
|---|---|---|---|---|---|---|---|
| conditioned medium | 1.1348 | 1.0099 | 1.1092 | 1.0846 | 0.0660 | 6.1 | 116.5 |
| no treatment | 0.9344 | 0.5977 | 0.8454 | 0.7925 | 0.1745 | 22.0 | 85.2 |
| AA/DMSO | 0.3878 | 0.2434 | 0.2252 | 0.2855 | 0.0891 | 31.2 | 30.7 |
| AA/Wnt3a/DMSO | 0.6098 | 1.0804 | 0.7635 | 0.8179 | 0.2403 | 25.8 | 100.0 |
| RWJ351001 | 0.3418 | 0.4276 | 0.5751 | 0.4482 | 0.1180 | 26.3 | 48.2 |
| RWJ351958 | 0.1362 | 0.1531 | 0.1532 | 0.1475 | 0.0098 | 6.6 | 15.8 |
| RWJ352190 | 1.3764 | 1.2753 | 1.3208 | 1.3242 | 0.0506 | 3.8 | 142.3 |
| RWJ352244 | 0.6923 | 0.5994 | 0.6134 | 0.6350 | 0.0501 | 7.9 | 68.2 |
| RWJ352628 | 1.7896 | 1.4721 | 2.1908 | 1.8175 | 0.3602 | 19.8 | 195.3 |
| RWJ353258 | 1.7591 | 1.6274 | 1.6518 | 1.6794 | 0.0701 | 4.2 | 180.4 |
| RWJ355131 | 0.3702 | 0.3193 | 0.3368 | 0.3421 | 0.0259 | 7.6 | 36.8 |
| RWJ355923 | 0.5876 | 0.6384 | 0.9154 | 0.7138 | 0.1764 | 24.7 | 76.7 |
| RWJ356205 | 0.3074 | 0.2328 | 0.2920 | 0.2774 | 0.0394 | 14.2 | 29.8 |
| RWJ382867 | 0.1311 | 0.1245 | 0.1288 | 0.1281 | 0.0034 | 2.6 | 13.8 |
| RWJ395477 | 0.1270 | 0.2778 | 0.1916 | 0.1988 | 0.0757 | 38.1 | 21.4 |
| RWJ414342 | 0.2166 | 0.3062 | 0.2915 | 0.2714 | 0.0481 | 17.7 | 29.2 |
| RWJ414984 | 0.4362 | 0.3728 | 0.2481 | 0.3524 | 0.0957 | 27.2 | 37.9 |
| RWJ425264 | 0.1560 | 0.1481 | 0.1359 | 0.1467 | 0.0101 | 6.9 | 15.8 |
| RWJ425268 | 0.2932 | 0.3883 | 0.6258 | 0.4358 | 0.1713 | 39.3 | 46.8 |
| RWJ425271 | 0.1362 | 0.1479 | 0.1298 | 0.1380 | 0.0092 | 6.7 | 14.8 |
| RWJ425348 | 0.2198 | 0.2159 | 0.2300 | 0.2219 | 0.0073 | 3.3 | 23.8 |
| RWJ445224 | 0.7624 | 0.2705 | 0.2478 | 0.4269 | 0.2908 | 68.1 | 45.9 |
| RWJ447228 | 0.1239 | 0.1233 | 0.1269 | 0.1247 | 0.0019 | 1.5 | 13.4 |
| RWJ553709 | 0.1277 | 0.1254 | 0.6980 | 0.3170 | 0.3299 | 104.1 | 34.1 |
| RWJ659780 | 0.2665 | 0.3215 | 0.2605 | 0.2828 | 0.0336 | 11.9 | 30.4 |
| RWJ662440 | 0.2395 | 0.3235 | 0.1333 | 0.2321 | 0.0953 | 41.1 | 24.9 |
| RWJ663860 | 0.2646 | 0.1873 | 0.1293 | 0.1937 | 0.0679 | 35.0 | 20.8 |
| RWJ664545 | 0.3590 | 0.2790 | 0.1515 | 0.2632 | 0.1047 | 39.8 | 28.3 |
| RWJ665436 | 0.4690 | 0.5805 | 0.3349 | 0.4615 | 0.1230 | 26.6 | 49.6 |
| conditioned medium | 1.1525 | 1.1269 | 1.1140 | 1.1311 | 0.0196 | 1.7 | 71.0 |
| no treatment | 1.2057 | 1.2358 | 1.3132 | 1.2516 | 0.0555 | 4.4 | 78.6 |
| AA/DMSO | 0.2622 | 0.2073 | 0.2830 | 0.2508 | 0.0391 | 15.6 | 15.8 |
| AA/Wnt3a/DMSO | 1.3943 | 1.7976 | 1.8000 | 1.5922 | 0.2136 | 13.4 | 100.0 |
| RWJ665588 | 0.1930 | 0.2223 | 0.2167 | 0.2107 | 0.0156 | 7.4 | 13.2 |
| RWJ665862 | 0.1757 | 0.1813 | 0.1835 | 0.1802 | 0.0040 | 2.2 | 11.3 |
| RWJ666167 | 0.1473 | 0.1880 | 0.1732 | 0.1695 | 0.0206 | 12.2 | 10.6 |
| RWJ666168 | 0.1330 | 0.1362 | 0.1867 | 0.1520 | 0.0301 | 19.8 | 9.5 |
| RWJ666205 | 0.8191 | 0.5493 | 0.6526 | 0.6737 | 0.1361 | 20.2 | 42.3 |
| RWJ666213 | 0.4008 | 0.2779 | 0.3869 | 0.3552 | 0.0673 | 18.9 | 22.3 |
| RWJ667045 | 0.1220 | 0.1248 | 0.1251 | 0.1240 | 0.0017 | 1.4 | 7.8 |
| RWJ667046 | 0.2883 | 0.3308 | 0.5503 | 0.3898 | 0.1406 | 36.1 | 24.5 |
| RWJ667069 | 0.2835 | 0.4024 | 0.5698 | 0.4186 | 0.1438 | 34.4 | 26.3 |
| RWJ669182 | 0.3704 | 0.6073 | 0.5280 | 0.5019 | 0.1206 | 24.0 | 31.5 |
| RWJ669327 | 0.2266 | 0.1815 | 0.2289 | 0.2123 | 0.0267 | 12.6 | 13.3 |
| RWJ670804 | 1.0820 | 1.1862 | 1.1076 | 1.1253 | 0.0543 | 4.8 | 70.7 |
| RWJ670908 | 0.3590 | 0.5457 | 0.6123 | 0.5057 | 0.1313 | 26.0 | 31.8 |
| RWJ670984 | 0.2198 | 0.3564 | 0.3202 | 0.2988 | 0.0708 | 23.7 | 18.8 |
| RWJ671232 | 0.2928 | 0.2920 | 0.3659 | 0.3169 | 0.0424 | 13.4 | 19.9 |
| RWJ672667 | 0.3349 | 0.3013 | 0.3507 | 0.3290 | 0.0252 | 7.7 | 20.7 |
| RWJ672932 | 0.1852 | 0.1924 | 0.2349 | 0.2042 | 0.0269 | 13.2 | 12.8 |
| RWJ672934 | 0.2170 | 0.3003 | 0.1877 | 0.2350 | 0.0584 | 24.9 | 14.8 |
| RWJ673313 | 0.3094 | 0.2515 | 0.1881 | 0.2497 | 0.0607 | 24.3 | 15.7 |
| RWJ673515 | 1.8452 | 1.7710 | 1.5591 | 1.7251 | 0.1485 | 8.6 | 108.3 |
| RWJ673829 | 0.7305 | 0.7067 | 0.6250 | 0.6874 | 0.0553 | 8.0 | 43.2 |
| RWJ673830 | 0.2113 | 0.1800 | 0.1547 | 0.1820 | 0.0284 | 15.6 | 11.4 |
| RWJ674239 | 1.5225 | 1.5912 | 0.1081 | 1.0739 | 0.8371 | 78.0 | 67.4 |
| RWJ674240 | 0.4006 | 1.2807 | 0.1162 | 0.5992 | 0.6071 | 101.3 | 37.6 |
| RWJ674241 | 0.1972 | 0.1839 | 0.1162 | 0.1658 | 0.0434 | 26.2 | 10.4 |
| RWJ674320 | 0.1351 | 0.1318 | 0.1169 | 0.1279 | 0.0097 | 7.6 | 8.0 |
| conditioned medium | 1.0568 | 1.0604 | | 1.0586 | 0.0025 | 0.2 | 71.9 |
| no treatment | 1.1544 | 0.9576 | | 1.0560 | 0.1392 | 13.2 | 71.7 |

TABLE VI-continued

EFFECTS OF INHIBITORS OF GSK-3B ENZYME ACTIVITY ON THE PROLIFERATION OF HUMAN EMBRYONIC STEM CELLS.

| JNJ number | Raw Data | | Average | S.D. | % CV | % Control |
|---|---|---|---|---|---|---|
| AA only+ DMSO | 0.6329 | 0.8434 | 0.7382 | 0.1488 | 20.2 | 47.1 |
| AA + Wnt3a + DMSO | 1.2704 | 1.8669 | 1.4229 | 0.2960 | 20.8 | 100.0 |
| RWJ674817 | 0.5617 | 0.2098 | 0.3858 | 0.2488 | 64.5 | 19.9 |
| RWJ674855 | 0.6850 | 0.5853 | 0.6352 | 0.0705 | 11.1 | 39.2 |
| RWJ674855 | 0.7496 | 0.9187 | 0.8342 | 0.1196 | 14.3 | 54.5 |
| RWJ675104 | 0.2320 | 0.2124 | 0.2222 | 0.0139 | 6.2 | 7.3 |
| RWJ675260 | 0.8079 | 1.4391 | 1.1235 | 0.4463 | 39.7 | 76.9 |
| RWJ675261 | 0.8310 | 0.7318 | 0.7814 | 0.0701 | 9.0 | 50.5 |
| RWJ675266 | 1.0646 | 1.1384 | 1.1015 | 0.0522 | 4.7 | 75.2 |
| RWJ675366 | 0.6344 | 1.0400 | 0.8372 | 0.2868 | 34.3 | 54.8 |
| no cells | 0.1335 | 0.2070 | 0.1703 | 0.0520 | 30.5 | 3.3 |
| RWJ675369 | 0.8643 | 0.4060 | 0.6352 | 0.3241 | 51.0 | 39.2 |
| RWJ675430 | 1.7922 | 1.8533 | 1.8228 | 0.0432 | 2.4 | 130.9 |
| RWJ675578 | 0.1914 | 0.2371 | 0.2143 | 0.0323 | 15.1 | 6.7 |
| RWJ675605 | 1.8401 | 1.7563 | 1.7982 | 0.0593 | 3.3 | 129.0 |
| RWJ675881 | 1.0301 | 1.0356 | 1.0329 | 0.0039 | 0.4 | 69.9 |
| RWJ675946 | 0.1306 | 0.1338 | 0.1322 | 0.0023 | 1.7 | 0.3 |
| RWJ675948 | 1.7143 | 1.6506 | 1.6825 | 0.0450 | 2.7 | 120.0 |
| RWJ676061 | 0.4170 | 0.4956 | 0.4563 | 0.0556 | 12.2 | 25.4 |
| RWJ676085 | 0.1772 | 0.2348 | 0.2060 | 0.0407 | 19.8 | 6.0 |
| RWJ676137 | 1.0231 | 1.2392 | 1.1312 | 0.1528 | 13.5 | 77.5 |
| RWJ676139 | 1.9718 | 2.0997 | 2.0358 | 0.0904 | 4.4 | 147.3 |
| RWJ676431 | 1.5168 | 1.6872 | 1.6020 | 0.1205 | 7.5 | 113.8 |
| RWJ676432 | 1.6935 | 1.9710 | 1.8323 | 0.1962 | 10.7 | 131.6 |
| RWJ67657 | 1.2655 | 1.1829 | 1.2242 | 0.0584 | 4.8 | 84.7 |
| RWJ676639 | 1.3481 | 1.3168 | 1.3325 | 0.0221 | 1.7 | 93.0 |
| JNJ26511966 | 0.6444 | 0.7239 | 0.6842 | 0.0562 | 8.2 | 43.0 |
| JNJ26511979 | 0.2046 | 0.3076 | 0.2561 | 0.0728 | 28.4 | 9.9 |
| JNJ26512005 | 1.3627 | 1.0693 | 1.2160 | 0.2075 | 17.1 | 84.0 |
| JNJ26533065 | 0.8722 | 0.9660 | 0.9191 | 0.0663 | 7.2 | 61.1 |
| JNJ26533091 | 1.0332 | 0.4554 | 0.7443 | 0.4086 | 54.9 | 47.6 |
| JNJ26533104 | 0.8775 | 0.7347 | 0.8061 | 0.1010 | 12.5 | 52.4 |
| JNJ26533156 | 1.7865 | 1.2008 | 1.4937 | 0.4142 | 27.7 | 105.5 |
| JNJ26714181 | 0.2396 | 0.1584 | 0.1990 | 0.0574 | 28.9 | 5.5 |
| JNJ26714194 | 0.8122 | 1.0827 | 0.9475 | 0.1913 | 20.2 | 63.3 |
| JNJ26714207 | 0.1342 | 0.1363 | 0.1353 | 0.0015 | 1.1 | 0.6 |
| JNJ26714220 | 1.0462 | 0.5838 | 0.8150 | 0.3270 | 40.1 | 53.1 |
| JNJ26875563 | 0.4586 | 0.2903 | 0.3745 | 0.1190 | 31.8 | 19.0 |
| JNJ22791671 | 0.1277 | 0.1402 | 0.1340 | 0.0088 | 6.6 | 0.5 |
| JNJ26893438 | 0.1258 | 0.1324 | 0.1291 | 0.0047 | 3.6 | 0.1 |
| JNJ26941226 | 0.1219 | 0.1216 | 0.1218 | 0.0002 | 0.2 | −0.5 |
| JNJ28572128 | 0.4223 | 0.4721 | 0.4472 | 0.0352 | 7.9 | 24.7 |
| JNJ28850601 | 0.1514 | 0.1396 | 0.1455 | 0.0083 | 5.7 | 1.4 |
| conditioned medium | 0.7423 | 0.7081 | 0.7252 | 0.0242 | 3.3 | 87.7 |
| no treatment | 0.4936 | 0.5689 | 0.5313 | 0.0532 | 10.0 | 59.8 |
| AA only + DMSO | 0.1433 | 0.1939 | 0.1686 | 0.0358 | 21.2 | 7.6 |
| AA + Wnt3a + DMSO | 0.6808 | 0.9406 | 0.8107 | 0.1837 | 22.7 | 100.0 |
| JNJ17994873 | 0.2447 | 0.1331 | 0.1889 | 0.0789 | 41.8 | 10.6 |
| JNJ17994899 | 0.1537 | 0.1302 | 0.1420 | 0.0166 | 11.7 | 3.8 |
| no cells | 0.1163 | 0.1147 | 0.1155 | 0.0011 | 1.0 | 0.0 |
| JNJ17994912 | 0.2994 | 0.2592 | 0.2793 | 0.0284 | 10.2 | 23.6 |
| JNJ17994925 | 0.1353 | 0.2121 | 0.1737 | 0.0543 | 31.3 | 8.4 |
| JNJ180125 | 0.1267 | 0.1419 | 0.1343 | 0.0107 | 8.0 | 2.7 |
| JNJ18014061 | 0.1376 | 0.1676 | 0.1526 | 0.0212 | 13.9 | 5.3 |
| JNJ18014074 | 0.1134 | 0.1103 | 0.1119 | 0.0022 | 2.0 | −0.5 |
| JNJ18018338 | 0.1318 | 0.1478 | 0.1398 | 0.0113 | 8.1 | 3.5 |
| JNJ18018351 | 0.2569 | 0.2124 | 0.2347 | 0.0315 | 13.4 | 17.1 |
| JNJ18047991 | 0.2674 | 0.2636 | 0.2655 | 0.0027 | 1.0 | 21.6 |
| JNJ18055726 | 0.4357 | 0.3467 | 0.3912 | 0.0629 | 16.1 | 39.7 |
| JNJ18077800 | 0.1265 | 0.1588 | 0.1427 | 0.0228 | 16.0 | 3.9 |
| JNJ18157074 | 0.1662 | 0.2521 | 0.2092 | 0.0607 | 29.0 | 13.5 |
| JNJ18157087 | 0.1596 | 0.1566 | 0.1581 | 0.0021 | 1.3 | 6.1 |
| JNJ18157646 | 0.2725 | 0.1636 | 0.2181 | 0.0770 | 35.3 | 14.8 |
| JNJ18157711 | 1.2256 | 1.0636 | 1.1446 | 0.1146 | 10.0 | 148.0 |
| JNJ18157711 | 0.1134 | 0.1070 | 0.1102 | 0.0045 | 4.1 | −0.8 |
| JNJ19363357 | 0.1469 | 0.1495 | 0.1482 | 0.0018 | 1.2 | 4.7 |
| JNJ19369233 | 0.1169 | 0.1122 | 0.1146 | 0.0033 | 2.9 | −0.1 |
| JNJ19369246 | 0.1595 | 0.1422 | 0.1509 | 0.0122 | 8.1 | 5.1 |
| JNJ19370026 | 1.0484 | 1.0749 | 1.0617 | 0.0187 | 1.8 | 136.1 |
| JNJ19376240 | 0.3012 | 0.2347 | 0.2680 | 0.0470 | 17.5 | 21.9 |
| JNJ19386042 | 0.1267 | 0.1510 | 0.1389 | 0.0172 | 12.4 | 3.4 |
| JNJ19410833 | 1.1902 | 1.1487 | 1.1695 | 0.0293 | 2.5 | 151.6 |
| JNJ19410859 | 0.6400 | 0.7076 | 0.6738 | 0.0478 | 7.1 | 80.3 |
| JNJ19410872 | 0.1701 | 0.1752 | 0.1727 | 0.0036 | 2.1 | 8.2 |
| JNJ19558929 | 0.3435 | 0.3488 | 0.3462 | 0.0037 | 1.1 | 33.2 |

TABLE VI-continued

EFFECTS OF INHIBITORS OF GSK-3B ENZYME ACTIVITY ON
THE PROLIFERATION OF HUMAN EMBRYONIC STEM CELLS.

| JNJ number | Raw Data | | Average | S.D. | % CV | % Control |
|---|---|---|---|---|---|---|
| JNJ19567314 | 0.4032 | 0.3548 | 0.3790 | 0.0342 | 9.0 | 37.9 |
| JNJ19567327 | 0.1602 | 0.1502 | 0.1552 | 0.0071 | 4.6 | 5.7 |
| JNJ19567340 | 0.1604 | 0.2079 | 0.1842 | 0.0336 | 18.2 | 9.9 |
| JNJ19567405 | 0.1646 | 0.1592 | 0.1619 | 0.0038 | 2.4 | 6.7 |
| JNJ19573541 | 0.1779 | 0.2273 | 0.2026 | 0.0349 | 17.2 | 12.5 |
| JNJ19574867 | 0.1225 | 0.1443 | 0.1334 | 0.0154 | 11.6 | 2.6 |
| JNJ19574880 | 0.1300 | 0.1291 | 0.1296 | 0.0006 | 0.5 | 2.0 |
| JNJ20948798 | 0.1263 | 0.1336 | 0.1300 | 0.0052 | 4.0 | 2.1 |
| JNJ21192730 | 0.2778 | 0.1326 | 0.2052 | 0.1027 | 50.0 | 12.9 |
| JNJ21194667 | 0.2569 | 0.1219 | 0.1894 | 0.0955 | 50.4 | 10.6 |
| JNJ21196227 | 0.1640 | 0.1158 | 0.1399 | 0.0341 | 24.4 | 3.5 |
| JNJ24843611 | 1.1486 | 0.8970 | 1.0228 | 0.1779 | 17.4 | 130.5 |
| JNJ24843611 | 0.1358 | 0.1201 | 0.1280 | 0.0111 | 8.7 | 1.8 |
| JNJ24326185 | 0.1257 | 0.1257 | 0.1257 | 0.0000 | 0.0 | 1.5 |
| JNJ24843572 | 0.4676 | 0.4803 | 0.4740 | 0.0090 | 1.9 | 51.6 |
| conditioned medium | 0.6935 | 0.7803 | 0.7369 | 0.0614 | 8.3 | 104.8 |
| no treatment | 0.4735 | 0.6069 | 0.5402 | 0.0943 | 17.5 | 71.5 |
| AA only+ DMSO | 0.1428 | 0.1656 | 0.1542 | 0.0161 | 10.5 | 6.3 |
| AA + Wnt3a + DMSO | 0.5702 | 0.8468 | 0.7085 | 0.1956 | 27.6 | 100.0 |
| JNJ24843585 | 0.1599 | 0.2380 | 0.1990 | 0.0552 | 27.8 | 13.8 |
| JNJ25753520 | 0.1287 | 0.1244 | 0.1266 | 0.0030 | 2.4 | 1.6 |
| no cells | 0.1241 | 0.1100 | 0.1171 | 0.0100 | 8.5 | 0.0 |
| JNJ25753403 | 0.1235 | 0.1152 | 0.1194 | 0.0059 | 4.9 | 0.4 |
| JNJ25757173 | 0.1199 | 0.1278 | 0.1239 | 0.0056 | 4.5 | 1.1 |
| JNJ25757173 | 0.1174 | 0.1162 | 0.1168 | 0.0008 | 0.7 | −0.1 |
| JNJ25757238 | 1.1100 | 0.9464 | 1.0282 | 0.1157 | 11.3 | 154.1 |
| JNJ25758707 | 0.1247 | 0.1115 | 0.1181 | 0.0093 | 7.9 | 0.2 |
| JNJ25758785 | 0.2640 | 0.1688 | 0.2164 | 0.0673 | 31.1 | 16.8 |
| JNJ25758850 | 0.2313 | 0.1307 | 0.1810 | 0.0711 | 39.3 | 10.8 |
| JNJ25758863 | 0.8639 | 0.9218 | 0.8929 | 0.0409 | 4.6 | 131.2 |
| JNJ25873419 | 0.2540 | 0.2320 | 0.2430 | 0.0156 | 6.4 | 21.3 |
| JNJ25887537 | 0.1809 | 0.3077 | 0.2443 | 0.0897 | 36.7 | 21.5 |
| JNJ25900641 | 0.1892 | 0.1872 | 0.1882 | 0.0014 | 0.8 | 12.0 |
| JNJ25900654 | 0.1967 | 0.2492 | 0.2230 | 0.0371 | 16.7 | 17.9 |
| JNJ25900706 | 0.3346 | 0.1619 | 0.2483 | 0.1221 | 49.2 | 22.2 |
| JNJ26047723 | 0.1106 | 0.1138 | 0.1122 | 0.0023 | 2.0 | −0.8 |
| JNJ26054912 | 0.1224 | 0.1445 | 0.1335 | 0.0156 | 11.7 | 2.8 |
| JNJ26064571 | 0.1312 | 0.1270 | 0.1291 | 0.0030 | 2.3 | 2.0 |
| JNJ26067626 | 0.1653 | 0.2114 | 0.1884 | 0.0326 | 17.3 | 12.0 |
| JNJ26067652 | 0.1732 | 0.1467 | 0.1600 | 0.0187 | 11.7 | 7.2 |
| JNJ26069901 | 0.1618 | 0.2754 | 0.2186 | 0.0803 | 36.7 | 17.2 |
| JNJ26077883 | 1.0006 | 0.9631 | 0.9819 | 0.0265 | 2.7 | 146.2 |
| JNJ26116922 | 0.6472 | 0.4319 | 0.5396 | 0.1522 | 28.2 | 71.4 |
| JNJ26120601 | 0.1539 | 0.1469 | 0.1504 | 0.0049 | 3.3 | 5.6 |
| JNJ26120614 | 0.1127 | 0.1309 | 0.1218 | 0.0129 | 10.6 | 0.8 |
| JNJ26128726 | 0.6887 | 0.5860 | 0.6374 | 0.0726 | 11.4 | 88.0 |
| JNJ26130403 | 0.1141 | 0.1094 | 0.1118 | 0.0033 | 3.0 | −0.9 |
| JNJ26134771 | 0.2774 | 0.1690 | 0.2232 | 0.0767 | 34.3 | 17.9 |
| JNJ26150202 | 0.9482 | 1.1150 | 1.0316 | 0.1179 | 11.4 | 154.6 |
| JNJ26153647 | 0.7687 | 0.6804 | 0.7246 | 0.0624 | 8.6 | 102.7 |
| JNJ26158015 | 0.7125 | 0.3347 | 0.5236 | 0.2671 | 51.0 | 68.7 |
| JNJ26158054 | 0.1446 | 0.1221 | 0.1334 | 0.0159 | 11.9 | 2.7 |
| JNJ26158093 | 1.0968 | 1.3108 | 1.2038 | 0.1513 | 12.6 | 183.8 |
| JNJ26158106 | 0.3167 | 0.3415 | 0.3291 | 0.0175 | 5.3 | 35.8 |
| JNJ26161343 | 0.1261 | 0.1144 | 0.1203 | 0.0083 | 6.9 | 0.5 |
| JNJ26170794 | 0.2223 | 0.2930 | 0.2577 | 0.0500 | 19.4 | 23.8 |
| JNJ26170820 | 0.1265 | 0.1236 | 0.1251 | 0.0021 | 1.6 | 1.3 |
| JNJ26170833 | 1.1940 | 0.9431 | 1.0686 | 0.1774 | 16.6 | 160.9 |
| JNJ26177086 | 1.0689 | 0.6879 | 0.8784 | 0.2694 | 30.7 | 128.7 |
| JNJ26177762 | 1.0444 | 0.7603 | 0.9024 | 0.2009 | 22.3 | 132.8 |
| JNJ26184457 | 0.1443 | 0.1209 | 0.1326 | 0.0165 | 12.5 | 2.6 |
| JNJ26219050 | 0.1152 | 0.1309 | 0.1231 | 0.0111 | 9.0 | 1.0 |
| conditioned medium | 0.7590 | 0.7451 | 0.7521 | 0.0098 | 1.3 | 98.0 |
| no treatment | 0.5687 | 0.4490 | 0.5089 | 0.0846 | 16.6 | 60.4 |
| AA only + DMSO | 0.1988 | 0.1522 | 0.1755 | 0.0330 | 18.8 | 8.9 |
| AA + Wnt3a + DMSO | 0.6837 | 0.8460 | 0.7649 | 0.1148 | 15.0 | 100.0 |
| JNJ26219063 | 0.1911 | 0.1101 | 0.1506 | 0.0573 | 38.0 | 5.0 |
| JNJ26220454 | 0.2772 | 0.1151 | 0.1962 | 0.1146 | 58.4 | 12.1 |
| no cells | 0.1278 | 0.1084 | 0.1181 | 0.0137 | 11.6 | 0.0 |
| JNJ26241774 | 0.1443 | 0.2120 | 0.1782 | 0.0479 | 26.9 | 9.3 |
| JNJ26241917 | 0.4413 | 0.2238 | 0.3326 | 0.1538 | 46.2 | 33.2 |
| JNJ26243204 | 0.1098 | 0.1085 | 0.1092 | 0.0009 | 0.8 | −1.4 |
| JNJ26247143 | 0.1389 | 0.2147 | 0.1768 | 0.0536 | 30.3 | 9.1 |
| JNJ26248729 | 0.1852 | 0.1342 | 0.1597 | 0.0361 | 22.6 | 6.4 |
| JNJ26261105 | 0.1114 | 0.1295 | 0.1205 | 0.0128 | 10.6 | 0.4 |

TABLE VI-continued

EFFECTS OF INHIBITORS OF GSK-3B ENZYME ACTIVITY ON THE PROLIFERATION OF HUMAN EMBRYONIC STEM CELLS.

| JNJ number | Raw Data | | Average | S.D. | % CV | % Control |
|---|---|---|---|---|---|---|
| JNJ26361712 | 0.5375 | 0.6158 | 0.5767 | 0.0554 | 9.6 | 70.9 |
| JNJ26361725 | 0.1259 | 0.1441 | 0.1350 | 0.0129 | 9.5 | 2.6 |
| JNJ26366730 | 0.1206 | 0.1312 | 0.1259 | 0.0075 | 6.0 | 1.2 |
| JNJ26367991 | 0.2269 | 0.2857 | 0.2563 | 0.0416 | 16.2 | 21.4 |
| JNJ26367991 | 0.1140 | 0.1079 | 0.1110 | 0.0043 | 3.9 | −1.1 |
| JNJ26399906 | 0.9589 | 0.8868 | 0.9229 | 0.0510 | 5.5 | 124.4 |
| JNJ26399906 | 1.0442 | 0.9622 | 1.0032 | 0.0580 | 5.8 | 136.8 |
| JNJ26399945 | 0.1961 | 0.1735 | 0.1848 | 0.0160 | 8.6 | 10.3 |
| JNJ26399971 | 0.5732 | 0.5216 | 0.5474 | 0.0365 | 6.7 | 66.4 |
| JNJ26399984 | 0.1273 | 0.1217 | 0.1245 | 0.0040 | 3.2 | 1.0 |
| JNJ26399997 | 0.5932 | 0.6671 | 0.6302 | 0.0523 | 8.3 | 79.2 |
| JNJ26400049 | 0.1444 | 0.1368 | 0.1406 | 0.0054 | 3.8 | 3.5 |
| JNJ26483197 | 1.0786 | 1.0891 | 1.0839 | 0.0074 | 0.7 | 149.3 |
| JNJ26483310 | 0.5418 | 0.2338 | 0.3878 | 0.2178 | 56.2 | 41.7 |
| JNJ26483223 | 0.1268 | 0.2052 | 0.1660 | 0.0554 | 33.4 | 7.4 |
| JNJ26483236 | 0.1169 | 0.1184 | 0.1177 | 0.0011 | 0.9 | −0.1 |
| JNJ26483249 | 0.8618 | 1.0400 | 0.9509 | 0.1260 | 13.3 | 128.8 |
| JNJ26483249 | 0.8430 | 1.0187 | 0.9309 | 0.1242 | 13.3 | 125.7 |
| JNJ26483262 | 0.3659 | 0.3168 | 0.3414 | 0.0347 | 10.2 | 34.5 |
| JNJ26511901 | 0.9184 | 0.8116 | 0.8650 | 0.0755 | 8.7 | 115.5 |
| JNJ26511927 | 0.2384 | 0.3156 | 0.2770 | 0.0546 | 19.7 | 24.6 |
| JNJ26511953 | 0.2297 | 0.1469 | 0.1883 | 0.0585 | 31.1 | 10.9 |
| RWJ67694 | 0.1955 | 0.1256 | 0.1606 | 0.0494 | 30.8 | 6.6 |
| RWJ676940 | 0.1658 | 0.1704 | 0.1681 | 0.0033 | 1.9 | 7.7 |
| RWJ677545 | 0.1399 | 0.1303 | 0.1351 | 0.0068 | 5.0 | 2.6 |
| RWJ678986 | 0.1234 | 0.1236 | 0.1235 | 0.0001 | 0.1 | 0.8 |
| RWJ680665 | 0.1397 | 0.2147 | 0.1772 | 0.0530 | 29.9 | 9.1 |
| RWJ680667 | 0.1218 | 0.1310 | 0.1264 | 0.0065 | 5.1 | 1.3 |
| RWJ680668 | 0.1456 | 0.1981 | 0.1719 | 0.0371 | 21.6 | 8.3 |
| RWJ680669 | 0.5412 | 0.1898 | 0.3655 | 0.2485 | 68.0 | 38.2 |
| RWJ680858 | 0.1996 | 0.1245 | 0.1621 | 0.0531 | 32.8 | 6.8 |
| RWJ680858 | 0.1418 | 0.2014 | 0.1716 | 0.0421 | 24.6 | 8.3 |
| RWJ680879 | 0.1106 | 0.1197 | 0.1152 | 0.0064 | 5.6 | −0.5 |
| RWJ680885 | 0.1159 | 0.1272 | 0.1216 | 0.0080 | 6.6 | 0.5 |
| conditioned medium | 0.8077 | 0.7210 | 0.7644 | 0.0613 | 8.0 | 74.7 |
| no treatment + DMSO | 0.4638 | 0.4073 | 0.4356 | 0.0400 | 9.2 | 36.7 |
| AA/Wnt3a | 0.8466 | 0.9935 | 0.9830 | 0.2592 | 26.4 | 100.0 |
| JNJ10222784 | 0.8095 | 0.9055 | 0.8575 | 0.0679 | 7.9 | 85.5 |
| JNJ10222927 | 0.3519 | 0.4708 | 0.4114 | 0.0841 | 20.4 | 33.9 |
| JNJ10231273 | 0.1609 | 0.1275 | 0.1442 | 0.0236 | 16.4 | 3.1 |
| JNJ10259847 | 0.5020 | 0.2733 | 0.3877 | 0.1617 | 41.7 | 31.2 |
| JNJ10259847 | 0.3413 | 0.4146 | 0.3780 | 0.0518 | 13.7 | 30.1 |
| JNJ17154215 | 0.1176 | 0.1174 | 0.1175 | 0.0001 | 0.1 | 0.0 |
| JNJ17154215 | 0.1148 | 0.1410 | 0.1279 | 0.0185 | 14.5 | 1.2 |
| JNJ17157659 | 0.2394 | 0.2450 | 0.2422 | 0.0040 | 1.6 | 14.4 |
| JNJ17163042 | 0.3672 | 0.3098 | 0.3385 | 0.0406 | 12.0 | 25.5 |
| JNJ10166565 | 0.2722 | 0.1593 | 0.2158 | 0.0798 | 37.0 | 11.3 |
| JNJ17174664 | 0.5079 | 0.4349 | 0.4714 | 0.0516 | 11.0 | 40.9 |
| JNJ17187027 | 0.1076 | 0.1168 | 0.1122 | 0.0065 | 5.8 | −0.6 |
| JNJ17187053 | 0.2569 | 0.2151 | 0.2360 | 0.0296 | 12.5 | 13.7 |
| JNJ17193774 | 0.2846 | 0.4376 | 0.3611 | 0.1082 | 30.0 | 28.1 |
| JNJ17200976 | 0.1168 | 0.1136 | 0.1152 | 0.0023 | 2.0 | −0.3 |
| JNJ17205955 | 0.1168 | 0.1152 | 0.1160 | 0.0011 | 1.0 | −0.2 |
| JNJ17205955 | 0.1137 | 0.1195 | 0.1166 | 0.0041 | 3.5 | −0.1 |
| JNJ17205994 | 0.1154 | 0.1152 | 0.1153 | 0.0001 | 0.1 | −0.3 |
| JNJ17226703 | 0.2188 | 0.2353 | 0.2271 | 0.0117 | 5.1 | 12.6 |
| JNJ17982133 | 0.4588 | 0.2521 | 0.3555 | 0.1462 | 41.1 | 27.5 |
| JNJ17989049 | 0.3081 | 0.1961 | 0.2521 | 0.0792 | 31.4 | 15.5 |
| conditioned medium | 0.7914 | 1.1189 | 0.9552 | 0.2316 | 24.2 | 93.3 |
| no treatment | 0.4215 | 0.5259 | 0.4737 | 0.0738 | 15.6 | 39.8 |
| no cells | 0.1152 | 0.1160 | 0.1156 | 0.0006 | 0.5 | 0.0 |
| AA/Wnt3a | 0.7168 | 0.8836 | 1.0151 | 0.2016 | 19.9 | 100.0 |
| RWJ680991 | 0.2882 | 0.2308 | 0.2844 | 0.0499 | 17.6 | 18.8 |
| RWJ680992 | 0.3049 | 0.2845 | 0.3127 | 0.0282 | 9.0 | 21.9 |
| RWJ680993 | 0.5403 | 0.2570 | 0.3855 | 0.1332 | 34.6 | 30.0 |
| RWJ681140 | 0.7323 | 0.3034 | 0.4388 | 0.2041 | 46.5 | 35.9 |
| RWJ681142 | 0.1185 | 0.1216 | 0.1199 | 0.0018 | 1.5 | 0.5 |
| RWJ681146 | 0.2496 | 0.2683 | 0.2302 | 0.0376 | 16.3 | 12.7 |
| RWJ681945 | 0.1548 | 0.1356 | 0.1513 | 0.0134 | 8.8 | 4.0 |
| RWJ68198 | 0.1555 | 0.1450 | 0.1581 | 0.0161 | 10.2 | 4.7 |
| RWJ682205 | 0.2347 | 0.1920 | 0.3785 | 0.2589 | 68.4 | 29.2 |
| RWJ447228 | 0.1842 | 0.2093 | 0.3793 | 0.2585 | 68.2 | 29.3 |
| RWJ675430 | 0.7223 | 0.8707 | 0.4291 | 0.2452 | 57.2 | 34.8 |
| RWJ355923 | 0.6268 | 0.3192 | 0.3354 | 0.1667 | 49.7 | 24.4 |

TABLE VII

EFFECTS OF INHIBITORS OF GSK-3B ENZYME ACTIVITY ON THE PROLIFERATION OF HUMAN EMBRYONIC STEM CELLS.

| JNJ Number | % Control Value |
|---|---|
| List Strong Hits >= 120% control | |
| RWJ352628 | 195.3 |
| JNJ26158093 | 183.8 |
| RWJ353258 | 180.4 |
| JNJ26170833 | 160.9 |
| JNJ26150202 | 154.6 |
| JNJ25757238 | 154.1 |
| JNJ19410833 | 151.6 |
| JNJ26483197 | 149.3 |
| JNJ18157711 | 148.0 |
| RWJ676139 | 147.3 |
| JNJ26077883 | 146.2 |
| RWJ352190 | 142.3 |
| JNJ26399906 | 136.8 |
| JNJ19370026 | 136.1 |
| JNJ26177762 | 132.8 |
| RWJ676432 | 131.6 |
| JNJ25758863 | 131.2 |
| RWJ675430 | 130.9 |
| JNJ24843611 | 130.5 |
| RWJ675605 | 129.0 |
| JNJ26483249 | 128.8 |
| JNJ26177086 | 128.7 |
| JNJ26483249 | 125.7 |
| JNJ26399906 | 124.4 |
| RWJ675948 | 120.0 |
| List Moderate Hits 60-120% control | |
| JNJ26511901 | 115.5 |
| RWJ676431 | 113.8 |
| RWJ673515 | 108.3 |
| JNJ26533156 | 105.5 |
| JNJ26153647 | 102.7 |
| RWJ676639 | 93.0 |
| JNJ26128726 | 88.0 |
| JNJ10222784 | 85.5 |
| RWJ67657 | 84.7 |
| JNJ26512005 | 84.0 |
| JNJ19410859 | 80.3 |
| JNJ26399997 | 79.2 |
| RWJ676137 | 77.5 |
| RWJ675260 | 76.9 |
| RWJ355923 | 76.7 |
| RWJ675266 | 75.2 |
| JNJ26116922 | 71.4 |
| JNJ26361712 | 70.9 |
| RWJ670804 | 70.7 |
| RWJ675881 | 69.9 |
| JNJ26158015 | 68.7 |
| RWJ352244 | 68.2 |
| RWJ674239 | 67.4 |
| JNJ26399971 | 66.4 |
| JNJ26714194 | 63.3 |
| JNJ26533065 | 61.1 |

TABLE VIII

DOSE-DEPENDANT EFFECTS OF INHIBITORS OF GSK-3B ENZYME ACTIVITY ON THE PROLIFERATION OF CELLS OF THE HUMAN EMBRYONIC STEM CELL LINE H1.

| Concentration [uM] | Cell number | SD | Cell number | SD | Cell number | SD | Cell number | SD | Cell number | SD |
|---|---|---|---|---|---|---|---|---|---|---|
| | JNJ10220067 | | JNJ17163796 | | JNJ17189731 | | JNJ17223375 | | JNJ18157698 | |
| 10 | 1.006 | 0.051 | 0.039 | 0.049 | 0.193 | 0.147 | 1.280 | 0.014 | 1.049 | 0.062 |
| 5 | 1.058 | 0.047 | 1.164 | 0.018 | 0.889 | 0.035 | 1.348 | 0.007 | 1.104 | 0.014 |
| 2.5 | 1.031 | 0.054 | 1.022 | 0.023 | 0.896 | 0.035 | 1.318 | 0.028 | 0.932 | 0.087 |
| 1.25 | 0.899 | 0.040 | 1.121 | 0.023 | 1.120 | 0.072 | 1.159 | 0.041 | 1.006 | 0.023 |
| 0.625 | 0.742 | 0.095 | 1.092 | 0.044 | 1.107 | 0.093 | 1.029 | 0.018 | 0.832 | 0.026 |
| 0.313 | 0.754 | 0.010 | 0.931 | 0.056 | 1.132 | 0.018 | 1.018 | 0.044 | 0.742 | 0.127 |
| 0.156 | 0.822 | 0.074 | 0.804 | 0.002 | 1.082 | 0.041 | 0.776 | 0.054 | 0.712 | 0.020 |
| | JNJ26158015 | | JNJ26483197 | | JNJ26483249 | | JNJ17225871 | | JNJ17228458 | |
| 10 | 0.001 | 0.001 | 0.096 | 0.103 | 0.058 | 0.074 | 0.290 | 0.307 | 0.000 | 0.000 |
| 5 | 0.034 | 0.035 | 0.262 | 0.268 | 0.173 | 0.207 | 0.458 | 0.263 | 0.089 | 0.067 |
| 2.5 | 0.566 | 0.461 | 0.592 | 0.019 | 0.428 | 0.326 | 0.640 | 0.104 | 0.438 | 0.050 |
| 1.25 | 0.897 | 0.103 | 1.124 | 0.101 | 0.850 | 0.238 | 0.739 | 0.129 | 0.636 | 0.016 |
| 0.625 | 0.921 | 0.122 | 1.106 | 0.056 | 0.910 | 0.061 | 0.805 | 0.036 | 0.736 | 0.025 |
| 0.313 | 1.028 | 0.069 | 0.888 | 0.213 | 0.868 | 0.131 | 0.785 | 0.094 | 0.791 | 0.038 |
| 0.156 | 1.027 | 0.067 | 0.890 | 0.079 | 0.742 | 0.051 | 0.774 | 0.027 | 0.832 | 0.005 |
| | JNJ19370026 | | JNJ26150202 | | JNJ26170833 | | JNJ26177086 | | JNJ26177762 | |
| 10 | 0.000 | 0.000 | 0.496 | 0.690 | 0.129 | 0.170 | 0.412 | 0.081 | 0.996 | 0.246 |
| 5 | 0.024 | 0.034 | 0.768 | 0.490 | 0.530 | 0.080 | 1.128 | 0.026 | 0.908 | 0.179 |
| 2.5 | 1.097 | 0.294 | 1.001 | 0.129 | 1.174 | 0.016 | 1.031 | 0.217 | 1.005 | 0.086 |
| 1.25 | 1.446 | 0.076 | 1.158 | 0.043 | 1.113 | 0.057 | 0.914 | 0.100 | 1.200 | 0.065 |
| 0.625 | 1.296 | 0.183 | 0.699 | 0.248 | 1.188 | 0.041 | 0.801 | 0.136 | 1.111 | 0.300 |
| 0.313 | 1.034 | 0.197 | 0.617 | 0.232 | 1.158 | 0.102 | 0.785 | 0.121 | 0.959 | 0.094 |
| 0.156 | 0.826 | 0.030 | 0.812 | 0.120 | 0.974 | 0.065 | 0.659 | 0.068 | 0.912 | 0.059 |
| | JNJ26512005 | | JNJ26533065 | | JNJ26533156 | | JNJ26714194 | | JNJ3026582 | |
| 10 | 0.000 | 0.000 | 0.021 | 0.027 | 0.002 | 0.002 | 0.052 | 0.067 | 0.053 | 0.024 |
| 5 | 0.000 | 0.000 | 0.339 | 0.254 | 1.011 | 0.499 | 1.161 | 0.134 | 0.905 | 0.036 |
| 2.5 | 0.192 | 0.233 | 1.350 | 0.170 | 1.724 | 0.042 | 1.293 | 0.020 | 1.019 | 0.015 |
| 1.25 | 0.552 | 0.458 | 1.277 | 0.101 | 1.652 | 0.032 | 1.213 | 0.087 | 1.163 | 0.062 |

TABLE VIII-continued

DOSE-DEPENDANT EFFECTS OF INHIBITORS OF GSK-3B
ENZYME ACTIVITY ON THE PROLIFERATION OF CELLS OF THE HUMAN
EMBRYONIC STEM CELL LINE H1.

| Concentration [uM] | Cell number | SD | Cell number | SD | Cell number | SD | Cell number | SD | Cell number | SD |
|---|---|---|---|---|---|---|---|---|---|---|
| 0.625 | 0.895 | 0.054 | 0.713 | 0.151 | 1.357 | 0.023 | 1.025 | 0.045 | 1.231 | 0.152 |
| 0.313 | 0.734 | 0.075 | 0.665 | 0.207 | 1.213 | 0.177 | 1.241 | 0.031 | 1.216 | 0.007 |
| 0.156 | 0.594 | 0.078 | 0.469 | 0.465 | 1.206 | 0.142 | 1.041 | 0.007 | 1.103 | 0.065 |

TABLE IX

DOSE-DEPENDANT EFFECTS OF INHIBITORS OF GSK-3B
ENZYME ACTIVITY ON THE DIFFERENTIATION OF CELLS OF THE
HUMAN EMBRYONIC STEM CELL LINE H1.

| Concentration [uM] | Sox17 Intensity | SD | Sox17 Intensity | SD | Sox17 Intensity | SD | Sox17 Intensity | SD | Sox17 Intensity | SD |
|---|---|---|---|---|---|---|---|---|---|---|
| | JNJ10220067 | | JNJ17163796 | | JNJ17189731 | | JNJ17223375 | | JNJ18157698 | |
| 10 | 0.889 | 0.144 | 0.029 | 0.034 | 0.140 | 0.095 | 1.183 | 0.044 | 0.969 | 0.040 |
| 5 | 1.004 | 0.021 | 0.824 | 0.035 | 0.785 | 0.077 | 1.171 | 0.010 | 1.013 | 0.002 |
| 2.5 | 1.023 | 0.092 | 0.849 | 0.003 | 0.842 | 0.032 | 1.169 | 0.031 | 0.838 | 0.068 |
| 1.25 | 0.954 | 0.100 | 0.985 | 0.082 | 1.028 | 0.043 | 1.106 | 0.006 | 0.940 | 0.071 |
| 0.625 | 0.793 | 0.135 | 0.986 | 0.059 | 1.016 | 0.000 | 0.931 | 0.033 | 0.767 | 0.014 |
| 0.313 | 0.803 | 0.048 | 0.916 | 0.028 | 1.058 | 0.017 | 0.943 | 0.056 | 0.692 | 0.167 |
| 0.156 | 0.941 | 0.106 | 0.822 | 0.036 | 1.039 | 0.015 | 0.789 | 0.074 | 0.651 | 0.032 |
| | JNJ26158015 | | JNJ26483197 | | JNJ26483249 | | JNJ17225871 | | JNJ17228458 | |
| 10 | 0.001 | 0.001 | 0.034 | 0.027 | 0.054 | 0.063 | 0.267 | 0.280 | 0.000 | 0.001 |
| 5 | 0.017 | 0.020 | 0.071 | 0.054 | 0.141 | 0.169 | 0.402 | 0.229 | 0.056 | 0.035 |
| 2.5 | 0.200 | 0.157 | 0.497 | 0.076 | 0.373 | 0.326 | 0.605 | 0.041 | 0.286 | 0.034 |
| 1.25 | 0.792 | 0.066 | 0.993 | 0.144 | 0.783 | 0.282 | 0.686 | 0.185 | 0.587 | 0.023 |
| 0.625 | 0.824 | 0.118 | 1.061 | 0.066 | 0.887 | 0.062 | 0.786 | 0.061 | 0.695 | 0.001 |
| 0.313 | 0.934 | 0.127 | 0.937 | 0.136 | 0.859 | 0.176 | 0.780 | 0.132 | 0.753 | 0.098 |
| 0.156 | 0.986 | 0.055 | 0.888 | 0.062 | 0.666 | 0.015 | 0.782 | 0.061 | 0.816 | 0.043 |
| | JNJ19370026 | | JNJ26150202 | | JNJ26170833 | | JNJ26177086 | | JNJ26177762 | |
| 10 | 0.000 | 0.000 | 0.491 | 0.681 | 0.281 | 0.358 | 0.330 | 0.059 | 0.701 | 0.307 |
| 5 | 0.035 | 0.049 | 0.158 | 0.224 | 0.460 | 0.189 | 0.846 | 0.036 | 0.728 | 0.146 |
| 2.5 | 1.336 | 0.192 | 0.800 | 0.201 | 1.018 | 0.139 | 0.887 | 0.191 | 0.928 | 0.019 |
| 1.25 | 1.238 | 0.030 | 0.910 | 0.045 | 0.960 | 0.106 | 0.819 | 0.179 | 1.159 | 0.093 |
| 0.625 | 0.997 | 0.095 | 0.567 | 0.190 | 1.050 | 0.038 | 0.755 | 0.126 | 1.136 | 0.186 |
| 0.313 | 0.791 | 0.172 | 0.515 | 0.276 | 1.032 | 0.063 | 0.667 | 0.125 | 1.006 | 0.009 |
| 0.156 | 0.669 | 0.037 | 0.708 | 0.148 | 0.950 | 0.087 | 0.628 | 0.053 | 0.922 | 0.096 |
| | JNJ26512005 | | JNJ26533065 | | JNJ26533156 | | JNJ26714194 | | JNJ3026582 | |
| 10 | 0.000 | 0.000 | 0.018 | 0.021 | 0.002 | 0.001 | 0.054 | 0.062 | 0.074 | 0.048 |
| 5 | 0.000 | 0.000 | 0.235 | 0.174 | 1.052 | 0.281 | 1.250 | 0.177 | 1.006 | 0.070 |
| 2.5 | 0.270 | 0.382 | 1.153 | 0.223 | 1.459 | 0.074 | 1.186 | 0.069 | 1.120 | 0.038 |
| 1.25 | 0.678 | 0.434 | 1.055 | 0.046 | 1.322 | 0.078 | 1.112 | 0.038 | 1.122 | 0.009 |
| 0.625 | 0.978 | 0.021 | 0.569 | 0.124 | 1.173 | 0.015 | 0.913 | 0.005 | 1.241 | 0.230 |
| 0.313 | 0.742 | 0.048 | 0.555 | 0.118 | 1.102 | 0.165 | 1.140 | 0.036 | 1.231 | 0.012 |
| 0.156 | 0.508 | 0.049 | 0.451 | 0.443 | 1.060 | 0.126 | 0.998 | 0.006 | 1.034 | 0.008 |

TABLE X

DOSE-DEPENDANT EFFECTS OF INHIBITORS OF GSK-3B
ENZYME ACTIVITY ON THE PROLIFERATION OF CELLS OF THE HUMAN
EMBRYONIC STEM CELL LINE H9.

| Concentration [uM] | Cell number | SD | Cell number | SD | Cell number | SD | Cell number | SD | Cell number | SD |
|---|---|---|---|---|---|---|---|---|---|---|
| | JNJ10220067 | | JNJ17163796 | | JNJ17189731 | | JNJ17223375 | | JNJ18157698 | |
| 10 | 0.164 | 0.209 | 0.001 | 0.000 | 0.049 | 0.028 | 0.123 | 0.106 | 0.770 | 0.077 |
| 5 | 0.147 | 0.141 | 0.616 | 0.497 | 0.583 | 0.155 | 0.954 | 0.146 | 0.496 | 0.011 |
| 2.5 | 0.140 | 0.112 | 1.295 | 0.402 | 1.108 | 0.170 | 0.795 | 0.101 | 0.384 | 0.247 |
| 1.25 | 0.307 | 0.198 | 1.233 | 0.058 | 1.195 | 0.147 | 0.541 | 0.051 | 0.395 | 0.002 |
| 0.625 | 0.138 | 0.071 | 0.606 | 0.121 | 1.100 | 0.014 | 0.332 | 0.049 | 0.221 | 0.009 |
| 0.313 | 0.063 | 0.008 | 0.397 | 0.020 | 0.887 | 0.078 | 0.206 | 0.085 | 0.172 | 0.071 |
| 0.156 | 0.069 | 0.001 | 0.214 | 0.025 | 0.699 | 0.109 | 0.142 | 0.039 | 0.138 | 0.048 |

TABLE X-continued

DOSE-DEPENDANT EFFECTS OF INHIBITORS OF GSK-3B
ENZYME ACTIVITY ON THE PROLIFERATION OF CELLS OF THE HUMAN
EMBRYONIC STEM CELL LINE H9.

| Concentration [uM] | Cell number | SD | Cell number | SD | Cell number | SD | Cell number | SD | Cell number | SD |
|---|---|---|---|---|---|---|---|---|---|---|
| | JNJ26158015 | | JNJ26483197 | | JNJ26483249 | | JNJ17225871 | | JNJ17228458 | |
| 10 | 0.001 | 0.000 | 0.785 | 0.192 | 0.208 | 0.134 | 0.377 | 0.040 | 0.000 | 0.000 |
| 5 | 0.023 | 0.024 | 1.067 | 0.236 | 0.320 | 0.087 | 0.336 | 0.081 | 0.052 | 0.009 |
| 2.5 | 0.681 | 0.223 | 1.368 | 0.025 | 0.388 | 0.019 | 0.296 | 0.016 | 0.089 | 0.003 |
| 1.25 | 1.011 | 0.461 | 1.477 | 0.147 | 0.334 | 0.113 | 0.222 | 0.035 | 0.106 | 0.003 |
| 0.625 | 0.927 | 0.108 | 0.899 | 0.108 | 0.267 | 0.148 | 0.282 | 0.096 | 0.169 | 0.041 |
| 0.313 | 0.686 | 0.022 | 0.540 | 0.094 | 0.192 | 0.056 | 0.208 | 0.003 | 0.119 | 0.026 |
| 0.156 | 0.458 | 0.001 | 0.206 | 0.089 | 0.147 | 0.067 | 0.174 | 0.051 | 0.067 | 0.015 |
| | JNJ19370026 | | JNJ26150202 | | JNJ26170833 | | JNJ26177086 | | JNJ26177762 | |
| 10 | 0.000 | 0.000 | 0.452 | 0.094 | 0.002 | 0.001 | 1.117 | 0.043 | 1.022 | 0.422 |
| 5 | 0.002 | 0.000 | 0.433 | 0.050 | 1.325 | 0.015 | 0.793 | 0.030 | 1.281 | 0.109 |
| 2.5 | 0.668 | 0.059 | 0.521 | 0.229 | 1.355 | 0.026 | 0.600 | 0.122 | 1.197 | 0.068 |
| 1.25 | 0.988 | 0.032 | 0.293 | 0.038 | 1.182 | 0.076 | 0.442 | 0.018 | 1.039 | 0.213 |
| 0.625 | 0.390 | 0.032 | 0.200 | 0.122 | 0.928 | 0.127 | 0.371 | 0.072 | 0.686 | 0.014 |
| 0.313 | 0.250 | 0.090 | 0.072 | 0.025 | 0.772 | 0.050 | 0.100 | 0.008 | 0.437 | 0.066 |
| 0.156 | 0.095 | 0.020 | 0.057 | 0.044 | 0.336 | 0.056 | 0.072 | 0.015 | 0.276 | 0.043 |
| | JNJ26512005 | | JNJ26533065 | | JNJ26533156 | | JNJ26714194 | | JNJ3026582 | |
| 10 | 0.007 | 0.002 | 0.000 | 0.000 | 0.000 | 0.000 | 0.044 | 0.038 | 0.004 | 0.001 |
| 5 | 0.002 | 0.001 | 0.127 | 0.069 | 0.415 | 0.023 | 0.382 | 0.110 | 0.017 | 0.003 |
| 2.5 | 0.001 | 0.001 | 0.151 | 0.059 | 0.425 | 0.082 | 0.345 | 0.001 | 0.033 | 0.037 |
| 1.25 | 0.090 | 0.097 | 0.108 | 0.051 | 0.325 | 0.042 | 0.284 | 0.076 | 0.044 | 0.028 |
| 0.625 | 0.248 | 0.058 | 0.230 | 0.168 | 0.314 | 0.062 | 0.266 | 0.021 | 0.100 | 0.099 |
| 0.313 | 0.264 | 0.048 | 0.086 | 0.033 | 0.267 | 0.098 | 0.347 | 0.084 | 0.057 | 0.032 |
| 0.156 | 0.133 | 0.069 | 0.063 | 0.004 | 0.218 | 0.012 | 0.192 | 0.014 | 0.070 | 0.048 |

TABLE XI

DOSE-DEPENDANT EFFECTS OF INHIBITORS OF GSK-3B
ENZYME ACTIVITY ON THE DIFFERENTIATION OF CELLS OF THE
HUMAN EMBRYONIC STEM CELL LINE H9.

| Concentration [μM] | Sox17 Intensity | SD | Sox17 Intensity | SD | Sox17 Intensity | SD | Sox17 Intensity | SD | Sox17 Intensity | SD |
|---|---|---|---|---|---|---|---|---|---|---|
| | JNJ10220067 | | JNJ17163796 | | JNJ17189731 | | JNJ17223375 | | JNJ18157698 | |
| 0.157 | 0.051 | 0.003 | 0.132 | 0.003 | 0.678 | 0.093 | 0.116 | 0.047 | 0.095 | 0.025 |
| 0.313 | 0.052 | 0.008 | 0.311 | 0.005 | 0.951 | 0.010 | 0.155 | 0.071 | 0.110 | 0.030 |
| 0.625 | 0.103 | 0.058 | 0.453 | 0.076 | 1.160 | 0.013 | 0.277 | 0.061 | 0.154 | 0.013 |
| 1.25 | 0.312 | 0.255 | 1.012 | 0.051 | 1.042 | 0.134 | 0.459 | 0.066 | 0.317 | 0.062 |
| 2.5 | 0.100 | 0.062 | 0.986 | 0.269 | 0.869 | 0.158 | 0.726 | 0.079 | 0.297 | 0.235 |
| 5 | 0.105 | 0.089 | 0.480 | 0.423 | 0.432 | 0.111 | 1.114 | 0.066 | 0.353 | 0.080 |
| 10 | 0.121 | 0.141 | 0.002 | 0.002 | 0.022 | 0.005 | 0.140 | 0.110 | 0.694 | 0.123 |
| | JNJ26158015 | | JNJ26483197 | | JNJ26483249 | | JNJ17225871 | | JNJ17228458 | |
| 0.157 | 0.364 | 0.044 | 0.149 | 0.058 | 0.125 | 0.051 | 0.132 | 0.063 | 0.039 | 0.010 |
| 0.313 | 0.577 | 0.062 | 0.398 | 0.166 | 0.129 | 0.018 | 0.146 | 0.005 | 0.070 | 0.027 |
| 0.625 | 0.985 | 0.072 | 0.678 | 0.197 | 0.212 | 0.134 | 0.196 | 0.084 | 0.137 | 0.049 |
| 1.25 | 0.943 | 0.419 | 1.110 | 0.042 | 0.202 | 0.103 | 0.129 | 0.029 | 0.075 | 0.017 |
| 2.5 | 0.559 | 0.238 | 0.857 | 0.012 | 0.209 | 0.045 | 0.177 | 0.030 | 0.053 | 0.005 |
| 5 | 0.019 | 0.019 | 0.194 | 0.007 | 0.154 | 0.023 | 0.174 | 0.070 | 0.038 | 0.001 |
| 10 | 0.001 | 0.001 | 0.129 | 0.037 | 0.129 | 0.067 | 0.200 | 0.022 | 0.000 | 0.000 |
| | JNJ19370026 | | JNJ26150202 | | JNJ26170833 | | JNJ26177086 | | JNJ26177762 | |
| 0.157 | 0.074 | 0.024 | 0.040 | 0.030 | 0.291 | 0.086 | 0.054 | 0.014 | 0.186 | 0.040 |
| 0.313 | 0.170 | 0.046 | 0.051 | 0.016 | 0.746 | 0.088 | 0.080 | 0.006 | 0.342 | 0.068 |
| 0.625 | 0.246 | 0.036 | 0.150 | 0.095 | 0.941 | 0.111 | 0.268 | 0.050 | 0.563 | 0.019 |
| 1.25 | 0.981 | 0.075 | 0.155 | 0.010 | 1.119 | 0.045 | 0.332 | 0.006 | 0.936 | 0.186 |
| 2.5 | 0.914 | 0.038 | 0.408 | 0.279 | 1.305 | 0.066 | 0.432 | 0.154 | 1.146 | 0.137 |
| 5 | 0.001 | 0.001 | 0.251 | 0.092 | 1.185 | 0.012 | 0.543 | 0.004 | 1.127 | 0.121 |
| 10 | 0.000 | 0.000 | 0.262 | 0.068 | 0.000 | 0.000 | 0.822 | 0.024 | 0.759 | 0.328 |
| | JNJ26512005 | | JNJ26533065 | | JNJ26533156 | | JNJ26714194 | | JNJ3026582 | |
| 0.157 | 0.085 | 0.041 | 0.049 | 0.011 | 0.173 | 0.009 | 0.146 | 0.041 | 0.059 | 0.051 |
| 0.313 | 0.240 | 0.030 | 0.068 | 0.010 | 0.203 | 0.061 | 0.282 | 0.135 | 0.054 | 0.040 |
| 0.625 | 0.165 | 0.043 | 0.222 | 0.201 | 0.220 | 0.070 | 0.202 | 0.013 | 0.073 | 0.066 |
| 1.25 | 0.114 | 0.134 | 0.076 | 0.034 | 0.202 | 0.002 | 0.165 | 0.030 | 0.053 | 0.035 |
| 2.5 | 0.001 | 0.001 | 0.120 | 0.066 | 0.299 | 0.019 | 0.205 | 0.002 | 0.042 | 0.049 |

TABLE XI-continued

DOSE-DEPENDANT EFFECTS OF INHIBITORS OF GSK-3B
ENZYME ACTIVITY ON THE DIFFERENTIATION OF CELLS OF THE
HUMAN EMBRYONIC STEM CELL LINE H9.

| Concentration [µM] | Sox17 Intensity | SD | Sox17 Intensity | SD | Sox17 Intensity | SD | Sox17 Intensity | SD | Sox17 Intensity | SD |
|---|---|---|---|---|---|---|---|---|---|---|
| 5 | 0.001 | 0.001 | 0.087 | 0.036 | 0.300 | 0.095 | 0.234 | 0.078 | 0.016 | 0.001 |
| 10 | 0.009 | 0.003 | 0.000 | 0.000 | 0.000 | 0.000 | 0.042 | 0.028 | 0.004 | 0.003 |

What is claimed is:

1. A method to expand and differentiate human embryonic stem cells, comprising the steps of:
   a. Culturing human embryonic stem cells, and
   b. Treating the human embryonic stem cells with an inhibitor of glycogen synthase kinase 3β (GSK-3B) enzyme activity, wherein the inhibitor is 3-[1-(3-hydroxy-propyl)-1H-pyrrolo[2,3-b]pyridin-3-yl]-4-pyrazin-2-yl-pyrrole-2,5-dione.

2. The method of claim 1, wherein the human embryonic stem cells express at least one of the following pluripotency markers: ATP-binding cassette, subfamily G, member 2 (ABCG2), crypto, forkhead box D3 (FoxD3), Connexin43, Connexin45, POU domain transcription factor Oct4, sex-determining region Y-box2 (SOX-2), Nanog, human telomerase reverse transcriptase (hTERT), undifferentiated embryonic cell transcription factor 1 (UTF-1), zinc finger protein 42 (ZFP42), stage-specific embryonic antigen 3 (SSEA-3), stage-specific embryonic antigen 4 (SSEA-4), tumor-related antigen 1-60 (Tra1-60), and tumor-related antigen 1-81 (Tra1-81).

3. The method of claim 1, wherein the human embryonic stem cells are differentiated into cells expressing markers characteristic of the definitive endoderm lineage.

4. The method of claim 1, wherein the human embryonic stem cells are treated with the inhibitor of GSK-3B enzyme activity for about one to about 72 hours.

5. The method of claim 1, wherein the human embryonic stem cells are treated with the inhibitor of GSK-3B enzyme activity for about 12 to about 48 hours.

6. The method of claim 1, wherein the human embryonic stem cells are treated with the inhibitor of GSK-3B enzyme activity for about 48 hours.

7. The method of claim 1, wherein the inhibitor of GSK-3B enzyme activity is used at a concentration of about 100 nM to about 10004.

8. The method of claim 1, wherein the inhibitor of GSK-3B enzyme activity is used at a concentration of about 1 µM to about 10 µM.

9. The method of claim 1, wherein the inhibitor of GSK-3B enzyme activity is used at a concentration of about 10 µM.

* * * * *